(12) United States Patent
Riedl et al.

(10) Patent No.: US 7,897,623 B2
(45) Date of Patent: Mar. 1, 2011

(54) ω-CARBOXYL ARYL SUBSTITUTED DIPHENYL UREAS AS P38 KINASE INHIBITORS

(75) Inventors: Bernd Riedl, Wuppertal (DE); Jacques Dumas, Carlisle, MA (US); Uday R. Khire, Orange, CT (US); Timothy B. Lowinger, Carlisle, MA (US); William J. Scott, Guilford, CT (US); Roger A. Smith, Chester Springs, PA (US); Jill E. Wood, Ft. Collins, CO (US); Mary-Katherine Monahan, Hamden, CT (US); Reina Natero, Hamden, CT (US); Joel Renick, Milford, CT (US); Robert N. Sibley, North Haven, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 361 days.

(21) Appl. No.: 11/845,597

(22) Filed: Aug. 27, 2007

(65) Prior Publication Data
US 2008/0027061 A1    Jan. 31, 2008

Related U.S. Application Data

(63) Continuation of application No. 10/086,417, filed on Mar. 4, 2002, which is a continuation of application No. 09/425,229, filed on Oct. 22, 1999, which is a continuation-in-part of application No. 09/257,265, filed on Feb. 25, 1999.

(60) Provisional application No. 60/115,878, filed on Jan. 13, 1999.

(51) Int. Cl.
*A61K 31/44* (2006.01)
(52) U.S. Cl. .................................................. 514/346
(58) Field of Classification Search .................. 514/346
See application file for complete search history.

(56) References Cited

U.S. PATENT DOCUMENTS

| | | |
|---|---|---|
| 502,504 A | 8/1893 | Thorns |
| 1,792,156 A | 2/1931 | Fitzky |
| 2,046,375 A | 7/1936 | Goldstein et al. |
| 2,093,265 A | 9/1937 | Coffby et al. |
| 2,288,422 A | 6/1942 | Rohm |
| 2,649,476 A | 8/1953 | Martin et al. |
| 2,683,082 A | 7/1954 | Hill et al. |
| 2,722,544 A | 11/1955 | Martin et al. |
| 2,745,874 A | 5/1956 | Schetty et al. |
| 2,781,330 A | 2/1957 | Downey |
| 2,797,214 A | 6/1957 | Werner-Bossard |
| 2,867,659 A | 1/1959 | Model et al. |
| 2,877,268 A | 3/1959 | Applegate et al. |
| 2,960,488 A | 11/1960 | Tamblyn et al. |
| 2,973,386 A | 2/1961 | Weldon |
| 3,151,023 A | 9/1964 | Martin |
| 3,200,035 A | 8/1965 | Martin et al. |
| 3,230,141 A | 1/1966 | Frick et al. |
| 3,284,433 A | 11/1966 | Becker et al. |
| 3,424,760 A | 1/1969 | Helsley et al. |
| 3,424,761 A | 1/1969 | Helsley et al. |
| 3,424,762 A | 1/1969 | Helsley et al. |
| 3,547,940 A | 12/1970 | Brantley |
| 3,639,668 A | 2/1972 | Alles et al. |
| 3,646,059 A | 2/1972 | Brantley |
| 3,668,222 A | 6/1972 | Hauser |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 3,860,645 A | 1/1975 | Nikawitz |
| 3,990,879 A | 11/1976 | Soper |
| 4,001,256 A | 1/1977 | Callahan et al. |
| 4,009,847 A | 3/1977 | Aldrich et al. |
| 4,042,372 A | 8/1977 | Harper |
| 4,062,861 A | 12/1977 | Yukinaga et al. |
| 4,063,928 A | 12/1977 | Johnston |
| 4,071,524 A | 1/1978 | Banitt |
| 4,103,022 A | 7/1978 | Sirrenberg et al. |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,279,639 A | 7/1981 | Okamoto et al. |
| 4,293,328 A | 10/1981 | Yukinaga et al. |
| 4,358,596 A | 11/1982 | Krüger |
| 4,405,644 A | 9/1983 | Kabbe et al. |
| 4,410,697 A | 10/1983 | Török et al. |
| 4,437,878 A | 3/1984 | Acker et al. |

(Continued)

FOREIGN PATENT DOCUMENTS

CA    2028536 A1    4/1991

(Continued)

OTHER PUBLICATIONS

Kubo, Hiroshi et al: "herbicidal activity . . . " J. Agr. Food Chem, (1970), 18(1), 60-5.

(Continued)

*Primary Examiner*—Raymond J Henley, III
(74) *Attorney, Agent, or Firm*—Millen, White, Zelano & Branigan, P.C.

(57) ABSTRACT

This invention relates to the use of a group of aryl ureas in treating p38 mediated diseases, and pharmaceutical compositions for use in such therapy.

8 Claims, No Drawings

U.S. PATENT DOCUMENTS

| | | | |
|---|---|---|---|
| 4,468,380 A | 8/1984 | O'Doherty et al. |
| 4,473,579 A | 9/1984 | Devries et al. |
| 4,499,097 A | 2/1985 | Tomcufcik et al. |
| 4,511,571 A | 4/1985 | Böger et al. |
| 4,514,571 A | 4/1985 | Nakai et al. |
| 4,526,997 A | 7/1985 | O'Doherty et al. |
| 4,540,566 A | 9/1985 | Davis et al. |
| 4,546,191 A | 10/1985 | Nishiyama et al. |
| 4,587,240 A | 5/1986 | Hider et al. |
| 4,623,662 A | 11/1986 | De Vries |
| 4,643,849 A | 2/1987 | Hirai et al. |
| 4,740,520 A | 4/1988 | Hallenbach et al. |
| 4,760,063 A | 7/1988 | Hallenbach et al. |
| 4,775,763 A | 10/1988 | Dalton et al. |
| 4,808,588 A | 2/1989 | King |
| 4,820,871 A | 4/1989 | Kissener et al. |
| 4,863,924 A | 9/1989 | Haga et al. |
| 4,921,525 A | 5/1990 | Grossman et al. |
| 4,973,675 A | 11/1990 | Israel et al. |
| 4,977,169 A | 12/1990 | Häusermann et al. |
| 4,983,605 A | 1/1991 | Kondo et al. |
| 4,985,449 A | 1/1991 | Haga et al. |
| 4,996,325 A | 2/1991 | Kristinsson |
| 5,036,072 A | 7/1991 | Nakajima et al. |
| 5,059,614 A | 10/1991 | Lepage et al. |
| 5,063,247 A | 11/1991 | Sekiya et al. |
| 5,098,907 A | 3/1992 | Kondo et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,331 A | 7/1992 | Pascual |
| 5,151,344 A | 9/1992 | Abe et al. |
| 5,151,413 A | 9/1992 | Caufield et al. |
| 5,162,360 A | 11/1992 | Creswell et al. |
| 5,177,110 A | 1/1993 | Oechslein et al. |
| 5,185,358 A | 2/1993 | Creswell |
| 5,256,790 A | 10/1993 | Nelson |
| 5,258,389 A | 11/1993 | Goulet et al. |
| 5,270,458 A | 12/1993 | Lemischka |
| 5,283,354 A | 2/1994 | Lemischka |
| 5,312,820 A | 5/1994 | Ashton et al. |
| 5,319,099 A | 6/1994 | Kamata et al. |
| 5,378,725 A | 1/1995 | Bonjouklian et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,441,947 A | 8/1995 | Dodge et al. |
| 5,447,957 A | 9/1995 | Adams et al. |
| 5,456,920 A | 10/1995 | Matoba et al. |
| 5,468,773 A | 11/1995 | Dodge et al. |
| 5,470,882 A | 11/1995 | Dixon et al. |
| 5,480,906 A | 1/1996 | Creemer et al. |
| 5,500,424 A | 3/1996 | Nagamine et al. |
| 5,508,288 A | 4/1996 | Forbes et al. |
| 5,547,966 A | 8/1996 | Atwal et al. |
| 5,559,137 A | 9/1996 | Adams et al. |
| 5,596,001 A | 1/1997 | Hamanaka |
| 5,597,719 A | 1/1997 | Freed et al. |
| 5,624,937 A | 4/1997 | Reel et al. |
| 5,656,612 A | 8/1997 | Monia |
| 5,658,903 A | 8/1997 | Adams et al. |
| 5,667,226 A | 9/1997 | Janich |
| 5,696,138 A | 12/1997 | Olesen et al. |
| 5,698,581 A | 12/1997 | Kleemann et al. |
| 5,710,094 A | 1/1998 | Minami et al. |
| 5,721,237 A | 2/1998 | Myers et al. |
| 5,726,167 A | 3/1998 | Dodge et al. |
| 5,747,498 A | 5/1998 | Schnur et al. |
| 5,773,459 A | 6/1998 | Tang et al. |
| 5,777,097 A | 7/1998 | Lee et al. |
| 5,780,262 A | 7/1998 | Brent et al. |
| 5,780,483 A | 7/1998 | Widdowson et al. |
| 5,783,664 A | 7/1998 | Lee et al. |
| 5,786,362 A | 7/1998 | Krongrad |
| 5,801,794 A | 9/1998 | Lehureau et al. |
| 5,807,876 A | 9/1998 | Armistead et al. |
| 5,807,891 A | 9/1998 | Bold et al. |
| 5,808,080 A | 9/1998 | Bell et al. |
| 5,814,646 A | 9/1998 | Heinz |
| 5,869,043 A | 2/1999 | McDonnell et al. |
| 5,871,934 A | 2/1999 | Lee et al. |
| 5,886,044 A | 3/1999 | Widdowson et al. |
| 5,891,895 A | 4/1999 | Shiraishi et al. |
| 5,908,865 A | 6/1999 | Doi et al. |
| 5,919,773 A | 7/1999 | Monia et al. |
| 5,929,250 A | 7/1999 | Widdowson et al. |
| 5,955,366 A | 9/1999 | Lee et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,017,692 A | 1/2000 | Brent et al. |
| 6,020,345 A | 2/2000 | Vacher et al. |
| 6,022,884 A | 2/2000 | Mantlo et al. |
| 6,025,151 A | 2/2000 | Peterson |
| 6,033,873 A | 3/2000 | McDonnell et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,103,692 A | 8/2000 | Avruch et al. |
| 6,114,517 A | 9/2000 | Monia et al. |
| 6,130,053 A | 10/2000 | Thompson et al. |
| 6,133,319 A | 10/2000 | Widdowson |
| 6,136,779 A | 10/2000 | Foulkes et al. |
| 6,143,764 A | 11/2000 | Kubo et al. |
| 6,147,107 A | 11/2000 | Dent et al. |
| 6,147,116 A | 11/2000 | Barbachyn et al. |
| 6,150,415 A | 11/2000 | Hammock et al. |
| 6,159,901 A | 12/2000 | Kanno et al. |
| 6,174,901 B1 | 1/2001 | Mantlo et al. |
| 6,177,401 B1 | 1/2001 | Ullrich et al. |
| 6,178,399 B1 | 1/2001 | Takebayashi et al. |
| 6,180,631 B1 | 1/2001 | McMahon et al. |
| 6,180,675 B1 | 1/2001 | Widdowson et al. |
| 6,187,799 B1 | 2/2001 | Wood et al. |
| 6,193,965 B1 | 2/2001 | Karin et al. |
| 6,204,267 B1 | 3/2001 | Tang et al. |
| 6,210,710 B1 | 4/2001 | Skinner |
| 6,211,373 B1 | 4/2001 | Widdowson et al. |
| 6,218,539 B1 | 4/2001 | Widdowson |
| 6,228,881 B1 | 5/2001 | Regan et al. |
| 6,235,764 B1 | 5/2001 | Larson et al. |
| 6,236,125 B1 | 5/2001 | Oudet et al. |
| 6,242,601 B1 | 6/2001 | Breu et al. |
| 6,262,113 B1 | 7/2001 | Widdowson et al. |
| 6,271,261 B1 | 8/2001 | Widdowson |
| 6,294,350 B1 | 9/2001 | Peterson |
| 6,297,381 B1 | 10/2001 | Cirillo et al. |
| 6,310,068 B1 | 10/2001 | Böttcher et al. |
| 6,316,462 B1 | 11/2001 | Bishop et al. |
| 6,319,921 B1 | 11/2001 | Cirillo et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,352,977 B1 | 3/2002 | Astles et al. |
| 6,358,525 B1 | 3/2002 | Guo et al. |
| 6,358,945 B1 | 3/2002 | Breitfelder et al. |
| 6,361,773 B1 | 3/2002 | Lee et al. |
| 6,372,773 B1 | 4/2002 | Regan |
| 6,372,933 B1 | 4/2002 | Baine et al. |

| | | |
|---|---|---|
| 6,380,218 B1 | 4/2002 | Marfat et al. |
| 6,383,734 B1 | 5/2002 | Marshall et al. |
| 6,387,900 B1 | 5/2002 | Pevarello et al. |
| 6,391,917 B1 | 5/2002 | Petrie et al. |
| 6,403,588 B1 | 6/2002 | Hayakawa et al. |
| 6,414,011 B1 | 7/2002 | Hogenkamp et al. |
| 6,444,691 B1 | 9/2002 | Oremus et al. |
| 6,448,079 B1 | 9/2002 | Monia et al. |
| 6,479,519 B1 | 11/2002 | Astles et al. |
| 6,492,393 B1 | 12/2002 | Breitfelder et al. |
| 6,495,331 B1 | 12/2002 | Gelfand et al. |
| 6,500,863 B1 | 12/2002 | Jin et al. |
| 6,511,800 B1 | 1/2003 | Singh |
| 6,511,997 B1 | 1/2003 | Minami et al. |
| 6,521,407 B1 | 2/2003 | Warenius et al. |
| 6,521,592 B2 | 2/2003 | Ko et al. |
| 6,524,832 B1 | 2/2003 | Kufe et al. |
| 6,525,046 B1 | 2/2003 | Cirillo et al. |
| 6,525,065 B1 | 2/2003 | Caldwell et al. |
| 6,525,091 B2 | 2/2003 | Robinson et al. |
| 6,583,282 B1 | 6/2003 | Zhang et al. |
| 6,608,052 B2 | 8/2003 | Breitfelder et al. |
| 6,617,324 B1 | 9/2003 | Naraian et al. |
| 6,635,421 B1 | 10/2003 | Klagsbrun et al. |
| 6,653,320 B2 | 11/2003 | Hayakawa et al. |
| 6,656,963 B2 | 12/2003 | Firestone et al. |
| 6,673,777 B1 | 1/2004 | Tracey et al. |
| 6,689,560 B1 | 2/2004 | Rapp et al. |
| 6,797,823 B1 | 9/2004 | Kubo et al. |
| 6,958,333 B1 | 10/2005 | Hayama et al. |
| 7,070,968 B2 | 7/2006 | Kufe et al. |
| 7,235,576 B1 | 6/2007 | Riedl et al. |
| 7,253,286 B2 | 8/2007 | Funahashi et al. |
| 7,307,071 B2 | 12/2007 | Lyons et al. |
| 7,329,670 B1 | 2/2008 | Dumas et al. |
| 7,351,834 B1 | 4/2008 | Riedl et al. |
| 7,371,763 B2 | 5/2008 | Dumas et al. |
| 7,517,880 B2 | 4/2009 | Miller et al. |
| 7,528,255 B2 | 5/2009 | Riedl et al. |
| 7,547,695 B2 | 6/2009 | Hoelzemann et al. |
| 7,557,129 B2 | 7/2009 | Scott et al. |
| 7,605,261 B2 | 10/2009 | Deprez et al. |
| 7,612,092 B2 | 11/2009 | Funahashi et al. |
| 7,678,811 B2 | 3/2010 | Dumas et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2001/0038842 A1 | 11/2001 | Achen et al. |
| 2002/0037276 A1 | 3/2002 | Ptasznik et al. |
| 2002/0042517 A1 | 4/2002 | Uday et al. |
| 2002/0062763 A1 | 5/2002 | Macholdt et al. |
| 2002/0065283 A1 | 5/2002 | McMahon et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0111495 A1 | 8/2002 | Magee et al. |
| 2002/0128321 A1 | 9/2002 | Widdowson et al. |
| 2002/0137774 A1 | 9/2002 | Riedl et al. |
| 2002/0161014 A1 | 10/2002 | Sadhu et al. |
| 2002/0165275 A1 | 11/2002 | Wu et al. |
| 2002/0165349 A1 | 11/2002 | Kirsch et al. |
| 2002/0165394 A1 | 11/2002 | Dumas et al. |
| 2002/0173507 A1 | 11/2002 | Santora et al. |
| 2002/0188027 A1 | 12/2002 | Robinson et al. |
| 2002/0197256 A1 | 12/2002 | Grewal |
| 2003/0069284 A1 | 4/2003 | Keegan et al. |
| 2003/0105091 A1 | 6/2003 | Riedl et al. |
| 2003/0125359 A1 | 7/2003 | Lyons et al. |
| 2003/0130309 A1 | 7/2003 | Moss et al. |
| 2003/0139605 A1 | 7/2003 | Riedl et al. |
| 2003/0144278 A1 | 7/2003 | Riedl et al. |
| 2003/0157104 A1 | 8/2003 | Waksal |
| 2003/0181442 A1 | 9/2003 | Riedl et al. |
| 2003/0207870 A1 | 11/2003 | Dumas et al. |
| 2003/0207872 A1 | 11/2003 | Riedl et al. |
| 2003/0207914 A1 | 11/2003 | Dumas et al. |
| 2003/0216396 A1 | 11/2003 | Dumas et al. |
| 2003/0216446 A1 | 11/2003 | Dumas et al. |
| 2003/0232400 A1 | 12/2003 | Radka et al. |
| 2003/0232765 A1 | 12/2003 | Carter et al. |
| 2004/0023961 A1 | 2/2004 | Dumas et al. |
| 2004/0052880 A1 | 3/2004 | Kobayashi et al. |
| 2004/0096855 A1 | 5/2004 | Stratton et al. |
| 2004/0147541 A1 | 7/2004 | Lane et al. |
| 2004/0192770 A1 | 9/2004 | Kozikowski et al. |
| 2004/0197256 A1 | 10/2004 | Rogers et al. |
| 2004/0209905 A1 | 10/2004 | Kubo et al. |
| 2004/0224937 A1 | 11/2004 | Furness et al. |
| 2004/0229937 A1 | 11/2004 | Dumas et al. |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0038080 A1 | 2/2005 | Boyer et al. |
| 2005/0059703 A1 | 3/2005 | Wilhelm et al. |
| 2005/0069963 A1 | 3/2005 | Lokshin et al. |
| 2005/0096344 A1 | 5/2005 | Fraley et al. |
| 2005/0175737 A1 | 8/2005 | Knobel |
| 2005/0256174 A1 | 11/2005 | Wood et al. |
| 2005/0288286 A1 | 12/2005 | Flynn et al. |
| 2006/0058358 A1 | 3/2006 | Dumas et al. |
| 2006/0078617 A1 | 4/2006 | Schueckler |
| 2006/0211738 A1 | 9/2006 | Mitchell et al. |
| 2006/0234931 A1 | 10/2006 | Biggs et al. |
| 2006/0241301 A1 | 10/2006 | Hoelzemann et al. |
| 2006/0247186 A1 | 11/2006 | Carter et al. |
| 2006/0281762 A1 | 12/2006 | Staehle et al. |
| 2007/0020704 A1 | 1/2007 | Wilhelm et al. |
| 2007/0037224 A1 | 2/2007 | Hamer et al. |
| 2007/0066660 A1 | 3/2007 | Stahle et al. |
| 2007/0105142 A1 | 5/2007 | Wilhelm |
| 2007/0149594 A1 | 6/2007 | Finsinger et al. |
| 2007/0173514 A1 | 7/2007 | Moss et al. |
| 2007/0178494 A1 | 8/2007 | Elting et al. |
| 2007/0244120 A1 | 10/2007 | Dumas et al. |
| 2007/0254295 A1 | 11/2007 | Harvey et al. |
| 2007/0265315 A1 | 11/2007 | Dumas et al. |
| 2008/0009527 A1 | 1/2008 | Dumas et al. |
| 2008/0027061 A1 | 1/2008 | Riedl et al. |
| 2008/0032979 A1 | 2/2008 | Riedl et al. |
| 2008/0045546 A1 | 2/2008 | Bouchon et al. |
| 2008/0045589 A1 | 2/2008 | Kelley |
| 2008/0085902 A1 | 4/2008 | Bold et al. |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0207699 A1 | 8/2008 | Hoelzemann et al. |
| 2008/0214545 A1 | 9/2008 | Lee et al. |
| 2008/0227828 A1 | 9/2008 | Dumas et al. |
| 2008/0242707 A1 | 10/2008 | Schuckler et al. |
| 2008/0262236 A1 | 10/2008 | Logers et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2008/0311604 A1 | 12/2008 | Elting et al. |
| 2009/0068146 A1 | 3/2009 | Wilhelm |
| 2009/0093526 A1 | 4/2009 | Miller et al. |
| 2009/0118268 A1 | 5/2009 | Riedl et al. |
| 2009/0176791 A1 | 7/2009 | Sandner et al. |
| 2009/0192127 A1 | 7/2009 | Scheuring et al. |
| 2009/0215833 A1 | 8/2009 | Grunenberg et al. |
| 2009/0215835 A1 | 8/2009 | Wilhelm |

| | | | | | | |
|---|---|---|---|---|---|---|
| 2009/0221010 | A1 | 9/2009 | Elting et al. | EP | 0425443 A1 | 10/1990 |
| 2009/0227637 | A1 | 9/2009 | Weber et al. | EP | 0 405 233 | 1/1991 |
| 2009/0306020 | A1 | 12/2009 | Scheuring et al. | EP | 0405233 A1 | 1/1991 |
| 2010/0035888 | A1 | 2/2010 | Sandner et al. | EP | 0405233 A1 | 1/1991 |
| 2010/0063088 | A1 | 3/2010 | Wood et al. | EP | 0425443 A1 | 5/1991 |

FOREIGN PATENT DOCUMENTS

| | | | | | |
|---|---|---|---|---|---|
| | | | EP | 459887 | 5/1991 |
| | | | EP | 0459887 A1 | 12/1991 |
| CA | 2 146 707 A1 | 10/1995 | EP | 0233559 B1 | 5/1992 |
| CA | 2146707 | 10/1995 | EP | 0192263 B1 | 7/1992 |
| CH | 47/9557 | 11/1969 | EP | 0 502 504 A1 | 9/1992 |
| CH | 479557 | 11/1969 | EP | 0502504 A1 | 9/1992 |
| CL | 38688 | 6/1993 | EP | 0509795 A2 | 10/1992 |
| DD | 253997 A1 | 2/1988 | EP | 0709225 A1 | 5/1995 |
| DD | 253997 A1 | 2/1998 | EP | 0690344 | 6/1995 |
| DE | 487 014 C1 | 11/1929 | EP | 0690344 A1 | 6/1995 |
| DE | 487014 C1 | 11/1929 | EP | 0676395 A2 | 10/1995 |
| DE | 511468 C1 | 11/1929 | EP | 0709225 A1 | 10/1995 |
| DE | 0 487 014 | 12/1929 | EP | 0 690 344 A1 | 1/1996 |
| DE | 0 511 468 | 10/1930 | EP | 0690344 A1 | 1/1996 |
| DE | 511 468 C1 | 10/1930 | EP | 0709220 A1 | 5/1996 |
| DE | 511468 C1 | 10/1930 | EP | 0709225 A1 | 5/1996 |
| DE | 523 437 C1 | 4/1931 | EP | 676395 | 7/1996 |
| DE | 523437 C1 | 4/1931 | EP | 0 860 433 A1 | 8/1998 |
| DE | 0 523 437 | 5/1931 | EP | 98/963310 | 8/1998 |
| DE | 2436179 | 2/1975 | EP | 0709225 B1 | 8/1998 |
| DE | 2436179 A1 | 2/1975 | EP | 0860433 A1 | 8/1998 |
| DE | 2436179 C2 | 2/1975 | EP | 0860433 A1 | 8/1998 |
| DE | 25 01 648 | 7/1975 | EP | 116932 A1 | 8/2000 |
| DE | 25 01 648 A1 | 7/1975 | EP | 1056725 A1 | 12/2000 |
| DE | 2501648 A1 | 7/1975 | EP | 98963810 | 12/2000 |
| DE | 2436179 A1 | 10/1981 | EP | 0425443 | 2/2001 |
| DE | 3305866 A1 | 2/1983 | EP | 0690344 | 5/2001 |
| DE | 3305866 A1 | 8/1984 | EP | 0709225 | 1/2002 |
| DE | 2436179 C2 | 4/1986 | EP | 1199306 A1 | 4/2002 |
| DE | 35 29 247 A1 | 11/1986 | EP | 903239.2-2103 R | 8/2002 |
| DE | 3529247 A1 | 11/1986 | EP | 1256587 A1 | 11/2002 |
| DE | 35 29 247 A1 | 2/1987 | EP | 1537075 A0 | 6/2005 |
| DE | 3529247 A1 | 2/1987 | EP | 1537075 | 8/2005 |
| DE | 35 40 377 A1 | 5/1987 | EP | 905597.1-2123 R | 7/2008 |
| DE | 3540377 A1 | 5/1987 | FR | 1 457 172 | 9/1966 |
| DE | 0 253 997 | 2/1988 | FR | 1 457 172 A | 9/1966 |
| DE | 253997 A1 | 2/1988 | FR | 1457172 A | 9/1966 |
| EP | 16371 | 3/1980 | GB | 0 828 231 | 10/1956 |
| EP | 0016371 A1 | 10/1980 | GB | 828 231 | 10/1956 |
| EP | 0107214 A1 | 5/1984 | GB | 0 771 333 | 3/1957 |
| EP | 0107214 A2 | 5/1984 | GB | 771 333 | 3/1957 |
| EP | 0116932 A1 | 8/1984 | GB | 771333 | 3/1957 |
| EP | 0192263 A2 | 8/1986 | GB | 828231 | 2/1960 |
| EP | 0192263 B1 | 8/1986 | GB | 0 921 682 | 3/1963 |
| EP | 0202538 A1 | 11/1986 | GB | 921 682 | 3/1963 |
| EP | 0230400 A2 | 7/1987 | GB | 921682 | 3/1963 |
| EP | 0230400 A2 | 7/1987 | GB | 1110099 | 6/1966 |
| EP | 0233559 A1 | 8/1987 | GB | 1110099 | 4/1968 |
| EP | 0233559 B1 | 8/1987 | GB | 1110099 A | 4/1968 |
| EP | 242666 | 10/1987 | GB | 1111554 | 5/1968 |
| EP | 0242666 A1 | 10/1987 | GB | 1 590 870 | 6/1981 |
| EP | 0264904 A2 | 4/1988 | GB | 1590870 | 6/1981 |
| EP | 0264904 A2 | 4/1988 | HU | P0004437 | 12/1998 |
| EP | 335156 | 3/1989 | HU | P0004437 | 6/2001 |
| EP | 0314615 A2 | 5/1989 | IR | 26555 | 1/2000 |
| EP | 0314615 W | 5/1989 | IR | 26555 | 7/2000 |
| EP | 0335156 A1 | 10/1989 | JP | 44 2569 | 2/1944 |
| EP | 371876 | 11/1989 | JP | 44 2569 | 2/1969 |
| EP | 0359148 A1 | 3/1990 | JP | 44-2569 B | 2/1969 |
| EP | 0359148 A1 | 3/1990 | JP | 50-76072 | 6/1975 |
| EP | 0371876 A1 | 6/1990 | JP | 50-76072 A | 6/1975 |
| EP | 0379915 A1 | 8/1990 | JP | 50-77375 | 6/1975 |
| EP | 0379915 A1 | 8/1990 | JP | 50-77375 A | 6/1975 |
| EP | 0380048 A2 | 8/1990 | JP | 50-149668 | 11/1975 |
| EP | 0380048 A2 | 8/1990 | JP | 50-149668 A | 11/1975 |
| EP | 0381987 A1 | 8/1990 | JP | 51-63170 A | 6/1976 |
| EP | 0381987 A1 | 8/1990 | JP | 51063170 | 6/1976 |
| | | | JP | 51-80862 | 7/1976 |

| | | | | | | |
|---|---|---|---|---|---|---|
| JP | 51-080862 A | 7/1976 | | WO | 93/24458 A1 | 12/1993 |
| JP | 51-80862 A | 7/1976 | | WO | 94/02136 A1 | 2/1994 |
| JP | 53-86033 A | 7/1978 | | WO | 94/02485 A1 | 2/1994 |
| JP | 53086033 | 7/1978 | | WO | 94/04541 | 3/1994 |
| JP | 54-032468 | 9/1979 | | WO | 94/04541 A2 | 3/1994 |
| JP | 54-32468 A | 9/1979 | | WO | 94/14801 | 7/1994 |
| JP | 55 98152 | 7/1980 | | WO | 94/14801 A1 | 7/1994 |
| JP | 55-98152 A | 7/1980 | | WO | 94/18170 | 8/1994 |
| JP | 55-124763 | 9/1980 | | WO | 94/18170 A1 | 8/1994 |
| JP | 55-124763 A | 9/1980 | | WO | 94 22807 | 10/1994 |
| JP | 55-162772 | 12/1980 | | WO | 94/22807 A1 | 10/1994 |
| JP | 55-162772 A | 12/1980 | | WO | 94/23755 | 10/1994 |
| JP | 57-53785 B2 | 11/1982 | | WO | 94/23755 A1 | 10/1994 |
| JP | 57053785 | 11/1982 | | WO | WO 94/22807 A1 | 10/1994 |
| JP | 58-21626 B2 | 5/1983 | | WO | 94/25012 | 11/1994 |
| JP | 61020039 A | 7/1984 | | WO | 94/25012 A1 | 11/1994 |
| JP | 61-20039 A | 1/1986 | | WO | 95/02136 A1 | 1/1995 |
| JP | 02035450 A | 7/1988 | | WO | 95/02591 | 1/1995 |
| JP | 63-214752 A | 9/1988 | | WO | 95/02591 A1 | 1/1995 |
| JP | 06075172 A | 9/1988 | | WO | 95/07922 | 3/1995 |
| JP | 64-9455 A | 1/1989 | | WO | 95/07922 A1 | 3/1995 |
| JP | 01009455 A | 1/1989 | | WO | 95/13067 | 5/1995 |
| JP | 1-102461 A | 4/1989 | | WO | 95/13067 A1 | 5/1995 |
| JP | 01102461 A | 4/1989 | | WO | 95/14023 A1 | 5/1995 |
| JP | 1-132580 A | 5/1989 | | WO | 95/16691 A1 | 6/1995 |
| JP | 1132580 A | 5/1989 | | WO | 95/19169 A2 | 7/1995 |
| JP | 1-200254 A | 8/1989 | | WO | 95/31451 | 11/1995 |
| JP | 01200254 | 8/1989 | | WO | 95/31451 A1 | 11/1995 |
| JP | 1-259360 A | 10/1989 | | WO | 95/33458 | 12/1995 |
| JP | 01259360 | 10/1989 | | WO | 95/33458 A1 | 12/1995 |
| JP | 03198049 A | 12/1989 | | WO | 95/33460 | 12/1995 |
| JP | 2-22650 A | 1/1990 | | WO | 95/33460 A1 | 12/1995 |
| JP | 2-23337 A | 1/1990 | | WO | WO 95/33458 A1 | 12/1995 |
| JP | 2022650 | 1/1990 | | WO | 96/02112 A1 | 1/1996 |
| JP | 2023337 | 1/1990 | | WO | WO 96/02112 A1 | 1/1996 |
| JP | 2023337 A | 1/1990 | | WO | 96/10559 | 4/1996 |
| JP | 2023337 W | 1/1990 | | WO | 96/10559 A1 | 4/1996 |
| JP | 2-35450 A | 2/1990 | | WO | WO 96/10559 A1 | 4/1996 |
| JP | 2-105146 A | 4/1990 | | WO | 96/13632 A1 | 5/1996 |
| JP | 2-108048 A | 4/1990 | | WO | WO 96/13632 | 5/1996 |
| JP | 2-150840 A | 4/1990 | | WO | 96/25157 A1 | 8/1996 |
| JP | 02105016 A | 4/1990 | | WO | 96/40673 | 12/1996 |
| JP | 02108048 A | 4/1990 | | WO | 96/40673 A1 | 12/1996 |
| JP | 2-150840 A | 6/1990 | | WO | 96/40675 A1 | 12/1996 |
| JP | 02150840 A | 6/1990 | | WO | 96/41807 A1 | 12/1996 |
| JP | 3 532 47 | 3/1991 | | WO | A1 96/40675 | 12/1996 |
| JP | 3 532 47 A | 3/1991 | | WO | 97/03069 | 1/1997 |
| JP | 3-53247 A | 3/1991 | | WO | 97/03069 A1 | 1/1997 |
| JP | 3-144634 A | 6/1991 | | WO | 97/09973 A2 | 3/1997 |
| JP | 03144634 A | 6/1991 | | WO | WO 97/09973 | 3/1997 |
| JP | 3-198049 A | 8/1991 | | WO | WO 97/09973 A2 | 3/1997 |
| JP | 06120039 A | 10/1992 | | WO | 97/17267 A1 | 5/1997 |
| JP | 6-75172 B2 | 9/1994 | | WO | 97/17329 A1 | 5/1997 |
| JP | 8 301841 | 11/1996 | | WO | WO 97/17267 A1 | 5/1997 |
| JP | 8-301841 A | 11/1996 | | WO | WO 97/17329 | 5/1997 |
| JP | 08-301841 A | 11/1996 | | WO | WO 97/17329 A1 | 5/1997 |
| JP | 56029871 | 9/1998 | | WO | 97/29743 | 8/1997 |
| JP | 10-306078 | 11/1998 | | WO | 97/29743 A1 | 8/1997 |
| JP | 10-306078 A | 11/1998 | | WO | 97/30992 A1 | 8/1997 |
| JP | 5821626 | 11/1998 | | WO | WO 97/30992 | 8/1997 |
| JP | 2022650 | 1/2002 | | WO | WO 97/30992 A1 | 8/1997 |
| JP | 2023337 | 1/2002 | | WO | 97/34146 A1 | 9/1997 |
| JP | 57053785 | 11/2003 | | WO | 97/40028 A1 | 10/1997 |
| LB | 6124 | 1/2000 | | WO | 97/40842 A1 | 11/1997 |
| WO | 90/02112 | 3/1990 | | WO | 97/45400 | 12/1997 |
| WO | 90/02112 A1 | 3/1990 | | WO | 97/45400 A1 | 12/1997 |
| WO | 92/03413 A1 | 3/1992 | | WO | 97/49399 | 12/1997 |
| WO | WO 92/03413 A1 | 3/1992 | | WO | 97/49399 A1 | 12/1997 |
| WO | 92/05179 A1 | 4/1992 | | WO | 97/49400 | 12/1997 |
| WO | 93/04170 A1 | 3/1993 | | WO | 97/49400 A1 | 12/1997 |
| WO | 93/18028 | 9/1993 | | WO | 98/17207 A1 | 4/1998 |
| WO | 93/18028 A1 | 9/1993 | | WO | 98/17267 A1 | 4/1998 |
| WO | 93/24458 | 12/1993 | | WO | WO 98/17267 | 4/1998 |

| | | | | | | |
|---|---|---|---|---|---|---|
| WO | WO 98/17267 A1 | 4/1998 | | WO | WO 99/32437 A1 | 7/1999 |
| WO | 98/20868 A1 | 5/1998 | | WO | WO 99/32455 A1 | 7/1999 |
| WO | 98/22103 | 5/1998 | | WO | WO 99/32463 | 7/1999 |
| WO | 98/22103 A1 | 5/1998 | | WO | WO 99/32463 A1 | 7/1999 |
| WO | 98/22432 | 5/1998 | | WO | WO 99/33458 | 7/1999 |
| WO | 98/22432 A1 | 5/1998 | | WO | WO 99/33458 A1 | 7/1999 |
| WO | WO 98/20868 | 5/1998 | | WO | 99/40673 A1 | 8/1999 |
| WO | WO 98/20868 A1 | 5/1998 | | WO | WO 99/40673 | 8/1999 |
| WO | WO 98/22103 | 5/1998 | | WO | WO 99/40673 A1 | 8/1999 |
| WO | WO 98/22103 A1 | 5/1998 | | WO | 99/58502 A1 | 11/1999 |
| WO | 98/32439 A1 | 7/1998 | | WO | 99/62890 A1 | 12/1999 |
| WO | WO 98/32439 A1 | 7/1998 | | WO | WO 99/62890 A1 | 12/1999 |
| WO | 98/34929 A1 | 8/1998 | | WO | 00/12497 | 3/2000 |
| WO | WO 98/34929 A1 | 8/1998 | | WO | 00/12497 A2 | 3/2000 |
| WO | 98/45268 A1 | 10/1998 | | WO | 00/17175 | 3/2000 |
| WO | WO 98/45268 | 10/1998 | | WO | 00/17175 A1 | 3/2000 |
| WO | WO 98/45268 A1 | 10/1998 | | WO | WO 00/17175 A1 | 3/2000 |
| WO | 98/49150 A1 | 11/1998 | | WO | 00/19205 A1 | 4/2000 |
| WO | 98/52558 A1 | 11/1998 | | WO | 00/26203 A1 | 5/2000 |
| WO | 98/52559 | 11/1998 | | WO | 00/27414 A2 | 5/2000 |
| WO | 98/52559 A1 | 11/1998 | | WO | PCT/US00/00648 R | 5/2000 |
| WO | 98/52937 A2 | 11/1998 | | WO | PCT/US00/00768 R | 5/2000 |
| WO | 98/52941 A1 | 11/1998 | | WO | WO 00/26203 A1 | 5/2000 |
| WO | WO 98/52558 | 11/1998 | | WO | 00/31238 A2 | 6/2000 |
| WO | WO 98/52558 A1 | 11/1998 | | WO | 00/34303 A1 | 6/2000 |
| WO | WO 98/52559 A1 | 11/1998 | | WO | 00/35454 A1 | 6/2000 |
| WO | 98/56377 | 12/1998 | | WO | 00/35455 A1 | 6/2000 |
| WO | 98/56377 A1 | 12/1998 | | WO | 00/39116 | 6/2000 |
| WO | 99/00357 | 1/1999 | | WO | WO 00/35454 A1 | 6/2000 |
| WO | 99/00357 A1 | 1/1999 | | WO | 00/39101 | 7/2000 |
| WO | 99/00370 | 1/1999 | | WO | 00/39101 A1 | 7/2000 |
| WO | 99/00370 A1 | 1/1999 | | WO | 00/39116 A1 | 7/2000 |
| WO | 99/20617 A1 | 4/1999 | | WO | 00/41698 A1 | 7/2000 |
| WO | WO 99/20617 | 4/1999 | | WO | 00/42012 A1 | 7/2000 |
| WO | 99/21835 A1 | 5/1999 | | WO | 00/43366 | 7/2000 |
| WO | 99/23091 | 5/1999 | | WO | 00/43366 A1 | 7/2000 |
| WO | 99/23091 A1 | 5/1999 | | WO | 00/43384 | 7/2000 |
| WO | 99/24035 | 5/1999 | | WO | 00/43384 A1 | 7/2000 |
| WO | 99/24035 A1 | 5/1999 | | WO | WO 00/41698 | 7/2000 |
| WO | 99/24398 | 5/1999 | | WO | WO 00/42012 | 7/2000 |
| WO | 99/24398 A2 | 5/1999 | | WO | WO 00/43366 A1 | 7/2000 |
| WO | 99/24635 A1 | 5/1999 | | WO | WO 00/43384 A1 | 7/2000 |
| WO | WO 99/21835 | 5/1999 | | WO | 00/47577 A1 | 8/2000 |
| WO | WO 99/23091 A1 | 5/1999 | | WO | 00/50425 A1 | 8/2000 |
| WO | WO 99/24398 A2 | 5/1999 | | WO | WO 00/50425 A1 | 8/2000 |
| WO | WO 99/24635 | 5/1999 | | WO | WO 0047577 | 8/2000 |
| WO | WO 99/24635 A1 | 5/1999 | | WO | 00/55139 | 9/2000 |
| WO | 99/26657 A1 | 6/1999 | | WO | 00/55139 A2 | 9/2000 |
| WO | 99/28305 A1 | 6/1999 | | WO | 00/55152 | 9/2000 |
| WO | WO 99/28305 | 6/1999 | | WO | 00/55152 A1 | 9/2000 |
| WO | WO 99/28305 A1 | 6/1999 | | WO | 00/56331 A1 | 9/2000 |
| WO | 99/32106 A1 | 7/1999 | | WO | WO 00/55139 | 9/2000 |
| WO | 99/32109 | 7/1999 | | WO | WO 00/55152 A1 | 9/2000 |
| WO | 99/32109 A1 | 7/1999 | | WO | WO 00/56331 | 9/2000 |
| WO | 99/32110 A1 | 7/1999 | | WO | 00/71506 A2 | 11/2000 |
| WO | 99/32111 | 7/1999 | | WO | 00/71532 A1 | 11/2000 |
| WO | 99/32111 A1 | 7/1999 | | WO | WO 00/71532 A1 | 11/2000 |
| WO | 99/32436 A1 | 7/1999 | | WO | 01/04115 A2 | 1/2001 |
| WO | 99/32437 A1 | 7/1999 | | WO | 02/07772 A2 | 1/2001 |
| WO | 99/32455 | 7/1999 | | WO | WO 01/04115 A2 | 1/2001 |
| WO | 99/32455 A1 | 7/1999 | | WO | 01/07411 A1 | 2/2001 |
| WO | 99/32463 A1 | 7/1999 | | WO | 01/09088 A1 | 2/2001 |
| WO | 99/33458 A1 | 7/1999 | | WO | 01/12188 A1 | 2/2001 |
| WO | 99/35132 | 7/1999 | | WO | WO 01/07411 A1 | 2/2001 |
| WO | 99/35132 A1 | 7/1999 | | WO | WO 01/09088 A1 | 2/2001 |
| WO | WO 99/32106 | 7/1999 | | WO | WO 01/12188 A1 | 2/2001 |
| WO | WO 99/32106 A1 | 7/1999 | | WO | 01/36403 A1 | 5/2001 |
| WO | WO 99/32110 | 7/1999 | | WO | WO 01/36403 A1 | 5/2001 |
| WO | WO 99/32110 A1 | 7/1999 | | WO | WO 01/36403 A1 | 5/2001 |
| WO | WO 99/32111 A1 | 7/1999 | | WO | 01/4789 A1 | 7/2001 |
| WO | WO 99/32436 | 7/1999 | | WO | 01/47892 A1 | 7/2001 |
| WO | WO 99/32436 A1 | 7/1999 | | WO | 01/54723 A1 | 8/2001 |
| WO | WO 99/32437 | 7/1999 | | WO | 01/54727 A1 | 8/2001 |

| | | | | | | |
|---|---|---|---|---|---|---|
| WO | | 01/57008 A1 | 8/2001 | WO | | 03/065995 A2 | 8/2003 |
| WO | | 01/63403 A2 | 8/2001 | WO | | 03/068223 A1 | 8/2003 |
| WO | WO 01/57008 A1 | 8/2001 | WO | | 03/068228 A1 | 8/2003 |
| WO | | 01/66099 | 9/2001 | WO | | 03/068229 A1 | 8/2003 |
| WO | | 01/66099 A2 | 9/2001 | WO | | 03/068746 A1 | 8/2003 |
| WO | | 01/66540 A1 | 9/2001 | WO | WO 03/068223 | 8/2003 |
| WO | | 01/80843 A2 | 11/2001 | WO | WO 03/068228 A1 | 8/2003 |
| WO | | 02/06382 A1 | 1/2002 | WO | WO 03/068229 A1 | 8/2003 |
| WO | | 02/07008 A1 | 1/2002 | WO | WO 03/068746 A1 | 8/2003 |
| WO | | 02/07747 A1 | 1/2002 | WO | WO 03/094626 A | 9/2003 |
| WO | | 02/07772 A2 | 1/2002 | WO | | 03/082272 A1 | 10/2003 |
| WO | WO 02/07747 A1 | 1/2002 | WO | WO 03/082272 A2 | 10/2003 |
| WO | WO 02/07772 | 1/2002 | WO | | 03/094626 A1 | 11/2003 |
| WO | | 02/10141 A1 | 2/2002 | WO | | 03/097854 A2 | 11/2003 |
| WO | | 02/14281 A1 | 2/2002 | WO | | 03/099771 A2 | 12/2003 |
| WO | | 02/14311 A2 | 2/2002 | WO | WO 03/099771 | 12/2003 |
| WO | WO 02/10141 A1 | 2/2002 | WO | WO 03/099771 A2 | 12/2003 |
| WO | WO 02/14281 A1 | 2/2002 | WO | | 2004/004720 A1 | 1/2004 |
| WO | WO 02/14311 | 2/2002 | WO | | 2004/004720 A1 | 3/2004 |
| WO | WO 02/14311 A2 | 2/2002 | WO | | 2004/019941 A1 | 3/2004 |
| WO | | 02/18346 A1 | 3/2002 | WO | | 2004/019941 A1 | 3/2004 |
| WO | | 02/24635 A2 | 3/2002 | WO | | 2004/037789 A2 | 5/2004 |
| WO | | 02/25286 | 3/2002 | WO | | 2004/043374 A2 | 5/2004 |
| WO | | 02/25286 A2 | 3/2002 | WO | A22004/037789 | 5/2004 |
| WO | WO 02/18346 A1 | 3/2002 | WO | WO 2004/037789 A2 | 5/2004 |
| WO | WO 02/24635 A2 | 3/2002 | WO | WO 2004/043374 A2 | 5/2004 |
| WO | | 02/32872 A1 | 4/2002 | WO | | 04/045578 | 6/2004 |
| WO | WO 02/32872 A1 | 4/2002 | WO | | 04/052880 | 6/2004 |
| WO | | 02/40445 A1 | 5/2002 | WO | | 2004/045578 A2 | 6/2004 |
| WO | | 02/42012 A1 | 5/2002 | WO | | 2004/052880 A1 | 6/2004 |
| WO | WO 02/42012 | 5/2002 | WO | | 2004/052882 A1 | 6/2004 |
| WO | WO 02/42012 A1 | 5/2002 | WO | | 04/078128 | 9/2004 |
| WO | | 02/44156 A2 | 6/2002 | WO | | 04/078748 | 9/2004 |
| WO | | 02/44158 A1 | 6/2002 | WO | | 2004/078128 A2 | 9/2004 |
| WO | | 02/50091 A1 | 6/2002 | WO | | 2004/078746 A2 | 9/2004 |
| WO | WO 02/44156 A2 | 6/2002 | WO | | 2004/078747 A1 | 9/2004 |
| WO | WO 02/44158 A1 | 6/2002 | WO | | 2004/078748 A1 | 9/2004 |
| WO | | 02/059081 A2 | 8/2002 | WO | WO 2004/078746 A2 | 9/2004 |
| WO | | 02/059102 A2 | 8/2002 | WO | WO 2004/078747 A1 | 9/2004 |
| WO | | 02/060900 A2 | 8/2002 | WO | | 2004/078748 A1 | 10/2004 |
| WO | | 02/062763 A2 | 8/2002 | WO | | 2004/085399 A1 | 10/2004 |
| WO | WO 02/059081 A2 | 8/2002 | WO | | 2004/085425 A1 | 10/2004 |
| WO | WO 02/059102 A2 | 8/2002 | WO | WO 2004/085399 A1 | 10/2004 |
| WO | WO 02/062763 A2 | 8/2002 | WO | WO 2004/085425 A1 | 10/2004 |
| WO | | 02/070008 | 9/2002 | WO | | 2004/108713 A1 | 12/2004 |
| WO | | 02/070008 A1 | 9/2002 | WO | | 2004/108715 A1 | 12/2004 |
| WO | | 02/76930 A2 | 10/2002 | WO | | 2004/113274 A2 | 12/2004 |
| WO | | 02/076930 A2 | 10/2002 | WO | WO 2004/113274 A | 12/2004 |
| WO | | 02/076977 | 10/2002 | WO | | 05/000284 | 1/2005 |
| WO | | 02/076977 A2 | 10/2002 | WO | | 2005/000284 A2 | 1/2005 |
| WO | | 02/083628 A1 | 10/2002 | WO | | 2005/002673 A1 | 1/2005 |
| WO | | 02/083642 A1 | 10/2002 | WO | | 2005/004863 A1 | 1/2005 |
| WO | | 02/085857 A2 | 10/2002 | WO | | 2005/004864 A1 | 1/2005 |
| WO | | 02/085859 A1 | 10/2002 | WO | | 2005/005389 A2 | 1/2005 |
| WO | WO 02/083628 A1 | 10/2002 | WO | | 2005/005434 A1 | 1/2005 |
| WO | WO 02/083642 A1 | 10/2002 | WO | WO 2005/002673 A1 | 1/2005 |
| WO | WO 02/085857 A2 | 10/2002 | WO | WO 2005/004863 A1 | 1/2005 |
| WO | WO 02/085859 A1 | 10/2002 | WO | WO 2005/004864 A1 | 1/2005 |
| WO | | 02/088090 A2 | 11/2002 | WO | WO 2005/005389 A2 | 1/2005 |
| WO | | 02/092576 A1 | 11/2002 | WO | | 2005/009367 A2 | 2/2005 |
| WO | WO 02/092576 | 11/2002 | WO | | 2005/009961 A2 | 2/2005 |
| WO | | 03/004523 A1 | 1/2003 | WO | | 2005/011700 A1 | 2/2005 |
| WO | | 03/005999 A2 | 1/2003 | WO | | 2005/016252 A2 | 2/2005 |
| WO | | 03/047523 A1 | 1/2003 | WO | WO 2005/009367 A | 2/2005 |
| WO | WO 03/005999 A2 | 1/2003 | WO | WO 2005/009367 A2 | 2/2005 |
| WO | WO 03/099771 A2 | 5/2003 | WO | WO 2005/009961 A2 | 2/2005 |
| WO | | 03/047523 A2 | 6/2003 | WO | | 2005/019192 A1 | 3/2005 |
| WO | | 03/047579 A1 | 6/2003 | WO | WO 2005/019192 A1 | 3/2005 |
| WO | WO 03/047523 A1 | 6/2003 | WO | | 2005/032548 A1 | 4/2005 |
| WO | | 03/056036 A2 | 7/2003 | WO | | 2005/037273 A1 | 4/2005 |
| WO | | 03/059373 A2 | 7/2003 | WO | | 2005/037285 A1 | 4/2005 |
| WO | | 03/060111 A2 | 7/2003 | WO | | 2005/037829 A1 | 4/2005 |
| WO | WO 2004/019941 A1 | 7/2003 | WO | WO 2005/032548 A1 | 4/2005 |

| | | | |
|---|---|---|---|
| WO | WO 2005/037273 A1 | 4/2005 |
| WO | WO 2005/037285 A1 | 4/2005 |
| WO | WO 2005/037829 A1 | 4/2005 |
| WO | 2005/042520 A1 | 5/2005 |
| WO | 2005/047283 A1 | 5/2005 |
| WO | WO 2005/042520 A1 | 5/2005 |
| WO | WO 2005/047283 A1 | 5/2005 |
| WO | 2005/048948 A2 | 6/2005 |
| WO | 2005/049603 A1 | 6/2005 |
| WO | 2005/056764 A2 | 6/2005 |
| WO | 2005/058832 A1 | 6/2005 |
| WO | 2005/059179 A1 | 6/2005 |
| WO | WO 2005/048948 A2 | 6/2005 |
| WO | WO 2005/049603 A1 | 6/2005 |
| WO | WO 2005/058832 A1 | 6/2005 |
| WO | 2005/075425 A2 | 8/2005 |
| WO | WO 2005/075425 A2 | 8/2005 |
| WO | 2005/089443 A2 | 9/2005 |
| WO | WO 2005/089443 A | 9/2005 |
| WO | 2005/110994 A2 | 11/2005 |
| WO | WO 2005/110994 A2 | 11/2005 |
| WO | 06/026500 | 3/2006 |
| WO | 2006/026500 A1 | 3/2006 |
| WO | 2006/026501 A1 | 3/2006 |
| WO | 2006/027346 A2 | 3/2006 |
| WO | WO 2006/026501 | 3/2006 |
| WO | 2006/034797 A1 | 4/2006 |
| WO | WO 2006/034797 A | 4/2006 |
| WO | 2006/094262 A1 | 9/2006 |
| WO | 2006/094626 A1 | 9/2006 |
| WO | 2006/105844 A1 | 10/2006 |
| WO | WO 2006/105844 A1 | 10/2006 |
| WO | 06/125540 A1 | 11/2006 |
| WO | 2006/125540 A1 | 11/2006 |
| WO | 2007/015947 A2 | 2/2007 |
| WO | WO 2007/015947 A | 2/2007 |
| WO | 2007/039403 A1 | 4/2007 |
| WO | 2007/039404 A1 | 4/2007 |
| WO | 2007/047955 A2 | 4/2007 |
| WO | WO 2007/039403 A1 | 4/2007 |
| WO | WO 2007/039404 A1 | 4/2007 |
| WO | 07/053573 A2 | 5/2007 |
| WO | 07/054215 A1 | 5/2007 |
| WO | 07/059094 | 5/2007 |
| WO | 07/059154 | 5/2007 |
| WO | 07/059155 | 5/2007 |
| WO | 2007/053573 A2 | 5/2007 |
| WO | 2007/054215 A1 | 5/2007 |
| WO | 2007/056011 A2 | 5/2007 |
| WO | 2007/056012 A2 | 5/2007 |
| WO | 2007/059094 A2 | 5/2007 |
| WO | 2007/059154 A2 | 5/2007 |
| WO | 2007/059155 A1 | 5/2007 |
| WO | 2007/064872 A2 | 6/2007 |
| WO | WO 2007/064872 A2 | 6/2007 |
| WO | 07/087575 | 8/2007 |
| WO | 2007/087575 A2 | 8/2007 |
| WO | 2007/096393 A1 | 8/2007 |
| WO | 2007/096395 A1 | 8/2007 |
| WO | WO 2007/096393 A1 | 8/2007 |
| WO | WO 2007/096395 A1 | 8/2007 |
| WO | 07/123722 | 11/2007 |
| WO | 2007/123722 | 11/2007 |
| WO | 2007/123722 A2 | 11/2007 |
| WO | 07/139930 | 12/2007 |
| WO | 2007/139930 A2 | 12/2007 |
| WO | 08/055966 A1 | 5/2008 |
| WO | 2008/055966 A1 | 5/2008 |
| WO | 08/079968 | 7/2008 |
| WO | 08/079972 | 7/2008 |
| WO | 08/089389 | 7/2008 |
| WO | 2008/055966 A1 | 7/2008 |
| WO | 2008/079968 A1 | 7/2008 |
| WO | 2008/079972 A2 | 7/2008 |
| WO | 2008/089389 A2 | 7/2008 |
| WO | 2009/034308 A2 | 3/2009 |
| WO | 2009/0343308 A2 | 3/2009 |
| WO | 2009/054004 A2 | 4/2009 |
| WO | 02/06382 A1 | 12/2009 |

OTHER PUBLICATIONS

Russo, F. et al. "Synthesis of 2,6-substituted derivatives of 5H-1,3,4-thiadiazolo'3,2-al-s triazine-5,7-dione" Farmaco, Ed.Sci. (1978), 33(12), 972-83.
Foussard-Blanpin, Odette: "Comparative pharmacodynamic study of variously substituted carboxamides of the central nervous ststem" Ann. Pharm. Fr. (1982), 40(4), 339-50.
Grant, A.M et al.: "Hypotensive thiadiazoles" J.Med. Chem. (1972), 15(10), 1082-4.
Murata et al. Chemical and Pharmaceutical Bulletin, vol. 22, 1974 pp. 1212-3.
Garcia-Lopez et al. Journal of the American Chemical Society, vol. 1978, 1978, pp. 438-7.
Abstract of DE 3305866 (EP equivalent 116,932).
Abstract of EP 202,538.
Blanco, "p38 MAPK signaling cascades: ancient roles and new functions," Bioassays, 22:637-645, 2000.
Carter et al. "Anti-tumor efficacy of the orally active RAF Kinase inhibitor BAY 43-9006 in human tumor Xenograft models," Proceedings of the annual meeting of the American Association for Cancer Res., 42: 923, 2001.
XP-002232130, "A Phase I Trial of H-ras Antisense Oligonucleotide ISIS 2503 Administered as a Continuous Intravenous Infusion in Patients with Advanced Carcinoma," C. Casey Cunningham et al., 2001 American Cancer Society, vol. 92, No. 5, pp. 1265-1271.
Dumas, J. "Protein Kinase Inhibitors from the urea class," Curr. Opin. In Drug Discovery and Dev., 5:718-727, 2002.
Facts and Comparisons (1994) pp. 2703-2705.
XP-001145779 "Antitumor Activity of a C-raf Antisense Oligonucleotide in Combination with Standard Chemotherapeutic Agents against Various Human Tumors Transplanted Subcutaneously into Nude Mice," Thomas Geiger et al., vol. 3, 1179-1185, Jul. 1997.
XP-002086152 "Pulmonary-Allergy, Dermatological, Gastrointestinal & Arthritis", Gunnar J. Hanson.
Hotte et al., "Bay 43-9006: Early clinical data in patients with advanced solid malignancies," Current Pharmaceutical Design, 8:2249-2253, 2002.
Iwadate et al. "Intra-arterial ACNU, CDDP Chemotherapy for brain metastases from lung cancer: comparison of cases with and without intra-arterial Mannitol infusion," Shinkei Geka. Neuro. Surg., 21:513-518, 1993.
Madwed et al., "Pharmacological Evaluation of BIRB 796, a selective inhibitor of P38 MAP kinase (MAPK), in animal models of endotoxic shock, inflammation and arthritis," Inflammation Res., 50:S184, 2001.
Regan et al., "Pyrazole urea-based inhibitors of P38 MAP kinase: from lead compound to clinical candidate," J. Med. Chem. 45:2994-3008, 2002.
XP-001145518 # 4956 Potent *Raf* Kinase Inhibitors from the Diphenylurea Class:Structure Activity Relationships, B. Riedl et al., Bayer Corporation.
XP-001145481 +2921 "Phase I and Pharmacokinetic Study of the Raf Kinase Inhibitor Bay 43-9006 in Patients with Locally Advanced or Metastic Cancer," Dirk Strumberg et al., Bayer AG.
Wild, Hanno, "Substructure #1," pp. 1-107, 1996.
Wilson, Keith et al., "The structural basis for the specificity of pyrimidinylimidazole inhibitors of p38 MAP Kinase" XP-002103155.
Dumas, "Preparation of pyrazolyl aryl ureas and related compounds as p38 kinase inhibitor," Jul. 1, 1999.
Bruder et al. "Adenovirus Infection Stimulates the Raf/MAPK Signaling Pathway and Induces Interleukin-8 Expression" Jour of Virology, 71(1):398-404, 1997.
Dumas, J., "CAS Substructure," May 6, 1997, pp. 1-29.

Scott, Bill, "substructure (Patent Families)," Aug. 11, 1997, pp. 1-19.
Scott, Bill, "substructure #2," Nov. 25, 1997, pp. 1-3.
"beilstein number" Collection, 28 pages.
"beilstein Collection," 4 pages.
Scott, Bill, "substructure Search," Dec. 2, 1997, pp. 1-51.
Substructure Search, pp. 1-30.
Derwent World Patents Index Search, pp. 20-26.
Abstract of EP 116,932.
Abstract of EP 676,395.
Abstract of EP 16,371.
Avruch et al., "Raf meets Ras: completing the framework of a signal transduction pathway", TIBS 19; Jul. 1994; pp. 279-2823.
White, A. D., et al., "Heterocyclic Ureas: Inhibitors of Acyl-CoA:Cholesterol O-Acyltransferase as Hypochelesterolemic Agents," Jun. 6, 1996, pp. 4382-4395.
Audia, James E., et al., "Potent, Selective Tetraphdro-β-carboline Antagonists of the Serotonin 2B ($5HT_{2B}$) Contractile Receptor in the Rat Stomach Fundus," Jan. 22, 1996, pp. 2773-2780.
Forbes, Ian T., "N-(1-Methyl-5-indolyl)-N-(3-methyl-5-isothiazolyl)urea: A Novel, High-Affinity $5\text{-}HT_{2B}$ Receptor Antagonist," Mar. 17, 1995, pp. 855-857.
Boulton, A. J., et al., "Heterocyclic Rearrangements. Part X.[1] A Generalised Monocyclic Rearrangement," 1967, 2005-07.
N. S. Magnuson, et al., "The Raf-1 serine/threonine protein kinase," Cancer Biology, vol. 5, 1994, pp. 247-253.
G. Daum, et al., The ins and outs of Raf Kinases,: TIBS 19, Nov. 1994, pp. 474-480.
W. Kolch, et al., "Raf-1 protein kinase is required for growth of induced NIH/3T3 cells," Letters to Nature, vol. 349, Jan. 31, 1991, p. 226-28.
M. Fridman, et al., "The Minimal Fragments of c-Raf-1 and NF1 That Can Suppress v-Ha-Ras-Induced Malignant Phenotype," The Journal of Biological Chemistry, vol. 269, No. 48, Dec. 2, 1994 pp. 30105-30108.
G. L. Bolton, et al., Chapter 17. Ras Oncogene Directed Approaches in Cancer Chemotherapy, Annual Reports In Medicinal Chemistry, vol. 29, 1994, pp. 165-174.
J. L. Bos, "ras Oncogenes in Human Cancer: A Review," Cancer Research, vol. 49, Sep. 1, 1989, pp. 4682-4689.
Michaelis, Justus, Liebigs Ann. Chem. (JLACBF) 397, 1913, 143.
B. P. Monia, et al., "Antitumor activity of a phosphorothioate antisense oligodeopxynucleotide targeted against C-raf kinase," Nature Medicine, vol. 2, No. 6, Jun. 1996, pp. 668-675.
Lee, et al., Bicyclic Imidazoles as a Novel Class of Cytokine Biosynthesis Inhiibitors, N.Y. Academy of Science, 1993, pp. 149-170.
F. Lepage et al., "New N-aryl isoxazolecarboxamides and N-isoxazolybenzamides as anticonvulsant agents," Eur. J. Med. Chem, vol. 27, 1992, pp. 581-593.
Ridley, et al., "Actions of IL-1 are Selectively Controlled by p38 Mitogen-Activated Protein Kinase," The American Association of Immunologists, 1997, p. 3165-73.
Chemical Abstract, vol. 116, No. 21, May 25, 1992, pp. 741-742.
Tarzia, G. et al. Whythesis and anti-inflammatory properties of some pyrrolo(1H,3H)[3,4]pyrimidin-2-ones and pyrrolo(1H,3H)[3 4-d]pyurimidin-2-ones and pyrrolo(1H,3H)-pyrimidin-2-ones. Chemical Abstracts. Aug. 27, 1979, No. 74558p; p. 594.
Garcia-Lopez et al. Journal of the American Chemical Society , vol. 1978, 1978, pp. 438-437.
Caplus 113:106314, Abstract of JP 2022650, Silver halide color photographic material containing a cyan coupler of 2-ureido-phenol type to improve dye developability and remove lecuo cyan dye, Noboru Mizukura et al. Jan. 25, 1990.
Caplus 113:142130, Abstract of JP 2023337, Silver halide photographic material containing phenolic cyan coupler a colorless cyan coupler, Toshihiko Yagi et al., Jan. 25, 1990.
Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat", Chemical Life Science, pp. 157-166, 1977.
Caplus 127:293717, "Optical properties of segmented oligourethane with azomethine terminal fragments", National Academy of Science of Ukraine, M. V. Kurik et al., pp. 2038-2041, 1996.

Caplus 127-273945, "Quantitative structure-biodegradability studies: an investigation of the MITI aromatic compound database", School of Pharmacy and Chemistry, J. C. Dearden, pp. 93-104, 1996.
Caplus 126:166148, "Inhibitors of coenzyme A-independent transacylase induce apoptosis in human HL-60 cells", James D. Winkler et al., J. Pharmacol. Exp. Ther. pp. 956-966, 1996.
Caplus 98:78152, Abstract of JP 57185219, "Antitumor benzophenone derivatives", Nov. 15, 1982.
Caplus 72:79046, Abstract of CH 479557, "Tuberculostatic and canoerostatic polybasic ureas", Dr. A. Wander, Oct. 15, 1969.
Caplus 125:245169, "Production of murine monoclonal antibodies against sulcofuron and flucofuron by in vitro immunization", G. A. Bonwick at al., J. Immunol. Methods, pp. 163-173, 1996.
Caplus 127:341371, "Preparation of quinoline an dquinazoline derivatives inhibiting platelet-derived growth factor receptor autophosphorylation", Kazuo Kubo et al., May 15, 1997.
Caplus 131:58658, "Inhibition of raf kinase using symmetrical and unsymmetrical substituted diphenyl ureas", Miller, Scott, Jul. 1, 1999.
Caplus 131:87909y, "Inhibition of p38 kinase activity using substituted heterocyclic ureas", Jacques Dumas, Jul. 1, 1999.
Caplus 131:73649b, "Preparation of pyrazolyl aryl ureas and related compounds as p38kinase inhibitor", Jacques Dumas, Jul. 1, 1999.
Joseph V. Simone, "Cecil Textbook of Medicine", 20th Edition, vol. 1, Feb. 3, 1997. pp. 1004-1010.
Cesar Raposo et al., "Catalysis of Nucleophilic Addition of Pyrrolidine to 2-(5H)-Furanone through Chromenone Cleft-Type Receptors", vol. 37, No. 38, pp. 6947-6950, 1996.
Jacqueline E. van Muijiwijk-Koezen et al., "Isoquinoline and Quinazoline Urea Analogues as Antagonists for the Human Adenosine $A_3$ Receptor", J. Ed. Chem. 2000, 43, pp. 2227-2238, Jan. 3, 2000.
Jacques Dumas et al., "1-Phenyl-5-pyrazolyl Ureas: Potent and Selective p38 Kinase Inhibitors", Bioorganic & Medicinal Chemistry Letters, pp. 2051-2054, May 2, 2000.
Robert W. Carling et el., "1-(3-Cyanobenxylpiperidin-4-yl)-5-methyl-4-phenyl-1,3-dihydroimidazol-2-one: A Selective High-Affinity Antagonist for the Human Dopamine $D_4$ Receptor with Excellent Selectivity over Ion Channels", J. Med. Chem., 1999, 42, pp. 2706-2715.
Abstract WO 9822103, May 28, 1998, John Philip Hedge et al.
Nickel et al., "Carboxylic Acid Analogues of Suramin, Potential Filaricides," *Indian Journal of Chemistry*, Feb. 1991, vol. 30B, pp. 182-187.
Moelling et al., "Signal Transuction as Target of Gene Therapy," Institute of Medical Virology, University of Zürich, *Recent Results in Cancer Research*, vol. 142, pp. 63-71.
Stein, Jay H., MD, Internal Medicine, 4th Edition, 1994, pp. 699-715.
Dumas et al., "Recent Developments in the Discovery of Protein Kinase Inhibitors from the Urea Class," *Current Opinion in Drug Discovery & Development*, 2004, vol. 7, No. 5, pp. 600-616.
Lee et al., "BAY-43-9006: Bayer/Onyx," *Current Opinion in Investigational Drugs*, 2003, vol. 4, No. 6, pp. 757-763.
Sorbara et al., "BAY-43-9006," *Drugs of the Future*, 2002, vol. 27, No. 12, pp. 1141-1147.
Khire et al., "Omega-Carboxypyridyl Substituted Ureas as Raf Kinase inhibitors: SAR of the Amid Substituent," *Bioorg. Med. Chem. Lett.*, 2004, vol. 14, pp. 783-786.
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," *Cancer Research*,. Oct. 1, 2004, vol. 64, pp. 7099-7109.
Smith, et al., "Discovery of Heterocyclic Ureas as a New Class of Raf Kinase Inhibitors: Identification of a Second Generation Lead by a Combinatorial Chemistry Approach." *Bloorganic & Medicinal Chemistry Letters*, 2001, vol. 11, pp. 2775-2778.
Bankston et al., "A Sealeable Synthesis of BAY 43-9006: a Potent Raf Kinase Inhibitor for the Treatment of Cancer," *Organic Process Research & Development*, 2002, vol. 6, pp. 777-781.
Strumberg et al., "Results of Phase I Pharmacokinetic and Pharmacodynamic Studies of the Raf Kinase Inhibitor BAY 43-9006 in Patients with Solid Tumors," *International Journal of Clinical Pharmacology and Therapeutics*, 2002, vol. 40, No. 12, pp. 580-581.

Chang et al., "BAY 43-9006 (Sorafenib) Inhibitors Ectopic (s.c.) and Orthotopic Growth of a Murine Model of Renal Adenocarcinoma (Renca) Predominantly Through Inhibition of Tumor Angiogenesis," 96th Annual Meeting, Anaheim/Orange County, CA, Apr. 16-20, 2005.

Panka et al., "BAY 43-9006 Induces Apoptosis in Melanoma Cell Lines," 96th Annual Meeting, Anaheim/Orange County, CA, Apr. 16-20, 2005.

Auclair, et al., "BAY 43-9006 (Sorafenib) is a Potent Inhibitor of FLT3 Tyrosine Kinase Signaling and Proliferation in AML cells," 96th Annual Meeting, Anaheim/Orange County, CA, Apr. 16-20, 2005.

Murphy et al., "BAY 43-9006 Controls Tumor Growth Through Inhibition of Vascular Development," 96th Annual Meeting, Anaheim/Orange County, CA, Apr. 16-20, 2005.

Heim et al., "Antitumor Effect and Potentiation or Reduction in Cytotoxic Drug Activity in Human Colon Carcinoma Cells by the Raf Kinase Inhibitor (RKI) BAY 43-9006," *International Journal of Clinical Pharmacology and Therapeutics*, 2003, vol. 41, No. 12, pp. 616-617.

Richly et al., "Results of a Phase I Trial of BAY 43-9006 in Combination with Doxorubicin in Patients with Primary Hepatic Cancer," *International Journal of Clinical Pharmacology and Therapeutics*, 2004, vol. 42, No. 11, pp. 650-651.

Mross et al., "Drug-drug Reaction Pharmacokinetic Study with the Raf Kinase Inhibitor (RKI) BAY 43-9006 Administered in Combination with Irinotecan (CPT-11) in Patients with Solid Tumors," *International Journal of Clinical Pharmacology and Therapeutics*, 2003, vol. 41, No. 12, pp. 618-619.

Richly et al., "A Phase I Clinical and Pharmacokinetic Study of the Raf Kinase Inhibitor (RKI) BAY 43-9006 Administered in Combination with Doxorubicin in Patients with Solid Tumors," *International Journal of Clinical Pharmacology and Therapeutics*, 2003, vol. 41, No. 12, pp. 620-621.

DeGrendele, "Activity of the Raf Kinase Inhibitor BAY 43-9006 in Patients with Advanced Solid Tumors," *Clinical Colorectal Cancer*, May 2003, pp. 16-18.

Moore et al., "Phase I Study to Determine the Safety and Pharmacokinetics of the Novel Raf Kinase and VEGFR Inhibitor BAY 43-9006, Administered for 28 days on/7 days off in Patients with Advanced, Refractory Solid Tumors," Annals of Oncology, 2005, vol. 16, pp. 1688-1694.

Ahmad et al., "Kinase Inhibition with BAY 43-9006 in Renal Cell Carcinoma," *Clinical Cancer Research*, Sep. 15, 2004, vol. 10, pp. 6388s-6392s.

Clark et al., "Safety and Pharmacokinetics of the Dual Action RAF Kinase and Vascular Endothelial Growth Factor Receptor Inhibitor, BAY 43-9006, in Patients with Advanced, Refractory Solid Tumors," *Clinical Cancer Res.*, Aug. 1, 2005, vol. 11, No. 5, pp. 5472-5480.

Jeffcoat et al., "The Metabolism and Toxicity of Halogenated Carbanilides," *Drug Metabolism and Deposition*, vol. 5, No. 2, pp. 157-166.

Wilhelm et al., "BAY 43-9006: Preclinical Data,", *Curr Pharm Des*, 2002, vol. 8, No. 25, pp. 2255-2257.

Wright et al., "Clinical Trials Referral Resource. Current Clinical Trials of BAY 43-9006, Part 1," *Oncology*, Apr. 19, 2005, vol. 4: pp. 499-502.

828, Siu et all, "Phase I Study of Oral RAF-1 Kinase Inhibitor BAY 43-9006 with Gemcitabine in Patients with Advanced Solid Tumors," *Proc Am Soc Clinic Oncology*, 2003, vol. 22, p. 207.

4510, Escudier at al., "Randomized phase III trial of the raf kinase and VEGFR inhibitor sorafenib (BAY 43-9006) in patients with advanced renal cell carcinoma (RCC)," Meeting: *2005 ASCO Annual Meeting*, Category: Genitourinary Cancer, Subcategory: Kidney Cancer.

7508, Eisen et al., "Phase I trial of BAY 43-9006 (Sorafenib) Combined with Dacarbazine (DTIC) in Metastatic Melanoma Patients," Meeting: *2005 ASCO Annual Meeting*, Category: Melamona, Subcategory: Melamona.

4510, Adjei et al., "A Phase I Study of BAY 43-9006 and Gefitinib in Patients with Refractory or Recurrent Non-Small-Cell Lung Cancer (NSCLC)," Meeting: *2005 ASCO Annual Meeting*, Category: Developmental Therapeutics: Molecular Therapeutics, Subcategory: Antiangiogenic or Antimetastatic agents.

913, XP-001152608, Kubo et al., "Synthesis and Structure-Activity Relationship of Quinazoline-Urea Derivatives as Novel Orally Active VEGF Receptor Tyrosine Kinase Selective Inhibitors," Proceedings of the American Association of Cancer Res., 2002, vol. 43, p. 182.

Dumas et al., "1-Phenyl-5-Pyrazolyl Ureas: Potent and Selective p38 Kinase Inhibitors," *Bioorganic & Medicinal Chemistry Letters*, 2000, vol. 10, pp. 2051-2054.

Ridley et al., "Actions of IL-1 are Selectively Controlled by p38 Mitogen-Activated Protein Kinase, Regulation of Prostaglandin H Synthase-2, Metalloproteinases, and IL-6 at Different Levels," *The Journal of Immunology*, 1997, vol. 158, pp. 3165-3173.

Abstract of DE 3305866A1, Aug. 29, 1984, Dr. Acker Rolf-Dieter et al.

Abstract of EP 4931(equlvalent 4,240,820), K. Dickore e tal. (1980).

Dumas, J., "CAS Structure," May 6, 1997, pp. 1-29.

Scott, Bill, "Substructure (Patent Families)", Aug. 11, 1997, pp. 1-19.

Scott, Bill, "Substructure #2", Nov. 25, 1997, pp. 1-3.

"Beilstein number" Collection, 28 pages (1997).

"Bellstein Collection", 4 pages (1997).

Scott, Bill, "Substructure Search", Dec. 2, 1997, pp. 1-51.

Substructure Search, pp. 1-30. (1997).

Derwent World Patents Index Search, pp. 20-26. (1997).

Abstract of EP 116,932 (1984).

Abstract of EP 676,395 (1995).

Abstract of EP 202,538 (1986).

Abstract of EP 16,371 (1980).

Caplus 86: 72448, Abstract JP 57053785, Pyridine derivatives, Maeda Ryozo et al., Nov. 15, 1982.

Caplus 84:180049, Abstract JP 56029871, Hamada Yoshinori et al., Jul. 10, 1981.

Caplus 84:43857, Abstract JP 58021626, Maeda Ryozo et al., May 2, 1983.

Abstract of JP 55162772, Substituted acetic derivatives, Shionogi & Co., May 23, 1980.

Abstract of EP 0 202 538 A1, "Growth Promoting Agents," Nov. 26, 1986.

Abstract of DE 3305866 A (EP equivalent 116,932), R.D. Acker et al., Aug. 23, 1984.

Abstract of EP 116,932, Aug. 29, 1984.

Abstract of EP 16,371, Oct. 1, 1980.

Abstract of EP 4931A (Equivalent 4,240,820), Dickore, K. et al.

Abstract of EP 0405233A1, Tetsuo Sekiya et al.

Abstract of EP 0 676 395 (U.S. equivalent 5,698,581), Dec. 16, 1997.

A "Notice of References Cited" from the USPTO for U.S. Appl. No. 08/995,749, filed Dec. 2, 1998, Inhibition of P38 Kinase Using Symmetrical and Unsymmetrical Diphenyl Ureas.

A "Notice of References Cited" from the USPTO for U.S. Appl. No. 09/083,399, filed Jan. 8, 2001, Inhibition of Raf Kinase Activity Using Aryl Ureas.

A "Notice of References Cited" from the USPTO for U.S. Appl. No. 09/425,228, filed Sep. 10, 2001, Inhibition of Raf Kinase Using Symmetrical and Unsymmetrical Substituted Diphenyl Ureas.

A "Notice of References Cited" from the USPTO for U.S. Appl. No. 09/425,229, filed Mar. 4, 2002, Omega-Carboxy Aryl Substituted Diphenyl Ureas As P38 Kinase Inhibitors.

A "Notice of References Cited" from the USPTO for U.S. Appl. No. 09/458,015, filed Feb. 1, 2002, Inhibition of P38 Kinase Using Symmetrical and Unsymmetrical Diphenyl Ureas.

A "Notice of References Cited" from the USPTO for U.S. Appl. No. 09/472,232, filed Dec. 27, 1999, Inhibition of Raf Kinase Using Aryl and Heteroaryl Substituted Heterocyclic Ureas.

A "Notice of References Cited" from the USPTO for U.S. Appl. No. 09/773,604, filed Feb. 2, 2001, Publication No. US 2001-0034447-A1, Publication Date Oct. 25, 2001, Omega-carboxyaryl Substituted Diphenyl Ureas as Raf Kinase Inhibitors.

A "Notice of References Cited" from the USPTO for U.S. Appl. No. 09/773,659, filed Feb. 2, 2001, W-carboxyaryl Substituted Diphenyl Ureas As Raf Kinase Inhibitors.

A "Notice of References Cited" from the USPTO for U.S. Appl. No. 09/773,672, filed Feb. 2, 2001, Publication No. US 2001-0016659

A1, Publication Date: Aug. 23, 2001, Omega-carboxyaryl substituted Diphenyl Ureas as Raf Kinase Inhibitors.
A "Notice of References Cited" from the USPTO for U.S. Appl. No. 09/773,675, filed Feb. 2, 2001, Publication No. US 2001-0011136-A1, Publication Date: Aug. 2, 2001, Omega-Carboxyaryl Substituted Diphenyl Ureas as Raf Kinase Inhibitors.
A "Notice of References Cited" from the USPTO for U.S. Appl. No. 09/776,935, filed Dec. 22, 1998, Inhibition of P38 Kinase Using Aryl and Heteroaryl Substituted Heterocyclic Ureas.
A "Notice of References Cited" from the USPTO for U.S. Appl. No. 09/776,936, filed Dec. 22, 1998, Inhibition of Raf Kinase Using Symmetrical and Unsymmetrical Substituted Diphenyl Ureas.
A "Notice of References Cited" from the USPTO for U.S. Appl. No. 09/777,920, filed Feb. 7, 2002, Omega-Carboxyaryl Substituted Diphenyl Ureas As Raf Kinase Inhibitors.
A "Notice of References Cited" from the USPTO for U.S. Appl. No. 09/948,915, filed Feb. 11, 2002, Omega-Carboxyaryl Substituted Diphenyl Ureas As Raf Kinase Inhibitors.
A "Notice of References Cited" from the USPTO for U.S. Appl. No. 10/042,226, filed Jan. 1, 2002, Omega Carboxyaryl Substituted Diphenyl Ureas As Raf Kinase Inhibitors.
Supplemental search report from the EPO for European application EP 98/963809 dated Mar. 30, 2001, Inhibition of Raf Kinase Using Symmetrical and Unsymmetrical Substituted Diphenyl Ureas, publication No. 1049664, publication date Nov. 8, 2000.
Supplemental search report from the EPO for European application EP 98/963810 dated Dec. 21, 2000, Inhibition of Raf Kinase Using Aryl and Heteroaryl Substituted Heterocyclic Ureas, publication No. 1056725, publication date Dec. 6, 2000.
Supplemental search report from the EPO for European application EP 98/965981 dated Dec. 21, 2000, Inhibition of Raf Kinase Using Substituted Heterocyclic Ureas, publication No. 1047418, publication date Nov. 2, 2000.
Supplemental search report from the EPO for European application EP 00/903239 dated Aug. 7, 2002, Omega-Carboxyaryl Substituted Diphenyl Ureas As Raf Kinase Inhibitors.
International search report for International Application No. PCT/US98/10375 Dated Sep. 3, 1998, Inhibition of p38 Kinase Activity by Aryl Ureas, publication No. 98/52558, publication date Nov. 26, 1998.
International search report for International Application No. PCT/US98/10376 dated 7/30/98, Raf Kinase Inhibitors, publication No. Wo 98/52559, publication date Nov. 26, 1998.
International search report for International Application No. PCT/US98/26078 dated Apr. 2, 1999, Inhibition of Raf Kinase Using Substituted Heterocyclic Ureas, publication No. WO99/32106, publication date Jul. 1, 1999.
International search report for International Application No. PCT/US98/26079 dated Apr. 12, 1999, Inhibition of p38 Activity Using Aryl and Heteroaryl Substituted Heterocyclic Ureas, publication No. WO99/32110, publication date Jul. 1, 1999.
International search report for International Application No. PCT/US98/26080 dated Apr. 12, 1999, Inhibition of p38 Kinase Using Substituted Heterocyclic Ureas, publication No. WO99/32111, publication date Jul. 1, 1999.
International search report for International Application No. PCT/US98/26081 dated Apr. 2, 1999, Inhibition of Raf Kinase Using Symmetrical and Unsymmetrical Substituted Diphenyl Ureas, publication No. WO99/32436, publication date Jul. 1, 1999.
International search report for International Application No. PCT/US98/26082 dated May 12, 1999, Inhibition of Raf Kinase Using Aryl and Heteroaryl Substituted Heterocyclic Ureas, publication No. WO99/32455, publication date Jul. 1, 1999.
International search report for International Application No. PCT/US98/27265.
International search report for International Application No. PCT/US00/00648 dated Jun. 29, 2000, Omega-Carboxyaryl Substituted Diphenyl Ureas as Raf Kinase Inhibitors, publication No. WO00/42012A1, publication date Jul. 20, 2000.
International search report for International Application No. PCT/US00/00768 dated May 16, 2000, Omega-Carboxy Aryl Substituted Diphenyl Ureas as P38 Kinase Inhibitors, publication No. WO00/41698A1, publication date Jul. 20, 2000.
International search report for International Application No. PCT/US02/12064 dated Sep. 20, 2002, Omega-Carboxypyridyl Substituted Dephenyl Ureas As Raf Kinase Inhibitors, publication No. 02/085859, publication date Oct. 31, 2002.
International search report for International Application No. PCT/US02/12066 dated Sep. 13, 2002, Inhibition of Raf Kinase Quinolyl, Isoquinolyl or Pyridyl Ureas, publication No. 02/085857, publication date Oct. 31, 2002.
International search report for International Application No. PCT/US/26081 dated Apr. 2, 1999, Inhibition of Raf Kinase Using Symmetrical and Unsymmetrical Substituted Diphenyl Ureas, publication No. WO99/32436, publication date Jul. 1, 1999.
Co-pending U.S. Appl. No. 09/640,780, filed Aug. 18, 2000.
Co-pending U.S. Appl. No. 09/472,232, filed Dec. 27, 1999.
Co-pending U.S. Appl. No. 09/776,936, filed Dec. 22, 1998.
Co-pending U.S. Appl. No. 09/776,935, filed Dec. 22, 1998.
Co-pending U.S. Appl. No. 09/993,647, filed Nov. 27, 2001.
Co-pending U.S. Appl. No. 10/086,417, filed Mar. 4, 2002.
Co-pending U.S. Appl. No. 10/071,248, filed Feb. 11, 2002.
Co-pending U.S. Appl. No. 10/308,187, filed Dec. 3, 2002.
Co-pending U.S. Appl. No. 10/361,859, filed Feb. 11, 2003.
Co-pending U.S. Appl. No. 10/361,844, filed Feb. 11, 2003.
Co-pending U.S. Appl. No. 10/361,850, filed Feb. 11, 2003.
Co-pending U.S. Appl. No. 10/060,396, filed Feb. 1, 2002.
Co-pending U.S. Appl. No. 09/458,014, filed Dec. 10, 1999.
Co-pending U.S. Appl. No. 10/125,369, filed Apr. 19, 2002.
Co-pending U.S. Appl. No. 09/889,227, filed Jul. 12, 2001.
XP-002233466, Medline/NLM, NLM8336809—[Intra-arterial ACNU, CDDP chemotherapy for brain metastases from lung cancer: comparison of cases with and without intra-arterial mannitol infusion], Iwadate Y et al.
Kurik et al., "Optical Properties of Segmented Oligourethane with Azomethine Terminal Fragments," Institute of Physics, National Academy of Sciences of Ukraine, 1996, pp. 2038-2041.
Duam et al., "The Ins and Outs of Raf Kinases," TIBS 19, Nov. 1994, pp. 474-480.
Campbell et al., "Increasing Complexity of Ras Signaling," Oncogene, 1998, vol. 17, pp. 1395-1413.
Bolton et al., "Ras Oncogene Directed Approaches in Cancer Chemotherapy," Annual Reports in Medicinal Chemistry, vol. 29, pp. 165-174.
Bos et al., "Ras Oncogenes in Human Cancer: A Review," Cancer Research, Sep. 1, 1989, vol. 49, pp. 4682-4689.
Kempter et al., "Synthese potentieller Pflanzenschutz- und Schädlingsbekämpfungsmittel aus substituierten Anilinen," Pädagosische Hochschule, Eingegangen am Jan. 7, 1982, 101-120.
Lyons et al., "Discovery of a novel Raf Kinase Inhibitor," Endocrine-Related Cancer, 2001, vol. 8, pp. 219-225.
Lowinger et al., "Design and Discovery of Small Molecules Targeting Raf-1 Kinase," Current Pharmaceutical Design, 2002, vol. 8, pp. 2269-2278.
Lowinger et al., "Discovery of Novel Class of Potent Raf Kinase Inhibitors: Structure Activity Relationships," Clinical Cancer Research, Nov. 2000, vol. 6, p. 4533s.
Spronsen et al., "Novel Treatment Strategies in Clear-Cell Metastatic renal Cell Carcinoma," Anti-Cancer Drugs, 2005, vol. 16, pp. 709-717.
Thaimattam et al., "3D-QSAR CoMFA, CoMSIA Studies on Substituted Ureas as Raf-1 Kinase Inhibitors and its Confirmation with Structure-Based Studies," Bioorganic & Medicinal Chemistry, 2004, vol. 12, pp. 6415-6425.
Danson et al., "Improving Outcomes in Advanced Malignant Melanoma," Drugs, 2005, vol. 65, No. 6, pp. 733-743.
Hubbard, "Oncogenic Mutations in B-Raf: Some Losses Yield Gains," Skirball Institute of Biomolecular Medicine and Department of Pharmacology, New York University School of Medicine, New York, NY.
Thompson et al., "Recent Progress in Targeting the Raf/MEK/ERK Pathway with Inhibitors in Cancer Drug Discovery," Curr. Opin. Pharmacol., Aug. 2005, vol. 5, No. 4, pp. 350-356.
Wan et al., "Mechanism of Activation of the RAF-ERK Signaling Pathway by Oncogenic Mutations of B-RAF," Cell, Mar. 19, 2004, vol. 116, pp. 855-867.

XP-002086152, Hanson et al., "Pulmonary-Allergy, Dermatological, Gastrointestinal & Arthritis, Inhibitors of p38 Kinase," *Exp. Opin. Ther. Patents*, 1997, vol. 7, No. 7, pp. 729-733.
Strumberg et al., "Phase I Clinical and Pharmacokinetic Study of the Novel Raf Kinase and Vascular Endothelial Growth Factor Receptor Inhibitor BAY 43-9006 in Patients with Advanced Refractory Solid Tumors," *Journal of Clinical Oncology*, Feb. 10, 2005, vol. 23, No. 5, pp. 965-972.
XP-000973679, Murata et al., "Facile Synthesis of New Pyrrolo[3,4-d]Pyrimidine-2,4-Diones," *Chemical and Pharmaceutical Bulletin*, 1974, vol. 22, No. 5, pp. 1212-1213.
Yasuo et al, "Intra-Arterial ACNU, CDDP Chemotherapy for Brain Metastases from Lung Cancer: Comparison of Cases With and Without Intra-Arterial Mannitol Infusion," *Neurol. Surg.*, 1993, vol. 21, No. 6, pp. 513-518.
Hanson, "Inhibitors of p38 Kinase," *Expert Opinion on Therapeutic Patents*, Jul. 1997, vol. 7, No. 7, pp. 729-733(5).
Garcia-Lopez et al., "New routes for the Synthesis of Pyrrolo[3,2-d]- and [2,3-d]- Pyrimidine Systems Starting from a Common Pyrrole Derivative," *Journal of the Chemical Society*, Perkin Transactions 1: Organic and Bio-Organic Chemistry (1972-1999), 1978, pp. 483-487.
02-022650, Patent Abstracts of Japan, Jan. 25, 1990.
02-023337, Patent Abstracts of Japan, Jan. 25, 1990.
XP-000676688, WisSner et al., "Analogues of Platelet Activating Factor. 7. Bis-Aryl Amide and Bis-Aryl Urea Receptor Antagonists of PAF," *J. Med. Chem.*, 1992, vol. 35, pp. 4779-4789.
Ravi et al., "Activated RAF-1 Causes Growth Arrest in Human Small Cell Lung Cancer Cells," *J. Clinical. Investigation*, pp. 153-159.
Lemoine, "Overview of ras oncogenes and their clinical potential," Chapter 10, pp. 85-91.
XP-001093697, Carling et al., "1-(3-Cyanobenzylpiperidin-4-yl)-5-Methyl-4-Phenyl-1,3-Dihydroimidazol-2-One: A Selective High-Affinity Antagonist for the Human Dopamine $D_4$ Receptor with Excellent Selectivity over Ion Channels," *J. Med. Chem.*, 1999, vol. 42, pp. 2706-2715.
XP-002147879, Muijlwijkl-Koezen et al., "Isoquinoline and Quinazoline Urea Analogues as Antagonists for the Human Adenosine A3 Receptor," *J. Med. Chem.*, 2000, vol. 43, pp. 2227-2238.
XP-001062441, Eisenhauer et al., "Impact of New Non-Cytotoxics in the Treatment in Ovarian Cancer," *Inernational J. Gynecol Cancer*, 2001, vol. 11, Supplement 1, pp. 68-72.
Canetta et al., "Carboplatin: current status and future prospects," 1998, p. 17-32.
Ozols, "New Developments With Carboplatin in the Treatment of Ovarian Cancer," *Seminars in Oncology*, vol. 19, No. 1, Supplement 2, Feb. 1992, pp. 85-89.
Rowinsky et al., "Taxol: The First of the Taxanes, an Important New Class of Anitumor Agents," *Seminars in Oncology*, vol. 19, No. 6, Dec. 1992, pp. 646-662.
Rowinsky et al., "Sequences of Taxol and Cisplatin: A Phase I and Pharmacologic Study," *Journal of Clinical Oncology*, vol. 19, No. 9, Sep. 1991, pp. 1692-1703.
Raez et al., "New Developments in chemotherapy for advanced non-small lung cancer," *Current Opinion in Oncology*, vol. 18, 2006, pp. 156-161.
Cortes et al., "Targeting the Microtubules in Breast Cancer Beyond Taxanes: The Epothilones," *The Oncologist*, 2007, vol. 12, pp. 271-280.
Bergstralh et al., "Microtubule stabilizing agents: Their molecular signaling consequences and the potential for enhancement by drug combination," *Cancer Treatment Reviews*, 2006, vol. 32, pp. 166-179.
Kempter et al., "Synthesis of potential plant protective agents and pesticides from . . . ," 1983, vol. 27, Issue 1, pp. 101-120.
"795 Oral Phase II trail of sorafenib (BAY 43-9006) in combination with interferon alpha 2b in patients with metastatic renal cell carcinoma", *European Journal of Cancer*, 2005, vol. 3, No. 2, pp. 226-227.
"883 Poster Phase I trial of sorafenib (BAY 43-9006) in combination with interferon alpha-2a in patients with unresectable and/or metastatic renal cell carcinoma and malignant melanoma", *European Journal of Cancer*, 2005, vol. 3, No. 2, p. 254.
Bando et al., "Association between intratumoral free and total VEGF, soluble VEGFR-1, VEGFR-2 and prognosis in breast cancer" *British Journal of Cancer*, 2005, vol. 92, pp. 553-561.
Carlomagno et al., "BAY 43-9006 Inhibition of Onconogenic RET Mutants", *Journal of the National Cancer Institute*, 2006, vol. 98, No. 5, pp. 326-334.
Chang et al., "Sorafenib (BAY 43-9006) inhibits tumor growth and vascularization and induces tumor apoptosis and hypoxia in RCC xenograft models" *Cancer Chemother Pharmacol*, 2007, vol. 50, pp. 561-574.
Foekens et al., "High Tumor Levels of Vascular Endothelial Growth Factor Predict Poor Response to Systemic Therapy in Advanced Breast Cancer," *Cander Research*, 2001, vol. 61, pp. 5407-5414.
Forbes et al., "N-(1-Methyl-5-indolyl)-N'-(3-methyl-5-isothiazolyl)urea: A Novel, High-Affinity 5-$HT_{2B}$ Receptor Antagonist" *Journal of Medicinal Chemistry*, 1995, vol. 38, No. 6, pp. 854-857.
Gomez-Esquer et al., "mRNA expression of the angiogenesis markers VEGF and CD105 (endoglin) in human breast cancer," *US National Library of Medicine*, 2004, vol. 24, No. 3a, pp. 1581-1585, XP002455577.
Gura, "Systems for identifying new drugs are often faulty." *Science*, 1997, vol. 278 (5340), pp. 1041-1042.
Heim et al., The Raf kinase inhibitor BAY 43-9006 reduces cellular uptake of platinum compounds and cytotoxicity in human colorectal carcinoma cell lines, *Anti-Cancer Drugs*, 2005, vol. 16, pp. 129-136.
Quinglong et al., "Soluble Vascular Endothelial Growth Factor Receptor 1, and Not Receptor 2, Is an Independent Prognostic Factor in Acute Myeloid Leukemia and Myelodysplastic Syndromes," *Wiley InterScience*, 2004, vol. 100, No. 9, pp. 1884-1891.
Dumas et al., "Synthesis and Pharmacological Characterization of a Potent, Orally Active p38 Kinase Inhibitor," *Bioorganic & Medicinal Chemistry Letters*, 2002, vol. 12, pp. 1559-1562.
Johnson et al., "Relationships between drug activity in NCI preclinical in vitro and in vivo models and early clinical trials," *British Journal of Cancer*, 2001, vol. 84, No. 10, pp. 1424-1431.
Kuefer et al., "Translational research in renal cell cancer. Illustrated by the example of the vascular endothelial growth factor pathway," *Der Urologe*, 2006, vol. 45, No. 3, pp. 328, 330-335.
Leuner et al., "Inmproving drug solubility for oral delivery using solic dispersions," *European Journal of Pharmaceutics and Biopharmaceutics*.
Luo et al., "Enhancement of radiation effects by pXLG-mENDO in a lung carcinoma model," *I.J. Radiation Oncology Biology Physics*, 2005, vol. 63, No. 2, pp. 553-564.
Shi et al., "Constitutive and Inducible Interleukin 8 Expression by Hypoxia and Acidosis Renders Human Pancreatic Cancer Cells More Tumorigenic and Metastatic," *Clinical Cancer Research*, 1999, vol. 5, pp. 3711-3721.
Veronese et al., "Mechanisms of Hypertension Associated with BAY 43-9006," *Journal of Clinical Oncology*, 2006, vol. 24, No. 9, pp. 1363-1369.
Xu et al., "Hypoxia-induced Elevation in Interleukin-8 Expression by Human Ovarian Carcinoma Cells," *Cancer Research*, 1999, vol. 59, pp. 5822-5829.
Hardmann et al., "Goodman & Gilman's The Pharmacological Basis of Therapeutics," 9$^{th}$ ed., 1996, pp. 51 and 57-58.
Yu et al, "The role of Mcl-1 downregulation in the proapoptotic activity of the multikinase inhibitor BAY 43-9006." PMID: 16007148.
Rahmani et al, "Apoptosis induced by the kinase inhibitor BAY 43-9006 in human leukemia cells involves downregulation of MCL-1 through inhibition of translation." JBC Papers in Press Manuscript M506551200 (Aug. 18, 2005).
Milano Et Al, "New molecular targeted therapies in thyroid cancer" Anti-Cancer Drugs (2006) © Lippincott Williams & Wilkins.
Chustecka Et Al, "Bortezomib and Sorafenib Show Activity in Thyroid Cancer" Medscape (Nov. 2, 2006).
Tanaka Et Al, "Current status and perspective of antiangiogenic therapy for cancer: hepatocellular carcinoma" Int J Clin Oncol (2006) 11:82-89 (Jan. 31, 2006).

Strumberg Et Al, "Phase I Clinical, Pharmacokinetic and Pharmacodynamic Study of the Raf Kinase Inhibitor Bay 43-9006 in Patients with Locally Advanced or Metastatic Cancer" Proc Am Soc Clin Oncol 20: 2001 (abstr 330).

Lorigan Et Al, "Phase II trial of sorafenib combined with dacarbazine in metastatic melanoma patients" ASCO DTIC abstract (Jan. 11, 2006).

Vandana Et Al, "Phase II Trial of Sorafenib in Advanced Thyroid Cancer" Journal of Clinical Oncology vol. 26, No. 29 (Oct. 10, 2008).

Sternberg Et Al, "Conspiracy Theory: RAS and RAF Do Not Act Alone" Cell, vol. 95, 447-450 (Nov. 13, 1998).

Kolch Et Al, "The Role of RAF Kinases in malignant transformation" Expert reviews in molecular medicine (Apr. 25, 2002).

Kyriakis Et Al, "RAF-1 activates MAP kinase-kinase" Nature, 358, 6385 Research Library pg. 417 (Jul. 30, 1992).

Board Et Al, "Platelet-derived growth factor receptor (PDGFR): A target for anticancer therapeutics" Drug Resistance Updates 8 (2005) 75-83.

Bollag Et Al, "Raf pathway inhibitors in oncology" Current Opinion in Investigational Drugs (2003) 4(12): 1436-1441.

Gupta Et Al, "Sorafenib targets BRAF and VEGFR in metastatic thyroid carcinoma" Journal of Clinical Oncology, 2007 ASCO Annual Meeting Proceedings (Post-Meeting Edition) vol. 25, No. 18S (Jun. 20 Supplement), 2007: 6019.

Naumann Et Al, "Raf protein serine/threonine kinases" Chapter 7.

Storm Et Al, "raf Oncogenes in Carcinogenesis" Critical Reviews in Oncogenesis, vol. 2, Issue 1.

Naumann Et Al, "The Role of Raf Kinases in Development and Growth of Tumors" Recent Results in Cancer Research, vol. 143 (1997).

European Medicines Agency, "Chimp Assessment Report for Nexavar" Doc Ref: EMEA/CHMP/140610/2006.

Gatzemeier Et Al, "Phase II trial of single-agent sorafenib in patients with advanced non-cell lung carcinoma." Journal of Clinical Oncology, 2006 ASCO Annual Meeting Proceedings Part I vol. 24, No. 18S (Jun. 20 Supplement) 2006.

Gridelli Et Al, "Sorafenib and Sunitinib in the treatment of advanced non-small cell lung cancer" The Oncologist Lung Cancer (2007) 12:191-200.

Hilger Et Al, "ERK1/2 Phosphorylation: a biomarker analysis within a phase I study with the new Raf kinase inhibitor Bay 43-9006"International journal of clinical pharmacology and therapeutics, vol. 40, No. 12 567-568 (2002).

Hilger Et Al, "Correlation of ERK-phosphorylation and toxicities in patients treated with the Raf kinase inhibitor BAY 43-9006" International journal of clinical pharmacology and therapeutics, vol. 42, No. 11, 648-649 (2004).

Flaherty Et Al, "A Phase I Trial of the Oral, Multikinase Inhibitor Sorafenib in Combination with Carboplatin and Paclitaxel" Clin Cancer Res 41(15) (Aug. 1, 2008).

Mross Et Al, "Results from an in vitro and a clinical/pharmacological phase I study with the combination irinotecan and sorafenib" European journal of cancer 43, 55-63 (Nov. 13,2006).

Tong Et Al, "Pharmacodynamic Monitoring of BAY 43-9006 (Sorafenib) in Phase I clinical trials involving solid tumor and AML/ MDS patients, using flow cytometry to monitor activation of the ERK pathway in peripheral blood cells" Cytometry Part B (Clinical Cytometry) 70B: 107-114 (2006).

Kupsch Et Al, "Results of a Phase I Trial of Sorafenib (BAY 43-9006) in Combination with Oxaliplatin in Patients with Refractory Solid Tumors, Including Colorectal Cancer." Clinical Colorectal Cancer-Cancer Information Group Journal, vol. 5 Issue 3, (Sep. 2005).

Ghassan Et Al, "Phase II Study of Sorafenib in Patients with Advanced Hepatocellular Carcinoma." Journal of Clinical Oncology, vol. 24 No. 26 (Sep. 10, 2006).

Ratain Et Al, "Phase II Placebo-Controlled Randomized Discontinuation Trial of Sorafenib in patients with Metastatic Renal Cell Carcinoma" Journal of Clinical Oncology vol. 24 No. 16, (Jun. 1, 2006).

Awada Et Al, "Phase I safety and pharmacokinetics of BAY 43-9006 administered for 21 days on/7 days off in patients with advanced, refractory solid tumors" British Journal of Cancer 92, 1855-1861 (2005).

Escudier Et Al, "Sorafenib in Advanced Clear-Cell Renal-Cell Carcinoma" New England Journal of Medicine vol. 356: 125-134 (Jan. 11, 2007).

"Nexavar Receives FDA Fast Track Designation for Skin Cancer" (Jul. 21, 2006) http://www.medicalnewstoday.com/ articles/47793.php (last visited on Jun. 16, 2008).

Wilhelm Et Al, "Sorafenib (Nexavar; Bay 43-9006): discovery and development of the first oral multi-kinase inhibitor that targets Raf and angiogenesis for the treatment of advanced renal cancer" Sorafenib (Nature Reviews Drug Discovery) Review (Apr. 12, 2006).

Bianchi Et Al, "Phase II multicenter uncontrolled trial of sorafenib (Bay 43-9006) in patients with metastatic breast cancer" Journal of Clinical Oncology (Presented Mar. 21-26, 2006).

Smith Et Al, (Abstract) "Recent Advances in the Research and Development of RAF Kinase Inhibitors".

Jain Et Al, Randomized Discontinuation Trial of Sorafenib (BAY 43-9006) Cancer Biology & Therapy, vol. 5 Issue 10 (2006).

Siu Et Al, "Phase I Trial of Sorafenib and Gemcitabine in Advanced Solid Tumors with an Expanded Cohort in Advanced Pancreatic Cancer" Clin Cancer Res 12(1) (2006).

Eisen Et Al, "Sorafenib in advanced melanoma: a Phase II randomized discontinuation trial analysis" British Journal of Cancer 95, 581-586 (2006).

Marshall, "MAP kinase Kinase, MAP kinase kinase, and MAP kinase" Curr Opin Genet Dev. 4: 82-9, 1994.

Doanes Et Al, "VEGF stimulates MAPK through a pathway that is unique for receptor tyrosine kinases" Bichem Biochem Biophys Res Commun. 225: 545-548 1999.

Smyth R M Et Al, "Anchimeric assistance in the specific acid-catalysed hydration of bensonitriles", J Chem. Soc. Perkin Trans. 2 1993 pages, 2171-2173. XP-001189455.

Chemical Abstracts vol. 117 No. 25 1992 ab. No. 251318p.

Stavchansky S. Et Al, "Evaluation of the Bioavailability of a solid dispersion of Phenytoin in Polyethylene glycol 6000 and a commercial phenytoin sodium capsule in the dog", Journal of pharmaceutical sciences/733 vol. 73 No. 6, (Jun. 1984).

Franco M. Et Al, "Dissolution properties and anticonvulsant activity of phenytoin-polyethylene glycol 6000 and polyvinylpyrrolidone K-30 solid dispersions"International journal of pharmaceutics 225 (2001) 63-73 © 2001 Elsevier Sciences B.V.

Craig D Et Al, "The mechanisms of drug release from solid dispersions in water-soluble polymers" International journal of pharmaceutics 231 (2002) 131-144 © 2002 Elsevier Sciences B.V.

Serajuddin Et Al, "Solid dispersions of poorly water-soluble drugs: Early promises subsequent problems, and recent breakthroughs" 1058 / Journal of pharmaceutical sciences vol. 88, No. 10, (Oct. 1999).

Yan He Et Al, "Oral formulation of a Novel Antiviral Agent. PG301029, in a mixture of Gelucine 44/14 amd DMA (2:1, wt/wt)" AAPS PharmSciTech 2005; vol. No. 6 (1) Article 1 (http://www.aapspharmscitech.org) (visited on Nov. 20, 2009) College of Pharmacy, The University of Arizona.

Choi Yun-Jung Et Al, "Imatinib-Resistant cell lines are sensitive to the RAF inhibitor Bay 43-9006" Blood, W.B. Saunders Company, Orlando, FL, US, vol. 100, No. 11, (Dec.10, 2002).

Guido Et Al, "International Melanoma Research Congress—Foundation for Melanoma Research. Jun. 21-24 2003, Philadelphia, PA USA. "IDRUGS: The investigational drugs journal Aug. 2003, vol. 6, No. 8, Aug. 2003 (2003-2008), pp. 752-754, XP002402150.

Hahn Et Al, "Sorafenib" Current Opinion in Oncology 18:615-621.

Elting, James Et Al, "Biomarkers associated with clinical outcomes in targets, a Phase III single-agent, placebo-controlled study of sorafenib in advanced renal cell carcinoma" vol. 47, Apr. 2006 (2006-2004), pp. 683-684, XP001245679 & 97th annual meeting of the American-Association-for-cancer-research (AACR); Washington, DC, USA; Apr. 1-5, 2006. ISSN: 0197-016X.

Anat Norden-Zfoni, "Blood-Based Biomarkers of SU11248 Activity and clinical outcome in patients with metastatic Imatinib-Resistant Gastrointestinal Stromal Tumor" Clin Cancer Res 2007;13(9) May 1, 2007 (www. aacrjournals.org).

John Ebos Et Al, "Multiple circulation proangiogenic factors induced by sunitinib malate are tumor-independent and correlated with antitumor efficacy" PNAS vol. 104, No. 43, 17069-17074 (Oct. 23, 2007).

Sandrine Faivre Et Al, "Molecular basis for sunitinib efficacy and future clinical development" Nature Publishing Group, 734, vol. 6 (Sep. 2007).

Michael Tamm Et Al, "Hypoxia induced interleukin-6 and inerleukin-8 production is mediated by platelet activation factor and platelet derived growth factor in primary human lung cells" Am. J. Respir. Cell Mol. Biol. vol. 19, pp. 653-661, (1998).

Bhagwat Et Al, "The angiogenic regulator CD13/APN is a transcriptional target of Ras signaling pathways endothelial morphogenesis," Blood 1, vol. 101 No. 5 (Mar. 1, 2003).

Rak Et Al, "Oncogenes as inducers of tumor angiogenesis" Cancer and Metastasis Reviews 14: 263-277, 1995. © 1995 Kluwer Academic Publishers. Printed in the Netherlands.

Rak Et Al, "Oncogenes and tumor Angiogenesis: Differential Modes of vascular Endothelial growth factor up Regulation in rastrasformed Epithelial cells and Fibroblast" Cancer Research 60, 490-498, Jan. 15, 2000).

Rak Et al, "Oncogenes and Angiogenesis: Signaling Three-Dimensional Tumor Growth" Cancer Biology research division, Sunnybrook amd women's college hospital health center, Toronto Sunnybrook Regional cancer Centre Department of Medical Biophysics, University of Toronto, Toronto, Ontario, Canada. 1087-0024/00/15. 00 © The Society for Investigative Dermatology, Inc.

Flaherty Et Al "Phase I/II trial of Bay 43-9006 carboplatin (c) and paclitaxel (P) demonstrates preliminary antitumor activity in the expansion cohort of patents with metastiatic melanoma." Journal of Clinical Oncology, 2004 ASCO annual meeting proceedings, vol. 22, No. 145 (Jul. 15, 2004) Supplement: 7507.

Guido Et Al, "Internation melanoma research congress - Foundation fo melanoma research" !Idrugs 2003 6(8): 752-754 © Current Drugs ISSN: 1369-7056.

Favaro Et Al, "Targeted therapy in renal cell carcinoma" Pub Med. PMID: 16185167.

Gollob Et Al, "Sorafenib: scientific rationales for single-agent and combination therapy in clear-cell renal cell carcinoma" Pub Med PMID: 16425993.

Reddy Et Al, "Sorafeninb: recent update on activity as a single agent and in combination with interferon-alpha2 in patients with advanced-stage renal cell carcinoma." Pub Med PMID: 16729906.

Takimoto Et Al, "Safety and anti-tumor activity of sorafenib (Nexavar ® ) in combination with other anti-cancer agents: a review of clinical trials." Cancer Chemotherapy and Pharmacology © Springer-Verlag 2007. 10.1007/s00280-007-0639-9.

Lago Et Al, "Selected combination therapy with Sorafenib: A Review of clinical data and perspectives in advanced solid tumors" The Oncologist, vol. 13, No. 8, 845-858 (Aug. 11, 2008) doi: 10.1634/theoncologist. 2007-0233 © 2008 AlphaMed Press.

Kolch Et Al, "The role of Raf kinases in malignant transformation" (Apr. 25, 2002) ISSN: 1462-3994 © Cambridge University Press.

Nicholas Et Al, "Overview of ras oncogenes and their clinical potential" (probally cited on PTO 892 by patent examiner in related case. Chapter 10 of a book. . . No way to tell what book).

Wald Et Al, "Involvement of the CXCL12/CXCR4 pathway in the advanced liver disease that is associated with hepatitis C virus or hepatitis B virus." Eur. J. Immunol, vol. 34, p. 1164-1174 (2004).

Thelen Et Al, "VEGF-D promotes tumor growth and lymphatic spread in a mouse model of hepatocellular carcinoma" Int. J. Cancer 122, 2471-2481 (2008) © 2008 Wiley-Liss, Inc.

Hilger Et Al, "Inhibition of ERK phosphorylation and clinical outcome in patients treated with the Raf kinase inhibitor Bay 43-9006" Proc Am Soc Clin Oncol 21: 922 (abstr 1916).

Oka Et Al, "Constitutive Activation of Mitogen-activated Protein (MAP) kinases in human renal cell carcinoma" Cancer Research 55, 4182-4187, (Sep. 15, 1995).

Chow Et Al, "Measurement of MAP kinase activation by flow cytometry using phospho-specific antibodies to MEK and ERK: potential for pharmacodynamic monitoring of signal transduction inhibitors" Cytometry (Communications in Clinical Cytometry) 46:72-78 (2001).

Kumar Et Al, "Drugs targeted against protein kinases" 2001 © Ashley publications ltd. ISSN: 1462-2416.

Carter Et Al, "Chemotherapy of Cancer (second edition)" Wiley Medical (Prior to Aug. 13, 1981).

Wood Et Al,"Novel RAF Kinase Inhibitor Bay 43-9006 Shows Early Signs of Tolerability and Activity in Phase 1B Combination Trials Reported at ASCO." (Press Release: Jun. 2, 2003).

Heim Martina Et Al, "The Raf kinase inhibitor Bay 43-9006 reduces cellular uptake of platinum compounds and cytotoxicity in human colorectal carcinoma cell lines." Anti-Cancer Drugs Feb. 2005, vol. 16, No. 2 Feb. 2005 pp. 129-136.

Tang Et Al, "Inhaled nitric oxide attenuates pulmonary hypertension and improves lung growth in infant rats after neonatal treatment with a VEGF receptor inhibitor." Am J Physiol Lung Cell Mol. Physiol 287: L344-L351.

Cras Et Al, "Treatment of newborn rats with a VEGF receptor inhibitor causes pulmonary hypertension and abnormal lung structure." Am J Physiol Lung Cell Mol Physiol vol. 283, Issue 3, L555-L562, 2002.

O'Dwyer Et Al, "c-raf-1 Depletion and tumor responses in patients treated with the c-raf-1 Antisense Olgodeoxynucleotide ISIS 5132 (CGP 69846A)." Clinical Cancer Research vol. 5 pp. 3977-3982 (Dec. 1999).

Mita Et Al, "The molecular target of rapamycin (mTOR) as a therapeutic target against cancer." Cancer Biology & Therapy 2:4 Suppl. 1, S169-S177 (Jul./Aug. 2003).

Herlaar Et Al, "p38 MAPK signaling cascades in inflammatory disease." Molecular Medicine Today, vol. 5 pp. 139-147 (Oct. 1999).

Stokoe Et Al, "Activation of c-Raf-1 by Ras and Src through different mechanisma: activation in vivo and in vitro." The EMBO Journal, vol. 16 No. 9 pp. 2384-2396 (1997).

Dorwald, "Side Reactions in Organic Synthesis: A Guide to Successful Synthesis Design. " Wiley-VCH Verlag GmbH & Co. KGaA (2005).

Siu Et Al, "Phase I study of oral raf-1 kinase inhibitor BAY 43-9006 with gemcitabine in patients with advanced solid tumors. " Proc Am Soc Oncol 22: p. 207, 2003 (abstr 828).

Redman Et Al, "p38 Kinase Inhibitors of the Treatment of Arthritis and Osteoporosis: Thieny, Furyl, and Pyrrolyl Ureas. " Bioorganic & Medicinal Chemistry Letters 11 (2001) 9-12.

Dumas Et Al, "Discovery of a New Class of p38 Kinases Inhibitors. " Bioorganic & Medicinal Chemistry Letters 10 (2000) 2047-2050.

Wojnowski Et Al, "Endothelial apoptosis in Braf-deficient mice" Nature Genetics vol. 16 (Jul. 1997).

Chialda Et Al, "Respiratory Research" 2005, 6:36, pp. 1-19.

Kapoun Et Al, Molecular Pharmacology, abstract, 2006, www.molpharmaspetjournals.org.

Feldmann, "Nature Immunology" 2001, vol. 2, No. 9, pp. 771-773.

National Cancer Institute, "Sorafenib With or Without Paclitaxel and Carboplatin in Treating Patients With Recurrent Ovarian Cancer, Primary Peritoneal Cancer, or Fallopian Tube Cancer", NCT0096200, www.clinicaltrials. gov.

National Cancer Institute, "Placlitaxel, Carboplatin, and Radiation Therapy in Treating Patients Who Are Undergoing Surgery for Stage III Non-Small Cell Lung Cancer", NCT00096226, www.clinicaltrials.gov.

Bayer Corporation, "Trial of BAY 43-9006 with Relapsed or Refractory Advanced Non-Small Cell Lung Carcinoma", NCT0010413, www.clinicaltrials.gov.

National Cancer Institute, "Carboplatin and Paclitaxel With or Without Sorafenib in Treating Patients With Unresectable Stage III or Stage IV Melanoma", NCT0011019, www.clinicaltrials.gov.

National Institutes of Health Clinical Center, "Bay 43-9006 (Sorafenib) to Treat Relapsed Non-Small Cell Lung Cancer", NCT00098254, www.clinicaltrials.gov.

Gressler, "The Importance of Solvates", Polymorphism in the Pharmaceutical Industry, Chapter 8, pg. 211, 2006, Wiley-VCH Verlug GmbH & Co., KGaA, Weinhelm.

Monia, "First-and second-generation antisense oligonucleotide inhibitors targeted against human c-raf kinase" Wiley, Chichester (Ciba Foundation Symposium 209) p. 107-123.

Nemunaitis Et Al, "Phase I Evaluation of ISIS 3521, an Antisense Oligodeoxynucleotide to Protein Kinase C-Alpha, in Patients with Advanced Cancer" Journal of Clinical Oncology, vol. 17, No. 11, pp. 3586-3595 (Nov. 1999).

Holmlund Et Al, Phase I Trial of C-raf Antisense Oligonucleotide ISIS 5132 (CGP 69846A) BY 21-day Continuous Intravenous Infusion (CIV) in patients with advanced cancer (Meeting abstract).

Cancer Weekly, "Antisense Technology (Clinical Trial) Phase II Trial of Second Antisense Cancer Drug Begins" Cancer Weekly, pg. 4 (Dec. 8, 1997).

Rudin Et Al, "Phase I Trial of ISIS 5132, an Antisense Oligonucleotide Inhibitor of c-raf 1, Administered by 24-hour weekly Infusion to Patients with Advanced Cancer" Clinical Cancer Research vol. 7, 1214-1220 (May 2001).

National Cancer Institute, Clinical Trials (PDQ), "Phase II Randomized Study of ISIS 5132 or ISIS 3521 in Women with Previously Treated Metastatic Breast Cancer" www.cancer.gov website (1998).

National Cancer Institute, Clinical Trials (PDQ), "Phase II Randomized Study of ISIS 5132 or ISIS 3521 for Locally Advanced or Metastatic Colorectal Cancer" www.cancer gov website (1998).

National Cancer Institute, Clinical Trials (PDQ), "Phase II Randomized Study of ISIS 5132 or ISIS 3521 in Patients with Hormone Refractory Prostate Cancer" www.cancer.gov website (1998).

Adjei et al., "A Phase I study of Bay 43-9006 and gefitinib in patients with refractory or recurrent non-small-cell lung cancer (NSCLC)," Abstract #43067, Meeting: *2005 ASCO Annual Meeting*, Category: Developmental Therapeutics: Molecular Therapeutics, Subcategory: Antiangiogenic or Antimetastatic agents.

Ahmad ad et al., "Kinase Inhibition with Bay 43-9006 in Renal Cell Carcinoma," *Clinical Cancer Research,* Sep. 15, 2004, vol. 10(suppl.), pp. 6388s-6392s.

Amornphimoltham et al., "Persistent Activation of the Akt Pathway in Head and Neck Squamous Cell Carcinoma: a Potential Target for UCN-01," Clinical Cancer Research, vol. 10, Jun. 15, 2004, pp. 4029-4037.

Arzneimitteltherapie, "Sorafenib" Oct. 6, 2006, Auflage 18498, 7 pages.

Arnone et al., "Selectivities in the Oxidation of Tertiary Amines and Pyridine Derivatives by Perfluoro *Cis*-2,3-dialkyloxaziridines," Tetrahedron, vol. 54, 1998, pp. 7831-7842.

Arora et al., "Stromelysin 3, Ets-1, and Vascular Endothelial Growth Factor Expression in Oral Precancerous and Cancerous Lesions: Correlation with Microvessel Density, Progression, and Prognosis," Clinical Cancer Research, 11: 2272-2284 (Mar. 15, 2005).

Ascierto et al., "Prognostic Value of Serum VEGF in Melanoma Patients: a Pilot Study" Anticancer Research, 24: 4255-4258 (2004).

Auclair et al., "BAY 43-9006 (Sorafenib) is a potent inhibitor of FLT3 tyrosine kinase signaling and proliferation in AML cells," Abstract #5991, 96th Annual Meeting, Anaheim/Orange County, CA, Apr. 16-20, 2005.

Audia et al., "Potent, Selective Tetrahydro-β-carboline Antagonists of the Serotonin 2B ($5HT_{2B}$) Contractile Receptor in the Rat Stomach Fundus," *J. Med. Chem.* 1996, 39, pp. 2773-2780.

Avruch et al., "Raf meets Ras: completing the framework of a signal transduction pathway," *TIBS* 19; Jul. 1994; pp. 279-283.

Awada et al., "Phase I safety and pharmacokinetics of BAY 43-9006 administered for 21 days on/7 days off in patients with advanced, refractory solid tumours" British Journal of Cancer 92, pp. 1855-1861 (2005).

Bachelot et al., "Prognostic value of serum levels of interleukin 6 and of serum and plasma levels of vascular endothelial growth factor in hormone-refractory metastatic breast cancer patients," British Journal of Cancer, 88: 1721-1726 (2003).

Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," JPET 279: pp. 1453-1461 (1996).

Baka et al., "A review of the latest clinical compounds to inhibit VEGF in pathological angiogenesis," Expert Opinion Therapeutic Targets, 2006, vol. 10, No. 6, pp. 867-876.

Balant et al., "Metabolic Considerations in Prodrug Design," Chapter Twenty-Three in: Burger's Medicinal Chemistry and Drug Discovery, 5th ed. John Wiley & Sons, Inc., New York, 1995: vol. 1,pp. 949-982.

Bando et al., "Association between intratumoral free and total VEGF, soluble VEGFR-1, VEGFR-2 and prognosis in breast cancer" British Journal of Cancer, 2005, vol. 92, pp. 553-561.

Banerjee et al., "Murine Coronavirus Replication-Induced p38 Mitogen-Activated Protein Kinase Activation Promotes Interleukin-6 Production and Virus Replication in Cultured Cells." Journal of Virology. American Society for Microbiology, 2002: vol. 76, pp, 5937-5948.

Bankston et al., "A Scaleable Synthesis of BAY 43-9006: A Potent Raf Kinase Inhibitor for the Treatment of Cancer," Organic Process Research & Development. 2002, vol. 6, pp. 777-781.

Barnett et al., "Identification and characterization of pleckstrin-homology-domain-dependent and isoenzyme-specific Akt inhibitors," Biochem J., vol. 385, 2005, pp. 399-408.

Baumann et al., "Raf induces $NF_{-\kappa}B$ by membrane shuttle kinase MEKK1, a signaling pathway critical for transformation," Proc. Natl. Acad. Sci. USA, vol. 97: No. 9: 4615-4620 (Apr. 25, 2000).

Bayer Corporation et al., "Trial of BAY 43-9006 in Patients with Relapsed or Refractory Advanced Non-Small Cell Lung Carcinoma", NCT0010413, clinicaltrials.gov, 3 pages Date not Available.

Bellacosa et al., "Molecular Alterations of the AKT2 Oncogene in Ovarian and Breast Carcinomas," Int. 1. Cancer (Pred. Oncol.), vol. 64, 1995, pp. 280-285.

Berge et al., "Pharmaceutical Salts." Journal of Pharmaceutical Sciences. Jan. 1977:1-19, vol. 66, No. 1.

Bergstralh et al, "Microtubule stabilizing agents: Their molecular signaling consequences and the potential for enhancement by drug combination," *Cancer Treatment Reviews,* 2006; vol. 32, pp. 166-179.

Bertrand et al., "Inhibition of PI3K, mTOR and MEK signaling pathways promotes rapid apoptosis in B-Lineage ALL in the presence of stromal cell support", Leukemia, vol. 19, pp. 98-102 (published online Oct. 21, 2004).

Bhagwat et al., "The angiogenic regulator CD13/APN is a transcriptional target of Ras signaling pathways in endothelial morphogenesis," Blood, vol. 101, No. 5, pp. 1818-1826, (Mar. 1, 2003).

Bianchi et: al., "A Phase II multi-center uncontrolled trial of sorafenib (BAY 43-9006) in patients with metastatic breast cancer" Journal of Clinical Oncology, Draft 33 pages (presented previously Oct. 30-Nov. 3, 2005).

Martin-Blanco, "p38 MAPK signalling cascades: ancient roles and new functions," BioEssays, 22:637- 645, 2000.

Foussard-Blanpin, Odette, "Comparative pharmacological study of substituted carboxamides upon central. nervous system," Ann. Pharm. Fr. (1982), 40 (4), )p. 339-350.

Board et al., "Platelet-derived growth factor receptor (PDGFR.): A target for anticancer therapeutics," Drug Resistance Updates 8 (2005) 75-83.

Bok et al., "Vascular Endothelial Growth Factor and Basic Fibroblast Growth Factor Urine Levels as Predictors of Outcome in Hormone-refractory Prostate Cancer Patients: A Cancer and Leukemia Group B Study," Cancer Research, 61: 2533-2536 (Mar. 15, 2001).

Bollag et al., "Raf pathway inhibitors in oncology," Current Opinion in Investigational Drugs (2003) 4(12): pp. 1436-1441.

Bolton et al., "Chapter 17. *Ras*Oncogene Directed Approaches in Cancer Chemotherapy," Annual Reports in Medicinal Chemistry, vol. 29, 1994, pp. 165-174.

Bono et al., "Serum KIT and KIT ligand levels in patients with gastrointestinal stromal tumors treated with itnatinib," Blood 103:2929-2935 (2004).

Bos, J.L. "*ras*Oncogenes in :Human Cancer: A Review," *Cancer Research,* vol. 49, Sep. 1, 1989, pp. 4682-4689.

Boulton et al., "Heterocyclic Rearrangements. Part X. A Generalised Monocyclic Rearrangement," J. Chem. Soc. (C), 1967, pp. 2005-2007.

Boyer, S.J., "Small Molecule Inhibitors of KDR (VEGFR-2) Kinase: An Overview of Structure Activity Relationships," Current Topics in Medicinal Chemistry, 2002, vol. 2, pp. 973-1000.

Boyd, et al. "Arene Oxides of Quinoline: Epoxidat on, N-Oxidation and N-Methylation Reactions," J. Chem. Soc. Perkin Trans. 1, 1991: pp. 2189-2192.

Braybrooke et al., "A Phase II Study of Razoxane, an Antiangiogenic Topoisomerase II Inhibitor, in Renal Cell Cancer with Assessment of Potential Surrogate Markers of Angiogenesis," Clin. Canc. Res. 6:4697-4704 (2000).

Broll et al., "Vascular endothelial growth factor (VEGF) — a valuable serum tumour marker in patients with colorectal cancer?" Ear. J. Surg. Ortcol, 27:37-42 (2001).

Bruder et al., "Adenovirus Infection Stimulates the Raf/MAPK Signaling Pathway and Induces Interleukin-8 Expression" Journal of Virology, vol. 71, pp. 398-404, 1997.

Bundgaard, Hans. "Design of prodrugs: Bioreversible derivatives for various functional groups and chemical entities," pp. 1-92, in Design of Prodrugs, Elsevier Science Publishers B,V., Amsterdam, The Netherlands, 1985.

Campbell et al., "Increasing complexity of Ras signaling," Oncogene, 1998, vol, 17, pp. 1395-1413.

Cancer Weekly. "Antisense Technology (Clinical Trial). Phase II Trial of Second Antisense Cancer Dg Begins," Cancer Weekly, p. 4 (Dec. 8, 1997).

Canetta et al., "Carboplatin: current status and finure prospects," Cancer Treatment Reviews, 1998, pp. 17- 32, vol. 15(Supplement B).

Caponigro et al., "Epidermal growth factor receptor as a major anticancer drug target,"Exp. Opin. Thera. Targets, 2006, vol. 10, No. 6, pp. 877-888.

Carey et al., "Contents of Part A," pp. vii-xi and "Contents of Part B," pp. xiii-xviii, in Advanced Organic Chemistry, Second Edition, Part A: Structure and Mechanisms, Plenum Press, NY (1984).

Carling et al., "1-(3-Cyanobenzylpiperiditi-4-y1)-5-methyl-4-pheny1-1,3-dihydroimidazol-2-one: A Selective High-Affinity Antagonist for the Human Dopamine $D_4$ Receptor with Excellent Selectivity over Ion Channels," J Med. Chem., 1999, 42, pp. 2706-2715.

Carlomagno et al., "BAY 43-9006 Inhibition of Oncogenic RET Mutants," Journal of the National Cancer Institute, 2006, vol. 98, No. 5, pp. 326-334.

Carney et al., "Monitoring the Circulating Levels of the HER2/neuOncoprotein in Breast Cancer," Clin Breast Cancer 5(2): 105-116, (2004).

Carter et al., "Anti-Tumor Efficacy of the Orally Active RafKinase Inhibitor BAY 43-9006 in Human Tumor Xenograft Models," Proceedings of the American Association for Cancer Res., vol. 42: p. 923, Mar. 2001, Abstract #4954.

Carter et al., "Drug-Tumor Interactions" pp. 362-365, in: Chemotherapy of Cancer, Second Edition, John Wiley & Sons, NY (1981).

Carter et al., "Sorafenib is efficacious and tolerated in combination with cytotoxic or cytostatic agents in preclinical models of human non-small cell lung carcinoma," Cancer Chemotherapy and Pharmacology, Springer Berlin/Heidelberg, vol. 59, No. 2, pp. 183-195 (Feb. 2007). Abstract.

Chang et al., "BAY 43-9006 (Sorafenib) inhibits ectopic (s.c.) and orthotopic growth of a murine model of renal adenocarcinoma (Renca) predominantly through inhibition of tumor angiogenesis," $96^{th}$ Annual Meeting, Anaheim/Orange County, CA, Apr. 16-20, 2005, 1 page.

Chang et al., "Sorafenib (BAY 43-9006) inhibits tumor growth and vascularization and induces tumor apoptosis and hypoxia in RCC xenograft models," Cancer Chemother. Pharmacol, 2007, vol. 59, pp. 561-574.

Chen et al., "Role of Regulatory Elements and the MAPK/ERK oR p38 MAPK Pathways for Activation of Human Cytomegalovirus Gene Expression," Journal of Virology, 2002: vol. 76, No. 10, pp. 4873-4885.

Chen et al., "Suppression of Japanese encephalitis virus infection by non- steroidial, anti-inflammatory drugs," Journal of General Virology, 2002, vol. 83, pp. 1897-1905.

Chen et al., "Expression of Proinflammatory and Proangiogenic Cytokines in Patients with Head and Neck Cancer," Clinical Cancer Research 5:1369-1379 (Jun. 1999).

Chialda et al., "Inhibitors of mitogen-activated protein kinases differentially regulate costimulated T cell cytokine production and mouse airway eosinophilia," Respiratory Research 2005, 6:36, pp. 1-19.

Chin et al., "Vascular endothelial growth factor and soluble Tie-2 receptor in colorectal cancer: associations with disease recurrence," European Journal of Surgical Oncology, 29:497-505 (2003).

Choi et al., "Imatinib-Resistant Cell Lines Are Sensitive to the Raf Inhibitor BAY 43-9006," Blood, W.E.B. Saunders Company, Orlando, FL, US, vol. 100, No. 11, Abstract #1427 (Dec. 10, 2002).

Choong et al., "Forthcoming receptor tyrosine kinase inhibitors," Exp. Opin. Ther. Targets, 2006, vol. 10, No. 6, pp. 793-797.

Chow et al., "Measurement of MAP Kinase Activation by Flow Cytometry Using Phospho-Specific Antibodies to MEK and ERK: Potential for Pharmacodynamic Monitoring of Signal Transduction Inhibitors," Cytometry (Communications in Clinical Cytometry) 46:72-78 (2001).

Christensen, et al., "Plasma vascular endothelial growth factor and interleukin-8 as biomarkers of antitumor efficacy of a prototypical erbB family tyrosine kinase inhibitor," Mol. Cancer Ther., 4(6):938-947 (Jun. 2005).

Chu et al., "Cardiotoxicity associated with tyrosine kinase inhibitor sunitinib," Lancet, 2007, vol. 370, pp. 2011-2019.

Chustecka et al., "Bortezomib and Sorafenib Show Activity in Thyroid Cancer," Medscape, 2 pages (Nov. 2, 2006).

Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," Clinical Cancer Res., Aug. 1, 2005, vol. 11, No. 15, pp. 5472-5480.

Garbe, "Auch cin Therapieplatz fur Sorafenib?" Medical Special (2006) 2 pages.

Copéret et al., "A Simple and Efficient Method for the Preparation of Pyridine-N-oxides II" Tetrahedron Letters, Elsevier Science Ltd., Pergamon Press, Oxford, UK 1998: vol.39, pp. 761-764.

Cortes et al., "Targeting the Microtubules in Breast Cancer Beyond Taxanes: The Epothilones" *The Oncologist*, 2007, vol. 12, pp. 271-280.

Craig, "The mechanisms of drug release from solid dispersions in water-soluble polymers." International Journal of Pharmaceutics 231 (2002) 131-144, Elsevier Science B.V.

Le Cras et al., "Treatment of newborn rats with a VEGF receptor inhibitor causes pulmonary hypertension and abnormal lung structure." Am. J. Physiol. Lung. Cell. Mol. Physiol. vol. 283, pp. L555-L562, 2002.

Crump, Micheal, "Inhibition of raf kinase in the treatment of acute myeloid leukemia," Medline Abstract ISSN:1381-6128, Current Pharmaceutical Design, vol. 8, Issue 25, 2002, pp. 2243-2248.

Cunningham et al., "A Phase I Trial of H-rasAntisense Oligonucleotide ISIS 2503 Administered as a Continuous intravenous Infusion in Patients with Advanced Carcinoma," Cancer, 2001, American Cancer Society, vol. 92, No. 5, pp. 1265-1271.

Danson et al., "Improving Outcomes in Advanced Malignant Melanoma. Update on Systemic Therapy," Drugs,2005, vol. 65, No. 6, pp. 733-743.

Dasmahapatra et al., "*In vitro*Combination Treatment with Perifosine and UCN-01 Demonstrates Synergism against Prostate (PC-3) and Lung (A549) Epithelial Adenocarcinoma Cell Lines," Clinical Cancer Research, vol. 10, Aug. 1, 2004, pp. 5242-5252.

Daum et al., "The ins and outs of Raf kinases," TIBS 19, Nov. 1994, pp, 474-480.

Dayan et al., "Tertiary Amine Oxidation using HOF-$CH_3$ CN: A Novel Synthesis of N-Oxides," Synthesis, 1999, No. SI, pp. 1427-1430.

DeGrendele, "Activity of the Raf Kinase Inhibitor BAY 43-9006 in Patients with Advanced Solid Tumors," Clinical Colorectal Cancer, May 2003, vol. 3, pp. 16-18.

Dehtling, J. "Groβe Onkologie-Pipeline" Medizinische Monatsschrift für Pharinazeuten, 2006, Auflage 12914, 2 pages.

Denny, "Prodrug strategies in cancer therapy," European Journal of Medicinal Chemistry. 2001: vol. 36, pp. 577-595.

DeVita et al., "Elevated Perioperative Serum Vascular Endothelial Growth Factor Levels in Patients with Colon Carcinoma," Cancer, 100 (2) pp. 270-278 (2004).

Devlin et al., "GATT and DISCOVERY: Significant Changes in U.S. Patent Law" Screening Fortran, vol. 3, No. 4, pp. 1, 3 and 6 (Dec. 1995).
Doanes et al., "VEGF Stimulates MAPK through a Pathway That Is Unique for Receptor Tyrosine Kinases," Biochem Biophys. Res. Commun. 255: pp. 545-548, 1999.
Dörwald, "Preface," p. IX, in Side Reactions in Organic Synthesis: A Guide to Successful Synthesis Design, Wiley-VCH Verlag GmbH & Co. KGaA (2005).
Downward, J., "Mechanisms and consequence of activation of protein kinase B/Akt," Current Opinion in Cell Biology, vol. 10, 1998, pp. 262-267.
Drevs et al., "Soluble markers for the assessment of biological activity with PTK787/ZK 222584 (PTK/ZK), a vascular endothelial growth factor receptor (VEGFR) tyrosine kinase inhibitor in patients with advanced colorectal cancer from two phase I trials," Annals of Oncology, 16: 558-565 (2005).
Drevs, J., "Soluble Markers for the Detection of Hypoxia under Antiangiogenic Treatment," Anticancer Research, 23: 1159-1162 (2003).
Drevs, J., Die Medizinische Welt, 2006, pp. 3/5, 4/5, 5/5.
"Doxorubicin HCl (ADR)," in drugs: facts and comparisons, 1994 Ed., pp. 2703-2705.
Dudek et al., "Circulating Angiogenic Cytokines in Patients with Advanced Non-Small Cell Lung Cancer: Correlation with Treatment Response and Survival," Cancer Investigation, 23: 193-200 (2005).
Dumas, J. "Protein kinase inhibitors from the urea class," Curr. Opin. In Drug Discovery and Dev., 5(s):718-727, 2002.
Dumas et al., "Discovery of a New Class of p38 Kinase Inhibitors," Bioorganic & Medicinal Chemistry Letters vol. 10, (2000), pp. 2047-2050.
Dumas et al., "1-Phenyl-5-pyrazolylUreas: Potent and Selective p38 Kinase Inhibitors," Bioorganic & Medicinal Chemistry Letters, 2000, vol. 10, pp. 2051-2054.
Dumas, J., "Growth factor receptor kinase inhibitors: Recent progress and clinical impact," Current Opinion in Drug Discovery & Development, 2001, vol. 4, No. 4, pp, 378-389.
Dumas, J., "Protein kinase inhibitors: emerging pharmacophores 1997-2000," Expert Opinion on Therapeutic Patents (2001) vol. 11, No. 3, pp. 405-429.
Dumas et al., "Orally Active p38 Kinase Inhibitors from the Urea Class," Poster, 222nd American Cancer Society National Meeting 2001, Med. I 256, 1 page.
Dumas, J., "Raf Kinase Inhibitors," Expert Opinion on Therapeutic Patients, vol. 8, No. 12, pp. 1749- 1750, 1998.
Dumas et al., "Recent developments in the discovery of protein kinase inhibitors from the urea class," *Current Opinion in Drug Discovery & Development*, 2004, vol. 7, No. 5, pp. 600-616.
Dumas et al., "Synthesis and Pharmacological Characterization of a Potent, Orally Active p38 Kinase Inhibitor," *Bioorganic & Medicinal Chemistry Letters*, 2002, vol. 12, pp. 1559-1562.
Dunst et al., "Tumor Hypoxia and Systemic Levels of Vascular Endothelial Growth Factor (VEGF) in Head and Neck Cancers," Strahlentherapie und Onkologie, 177(9): 469-473 (2001).
Ebos et al., "Multiple circulating proangiogenic factors induced by sunitinib malate are tumor-independent and correlated with antitumor efficacy" PNAS vol. 104, No. 43, pp. 17069-17074 (Oct. 23, 2007).
Ebrahimi et al., "Cytokines in Pancreatic Carcinoma. Correlation with Phenotypic Characteristics and Prognosis," Cancer, 101(12): 2727-2736 (Published on-line Nov 3, 2004).
Eisen et al., "Phase I trial of BAY 43-9006 (Sorafenib) combined with dacarbazine (DTIC) in metastatic melanoma patients," Abstract #7508, Meeting: *2005 ASCO Annual Meeting*, Category: Melamona, Subcategory: Melamona.
Eisen et al., "Sorafenib in advanced melanoma: a Phase II randomised discontinuation trial analysis" British Journal of Cancer 95, 581-586 (2006).
Eisenhauer et al., "Impact of new non-cytotoxics in the treatment in ovarian cancer," International J. Gynecol. Cancer, 2001, vol. 11, Supplement 1, pp. 68-72.

El-Deiry, Wafik S., "Meeting Report: The International Conference on Tumor Progression and Therapeutic Resistance", Cancer Research, 2005; vol. 65, No. 11, pp. 4475-4484.
Elting et al., "Biomarkers associated with clinical outcomes in TARGETs, a Phase III single-agent, placebo-controlled study of sorafenib in advanced renal cell carcinoma," .Proc. Amer. Assoc. Cancer Res. vol. 47, Abstract #2909, 2006, pp. 683-684.
Escudier et al., "Randomized Phase III trial of the Raf kinase and VEGFR inhibitor sorafenib (BAY 43-9006) in patients with advanced renal cell carcinoma (RCC)," Meeting: 2005 ASCO Annual Meeting, Category: Genitourinary Cancer, Subcategory: Kidney Cancer, 1 page.
Escudier et al., "Sorafenib in Advanced Clear-Cell Renal-Cell Carcinoma" New England Journal of Medicine vol. 356: 125-134 (Jan. 11, 2007).
European Medicines Agency, "CHMPAssessment Report for Nexavar" Doc Ref: EMEA/CHMP/140610/2006, 63 pages.
Fabian et al., "A small molecule-kinase interaction map for clinical kinase inhibitors," Nature Biotechnology, 2005, vol. 23, No. 3, pp. 329-336, 4 supplementary pages.
Faderl et al., "Angiogenic factors may have a different prognostic role in adult acute lymphoblastic leukemia," Blood, 2005 vol. 106 No. 13, pp. 4303-4307.
Faivre et al., "Molecular basis for sunitinib efficacy and future clinical development" Nature Reviews Drug Discovery, Nature Publishing Group, pp. 734-745, vol. 6 (Sep. 2007).
Fakhari et al., "Upregulation of Vascular Endothelial Growth Factor Receptors is Associated with Advanced Neuroblastoma," Journal of Pediatric Surgery, 37(4): 582-587 (Apr. 2002).
Favaro et al., "Targeted therapy in renal cell carcinoma," Expert Opin. Investig. Drugs 14( 10):1251- 258 (2005).
Fiedler et al. "A phase 2 clinical study of SU5416 in patients with refractory acute myeloid leukemia," Blood, 102(8): 2763-2767(prepublished online Jul. 3, 2003).
Feldmann, "Pathogenesis of arthritis: recent research progress," Nature Immunology 2001, vol. 2, No. 9, pp. 771-773.
Fields Virology Second Editon, "Contents,":vol. 1 , pp. ix-xiv, Raven Press, NY (1990).
Flaherty et al., "A Phase I Trial of the Oral, Multikinase Inhibitor Sorafenib in Combination with Carboplatin and Paclitaxel" Clin Cancer Res 41(15):4836-4842 (Aug. 1, 2008).
Flaherty et al., "Phase I/II trial of BAY 43-9006 carboplatin (C) and paclitaxel (P) demonstrates preliminary antitumor activity in the expansion cohort of patients with metastatic melanoma," Journal of Clinical Oncology, 2004 ASCO annual meeting proceedings, vol. 22, No. 14S (2004) Supplement: 7507, 4 pages.
Flaherty et al., "Antisense therapeutics: lessons from early clinical trials," Current Opin. In Oncol. 13: 499- 505 (2001).
Foekens et al,, "High Tumor Levels of Vascular Endothelial Growth Factor Predict Poor Response to Systemic Therapy in Advanced Breast Cancer," *Cancer Research*, 2001, vol. 61, pp. 5407-5414.
Forbes et al., "$N$-(1-Methyl-5-indolyl)-$N$-(3-methyl-5-isothiazoly)urea: A Novel, High-Affinity 5-HT$_{2B}$ Receptor Antagonist," Journal of Medicinal Chemistry, 1995, vol. 38, No. 6, pp. 855-857.
Franco et al., "Dissolution properties and anticonvulsant activity of phenytoin-polyethylene glycol 6000 and -polyvinylpyrrolidone K-30 solid dispersions," International Journal of Pharmaceutics 225 (2001) pp. 63-73.
Fridman et al., "The Minimal Fragments of c-Raf-1 and NF1 That Can Suppress v-Ha-Ras-Induced Malignant Phenotype," the Journal of Biological Chemistry, vol. 269, No. 48, 1994, pp. 30105-30108.
Garcia-López et al., "New Routes for the Synthesis of Pyrrolo[3,2-d]- and [2,3-d]-pyrimidine Systems starting from a Common Pyrrole Derivative," Journal of the Chemical Society, Perkin Transactions 1: Organic and Bio-Organic Chemistry (1972-1999), 1978, pp. 483-487.
Gatzemeier et al., "Phase II trial of single-agent sorafenib in patients with advanced non-small cell lung carcinoma," Journal of Clinical Oncology, 2006 ASCO Annual Meeting Proceedings Part I, vol. 24, No. 18S (Jun. 20 Supplement) 2006, abstract No. 7002, 4 pages.
Geiger et al., "Antitumor Activity of a C-raf Antisense Oligonucleotide in Combination with Standard Chemotherapeutic Agents against Various Human Tumors Transplanted Subcutaneously into Nude Mice," Clinical Cancer Research vol. 3, 1179-1185, Jul. 1997.

Geng et al., "A Specific Antagonist of the p110δ Catalytic Component of Phosphatidylinositol 3'-Kinase, IC486068, Enhances Radiation-Induced Tumor Vascular Destruction," Cancer Research,64, Jul. 2004, pp. 4893-4899.

Gennaro, Alfonso R. "Table of Contents," pp. xiv-xv, in Remington: The Science and Practice of Pharmacy, 20TH Ed. Remington. Lippincott Williams & Wilkins, 2000.

George et al., "VEGF-A, VEGF-C and VEGF-D in Colorectal Cancer Progression," Neoplasia, 3(5): 420- 427 (2001).

George et al., "Prognostic Significance of Plasma Vascular Endothelial Growth Factor Levels in Patients with Hormone-refractory Prostate Cancer Treated on Cancer and Leukemia Group B 9480," Clinical Cancer Research, 7: 1932-1936 (Jul. 2001).

Abou-Alfa et al., "Phase II Study of Sorafenib in Patients with. Advanced Hepatocellular Carcinoma" Journal of Clinical Oncology, vol. 24, No. 26, pp. 4293-4300 (Sep. 10, 2006).

Giambartolomei et al., "Sustained activation of the Raf/MEK/Erk pathway in response to EGF in stable cell lines expressing the Hepatitis C Virus (HCV) core protein," Oncogene, Nature Publishing Group, 2001: vol. 20, pp. 2606-2610.

Gills et al., "The development of phosphatidylinositol ether lipid analogues as inhibitors of the serine/threonine kinase, Akt," Expert Opin. Investig. Drugs, vol. 13, No. 7, 2004, pp. 787-797.

Gollob, "Sorafenib: scientific rationales for single-agent and combination therapy in clear-cell renal cell carcinoma" Pub Med PMID: 16425993, Clin. Genitourin. Cancer 4(3):167-174 (2005) abstract.

Gómez-Esquer et al., "mRNA expression of the angiogenesis markers VEGF and CD105 (endoglin) in human breast cancer," Anticancer Res., 2004, vol. 24, No. 3a, pp. 1581-1585, XP-002455577, abstract.

Grant et al., "Some Hypotensive ' Thiadiazoles," J. Med. Chem. (1972), 15(10), pp. 1082-1084.

Greene et al., "Contents," pp. xi -xii, in: Protective Groups in Organic Synthesis, 3rd Ed. John Wiley & Sons, Inc., New York, 1999.

Gelasser, "The Importance of Solvates," in: Polymorphism in the Pharmaceutical Industry, Chapter 8, p. 211, 2006, Wiley-VCH Verlug GmbH & Co., KGaA, Weinhelm.

Gridelli et al., "Sorafenib and Sunitinib in the Treatment of Advanced Non-Small Cell Lung Cancer" the Oncologist (2007) 12:191-200.

Guan et al., "H5N1 influenza: A protean pandemic threat," Proc. Natl. Acad, Sci. USA, May 25, 2004; vol. 101, pp. 8156-8161.

Gupta et al., "Sorafenib targets BRAF and VEGFR in metastatic thyroid carcinoma" Journal of Clinical Oncology, 2007 ASCO Annual Meeting Proceedings (Post-Meeting Edition) vol. 25, No. 185 (Jun. 20 Supplement), 2007: 6019 abstract.

Gura, "Systems for identifying new drugs are often faulty." Science,1997; vol. 278, (5340), pp. 1041- 1042, MEDLINE with Full text.

Hahn et al., "Sorafenib," Curr. Opin. Oncol. 18:615-621 (2006).

Hall-Jackson et al., "Paradoxical activation of Raf by a novel Raf inhibitor," Chemistry & Biology. 6: 559- 568 (Jul. 1999).

Han et al., "Targeted Prodrug Design to Optimize Drug Delivery." AAPS Pharmsci. 2000: vol. 2, No. 1, Article 6, 1-11.

Hanna, "Second-Line Treatment of Non-small Cell Lung Cancer: Big Targets, Small Progress; Small Targets, Big Progress?" Journal of Thoracic Oncology vol. 1, No. 9, pp. 927-928 (Nov. 2006).

Hansch et al., "Contents," 21 pages, in: Comprehensive Medicinal Chemistry. The Rational Design, Mechanistic Study & Therapeutic Application of Chemical Compounds, Pergamon Press, Oxford, Uk, 1990.

Hanson, "Pulmonary-Allergy, Dermatological, Gastrointestinal & Arthritis Inhibitors of p38 kinase," Exp. Opin. Ther. Patents,1997, vol. 7, No. 7, pp. 729-733.

Hardmann et al., excerpts from chapter 3. Principles of Therapeutics, in: Goodman & Gilman's the Pharmacological Basis of Therapeutics, 9th ed., 1996, pp. 51 and 57-58.

Harris et al., "Soluble Tie2 and Flt 1 Extracellular Domains in Serum of Patients with Renal Cancer and Response to Antiangiogenic Therapy," Chin. Cancer Res. 7:1992-1997 (2001).

Hayes et al., "Serum vascular endothelial growth factor as a tumour marker in soft tissue sarcoma," British Journal of Surgery, 91:242-247 (Published on-line Nov. 24, 2003).

Hegedus, L.S. "Contents," 4 pages in: Transition Metals in the Synthesis of Complex Organic Molecules, University Science Books, Mill Valley, California, 1994.

Heim et al., "Antitumor effect and potentiation or reduction in cytotoxic drug activity in human colon carcinoma cells by the Raf kinase inhibitor (RKI) Bay 43-9006," International Journal of Clinical Pharmacology and Therapeutics,2003, vol. 41, No. 12, pp. 616-617.

Heim et al., "The Raf kinase inhibitor BAY 43-9006 reduces cellular uptake of platinum compounds and cytotoxicity in human colorectal carcinoma cell lines," Anti-Cancer Drugs,2005, vol. 16, pp. 129-136.

Herlaar et al., "p38 MAPK signalling cascades in inflammatory disease," Molecular Medicine Today, vol. 5, pp. 439-447 (Oct. 1999).

Herrera et al., "Unraveling the complexities of the Raf/MAP kinase pathway for pharmacological intervention," Trends in Molecular Medicine, 2002, vol. 8, No. 4 (Suppl.), pp. S27-S31.

Higuchi T. et al., "Contents," in: Prodrugs as Novel Drug Delivery Systems, ACS Symposium Series 14, American Chemical Society, Washington, DC, 1975, p. vii.

Higuchi et: al., "Mitochondrial DNA determines androgen dependence in prostate cancer cell lines," Oncogene, 2006, vol. 25, pp. 1437-1445.

Hilger et: al., "Correlation of ERK-phosphorylation and toxicities in patients treated with the Raf kinase inhibitor BAY 43-9006" International Journal of Clinical Pharmacology and Therapeutics, vol. 42, No. 11, pp. 648-649 (2004).

Hilger et al., "ERK1/2 phosphorylation: a biomarker analysis within a phase I study with the new Raf kinase inhibitor BAY 43-9006" International Journal of Clinical Pharmacology and Therapeutics, vol. 40, No. 12, pp. 567-568 (2002).

Hilger et al., "Inhibition of ERK phosphorylation and clinical outcome in patients treated with the Raf kinasekinase inhibitor BAY 43-9006" Proc Am Sac Clin Oncol 21: 2002 (abstr 1916), 3 pages.

Hrasawa et al., "Effect of p38 Mitogen-Activated Protein Kinase on the Replication of Encephalomyocarditis Virus." Journal of Virology, May 2003: vol. 77, No. 10, pp. 5649-5656.

Holmlund et al., "Phase I Trial of C-raf Antisense Oligonucleotide ISIS 5132 (CGP 69846A) by 21-Day Continuous Intravenous infusion (CIV) In Patients With Advanced Cancer," (Meeting abstract), 1998 ASCO Annual Meeting, Abstract No. 811, 2 pages.

Hotte et al., "Bay 43-9006: Early clinical data in patients with advanced solid malignancies," Current Pharmaceutical Design, 8: 2249-2253, 2002.

Hu et al., "Soluble Vascular :Endothelial Growth Factor Receptor 1, and Not Receptor 2, Is an Independent Prognostic Factor in Acute Myeloid Leukemia and Myelodyslastic Syndromes," Cancer, 100(9): 1884-1891 (Published on-line Mar. 29, 2004).

Hubbard, "Oncogenic Mutations in B-Raf: Some Losses Yield Gains," Cell vol. 116, Issue 6, 764-766 (2004).

Hyodo et al., "Clinical Significance of Plasma Vascular Endothelial Growth Factor in Gastrointestinal Cancer," European Journal of Cancer, 34(13): 2041-2045 (1998).

Ihle et al., "Molecular pharmacology and antitumor activity of PX-866, a novel inhibitor of phosphoinositide-3-kinase signaling," Molecular Cancer Therapy, vol. 3, No. 7, 2004, pp. 763-772.

Ishigami et al, "Predictive Value of vascular endothelial growth factor (VEGF) in metastasis and prognosis of human colorectal cancer," British Journal of Cancer, 78(10): 1379-1384 (1998).

Jacobsen et al., "Vascular Endothelial Growth Factor as Prognostic Factor in Renal Cell Carcinoma," Journal of Urology, 163(1): 343-347 (Jan. 2000).

Jacobsen et al., "Prognostic importance of serum vascular endothelial growth factor in relation to platelet and leukocyte counts in human renal cell carcinoma," European Journal of Cancer Prevention, 2002, 11(3) pp. 245-252.

Jain et al, "Randomized Discontinuation Trial of Sorafenib (BAY 43-9006)," Cancer Biology & Therapy, vol. 5, Issue 10, pp. 1270-1272 (2006).

Jeffcoat et al., "The Metabolism and Toxicity of Halogenated Carbanilides," Drug Metabolism and. Disposition, vol. 5, No. 2, pp. 157-166 (1977).

Jimeno et al., "Analysis of Biologic Surrogate Markers from a Children's Oncology Group Phase 1 Trial of Gefitinib in Pediatric Patients with Solid Tumors," Pediatr. Blood Cancer, 49(3): 352-357 (2007).

Jin et al., "Inhibition of AKT survival pathway by a small molecule inhibitor in human endometrial cancer cells," British Journal of Cancer, vol. 91, 2004, pp. 1808-1812.

Johnson et al., "Relationships between drug activity in NCI preclinical in vitro and in vivo models and early clinical trials," British Journal of Cancer, 2001, vol. 84, No. 10, pp. 1424-1431.

Johnston, D, et al., "Elevation of the Epidermal Growth Factor Receptor and Dependent Signaling in Human Papillomavirus-infected Laryngeal Papillomas." Cancer Research, 1999: vol. 59, pp. 968-974.

Jungmayr, P., "Aktueller Stand der Krebstherapie," Deutsche Apotheker Zeitung, Sep. 30, 2004, Auflage ca. 36,000.

Kapoun et al., "TGFβR1 kinase activity, but not p38 activation is required for TGFβR1-induced myofibroblast differentiation and profibrotic gene expression," Molecular Pharmacology Fast Forward, abstract, 2006, www.molpharmaspetjoumals.org, 2 pages.

Karayiannakis et al., "Circulating VEGF Levels in the Serum of Gastric Cancer Patients," Annals of Surgery, 236(1): 37-42 (Jul. 2002).

Karayiannakis et al., "Clinical significance of preoperative serum vascular endothelial growth factor levels in patients with colorectal cancer and the effect of tumor surgery," Surgery, 131(5): 548-555 (May 2002).

Karp et al., "Targeting Vascular Endothelial Growth Factor for Relapsed and Refractory Adult Acute Myelogenous Leukemias: Therapy with Sequential 1-β-D Arabinofuranosylcytosine, Mitoxantrone, and Bevacizumab," Clinical Cancer Research, 10: 3577-3585 (Jun. 1, 2004).

Katritzky et al., "1.18. Azetidines. Azetines, and Azetes: Monocylcic" pp. 507-508 in: Comprehensive Heterocyclic Chemistry II, A Review of the Literature 1982-1995: The Structure, Reactions, Synthesis, and Uses of Heterocyclic; Compounds. Pergamon Press, Oxford, UK, 1996.

Katritzky, Alan R., Tables of Content, in: Comprehensive Organic Functional Group Transformations. Pergamon Press, Oxford, UK, 1995, 25 pages.

Katritzky et al., "Contents," 2 pages, in: Comprehensive Heterocyclic Chemistry, The Structure, Reactions, Synthesis, and Uses of Heterocyclic Compounds. Pergamon Press, Oxford, UK, 1984.

Keller et al., "The role of Raf kinase inhibitor protein (RKIP) in health and disease." Biochemical Pharmacology 68; pp. 1049-1053 (2004).

Kempter et al., "Synthese potentieller Pflanzenschutz- and Schällingsbekämpfungsmittel aus substituierten Anilinen," Pädagogsische Hochschule, Eingegangen am 1.7.1982, vol. 27, Issue 1, 101-120 (1983).

Kessler et al., "Use of the DNA Flow-Thru Chip, a Three-Dimensional Biochip, for Typing and Subtyping of Influenza Viruses." Journal of Clinical Microbiology. May 2004: vol. 42, pp. 2173-2185.

Khire et al., "Omega-carboxypyridyl substituted ureas as Raf kinase inhibitors: SAR of the amide substituent," Bioorg. Med. Chem. Lett., 2004, vol. 14, pp. 783-786.

Kido, Y., "Vascular Endothelial Growth. Factor (VEGF) Serum Concentration Changes during Chemotherapy in Patients with Lung Cancer," Kurume Medical Journal, 48(1): 43-47 (2001).

Klemm et al., "Chemistry of Thienopyridines. XXXVII. Syntheses in the Cyclopenta, Cyclohexa-, and Cycloheptathieno[2,3- b ]pyridine Series. Threee Analogs of 9-Amino-1,2,3,4-tetrahydroacridine [1]," J. Heterocyclic Chem., 27, 1990, pp. 1537-1541.

van Muijlwijk-Koezen et al., "Isoquinoline and Quinazoline Urea Analogues as Antagonists for the Human Adenosine A₃Receptor," J. Med. Chem. 2000, 43, pp. 2227-2238.

Kolch et al., "Raf-1 protein kinase is required for growth of induced NIH/3T3 cells," Nature, vol. 349, Jan. 31, 1991, pp. 426-428.

Kolch et al., "The role of Raf kinases in malignant transformation" Expert reviews in molecular medicine (Apr. 25, 2002) ISSN: 1462-3994 © Cambridge University Press, 18 pages.

Konecny et al., "Association between HER-2/neu and Vascular Endothelial Growth Factor Expression Predicts Clinical Outcome in Primary Breast Cancer Patients," Clinical Cancer Research, 10: 1706-1716 (Mar. 1, 2004).

Korfee et al., "New targeted treatments in lung cancer-overview of clinical trials," Lang Cancer, 45 (Supp. 2): S199-S208 (2004).

Kraft et al., "Vascular Endothelial Growth Factor in the Sera and Effusions of Patients with Malignant and Nonmalignant Disease," Cancer, 85(1): 178-187 (Jan 1, 1999).

Kubo et al., "Herbicidal Activity of 1,3,4-Thiadiazole Derivatives," J. Agr. Food Chem. (1970), 18(1), pp. 60-65.

Kubo et al., "Synthesis and structure-activity relationship of quinazoline-urea derivatives as novel orally active VEGF receptor tyrosine kinase selective inhibitors," Proceedings of the American Association of Cancer Res., 2002, vol. 43, p. 182, abstract No. 913.

Kuefer et al., "Translational research in renal cell cancer. Illustrated by the example of the vascular endothelial growth factor pathway," Der Urologe, 2006, vol. 45, No. 3, pp. 328, 330-335.

Kumar et al., "Drugs targeted against protein kinases" Expert Opin. Emerging Drugs 6(2):303-315 (2001).

Kupsch et al., "Restilts of a Phase 1 Trial of Sorafenib (BAY 43-9006) in Combination with Oxaliplatin in Patients with Refractory Solid Tumors, Including Colorectal Cancer," Clinical Colorectal Cancer, Cancer Information Group Journal, vol. 5 Issue 3, pp. 188-196, abstract (Sep. 2005).

Kurik et al., "Optical Properties of Segmented Oligourethane with Azomethine Terminal Fragments," Polymer Science, series B, 1996, vol. 38 pp. 2038-2041.

Kyriakis et al., "Raf-1 activates MAP kinase-kinase" Nature, 358, 6385, pp. 417-421 (Jul. 30, 1992).

Laack et al., "Pretreatment serum levels of matrix metalloproteinase-9 and vascular endothelial growth factor m non-small-cell lung cancer," Annals of Oncology, 13(10): 1550-1557 (Oct 2002).

Dal Lago et al., "Selected Combination Therapy with Sorafenib: A Review of Clinical Data and Perspectives in Advanced Solid Tumors" The Oncologist, vol. 13, No. 8, pp. 845-858 (Aug 11, 2008).

Lau et al., "Abrogation of c-Raf expression induces apoptosis in tumor cells," Oncogene 16, 1899-1902 (1998).

Lee et al., "BAY-43-9006 Bayer/Onyx," Current Opinion Investigational Drugs, 2003, vol. 4, No. 6, pp. 757-763.

Lee et al., "Bicyclic Imidazoles as a Novel Class of Cytokine Biosynthesis Inhibitors," Annals N.Y. Academy of Science, 1993, vol. 696, pp. 149-170.

Lee et al.: "FTY720 induces apoptosis of human hepatoma cell lines through PI3-K-mediated Akt dephosphorylation," Carcinogenesis, vol. 25, No. 12, 2004, pp. 2397-2405.

Lee et al., "Prognostic value of vascular endothelial growth factor expression in colorectal cancer patients," European Journal of Cancer, 36(6): 748-753 (Apr. 2000).

Lee and Heymach, "Emerging Antiangiogenic Agents in Lung Cancer," Clinical Lung Cancer, 7(5): 304- 308 (Mar. 2006).

Legros et al., "Imatinib mesylate (STI571) decreases the vascular endothelial growth factor plasma concentration in patients with chronic myeloid leukemia," Blood, 104(2): 495-501 (Prepublished on-line Feb. 19, 2004).

Lemoine, "Overview of ras oncogenes and their clinical potential," Chapter 10, In: Mutant Oncogenes: Targets for Therapy? (eds. Lemoine NR & Epeuetos A), Chapman & Hall, London. pp. 85-91.

Lepage et al., "New N-aryl isoxazolecarboxamides and N-isoxazolybenzamides as anticonvulsant agents," Eur. J. Med. Chem., vol. 27, 1992, pp. 581-593.

Leuner et al., "Improving drug solubility for oral delivery using solid dispersions," European Journal of Pharmaceutics and Biopharmaceutics, 50, 2000, pp. 47-60.

Liang et al., "Differential Expression of VEGF and Its Receptors in the Primary Cells of Various Risk Classified Acute Lymphoblastic Leukemia Patients," Blood 104: Abstract 4446 (2004).

Li et al. "Correlation of Serum VEGF Levels with Clinical Stage, Therapy Efficacy, Tumor Metastasis and Patient Survival in Ovarian Cancer," Anticancer Research, 24: 1973-1980 (2004).

Lin, "Synthesis of 1-(2-Pyridine-1-oxide)-2-(1-Methyl-2-Pyridinium)-Ethane Chloride," OPPI Briefs, vol. 23, No. 1, 1991, pp. 114-115.

Linderholm et al., "Correlation of Vascular Endothelial Growth Factor Content with Recurrences, Survival, and First Relapse Site in Primary Node-Positive Breast Carcinoma After Adjuvant Treatment," Journal of Clinical Oncology, 18(7): 1423-1431 (Apr. 2000).

Linderholm et al., "p53 and Vascular-Endothelial-Growth-Factor (VEGF) Expression Predicts Outcome in 833 Patients with Primary Breast Carcinoma," Int. J. Cancer (Pred. Oncol.): 89(1): 51-62 (2000).

Lissoni et al., "Anti-angiogenic activity of melatonin in advanced cancer patients," Neuroendocrinology-Letters, 2001, 22:45-47.

Lissoni et al., "Chemotherapy and angiogenesis in advanced cancer: vascular endothelial growth factor (VEGF) decline as predictor of disease control during taxol therapy in metastatic breast cancer," International Journal of Biological Markers, 15(4): 308-311 (Oct. 1, 2000).

Lissoni et al., "Abnormally enhanced blood concentrations of vascular endothelial growth factor (VEGF) in metastatic cancer patients and their relation to circulating dendritic cells, IL-12 and endothelin-1," Journal of Biological Regulators and Homeostatic Agents, 15(2): 140-144 (Apr. 2001).

Lissoni et al., "Changes in circulating VEGF levels in relation to clinical response during chemotherapy for metastatic cancer," International Journal of Biological Markers, 18(2): 152-155 (2003).

Llovet et al., "Molecular Targeted Therapies in Hepatocellular Carcinoma," Hepatology, vol. 48, No. 4, pp. 1312-1327, 2008.

Lockhart et al., "Phase I/Pilot Study of SU5416 (Semaxinib) in Combination With IrinotecanBolus 5- FU/LV (IFL) in Patients With Metastatic Colorectal Cancer," American Journal of Clinical Oncology, 29(2):109-115 (Apr. 2006).

Lorigan et al., "Phase II trial of sorafenib combined with dacarbazine in metastatic melanoma patients" ASCO 2006 DTIC abstract, 2 pages (Jan. 11, 2006).

Lowinger et al., "Design and Discovery of Small Molecules Targeting Raf-1 Kinase," Current Pharmaceutical Design, 2002, vol. 8, pp. 2269-2278.

Lowinger et al., "Discovery of novel class of potent Raf kinase inhibitors: structure activity relationships," Clinical Cancer Research, Nov. 2000, vol. 6 (Suppl.), p. 4533s, abstract No. 335.

Lowy et al., "Function and Regulation of RAS" Annual Review of Biochemistry, vol. 62, pp. 851-891, 1993.

Ludwig et al., "MEK inhibition impairs influenza B virus propagation without emergence of resistant variants," FEBS Letters, 2004, vol. 561, pp. 37-43.

Luo et al., "Enhancement of radiation effects by pXLG-mENDO in a lung carcinoma model," Int, J. Radiation Oncology Biol. Phys., 2005, vol. 63, No. 2, pp. 553-564.

Lyons et al., "Discovery of a novel Raf kinase inhibitor," *Endocrine-Related Cancer*,2001, vol. 8, pp. 219-225.

Madwed et al., "Pharmacological evaluation of BIRB 796, a selective inhibitor of p38 MAP kinase (MAPK), in animal models of endotoxic shock, inflammation and arthritis," Inflammation Res., 50:S184, abstract No. W22/03, 2001.

Magnuson et a "The Raf-1 serine/threonine protein kinase," Cancer Biology, vol. 5, 1994, pp. 247-253.

Manenti et al., "Circulating plasma vascular endothelial growth factor in mice bearing human ovarian carcinoma xengraft correlates with tumor progression and response to therapy," Molecular Cancer Therapeutics, 4(5): 715-725 (May 2005).

Mannováet al., "Activation of the N-Ras-PI3K-Akt-mTOR Pathway by Hepatitis C Virus: Control of Cell Survival and Viral Replication," Journal of Virology, Jul. 2005, vol. 79, No. 14, pp. 8742-8749.

Markgraf et al., "Strained Heterocyclic Systems. 19. 1-Azatriptycene and Derivatives," Tetrahedron, vol. 47, No. 2, 1991, pp. 183-188.

Marshall, "MAP kinase kinase kinase, MAP kinase kinase, and MAP kinase," Curr. Opin. Genet. Dev. 4: 82-89, 1994.

Marx, J., "Why a New Cancer Drug Works Well, in Some Patients." Science, vol. 304, pp. 658-659, 2004.

McGoon et al., "Screening, Early Detection, and Diagnosis of Pulmonary Arterial Hypertension," CHEST, 2004: 126, pp. 14S-34S.

Medinger et al., "Hemmung der Tumorangiogenese Neue Therapieoptionen in der Onkologie,"Med, Welt, 2006, 57, pp. 437-441.

Med Report Deutschland, "Sorafenib zur Therapie des fortgeschrittenen Nierenzellkarzinoms zugelassen," (2006), 1 page.

Meuillet et al., "In Vivo Molecular Pharmacology and Antitumor Activity of the Targeted Akt Inhibitor PX-316," Oncology Research, vol. 14, 2004. pp. 513-527.

Michaelis, "Phenylharnstoff des 1-Phenyl-3-methyl-1-5-aminopyrazols,"Justus Liebigs Ann. Chem. (JLACBF) 397, 1913, p. 143.

Milanini et al., "p42/p44 MAP Kinase Module Plays a Key Role in the Transcriptional Regulation of the Vascular Endothelial Growth Factor Gene in Fibroblasts," Journal of Biological Chemistry, 273(29): 18165-18172 (Jul. 17, 1998).

Milano et al., "New molecular targeted therapies in thyroid cancer" Anti-Cancer Drugs (2006) © Lippincott Williams & Wilkins , vol, 17:869-879.

Mills et al., "The Effects of Standard Anthracycline-Based Chemotherapy on Soluble ICAM-1 and Vascular Endothelial Growth Factor Levels in Breast Cancer," Clinical Cancer Research, 10: 4998-5003 (Aug. 1, 2004).

Milojokovic et al , "Immunohistochemical Characterisation of Vascular Endothelial Growth Factor (VEGF) and its Receptors Flt-1 and KDR in Chronic Myeloid Leukaemia (CML) Patients Treated with Imatinib Mesylate," Blood, 104 Abstract 1999 (2004).

Minna et al., "A Bull's Eye for Targeted Lung Cancer Therapy," Science, vol. 304, pp. 1458-1460, 2004.

Mita et al., "The Molecular Target of Rapamycin (mTOR) as a Therapeutic Target Against Cancer." Cancer Biology & Therapy 2:4 Suppl. 1, S169-S177 (Jul./Aug. 2003).

Moelling et al., "Signal Transduction as Target of Gene Therapy," Institute of Medical Virology, University of Zürich, Recent Results in Cancer Research, vol. 142, pp. 63-71 (1996).

Molhoek et al., "Synergistic inhibition of human melanoma proliferation by combination treatment with B-Raf inhibitor BAY 43-9006 and mTOR inhibitor rapamycin," Journal of Translational Medicine (2005) 3: 39, pp. 1-11.

Monia, "First-and second-generation antisense oligonucleotide inhibitors targeted against human c-*raf*kinase," (1997) Oligonucleotides as therapeutic agents Wiley, Chichester (Ciba Foundation Symposium 209) pp. 107-123.

Monia et al., "Antitumor activity of a phosphorothioate antisense oligodeoxynucleotide targeted against C- *raf*kinase," Nature Medicine, vol. 2, No. 6, Jun. 1996. pp. 668-675.

Monia et al., "Sequence-specific antitumor activity of a phosphorothioate oligodeoxyribouucleotide targeted to human C-*raf*kinase supports and antisense mechanism of action *in vivo*," Proc. Natl. Acad. Sci USA, vol. 93, 15481-15484 (Dec. 1996).

Morabito et al., Tyrosine Kinase Inhibitors of Vascular Endothelial Growth Factor Receptors I Clinical Trials: Current Status and Future Directions, The Oncologist, 11: 753-764 (2006).

Mori et al., "Differential activation of the c-Jun N-terminal kinase/stress-activated protein kinase and p38 mitogen-activated protein kinase signal transduction pathways in the mouse brain upon infection with neurovirulent influenza A virus," Journal of General Virology, 2003, 84, pp. 2401-2408.

Moore et al., "Phase I study to determine the safety and pharmacokinetics of the novel Raf kinase and VEGFR inhibitor BAY 43-9006, administered for 28 days on/7 days off in patients with advanced, refractory solid tumors," Annals of Oncology, 2005, vol. 16, pp. 1688-1694.

Motzer et al., "Survival and Prognostic Stratification of 670 Patients With Advanced Renal Cell Carcinoma", J. Chin. Oncol., 17(8):pp. 2530-2540 (1999).

Mross et al., "Drug-drug interaction pharmacokinetic study with the Raf kinase inhibitor (RKI) BAY 43-9006 administered in combination with irinotecan (CPT-11) in patients with solid tumors," International Journal of Clinical Pharmacology and Therapeutics, 2003, vol. 41, No. 12, pp. 618-619.

Mross et al., "Results from an in vitro and a clinical/pharmacological phase I study with the combination irinotecan and sorafenib" European Journal of Cancer 43, pp. 55-63 (2007).

Murata et al., "Facile Synthesis of New Pyrrolo[3,4-d]pyrimidine-2,4-diones," Chemical and Pharmaceutical Bulletin, vol. 22, No. 5, 1974, pp. 1212-1213.

Murphy et al., "BAY 43-9006 controls tumor growth through inhibition of vascular development," 96th Annual Meeting, Anaheim/Orange County, CA, Apr. 16-20, 2005, abstract No. 2985.

Muthumani et al., "Suppression of HIV-1 viral replication and cellular pathogensis by a novel p38/JNK kinase inhibitor," AIDS, Lippincott Williams & Wilkins, 2004: vol. 18, pp. 739-748.

National Cancer Institute, "Carboplatin and Paclitaxel With or Without Sorafenib in Treating Patients With Unresectable Stage III or Stage IV Melanoma", 7 pages, NCT00110019, clinicaltrials.gov, (2005).

National Cancer Institute, "Paclitaxel, Carboplatin, and Radiation Therapy in Treating Patients Who Are Undergoing Surgery for Stage III Non-Small Cell Lung Cancer," 5 pages, NCT00096226, (2005).

National Cancer Institute, "Sorafenib With or Without Paclitaxel and Carboplatin in Treating Patients With Recurrent Ovarian Cancer, Primary Peritoneal Cancer, or Fallopian Tube Cancer," 5 pages, NCT00096200, (2005).

National Cancer Institute, Clinical Trials (PDQ® ), "Phase II Randomized Study of ISIS 5132 or ISIS 3521 in Women with Previously Treated Metastatic Breast Cancer," 3 pages, www.cancer.gov website (1998).

National Cancer Institute, Clinical Trials (PDQ ® ), "Phase II Randomized Study of ISIS 3521 and ISIS 5132 for Locally Advanced or Metastatic Colorectal Cancer," 3 pages, www.cancer.gov website (1998).

National Cancer Institute, Clinical Trials (PDQ ® ), "Phase II Randomized Study of ISIS 3521 and ISIS 5132 in Patients with Hormone Refractory Prostate Cancer," 3 pages, www.cancer.gov website (1998).

National Cancer Institute, Clinical Trials (PDQ® ), "Phase II Study of ISIS 5132 in Patients with Advanced Pancreatic Cancer," 3 pages, www.cancer.gov website (1999).

National Institutes of Health Clinical Center, "BAY 43-9006 (Sorafenib) to Treat Relapsed Non-Small Cell Lung Cancer", 4 pages, NCT00098254, clinicaltrials.gov (2005).

Naumann et al., "Raf protein serine/threonine kinases" in: Protein Phosphorylation, VCH Verlagsgesellschaft mbH Chapter 7, pp. 203-236 (1996).

Naumann et al., "The Role of Raf Kinases in Development and Growth of Tumors" Recent Results in Cancer Research, vol. 143, pp. 237-244 (1997).

Nemunaitis et al., "Phase I Evaluation of ISIS 3521, an Antisense Oligodeoxynucleotide to Protein Kinase C-Alpha, in Patients with Advanced Cancer" Journal of Clinical Oncology, vol. 17, No. 11, pp. 3586-3595 (Nov. 1999).

Neufeld et al., "Vascular endothelial growth factor (VEGF) and its receptors, "The FASEB Journal, 13: 9-22 (Jan. 1999).

"Nexavar Receives FDA Fast Track Designation for Skin Cancer" 4 pages, (Jul. 21, 2006) http:// www.medicalnewstoday.com/articles/47793.php (last visited on Jun. 16, 2008).

Nicholson, K. M. et al,: "The protein kinase B/Akt signalling pathway in human malignancy," Cellular Signalling 14, 2004, pp. 381-395.

Nickel et al., "Carboxylic acid analogues of suramin, potential filaricides," Indian Journal of Chemistry, Feb. 1991, vol. 30B, pp. 182-187.

Nilsson et al., "Vascular Endothelial Growth Factor(VEGF) Pathway," Journal of Thoracic Oncology, 1(8): 768-770 (Oct. 2006).

Noble et al., "Protein Kinase Inhibitors: Insights into Drug Design From Structure," Science, (2004), vol. 303, pp. 1800-1805.

O'Dwyer et al., "c-raf Depletion and Tumor Responses in Patients Treated with the c-raf-1 Antisense Oligodeoxynucleotide ISIS 5132 (CGP 69846A)," Clinical Cancer Research vol. 5, pp. 3977-3982 (Dec. 1999).

Oka et al., "Constitutive Activation of Mitogen-activated Protein (MAP) Kinases in Human Renal Cell Carcinoma," Cancer Research 55. pp. 4182-4187, (Sep. 15, 1995).

Gollob et al., "Phase II trial of sorafenib (BAY 43-9006) in combination with interferon alpha 2b in patients with metastatic renal cell carcinoma," European Journal of Cancer, 2005, vol. 3, No. 2, pp. 226-227. abstract No. 795.

Osella-Abate et al., "VEGF-165 serum levels and tyrosinase expression in melanoma patients: correlation with the clinical course," Melanoma Research, 12: 325-334 (Aug. 2002).

Oza et al., "Phase II study of CGP 69846A (ISIS 5132) in recurrent epithelial ovarian cancer: an NCIC clinical trials group study (NCIC IND .116)," PubMed Abstract 12694666, Gynecol. Oncol. 2003 Apr: 89(1 ): 129-133.

Ozols, "New Developments With Carboplatin in the Treatment of Ovarian Cancer," Seminars in Oncology,vol. 19, No. 1, Supplement 2, Feb. 1992, pp. 85-89.

Panka et al., "BAY 43-9006 induces apoptosis in melanoma cell lines," 96th Annual Meeting, Anaheim/Orange County, CA, Apr. 16-20, 2005, abstract No. 5328.

Panteva et al., "Hepatitis viruses and the MAPK pathway: is this a survival strategy?" Virus Research, 2003, vol. 92: 131-140.

Paquette, Table of Contents for the Encyclopedia of Reagents for Organic Synthesis, John Wiley, New York, 1994 Table of Contents.

Pavlović-Lažetićet al., "Biointhrmatics analysis of SARS coronavinls genome polymorphism," May 25, 2004, BMC Biointhrmatics, vol. 5:65, 14 pages.

Pederson et al., "Early changes in serum IL-6 and VEGF levels predict clinical outcome following first-line therapy in aggressive non-Hodgkin's lymphoma," Ann. Hematol., 84:510-516 (2005).

Peters, H.D. "Sorafenib bei soliden Tumoren," Focus Onkologie, 2007, Auflage 12000, 6 pages.

Robert et al., "Phase I trial of sorafenib (BAY 43-9006) in combination with interferon alpha-2a in patients with unresectable and/or metastatic renal cell carcinoma and malignant melanoma," European Journal of Cancer, 2005, vol. 3, No. 2, p. 254, Abstract 883.

Hu et al., "Soluble Vascular Endothelial Growth Factor Receptor 1, and Not Receptor 2, Is an Independent Prognostic Factor in Acute Myeloid Leukemia and Myelodysplastic Syndromes," Cancer 2004, vol. 100, No. 9, pp. 1884-1891.

Raez et al., "New developments in chemotherapy for advanced non-small cell lung cancer," Current Opin. Oncol., vol. 18, 2006, pp. 156-161.

Ralunani et al., "Apoptosis Induced by the Kinase Inhibitor BAY 43-9006 in Human Leukemia Cells Involves Down-regulation of Mc1-1 through Inhibition of Translation," J. Biol, Chem. 280(42):35217-35227 (2005).

Rak et al., "Oncogenes and Angiogenesis: Signaling Three-Dimensional Tumor Growth," Journal of Investigative Dermatology Symposium Proceedings (2000) 5, 24-33.

Rak et al., "Oncogenes and Tumor Angiogenesis: Differential Modes of Vascular Endothelial Growth Factor Up-Regulation in ras-transformed Epithelial Cells and Fibroblasts," Cancer Research 60, pp. 490-498, (Jan. 15, 2000).

Rak et al., "Oncogenes as inducers of tumor angiogenesis," Cancer and Metastasis Reviews 14: 263-277, 1995.

Sturm-Ramirez et al., "Reemerging H5N1 Influenza Viruses in Hong Kong in 2002 Are Highly Pathogenic to Ducks," Journal of Virology, 2004-05, 78(9):4892-4901.

Raposo et al., "Catalysis of Nucleophilic Addition of Pyrrolidine to 2-(5H)-Furanone through Chromenone Cleft-Type Receptors," Tetrahedron Letters vol. 37, No. 38, pp. 6947-6950, 1996.

Ratain et al., "Phase II Placebo-Controlled Randomized Discontinuation Trial of Sorafenib in Patients with Metastatic Renal Cell Carcinoma," Journal of Clinical Oncology vol. 24 No. 16, pp. 2505-2512 (Jun. 1, 2006).

Ravi et al., "Activated Raf-1 Causes Growth Arrest in Human Small Cell Lung Cancer Cells," J. Clin. Invest., vol. 101, No. 1, pp. 153-159 (1998).

Reddy et al., "Sorafenib: recent update on activity as a single agent and in combination With interferon-alpha2 in patients with advanced-stage renal cell carcinoma," Clin. Genitourin. Cancer 4:246-248 (2006) abstract.

Redman et al., "p38 Kinase Inhibitors for the Treatment of Arthritis and Osteoporosis: Thienyl, Furyl, and Pyrrolyl Ureas," Bioorganic & Medicinal Chemistry Letters 11 (2001) 9-12.

Regan et al., "Pyrazole Urea-Based Inhibitors of p38 MAP kinase: From Lead Compound to Clinical Candidate." J. Med. Chem. 45:2994-3008, 2002.

Richly et al., "A phase I clinical and pharmacokinetic study of the Raf kinase inhibitor (RKI) BAY 43-9006 administered in combination with doxorubicin in patients with solid tumors," International Journal of Clinical Pharmacology and Therapeutics, 2003, vol. 41, No. 12, pp. 620-621.

Richly et al., "Results of a Phase I trial of sorafenib (BAY 43-9006) in combination with doxorubicin in patients with refractory solid tumors," Annals of Oncology, 2006, 17, pp. 866-873.

Richly et al., "Results of a phase I trial of BAY 43-9006 in combination with doxorubicin in patients with primary hepatic cancer," International Journal of Clinical Pharmacology and Therapeutics, 2004; vol. 42, No. 11, pp. 650-651.

Ridley et al., "Actions of IL-1 are Selectively Controlled by p38I Mitogen-Activated Protein Kinase, Regulation of Prostaglandin H Synthase-2, Metalloproteinases, and IL-6 at Different Levels," The American Association of Immunologists, 1997, J. Immunol. vol. 158, pp. 3165-3173.

Rini and Small, "Biology and Clinical Development of Vascular Endothelial Growth Factor-Targeted Therapy in Renal Cell Carcinoma," Journal of Clinical Oncology, 23(5): 1028-1043 (Feb. 10, 2005).

Robak et al., "Vascular endothelial growth factor and its soluble receptors VEGFR-1 and VEGFR-2 in the serum of patients with systemic lupus erythematosus," Mediators of Inflammation 12(5):293-298 (Oct. 2003).

Robertson et al. "HIV-1 Nomenclature Proposal," Science, Apr. 7. 2000, pp. 55-57. vol. 288.

Robinson et al., "Enhanced Radiosensitization with Gemcitabine in Mismatch Repair-Deficient HCT116 Cells," Cancer Research 63, 6935-6941 (Oct. 15, 2003).

Robke et al., "Conversion of Aminopyridines into $N$-Oxides by Caro's Acid Anion (Peroxymonosulfate)," J. Chem. Research (S), 1993, pp. 412-413.

Roche, E. B., "Structural Aspects of Selective Distribution," Chapter 3, in: Design of Biopharmaceutical Properties Through Prodrugs and Analogs, American Pharmaceutical Association, Washington, D.C., 1977, pp. 27-46.

Rodriguez et al., "A sensitive fluorometric enzyme-linked immunosorbent assay that measures vascular endothelial growth factor$_{165}$ in human plasma," Journal of Immunological Methods, 219(1-2): 45-55 (Oct. 1998).

Roman et al., "Human Papillomaviruses: Are We Ready to Type?" Clinical Microbiology Reviews. Apr. 1989: vol. 2, pp. 166-190.

Rowinsky et al., "Sequences of Taxol and Cisplatin: A Phase I and Pharmacologic Study," Journal of Clinical Oncology, vol. 9, No. 9, Sep. 1991, pp. 1692-1703.

Rowinsky et al., "Taxol: The First of the Taxanes, an Important New Class of Antitumor Agents," Seminars in Oncology,vol. 19, No. 6, Dec. 1992, pp. 646-662.

Rubin, Lewis J., "Primary Pulmonary Hypertension," New England Journal of Medicine, vol. 336, No. 2, pp. 111-117 (1997).

Rudin et al., "Phase I Trial of ISIS 5132, an Antisense Oligonucleotide Inhibitor of c-$raf$-1, Administered by 24-hour Weekly Infusion to Patients with Advanced Cancer" Clinical Cancer Research vol. 7, pp. 1214-1220 (May 2001).

Russo et al., "Sintesi Di Derivati 2,6-Sostituiti Del 5H-1 ,3,4-Tiadiazolo[3,2-a-]-s-Triazina-5,7-Dione," Il Farmaco, Ed.Sci. (1978), 33(12), 972-983.

Rydén et al., "Tumor specific VEGF-A and VEGFR2/KDR protein are co-expressed in breast cancer," Breast Cancer Research and Treatment, 82(3):147-154 (Dec. 2003).

Salvatore et al, "BRAF Is a Therapeutic Target in Aggressive Thyroid Carcinoma," Clin. Cancer Res. pp. 1623-1629; 12(5) (Mar. 1, 2006).

Sarkar et al., "Indole-3-Carbinol and Prostate Cancer " Journal of Nutrition 134, 2004, pp. 3493S-3498S.

Serajuddin, "Solid Dispersion of Poorly Water-Soluble Drugs: Early Promises Subsequent Problems, and Recent. Breakthroughs," Journal of Pharmaceutical Sciences vol. 88, No. 10, pp. 1058-1066 (Oct. 1999).

Shaked et al., "Cellular and Molecular Surrogate Markers to Monitor Targeted and Non-Targeted. Antiangiogenic Drug Activity and Determine Optimal Biologic Dose," Current Cancer Drug Targets, 5: 551-559 (Nov. 2005).

Shelton et al., "Effects of the RAF/MEK/Erk and PI3K/AKT signal transduction pathways on the abrogation of cytokine-dependence and prevention of apoptosis in hematopoietic cells," Oncogene, vol. 22, No. 16, Apr. 2003; pp. 2478-2492.

Shi et al., "Constitutive and Inducible Interleukin 8 Expression by Hypoxia and Acidosis Renders Human Pancreatic Cancer Cells More Tumorigenic and Metastatic," Clinical Cancer Research,1999, vol. 5, pp. 3711-3721.

Shimanuki et al., "Role of Serum Vascular Endothelial Growth Factor in the Prediction of Angiogenesis and Prognosis for Non-small Cell Lung Cancer," Lung, 183: 29-42 (2005).

Simone, Joseph, V., "Part XIV. Oncology," in: Cecil Textbook of Medicine, 20th Edition, vol. 1, 2-3- 1997. W.B. Saunders Company, pp. 1004-1010.

Sinkula et al., "Rationale for Design of Biologically Reversible Drug Derivatives: Prodrugs," Journal of Pharmaceutical Sciences, vol. 64, No. 2, Feb. 1975, pp. 181-210.

Siu et al., "Phase I study of oral raf-1 kinase inhibitor BAY 43-9006 with gerncitabine in patients with advanced solid tumors," Abstract No. 828, Proc. Am. Soc. Clin. Oncol., 2003, vol. 22, p. 207.

Siu et al., "Phase I Trial of Sorafenib and Gemcitabine in Advanced Solid Tumors with an Expanded Cohort in Advanced Pancreatic Cancer," Clin. Cancer Res. 12(1):144-151 (2006).

Smith et al., "Discovery of Heterocyclic Ureas as a New Class of Raf Kinase Inhibitors: Identification of a Second Generation Lead by a Combinatorial Chemistry Approach," Bioorganic & Medicinal Chemistry Letters, 2001, vol. 11, pp. 2775-2778.

Smith et al., (Abstract) "Recent Advances in the Research and Development of RAF Kinase Inhibitors," Current Topics in Medicinal Chemistry 6 (11):1071-1089 (2006).

Smyth, R.M. et al., "Anchimeric Assistance in the Specific Acid-catalysed Hydration of Benzonitriles" J. Chem. Soc. Perkin Trans. 2 1993 pp, 2171-2174.

Song, Huai-Dong et al., "Cross-host evolution of severe acute respiratory syndrome coronavirus in palm civet and human," Proc. Natl. Acad. Sci. USA 102(7):2430-2435 (2005).

Sorbara et al "BAY-43-9006," Drugs of the Future, 2002, vol. 27, No. 12, pp. 1141-1147.

van Spronsen et al., "Novel treatment strategies in clear-cell metastatic renal cell carcinoma," Anti-Cancer Drugs, 2005, vol. 16, pp. 709-717.

Stadler et al., "A Randomized Phase II Trial of the Antiangiogenic Agent SU5416 in Hormone-Refractory Prostate Cancer," Clinical Cancer Research, 10: 3365-3370 (May 15, 2004).

Stahl et al., "Deregulated Akt3 Activity Promotes Development of Malignant Melanoma," Cancer Research, vol. 64, No. 19; Oct. 2004; pp. 7002-7010.

Stavchansky et al., "Evaluation of the Bioavailability of a Solid Dispersion of Phenytoin m Polyethylene Glycol 6000 and a Commercial Phenytoin Sodium Capsule in the Dog," Journal of Pharmaceutical Sciences, vol. 73 , No. 6, Jun. 1984, pp. 733-736.

Krontiris, "Chapter 71. Molecular and Cellular Biology of Cancer," and Capizzi, "Chapter 72, Principles of Treatment of Cancer," in: Internal Medicine, 4th Edition, Stein, Jay H., MD, Ed., Mosby, 1994, pp. 699-715.

Sternberg et al., "Conspiracy Theory: RAS and RAF Do Not Act Alone" Cell, vol. 95, pp. 447-450 (Nov. 13, 1998).

Stella et al., "Prodrugs and Site-Specific Drug Delivery," Journal of Medicinal Chemistry, vol. 23, No. 12, Dec. 1980, pp. 1275-1282.

Stella et al., "Prodrugs as therapeutics," Exp. Opin. Ther. Patents 14(3): 277-280 (2004).

Stella et al., "Prodrugs. Do They Have Advantages in Clinical Practice?" Drugs, vol. 29, 1985, pp. 455- 473.

Stevenson et al., "Phase I Clinical/Pharmacokinetic and Pharmacodynamic Trial of the c-$raf$-1 Antisense Oligonucleotide ISIS 5132 (CGP 69846A)," The Journal of Clinical Oncology, vol. 17, No7: pp. 2227-2236 (Jul. 1999).

Stöckl et al., "Integrity of c-Raf-1/MEK signal transduction cascade is essential for hepatitis B virus gene expression," Oncogene. Nature Publishing Group, 2003: vol. 22, pp. 2604-2610.

Stokoe et al., "Activation of c-Raf-1 by Ras and Src through different mechanisms: activation in vivo and in vitro," The Embo Journal, vol. 16 No. 9 pp. 2384-2396 (1997).

Storm et al., "rafOncogenes in Carcinogenesis" Critical Reviews in Oncogenesis, vol. 2, Issue 1, pp. 1-8 (1990).

Strumherg, D., "Preclinical and Clinical Development of the Oral Multikinase Inhibitor Sorafenib in Cancer Treatment," Drugs of Today, 41(12): 773-784 (2005).

Strumberg et al., "Phase I Clinical and Pharmacokinetic Study of the Novel Raf Kinase and Vascular Endothelial Growth Factor Receptor Inhibitor BAY 43-9006 in Patients With Advanced Refractory Solid Tumors," Journal of Clinical Oncology, Feb. 10, 2005, vol. 23, No. 5, pp. 965-972.

Strumberg et al., "Phase I Clinical, Pharmacokinetic and Pharmacodynamic Study of the Raf Kinase Inhibitor BAY 43-9006 in Patients with Locally Advanced or Metastatic Cancer," Proc. Am. Soc. Clin. Oncol. 20: 2001 (abstr 330).

Strumberg et al., "Results of phase I pharmacokinetic and pharmacodynamic studies of the Raf kinase inhibitor BAY 43-9006 in patients with solid tumors," International Journal of Clinical Pharmacology and Therapeutics, 2002, vol. 40, No. 12, pp. 580-581.

Strumberg et al., "Sorafenib Neue Therapieoption in der Onkologie," Krankenhauspharmazie, 2007, vol. 28, pp. 93-97, pp. 1/5, 2/5, 3/5 and 4/5.

Suzuki et al., "The role of p38 mitogen-activated protein kinase in IL-6 and IL-8 production from the TNF-α- or IL-1β-stimulated rheumatoid synovial fibroblasts," FEBS Letters (2000), vol. 465, pp. 23-27.

Swarbrick et al., "Contents," pp. xvii—xviii in: Encyclopedia of Pharmaceutical Technology, 2nd Edition, Marcel Dekker, Inc. 2002.

Swart, Guido W.M., "International Melanoma Research Congress — Foundation for Melanoma Research," IDRUGS: The Investigational Drugs Journal, Aug. 2003; vol. 6, No. 8, pp. 752-754.

Tabellini et al., "Novel 2'-substituted, 3'-deoxy-phosphatidyl-myo-inositiol analogues reduce drug resistance in human leukaemia cell lines with an activated phosphoinositide 3-kinase/Akt pathway," British Journal of Haematology, 126, 2004, pp. 574-582.

Takimoto et al., "Safety and anti-tumor activity of sorafenib (Nexavar® ) in combination with other anticancer agents: a review of clinical trials," Cancer Chemotherapy and Pharmacology (2008) 61:535-548.

Tamm et al., "Hypoxia-Induced Interleukin-6 and Interleukin-8 Production Is Mediated by Platelet: Activation Factor and Platelet-Derived Factor in Primary Human Lung Cells," Am. J. Respir. Cell Mol. Biol. vol. 19, pp. 653-661, (1998).

Tanaka et al., "Current status and perspective of antiangiogenic therapy for cancer: hepatocellular carcinoma," Int. I. Clin. Oncol. (2006) 11:82-89 (2006).

Tang et al., "Inhaled nitric oxide attenuates pulmonary hypertension and improves lung growth in infant rats after neonatal treatment with a VEGF receptor inhibitor." Am. J. Physiol. Lung Cell, Mol. Physiol. 287:L344-L351 (2004).

Tarzia et al., "Synthesis and anti-inflammatory properties of some pyrrolo(1H,3H) [3,4-d]pyrimidin-2-ones and pyrrlo=(IH,6H)[3,4-d]pyrimidin-2-ones," Chemical Abstracts, vol. 91, 1979, 91:74558p.

Teknos et al., "Elevated Serum Vascular Endothelial Growth Factor and Decreased Survival in Advanced Laryngeal Carcinoma," Head & Neck, 24: 1004-1011 (Nov. 2002).

Thaimattam et al., "3D-QSAR CoMFA, CoMSIA studies on substituted ureas as Raf-1 kinase inhibitors and its confirmation with structure-based studies," Bioorganic & Medicinal Chemistry, 2004, vol. 12, pp. 6415-6425.

Thelen et al., "VEGF-D promotes tumor growth and lymphatic spread in a mouse model of hepatocellular carcinoma" Int. J. Cancer 122, 2471-2481 (2008) © 2008 Wiley-Liss, Inc.

Thompson et al., "Recent progress in targeting the Raf/MEK/ERK pathway with inhibitors in cancer drug discovery," Curr. Opin. Phannacol., Aug. 2005, vol. 5, No. 4, pp. 350-356.

Tong et al., "Pharmacodynamic Monitoring of BAY 43-9006 (Sorafenib) in Phase I Clinical Trials Involving Solid Tumor and AML/MDS Patients, Using Flow Cytometry to Monitor Activation of the ERK Pathway in Peripheral Blood Cells," Cytometry Part B (Clinical Cytometry) 70B: 107-114 (2006).

Trost et al., "Contents," vols. 1-9, 36 pages in: Comprehensive Organic Synthesis: Selectivity, Strategy & Efficiency in Modem Organic Chemistry, Pergamon Press, Oxford, UK. 1991.

Gupta-Abramson et al., "Phase II Trial of Sorafenib in Advanced Thyroid Cancer" Journal of Clinical Oncology vol. 26, No. 29, pp. 4714-4719 (Oct. 10, 2008).

Veronese et al., "Mechanisms of Hypertension Associated With BAY 43-9006," Journal of Clinical Oncology, 2006, vol. 24, No. 9, pp. 1363-1369.

Vivanco et al., "The Phosphatidylinositol 3-Kinase-AKT Pathway in Human Cancer," Nature Reviews Cancer, vol. 2, Jul. 2002. pp. 489-501.

Vlahos et al., "A Specific Inhibitor of Phosphatidylinositol 3-Kinase, 2-(4-Morpholinyl)-8-phenyl-4H-1- benzopyrart-4-one (LY294002)," The Journal of Biological Chemistry, vol. 269, No. 7, 1994, pp. 5241-5248.

Wakelee et al., "Targeting Angiogenesis with Vascular Endothelial Growth Factor Receptor Small Molecular Inhibitors: Novel Agents with Potential in Lung Cancer," Clinical Lung Cancer, 7(Suppl 1): S31-S38 (Sep. 2005).

Wald et al., "Involvement of the CXCL12/CXCR4 pathway in the advanced liver disease that is associated with hepatitis C virus or hepatitis B virus," Eur. J. Immunol., vol, 34, p. 1164-1174 (2004).

Wan et al., "Mechanism of Activation of the RAF-ERK Signaling Pathway by Oncogenic Mutations of B- Raf," Cell, Mar. 19, 2004, vol. 116, pp. 855-867.

Weekly Epidemiological Record, "Influenza," World Health. Organization. Apr. 1999; vol. 14, pp. 111-112.

Wermuth, C. G., "Designing Prodrugs and Bioprecursors II: Bioprecursor Prodrugs," in: The Practice of Medicinal Chemistry, Academic Press Limited 1996, pp. 697-715.

White et al., "Heterocyclic Ureas: Inhibitors of Acyl-CoA:Cholesterol O-Acyltransferase as Hypocholesterolemic Agents," J. Med. Chem. 1996, 39, pp. 4382-4395.

Wierzbowska et al., "Circulating VEGF and its soluble receptors sVEGFR-1 and sVEGFR-2 in patients with acute leukemia," Eur. Cytokine Netw., 14(3): 149-153 (Sep. 2003).

Wilhelm et al., "A Novel RAF Kinase Inhibitor Blocks the RAF/MEK/ERK Pathway in Tumor Cells," Poster, 92nd Annual Meeting of the American Association for Cancer Research, Mar. 24-28, 2001, New Orleans, LA USA, 1 page.

Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research, Oct. 1, 2004, vol. 64, pp. 7099-7109.

Wilhelm et al., "BAY 43-9006: Preclinical Data," Curr Pharm Des, 2002, vol. 8, No. 25, pp. 2255- 2257.

Wilhelm et al., "Discovery and development of sorafenib: a multtkinase inhibitor for treating cancer," Nature Reviews, Drug Discovery, 2006, vol. 5, pp. 835-844.

Wilhelm et al., "Preclinical overview of sorafenib, a multikinase inhibitor that targets both Raf and VEGF and PDGF receptor tyrosine kinase signaling," Mol. Cancer Ther., 2008, vol. 7, No. 10, pp. 3129-3140.

Wilkinson Geoffrey, "Contents," 7 pages in: Comprehensive Organometallic Chemistry. The Synthesis, Reactions, and Structures of Organometallic Compounds, Pergamon Press, Oxford, U.K. 1982: vol. 1-3.

Wilson et al., "The structural basis for the specificity of pyridinylimidazole inhibitors of p38 MAP kinase," Chemistry & Biology, 1997, vol. 4, No. 6, pp. 423-431,.

Stollorz, "Die Krebsformel, die der Zufall fand," Frankfurter Allgemeine Sonntagszeitung, Jul. 2, 2006, NR 26, pp. 68-69.

Wissner et al., "Analogues of Platelet Activating Factor. 7. Bis-Aryl Amide and Bis-Aryl Urea Receptor Antagonists of PAF," J. Med Chem., 1992, vol. 35, pp. 4779-4789.

Wojnowski et al., "Endothelial apoptosis in Braf-deficient mice," Nature Genetics vol. 16, pp. 293-297 (Jul. 1997).

Onyx Pharmaceuticals, Inc.,"Novel RAF Kinase Inhibitor Bay 43-9006 Shows Early Signs of Tolerability and Activity in Phase 1B Combination Trials Reported at ASCO," 1 page, (Press Release: Jun. 2, 2003).

Wright et al., "Bovine immunodeficiency Virus Expression *in Vitro* is Reduced in the Presence of β- Chemokines, MIP-1α, MIP-1 β and RANTES." Veterinary Research Communications. 2002: vol. 26, pp. 239-250.

Wright et al., "Clinical Trials Referral Resource. Current Clinical Trials of BAY 43-9006, Part 1," Oncology, Apr. 2005, vol. 19, No. 4: pp. 499-502.

Wu et al., "Plasma vascular endothelial growth factor is useful in assessing progression of breast cancer post surgery and during adjuvant treatment," International Journal of Oncology, 20: 509-516 (2002).

Xu et al., "Hypoxia-induced Elevation in Interleukin-8 Expression by Human Ovarian Carcinoma Cells," Cancer Research, 1999, vol. 59, pp. 5822-5829.

He et al., "Oral Formulation of a Novel Antiviral Agent, PG301029, in a :Mixture of Gelucire 44/14 and DMA (2:1, wt/wt)," AAPS PhannSciTech 2005; vol. 6 (1) Article 1, 5 pp., (http://www.aapsharmscitech.org).

Yamaguchi et al., "Expression of Vascular Endothelial Growth Factor in Human Hepatocellular Carcinoma," Hepatology, 28(1) pp. 68-77 (1998).

Yang et al. "Akt/Protein Kinase B Signaling Inhibitor-2, a Selective Small Molecule Inhibitor of a Akt Signaling with Antitutnor Activity in Cancer Cells Overexpressing Akt," Cancer Research, 64, Jul. 1, 2004, pp. 4394-4399.

Yang et al., "Antiviral chemotherapy control of poxvirus infections through inhibition of cellular signal transduction," The Journal of Clinical Investigation, 2005: 115(2):pp, 379-387.

Yeh et al., "Characterization of severe acute respiratory syndrome coronavirus genomes in Taiwan: Molecular epidemiology and genome evolution," Proc. Natl. Acad. Sci. USA Feb. 24, 2004, 101(8):2542-2547.

Yu et al., "The role of Mc1-1 downregulation in the proapoptotic activity of the multi kinase inhibitor BAY 43-9006," Oncogene 24:6861-6869 (2005).

Zachos et al., "Herpes Simplex Virus Type 1 Infection Stimulates p38/c-Jun N-terminal Mitogen-activated Protein Kinase Pathways and activates Transcription Factor AP-1," Journal of Biological Chemistry, The American Society for Biochemistry and Molecular Biology, Inc, 1999: vol. 274, pp. 5097-5103.

Zangari et al., "Phase II Study of SU5416, a Small Molecule Vascular Endothelial Growth Factor Tyrosine Kinase Receptor Inhibitor, in Patients with Refractory Multiple Myeloma," Clinical Cancer Research, 10: 88-95 (Jan. 1, 2004).

Norden-Zfoni, Anat. "Blood-Based Biomarkers of SU11248 Activity and Clinical Outcome in Patients with Metastatic Imatinib-Resistant Gastrointestinal Stromal Tumor," Clin. Cancer, Res. 2007; 13(9):2643-2650 May 1, 2007.

Zhao et al "Moderate mutation rate in the SARS coronavirus genome and its implications," BMC Evolutionary Biology, 2004, 4:21, 9 pages.

Zhu et al., "From the Cyclooxygenase-2 Inhibitor Celecoxib to a Novel Class of 3- Phosphoinositide-Dependent Protein Kinase-1 Inhibitors," Cancer Research 64, Jun. 15, 2004, pp. 4309-4318.

Carter et al., "Anti-tumor Efficacy of the Orally Active RAF Kinase Inhibitor Bay 43-90006 in Human Tumor Xenograft Model," #4954. Proceedings of the American Association for Cancer Res., 2001, vol. 42, p. 923.

Iwadate et al., MEDLINE/NLM, NLM8336809 "Intra-arterial ACNU, CDDP chemotherapy for brain metastases from lung cancer: comparison of cases with and without intra-arterial mannitol infusion," 1 page, abstract ( Date not available).

Kubo et al., "Synthesis and Structure-Activity Relationship of Quinazoline-Urea Derivatives as Novel Orally Active VEGF Receptor Tyrosine Kinase Selective Inhibitors," Proceedings of the American Association of Cancer Res., 2002, vol. 43, p. 182, abstract No. 913.

Riedl et al., #4956 "Potent *Raf*Kinase Inhibitors from the Diphenylurea Class: Structure Activity Relationships," Proceedings of the American Association for Cancer Research, vol. 42, Mar. 2001, p. 923, 92nd Annual Meeting of the American Association for Cancer Research; New Orleans, LA, USA; Mar. 24-28, 2001.

Strumberg et al., abstract No. #2921 "Phase I and Pharmacokinetic Study of the Raf Kinase Inhibitor Bay 43-9006 in Patients with Locally Advanced or Metastic Cancer," Proceedings of the American Association for Cancer Research, vol. 42, Mar. 2001, page 543, 92nd Annual Meeting of the American Association for Cancer Research;New Orleans, LA, USA; Mar. 24-28, 2001.

Abstract of DE 3305866 A1, Aug. 23, 1984, BASF AG et al.

Abstract of EP 4931 A (Equivalent 4,240,820), Bayer AG, 1 page 1996.

Abstract of EP 16371 (1980), 1 page, Hoffmann-La Roche AG.

Abstract of EP 16371, Oct. 1. 1980, 1 page.

Abstract of EP 116932, Aug. 29, 1984, 2 pages.

Abstract of EP 116932, (1984), 2 pages, BASF AG.

Abstract of EP 0202538, (1986), 3 pages.

Abstract of EP 0202538 A1, Growth Promoting Agents, Nov. 26, 1986, 4 pages, Bayer AG.

Abstract of EP 0405233A1, Mitsubishi Kasei Corp., 2 pages 1994.

Abstract of EP 0405233A1, Tetsuo Sekiya et al., 1 page 1994.

Abstract of EP 0676395A2, (1995), 3 pages, Hoechst AG.

Abstract of EP 676395, (U.S. equivalent 5,698,581), Dec. 16, 1997, 1 page.

Patent Abstracts of Japan 02-022650. Jan. 25, 1990, 2 pages, Konica Corp.

esp@cenet Abstracts of Japan 02-022650, Jan. 25, 1990, 1 page.

Patent Abstracts of Japan 02-023337, Jan. 25, 1990, 2 pages, Konica Corp.

Patent Abstracts of Japan 63-214752,Sep. 07, 1988, 2 pages, family member of JP 6-07512 B4, Fuji Photo Film Co. Ltd.

esp@cenet Abstract of Japan 02-023337, 1 page 1998.

Abstract of JP 55162772 A2, Preparation of Substituted Acetic Acid Derivatives, Shiongi & Co., Ltd. Dec. 1980. 1 page.

Esp@cenet Abstract of WO 9822103, May 28,1998, Philip Hedge et al.

Abstract of WO 9822098 A2, QLT Phototherapeutics Inc. et al., May 28, 1998, 1 page.

Abstract of WO 9822103 A1, Zeneca Limited, published May 28, 1998, 1 page.

Abstract of WO 9852559 A1, Bayer Corp. et al., published Nov. 26, 1998, 1 page.

Abstract of WO 9852562 A1, Verkaik, MSE, et al., published Nov. 26, 1998, 1 page.

Abstract of WO 9900357 A1, Vertex Pharm. Inc., published Jan. 7, 1999, 1 page.

Abstract of WO 9900364 A1, Pharmacia & Upjohn S.P.A. et al., published Jan. 7, 1999, 1 page.

Abstract of WO 9932098 A2, Janssen Pharm NV, published Jul. 1, 1999, 1 page.

Abstract of WO 9932106 A1, Bayer Corp., published Jul. 1, 1999, 1 page.

Abstract of WO 9932148 A1, Beth Israel Deaconess Medical Center et al., pub. Jul. 01, 1999. 1 page.

Abstract of WO 9932436 A1, Bayer Corp., published Jul. 1, 1999, 1 page.

Abstract of WO 9932455 A1, Bayer Corp., published Jul. 1, 1999, 1 page.

Abstract of WO 9932457 A1, Hoechst Marion Roussel Deutschland GmbH et al., published Jul. 1, 1999, 1 page.

Caplus 72:79046, Abstract of CH 479557, "Tuberculostatic and cancerostatic polybasic ureas," Dr. A. Wander, Oct. 15, 1969, 6 pages.

Caplus 84:180049, Abstract JP 56029871, "Substituted acetic acid derivatives," Hamada, Yoshinori et al., Jul. 10, 1981, 1 page.

Caplus 84:43857, Abstract JP 58021626, "Alkanoic acid derivatives containing a pyridine ring," Maeda, Ryozo et al., May 2, 1983, 1 page.

Caplus 86:72448, Abstract JP 57053785, "Pyridine derivatives," Maeda, Ryozo et al., Nov. 15, 1982, 1 page.

Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat," Chemical Life Science, pp. 157-66, 1977, 1 page.

Caplus 98:78152, Abstract of JP 57185219, "Antitumor benzophenone derivatives," Nov. 15, 1982, 1 page, Chugai Pharmaceutical Co., Ltd.

Caplus 113:106314, Abstract of JP 2022650, "Silver halide color photographic material containing a cyan coupler of 2-ureido-phenol type to improve dye developability and remove lecuo cyan dye," Noboru Mizukura et al. Jan. 25, 1990, 1 page.

Caplus 113:142130, Abstract of JP 2023337, "Silver halide photographic material containing phenolic cyan coupler a colorless cyan coupler," Toshihiko Yagi et al., Jan. 25, 1990, 1 page.

Caplus 125:245169, "Production of murine monoclonal antibodies against sulcofuron and flucofuron by in vitro immunization," G. A. Bonwick et al., J. Immunol, Methods, 196(2), pp. 163-173, 1996, 1 page.

Caplus 126:166148, "Inhibitors of coenzyme A-independent transacylase induce apoptosis in human HL-60 cells," James D. Winkler et al., J. Pharmacol. Exp. Ther. 279(2), pp. 956-966, 1996, 2 pages.

Dearden et al.,"Quantitative structure-biodegradability studies: an investigation of the MITI aromatic compound data-base," in: Biodegradability Prediction, Edited by Willie J.G.M. Peijnenburg et al., NATO ASI Series, 2. Environment - vol. 23, pp. 93-104, 1996.

Caplus 127:293717, "Optical properties of segmented oligourethane with azomethine terminal fragments," National Academy of Science of Ukraine, M. V. Kurik et al., pp. 2038-2041, 1996, 2 pages.

Caplus 127:34137f, "Preparation of quinoline and quinazoline derivatives inhibiting platelet-derived growth factor receptor autophosphorylation," Kazuo Kubo et al., May 15, 1997, WO 97/17329.

Caplus 131:58658k, "Inhibition of raf kinase using symmetrical and unsymmetrical substituted diphenyl ureas," Miller, Scott, et al. Jul. 1, 1999, WO 99 32,436.

Caplus 131:73649b, "Preparation of pyrazolyl aryl ureas and related compomds as p38 kinase inhibitors," Jacques Dumas et al., Jul. 1, 1999, WO 99/32110.

Caplus 131:87909y, "Inhibition of p38 kinase activity using substituted heterocyclic ureas," Jacques Dumas et al., Jul. 1, 1999, WO 99/32111.

Caplus 146:265643 Abstract of Strumberg et al., "Sorafenib - A novel opportunity in oncology," Arzneimitteltherapie 25(1):2-6 (2007) abstract, 1 page.

Kujundzic et al., "Synthesis of 8-methyl-1,2,3,4-tetrahydropyrido[3,4-d] pyrimidine-2,4-diones," Croat. Chem. Acta (1991) 64(4):599-606, Chemical Abstracts vol. 116, No. 21, May 25, 1992, (pp. 741-742) No. 116:214456.

Badran et al., "Novel piperazinyl-substituted pyrimidines as antihypertensive and vasodilators," Revue Roumaine de Chimie (1992). 37(2):238-288, Chemical Abstracts vol. 117:251318.

"Beilstein number" Collection, 28 pp. (1997).

"Beilstein number" Collection, 4 pp. (1997).

Derwent World Patents Index Search, pp. 20-26. (1997).

Dumas, J. "CAS Substructure," May 6, 1997, pp. 1-29.

Scott, Bill, "Substructure (Patent Families)," Aug. 11, 1997, pp. 1-19.

Scott, Bill, "Substructure {fourth root}2," Nov. 25, 1997, pp. 1-3.

Scott, Bill, "Substructure Search," Dec. 2, 1997. pp. 1-49.

Substructure Search, pp. 1-29. (1997).

Wild, Hanno, "Substructure {fourth root}1," search, pp. 1-150, 1996.

A "Notice of References Cited" from the USPTO for U.S. Appl. No. 08/995,749, filing date of Dec. 22, 1997, Inhibition of P38 Kinase Using Symmetrical and Unsymmetrical Diphenyl Ureas, 2 pages.

A "Notice of References Cited" from the USPTO for U.S. Appl. No. 09/083,399, filing date of May 22, 1998, Patent 6187799 issued Feb. 13, 2001, Inhibition of Raf. Kinase Activity Using Aryl Ureas, 1 page.

A "Notice of References Cited" from the USPTO for U.S. Appl. No. 09/425,228, filing date of Oct. 22, 1999, Omega-Carboxyaryl Substituted Diphenyl Ureas As Raf Kinase Inhibitors, 3 pages.

A "Notice of References Cited" from the USPTO for U.S. Appl. No. 09/425,229, filing date of Oct. 22, 1999, Omega-Carboxy Aryl Substituted Diphenyl Ureas As p38 Kinase Inhibitors, 1 page.

A "Notice of References Cited" from the USPTO for U.S. Appl. No. 09/458,015, filing date of Dec. 10, 1999, Inhibition of p38 Kinase Using Symmetrical and Unsymmetrical Diphenyl Ureas, 1 page.

A "Notice of References Cited" from the USPTO for U.S. Appl. No. 09/472,232, filed of Dec. 27, 1999, Patent 7329670 issued Feb. 12, 2008, Inhibition of Raf Kinase Using Aryl and Heteroaryl Substituted heterocyclic Ureas, 1 page.

A "Notice of References Cited" from the USPTO for U.S. Appl. No. 09/472,232, filing date of Dec. 27, 1999, Patent 7329670 issued Feb. 12, 2008, Inhibition of Raf Kinase Using Aryl and Heteroaryl Substituted Heterocyclic Ureas, 1 page.

A "Notice of References Cited" from the USPTO for U.S. Appl. No. 09/773,604, filing date of Feb. 2, 2001, Publication No. US 2001-0034447-A 1, Publication Date Oct. 25, 2001, Omega-carboxyaryl Substituted Diphenyl Ureas as Raf Kinase Inhibitors, 1 page.

A "Notice of References Cited" from the USPTO for U.S. Appl. No. 09/773,659, filing date of Feb. 2, 2001, Publication No.: US 2001-0011135 Al, Publication Date: Aug. 2, 2001, Omega-carboxyaryl Substituted Diphenyl Ureas As Raf Kinase Inhibitors, 1 page.

A "Notice of References Cited" from the USPTO for U.S. Appl. No. 09/773,672, filing date of Feb. 2, 2001, Publication No. US 2001-0016659 A1, Publication Date: Aug. 23, 2001, Omega-carboxyaryl substituted Diphenyl Ureas as Raf Kinase Inhibitors, 1 page.

A "Notice of References Cited" from the USPTO for U.S. Appl. No. 09/773,675, filed of Feb. 2, 2001, Publication No. US 2001-0011136-A1, Publication Date: Aug. 2, 2001, Omega-Carboxyaryl Substituted Diphenyl Ureas as Raf Kinase Inhibitors, 1 page.

A "Notice of References Cited" from the USPTO for U.S. Appl. No. 09/776,935 filing date of Dec. 22, 1998, Inhibition Of p38 Kinase Using Aryl and Heteroaryl Substituted Heterocyclic Ureas, 1 page.

A "Notice of References Cited" from the USPTO for U.S. Appl. No. 09/776,936, filing date of Dec. 22, 1998, Inhibition of Raf Kinase Using Symmetrical and Unsymmetrical Substituted Diphenyl Ureas, 1 page.

A "Notice of References Cited" from the USPTO for U.S. Appl. No. 09/777,920, filing date of Feb. 7, 2001, Inhibition of Raf kinase using quinolyl, isoquinolyl or pyridyl ureas, 1 page.

A "Notice of References Cited" from the USPTO for U.S. Appl. No. 09/948,915, filing date of Sep. 10, 2001, Omega-Carboxyaryl Substituted Diphenyl Ureas As Raf Kinase Inhibitors, 1 page.

A "Notice of References Cited" from the USPTO for U.S. Appl. No. 10/042,226, filing date of Jan. 11, 2002, Omega-Carboxyaryl Substituted Diphenyl Ureas As Raf Kinase Inhibitors, 1 page.

Co-pending U.S. Appl. No. 09/458,014, filed Dec. 10, 1999, Dumas et al.

Abandoned U.S. Appl. No. 09/776,935 filed Dec. 22, 1998, Dumas et al.

Co-pending U.S. Appl. No. 09/776,936 filed Dec. 22, 1998, Miller et al.

Issued U.S. Appl. No. 09/889,227 filed Jul. 12, 2000, Riedl et al., issued as 7351834, Apr. 1, 2008.

Co-pending U.S. Appl. No. 09/993,647 filed Nov. 27, 2001, Riedl et al, published as 2003-0181442, Sep. 25, 2003.

Issued U.S. Appl. No. 10/060,396 filed Feb. 1, 2002, Miller et al., patent 7517880, issued Apr. 14, 2009, also published as 2004-0102636, May 27, 2004.

Issued U.S. Appl. No. 10/071,248 filed Feb. 11, 2002, Riedl et al., patent 7528255, issued May 5, 2009, also published as 2003-139605, Jul. 24, 2003.

Abandoned U.S. Appl. No. 10/086,417 filed Mar. 4, 2002, Riedl et al., published as 2003-0105091, Jun. 5, 2003.

Abandoned U.S. Appl. No. 10/125,369 filed Apr. 19, 2002, Dumas et al., published as 2003-0207914, Nov. 6, 2003.

Abandoned U.S. Appl. No. 10/308,187 filed Dec. 3, 2002, Carter et al,, published as 2003-0232765, Dec. 18, 2003.

Abandoned U.S. Appl. No. 10/361,844 filed Feb. 11 2003, Dumas et al., published as 2004-0023961, Feb. 5, 2004.

Abandoned U.S. Appl. No. 10/361,850 filed Feb. 11, 2003, Dumas et al., published as US 2003-0216396. Nov. 20, 2003.

Co-pending U.S. Appl. No. 10/361,859 filed Feb. 11, 2003, Dumas et al., published as 2003-0216446.Nov. 20, 2003.

Co-Pending U.S. Appl. No. 10/895,985 filed Jul. 22, 2004. Boyer et al., published as US 2005-0038080, Feb. 17, 2005.

Co-Pending U.S. Appl. No. 11/932,548 filed Oct. 31, 2007, Dumas et al.,.

Co-Pending U.S. Appl. No. 12/084,662 filed May 7, 2008, Sandner et al., published as 2010-0035888, Feb. 11, 2010.
Co-Pending U.S. Appl. No. 12/086,454 filed Jun. 12, 2008, Weber et al.
Co-Pending U.S. Appl. No. 12/093,515 filed Nov. 13, 2008, Wilhelm et al.
Co-Pending U.S. Appl. No. 12/095,611 filed May 30, 2008, Smith et al.
Co-Pending U.S. No. 12/158,524 filed Jun. 20, 2008, Smith et al.
Co-Pending U.S. Appl. No. 12/294,979 filed Sep. 29, 2008, Wilhelm et al.
Co-Pending U.S. Appl. No. 12/421,690 filed Apr. 10, 2009. Dumas et al.
Co-Pending U.S. Appl. No. 12/444,974 filed Apr. 9, 2009; Grunenberg et al.
Co-Pending U.S. Appl. No. 12/514,129 filed May 8, 2009, Gruneriberg et al.
Co-Pending U.S. Appl. No. 12/514,715 filed May 13, 2009, Stiehl et al.
Co-Pending U.S. Appl. No. 12/520,618 filed Jun. 22, 2009, Smith et al.
Co-Pending U.S. Appl. No. 12/520,609 filed Jun. 22, 2009, Smith et al.
Co-pending U.S. Appl. No. 12/523,652 filed Jul. 17, 2009, Wilhelm et al.
Co-pending U.S. Appl. No. 12/523,697 filed Jul. 17, 2009, Wilhelm et al.
Co-Pending U.S. Appl. No. 12/628,735 filed Dec. 1, 2009, Dumas et al.
Co-Pending U.S. Appl. No. 12/692,845 filed Jan. 25, 2010, Dumas et al.
Co-Pending Application PCT/US09/61506, filed Oct. 21, 2009, Carol Pena.
International search report for International Application No. PCT/US98/10375 dated Sep. 3, 1998, Inhibition Of p38 Kinase Activity By Aryl Ureas, publication No. 98/52558, publication date Nov. 26, 1998, 1 page.
International search report for International Application No. PCT/US98/10376 dated Jul. 30, 1998, Raf Kinase Inhibitors, publication No. WO 98/52559, publication date Nov. 26, 1998, 1 page.
International search report for International Application No. PCT/US98/26078 dated Apr. 2, 1999, Inhibition of Raf Kinase Using Substituted Heterocyclic Ureas, publication No. WO 99/32106, publication date Jul. 1, 1999, 2 pages.
International search report for International Application No. PCT/US98/26079 dated Apr. 12, 1999, Inhibition Of p38 Kinase Activity Using Aryl and Heteroaryl Substituted Heterocyclic Ureas, publication No. WO 99/32110, publication date Jul. 1, 1999, 1 page.
International search report for International Application No. PCT/US98/26080 dated Apr. 12, 1999, Inhibition Of p38 Kinase Using Substituted Heterocyclic Ureas, publication No. WO 99/32111, publication date Jul. 1, 1999, 1 page.
International search report for International Application No. PCT/US98/26081 dated Apr. 2, 1999, Inhibition of Raf Kinase Using Symmetrical and Unsymmetrical Substituted Diphenyl Ureas, publication No. WO 99/32436, publication date Jul. 1, 1999, 1 page.
International search report for International Application No. PCT/US98/26082 dated May 12, 1999, Inhibition Of Raf Kinase Using Aryl and Heteroaryl Substituted Heterocyclic Ureas, publication No. WO 99/32455, publication date Jul. 1, 1999, 1 page.
International search report for International Application No. PCT/US98/27265, dated Mar. 2, 1999, Inhibition of p38 kinase using symmetrical and unsymmetrical diphenyl ureas, publication No. WO 99/32463, publication date Jul. 1, 1999, 1 page.
International search report for International Application No. PCTIUS00/00648 dated Jun. 29, 2000, Omega-Carboxyaryl Substituted Diphenyl Ureas as RAF Kinase Inhibitors, publication No. WO 00/42012 A1, publication date Jul. 20, 2000, 2 pages.
International search report for International Application No. PCT/US00100768 dated May 16, 2000, Omega-Carboxy Aryl Substituted Diphenyl Ureas As p38 Kinase Inhibitors, publication No. WO 00/41698 A1, publication date Jul. 20, 2000, 1 page.

International search report for International Application No. PCDUS02112064 dated Sep. 20, 2002, Heteroaryl Ureas Containing Nitrogen Fiftero-Atoms As p38 Kinase Inhibitors, publication No. 02/085859, publication date Oct. 31, 2002, 2 pages.
International search report for International Application No. PCT/US02/12066 dated Sep. 27, 2002, Inhibition of Raf Kinase Quinolyl, Isoquinolyl or Pyridyl Ureas, publication No. 02/085857, publication date Oct. 31, 2002, 2 pages.
Supplemental search report from the EPO for European application EP 98963809.3 dated Mar. 30, 2001, Inhibition of Raf Kinase Using Symmetrical and Unsymmetrical Substituted Diphenyl Ureas, publication No. 1049664, publication date Jul. 1, 1999, granted Mar. 16, 2005, 4 pages.
Supplemental search report from the EPO for European application EP 98963810.1 dated Dec. 21, 2000, Inhibition of Raf Kinase Using Aryl and Heteroaryl Substituted Heterocyclic Ureas, publication No. 1056725, publication date Jul. 1, 1999, granted Jun. 7, 2006, 4 pages.
Supplemental search report from the EPO for European application EP 98965981.8 dated Dec. 21, 2000, Inhibition Of Raf Kinase Using Substituted Heterocyclic Ureas, publication No. 1047418, publication date Jul. 1, 1999, granted Jul. 27, 2005, 8 pages.
Supplemental search report front the EPO for European application EP 00903239.2 dated Aug. 7, 2002, Omega-Carboxyaryl Substituted Diphenyl Ureas As Raf Kinase Inhibitors, publication No. EP 1140840, published. Jul. 20, 2000, granted Mar. 22, 2006, 6 pages.
Supplemental search report from the EPO for European application EP 00905597.1 dated Feb. 7, 2008, Omega-Carboxyaryl Substituted Diphenyl Ureas As p38 Kinase Inhibitors, publication No. EP 1158985, Jul. 20, 2000, 9 pages.
Belgore et al., "Measurement of free and complexed soluble vascular endothelial growth factor receptor, Flt-1, in fluid samples: development and application of two new immunoassays," Clinical Science, 100: 567-575 (2001).
Belgore et al., "Plasma Levels of Vascular Endothelial Growth Factor (VEGF) and Its Receptor, Flt-1, in Haematological Cancers: A Comparison With Breast Cancer," American Journal of Hematology, 66:59-61 (2001).
Coskun et al., "Significance of serum vascular endothelial growth factor, insulin-like growth factor-I levels and nitric oxide activity in breast cancer patients," The Breast, 12, 104-110 (2003).
Kaya et al., "The prognostic significance of vascular endothelial growth factor levels in sera of non-small cell lung cancer patients," Respiratory Medicine, 98:632-636 (2004).
Kumar et al., "Soluble FLT-1 is Detectable in the Sera of Colorectal and Breast Cancer Patients," Anticancer Research, 22:1877-1880 (2002).
Pasieka et al., "Evaluation of the Levels of bFGF, VEGF, sICAM-1, and sVCAM-1 in Serum of Patients with Thyroid Cancer," Recent Results in Cancer Research, 162:189-194 (2003).
Pegram et al., "Combined Biological Therapy of Breast Cancer Using Monoclonal Antibodies Directed Against HER2/*neu*Protein and Vascular Endothelial Growth Factor," Seminars in Oncology, 29(Suppl. 11):29-37 (2002).
Poon et al., "Prognostic significance of serum vascular endothelial growth factor an endostatin in patients with hepatocellular carcinoma," British Journal of Surgery, 91:1354-1360 (2004).
Ria et al., "Serum levels of angiogenic cytokines decrease after antineoplastic radiotherapy," Cancer Letters, 216:103-107 (2004).
Secord et al., "The relationship between serum vascular endothelial growth factor, persistent disease, and survival at second-look laparotom.y in Ovarian cancer," Gynecologic Oncology, 94:74-79 (2004).
English abstract of JP 10-306078, Nov. 17, 1998, Patent Abstracts of Japan, 2 pages.
English abstract of JP 08-301841, Nov. 19, 1996, Patent Abstracts of Japan, 2 pages.
English abstract of JP 03-198049, Aug. 29, 1991, Patent Abstracts of Japan, 1 page.
English abstract of JP 03-144634, Jun. 20, 1991, Patent Abstracts of Japan, 1 page.
English abstract of JP 03-053247, Mar. 7, 1991, Patent Abstracts of Japan, 1 page.

English abstract of JP 02-150840, Jun. 11, 1990, Patent Abstracts of Japan, 1 page.
English abstract of JP 02-108048, Apr. 19, 1990, Patent Abstracts of Japan, 1 page.
English abstract of JP 02-105146, Apr. 17, 1990, Patent Abstracts of Japan, 1 page.
English abstract of JP 02-035450, Feb. 6, 1990, Patent Abstracts of Japan, 1 page.
English abstract of JP 01-200254, Aug. 11, 1989, Patent Abstracts of Japan, 1 page.
English abstract of JP 01-259360, Oct. 17, 1989, Patent Abstracts of Japan, 2 pages.
English abstract of JP 01-102461, Apr. 20, 1989, Patent Abstracts of Japan, 1 page.
English abstract of JP 06-120039, Apr. 28, 1994, Patent Abstracts of Japan, 1 page.
English abstract of JP 05-180862, Jul. 23, 1993, Patent Abstracts of Japan, 1 page.
English abstract of JP 05-163170, Jul. 29, 1993, Patent Abstracts of Japan, 1 page.
English abstract of JP 05-077375, Mar. 30, 1993, Patent Abstracts of Japan, 1 page.
English abstract of JP 05-076072, Mar. 26, 1993, Patent Abstracts of Japan, 2 pages.
English abstract of JP 50-149668 A and JP 56-29871 B, Derwent World Patents Index, Dialog File No. 351, Acc. No. 1488399, 3 pages.
English abstract of JP 53-086033, Jul. 29, 1978, Patent Abstracts of Japan, 1 page.
English abstract of JP 54-032468, Mar. 9, 1979, Patent Abstracts of Japan, 1 page.
English abstract of JP 55-098152, Jul. 25, 1980, Patent Abstracts of Japan, 1 page.
English abstract of JP 64-009455, Jan. 12, 1989, Patent Abstracts of Japan, 1 page.
English abstract of JP 02-023337, Mar. 9, 1979, Patent Abstracts of Japan, 2 pages.
English abstract of EPA 0379915/EP-A1, Aug. 1, 1990, 2 pages.
English abstract of DD 253997 A, Feb. 10, 1988, 1 page.
English abstract of DE511468, European Patent Office, 2 pages.
Co-Pending U.S. Appl. No. 12/619,913, filed Nov. 17, 2009, Ranges et al.
Adjei et al., "A Phase I study of BAY 43-9006 and gefitinib in patients with refractory or recurrent non-small-cell lung cancer (NSCLC)," Abstract #3067, Meeting: *2005 ASCO Annual Meeting,* Category: Developmental Therapeutics: Molecular Therapeutics, Subcategory: Antiangiogenic or Antimetastatic agents.
Ahmad ad et al., "Kinase Inhibition with BAY 43-9006 in Renal Cell Carcinoma," *Clinical Cancer Research,* Sep. 15, 2004, vol. 10(suppl.), pp. 6388s-6392s.
Amornphimoltham et al., "Persistent Activation of the Akt Pathway in Head and Neck Squamous Cell Carcinoma: A Potential Target for UCN-01," Clinical Cancer Research, vol. 10, Jun. 15, 2004, pp. 4029-4037.
Arzneimitteltherapie, "Sorafenib" Oct. 6, 2006, Auflage 18498, 7 pages.
Arnone et al., "Selectivities in the Oxidation of Tertiary Amines and Pyridine Derivatives by Perfluoro *Cis*-2,3-dialkyloxaziridines," Tetrahedron, vol. 54, 1998, pp. 7831-7842.
Arora et al., "Stromelysin 3, Ets-1, and Vascular Endothelial Growth Factor Expression in Oral Precancerous and Cancerous Lesions: Correlation with Microvessel Density, Progression, and Prognosis," Clinical Cancer Research, 11: 2272-2284 (Mar. 15, 2005).
Ascierto et al., "Prognostic Value of Serum VEGF in Melanoma Patients: a Pilot Study" Anticancer Research, 24: 4255-4258 (2004).
Auclair et al., "BAY 43-9006 (Sorafenib) is a potent inhibitor of FLT3 tyrosine kinase signaling and proliferation in AML cells," Abstract #5991, 96th Annual Meeting, Anaheim/Orange County, CA, Apr. 16-20, 2005.
Audia et al., "Potent, Selective Tetrahydro-β-carboline Antagonists of the Serotonin 2B ($5HT_{2b}$) Contractile Receptor in the Rat Stomach Fundus," *J. Med. Chem.* 1996, 39, pp. 2773-2780.

Avruch et al., "Raf meets Ras: completing the framework of a signal transduction pathway," *TIBS*19; Jul. 1994; pp. 279-283.
Awada et al., "Phase I safety and pharmacokinetics of BAY 43-9006 administered for 21 days on/7 days off in patients with advanced, refractory solid tumours" British Journal of Cancer 92, pp. 1855-1861 (2005).
Bachelot et al., "Prognostic value of serum levels of interleukin 6 and of serum and plasma levels of vascular endothelial growth factor in hormone-refractory metastatic breast cancer patients," British Journal of Cancer, 88: 1721-1726 (2003).
Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," JPET 279: pp. 1453-1461 (1996).
Baka et al., "A review of the latest clinical compounds to inhibit VEGF in pathological angiogenesis," Expert Opinion Therapeutic Targets, 2006, vol. 10, No. 6, pp. 867-876.
Balant et al., "Metabolic Considerations in Prodrug Design," Chapter Twenty-Three In: Burger's Medicinal Chemistry and Drug Discovery, 5th ed. John Wiley & Sons, Inc., New York, 1995: vol. 1,pp. 949-982.
Bando et al., "Association between intratumoral free and total VEGF, soluble VEGFR-1, VEGFR-2 and prognosis in breast cancer" British Journal of Cancer, 2005, vol. 92, pp. 553-561.
Banerjee et al., "Murine Coronavirus Replication-Induced p38 Mitogen-Activated Protein Kinase Activation Promotes Interleukin-6 Production and Virus Replication in Cultured Cells." Journal of Virology. American Society for Microbiology, 2002: vol. 76, pp. 5937-5948.
Bankston et al., "A Scaleable Synthesis of BAY 43-9006: A Potent Raf Kinase Inhibitor for the Treatment of Cancer," Organic Process Research & Development. 2002, vol. 6, pp. 777-781.
Barnett et al., "Identification and characterization of pleckstrin-homology-domain-dependent and isoenzyme-specific Akt inhibitors," Biochem J., vol. 385, 2005, pp. 399-408.
Baumann et al., "Raf induces $NF_{-K}$ B by membrane shuttle kinase MEKK1, a signaling pathway critical for transformation," Proc. Natl. Acad. Sci. USA, vol. 97: No. 9: 4615-4620 (Apr. 25, 2000).
Bayer Corporation et al., "Trial of BAY 43-9006 in Patients with Relapsed or Refractory Advanced Non-Small Cell Lung Carcinoma", NCT0010413, clinicaltrials.gov, 3 pages 2006.
Bellacosa et al., "Molecular Alterations of the AKT2 Oncogene in Ovarian and Breast Carcinomas," Int. J. Cancer (Pred. Oncol.), vol. 64, 1995, pp. 280-285.
Berge et al., "Pharmaceutical Salts." Journal of Pharmaceutical Sciences. Jan. 1977:1-19, vol. 66, No. 1.
Bergstralh et al, "Microtubule stabilizing agents: Their molecular signaling consequences and the potential for enhancement by drug combination," *Cancer Treatment Reviews*, 2006; vol. 32, pp. 166-179.
Bertrand et al., "Inhibition of PI3K, mTOR and MEK signaling pathways promotes rapid apoptosis in B-Lineage ALL in the presence of stromal cell support", Leukemia, vol. 19, pp. 98-102 (published online Oct. 21, 2004).
Bhagwat et al., "The angiogenic regulator CD13/APN is a transcriptional target of Ras signaling pathways in endothelial morphogenesis," Blood, vol. 101, No. 5, pp. 1818-1826, (Mar. 1, 2003).
Bianchi et: al., "A Phase II multi-center uncontrolled trial of sorafenib (BAY 43-9006) in patients with metastatic breast cancer" Journal of Clinical Oncology, Draft 33 pages (presented previously Oct. 30-Nov. 3, 2005).
Martin-Blanco, "p38 MAPK signalling cascades: ancient roles and new functions," BioEssays, 22:637- 645, 2000.
Foussard-Blanpin, Odette, "Comparative pharmacological study of substituted carboxamides upon central nervous system," Ann. Pharm. Fr. (1982), 40 (4), ) pp. 339-350.
Board et al., "Platelet-derived growth factor receptor (PDGFR): A target for anticancer therapeutics," Drug Resistance Updates 8 (2005) 75-83.
Bok et al., "Vascular Endothelial Growth Factor and Basic Fibroblast Growth Factor Urine Levels as Predictors of Outcome in Hormone-refractory Prostate Cancer Patients: A Cancer and Leukemia Group B Study," Cancer Research, 61: 2533-2536 (Mar. 15, 2001).
Bollag et al., "Raf pathway inhibitors in oncology," Current Opinion in Investigational Drugs (2003) 4(12): pp. 1436-1441.
Bolton et al., "Chapter 17. RasOncogene Directed Approaches in Cancer Chemotherapy," Annual Reports in Medicinal Chemistry, vol. 29, 1994, pp. 165-174.
Bono et al., "Serum KIT and KIT ligand levels in patients with gastrointestinal stromal tumors treated with imatinib," Blood 103:2929-2935 (2004).
Bos, J.L. "rasOncogenes in Human Cancer: A Review," *Cancer Research*, vol. 49, Sep. 1, 1989, pp. 4682-4689.
Boulton et al., "Heterocyclic Rearrangements. Part X. A Generalised Monocyclic Rearrangement," J. Chem. Soc. (C), 1967, pp. 2005-2007.
Boyer, S.J., "Small Molecule Inhibitors of KDR (VEGFR-2) Kinase: An Overview of Structure Activity Relationships," Current Topics in Medicinal Chemistry, 2002, vol. 2, pp. 973-1000.
Boyd, et al. "Arene Oxides of Quinoline: Epoxidation, $N$-Oxidation and $N$-Methylation Reactions," J. Chem. Soc. Perkin Trans. 1, 1991: pp. 2189-2192.
Braybrooke et al., "A Phase II Study of Razoxane, an Antiangiogenic Topoisomerase II Inhibitor, in Renal Cell Cancer with Assessment of Potential Surrogate Markers of Angiogenesis," Clin. Canc. Res. 6:4697-4704 (2000).
Broll et al., "Vascular endothelial growth factor (VEGF) — a valuable serum tumour marker in patients with colorectal cancer?" Ear. J. Surg. Oncol, 27:37-42 (2001).
Bruder et al., "Adenovinls Infection Stimulates The Raf/MAPK Signaling Pathway and Induces Interleukin-8 Expression" Journal of Virology, vol. 71, pp. 398-404, 1997.
Bundgaard, Hans. "Design of prodrugs: Bioreversible derivatives for various functional groups and chemical entities," pp. 1-92, in Design of Prodrugs, Elsevier Science Publishers B,V., Amsterdam, The Netherlands, 1985.
Campbell et al., "Increasing complexity of Ras signaling," Oncogene, 1998, vol. 17, pp, 1395-1413.
Cancer Weekly, "Antisense Technology (Clinical Trial). Phase II Trial of Second Antisense Cancer Drug Begins," Cancer Weekly, p. 4 (Dec. 8, 1997).
Canetta et al., "Carboplatin: current status and future prospects," Cancer Treatment Reviews, 1998, pp. 17-32, vol. 15(Supplement B).
Caponigro et al., "Epidermal growth factor receptor as a major anticancer drug target," Exp. Opin. Thera. Targets, 2006, vol. 10, No. 6, pp. 877-888.
Carey et al., "Contents of Part A," pp. vii-xi and "Contents of Part B," pp. xiii-xviii, in Advanced Organic Chemistry, Second Edition, Part A: Structure and Mechanisms, Plenum Press, NY (1984).
Carling et al., "1-(3-Cyanobenzylpiperiditi-4-y1)-5-methyl-4-pheny1-1,3-dihydroimidazol-2-one: A Selective High-Affinity Antagonist for the Human Dopamine $D_4$ Receptor with Excellent Selectivity over Ion Channels," J Med. Chem., 1999, 42, pp. 2706-2715.
Carlomagno et al., "BAY 43-9006 Inhibition of Oncogenic RET Mutants," Journal of the National Cancer Institute, 2006, vol. 98, No. 5, pp. 326-334.
Carney et al., "Monitoring the Circulating Levels of the HER2/neuOncoprotein in Breast Cancer," Clin Breast Cancer 5(2): 105-116, (2004).
Carter et al., "Anti-Tumor Efficacy of the Orally Active *Raf*Kinase Inhibitor BAY 43-9006 in Human Tumor Xenograft Models," Proceedings of the American Association for Cancer Res., vol. 42: p. 923, Mar. 2001, Abstract #4954.
Carter et al., "Drug-Tumor Interactions" pp. 362-365, in: Chemotherapy of Cancer, Second Edition, John Wiley & Sons, NY (1981).
Carter et al., "Sorafenib is efficacious and tolerated in combination with cytotoxic or cytostatic agents in preclinical models of human non-small cell lung carcinoma," Cancer Chemotherapy and Pharmacology, Springer Berlin/Heidelberg, vol. 59, No. 2, pp. 183-195 (Feb. 2007). Abstract.
Chang et al.. "BAY 43-9006 (Sorafenib) inhibits ectopic (s.c.) and orthotopic growth of a murine model of renal adenocarcinoma (Renca) predominantly through inhibition of tumor angiogenesis," $96^{th}$ Annual Meeting, Anaheim/Orange County, CA, Apr. 16-20, 2005, 1 page.
Chang et al., "Sorafenib (BAY 43-9006) inhibits tumor growth and vascularization and induces tumor apoptosis and hypoxia in RCC xenograft models," Cancer Chemother. Pharmacol, 2007, vol. 59, pp. 561-574.
Chen et al., "Role of Regulatory Elements and the MAPK/ERK OR p38 MAPK Pathways for Activation of Human Cytomegalovirus Gene Expression," Journal of Virology, 2002: vol. 76, No. 10, pp. 4873-4885.
Chen et al., "Suppression of Japanese encephalitis virus infection by non- steroidial, anti-inflammatory drugs," Journal of General Virology, 2002, vol. 83, pp. 1897-1905.
Chen et al., "Expression of Proinflammatory and Proangiogenic Cytokines in Patients with Head and Neck Cancer," Clinical Cancer Research 5:1369-1379 (Jun. 1999).
Chialda et al., "Inhibitors of mitogen-activated protein kinases differentially regulate costimulated T cell cytokine production and mouse airway eosinophilia." Respiratory Research 2005, 6:36, pp. 1-19.
Chin et al., "Vascular endothelial growth factor and soluble Tie-2 receptor in colorectal cancer: associations with disease recurrence," European Journal of Surgical Oncology, 29:497-505 (2003).
Choi et al., "Imatinib-Resistant Cell Lines Are Sensitive to the Raf Inhibitor BAY 43-9006," Blood, W.E.B. Saunders Company, Orlando, FL, US, vol. 100, No. 11, Abstract # 1427 (Dec. 10, 2002).
Choong et al., "Forthcoming receptor tyrosine kinase inhibitors," Exp. Opin. Ther. Targets, 2006, vol. 10, No. 6, pp. 793-797.
Chow et al., "Measurement of MAP Kinase Activation by Flow Cytometry Using Phospho-Specific Antibodies to MEK and ERK: Potential for Pharmacodynamic Monitoring of Signal Transduction Inhibitors," Cytometry (Communications in Clinical Cytometry) 46:72-78 (2001).
Christensen, et al., "Plasma vascular endothelial growth factor and interleukin-8 as biomarkers of antitumor efficacy of a prototypical erbB family tyrosine kinase inhibitor," Mol. Cancer Ther., 4(6):938-947 (Jun. 2005).
Chu et al., "Cardiotoxicity associated with tyrosine kinase inhibitor sunitinib," Lancet, 2007, vol. 370, pp.2011-2019.
Chustecka et al., "Bortezomib and Sorafenib Show Activity in Thyroid Cancer," Medscape, 2 pages (Nov. 2, 2006).
Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," Clinical Cancer Res., Aug. 1, 2005, vol. 11, No. 15, pp. 5472-5480.
Garbe, "Auch cin Therapieplatz für Sorafenib?" Medical Special (2006) 2 pages.
Copéret et al., "A Simple and Efficient Method for the Preparation of Pyridine-$N$-oxides II" Tetrahedron Letters, Elsevier Science Ltd., Pergamon Press, Oxford, UK 1998: vol. 39, pp. 761-764.
Cortes et al., "Targeting the Microtubules in Breast Cancer Beyond Taxanes: The Epothilones." *The Oncologist*,2007, vol. 12, pp. 271-280.
Craig, "The mechanisms of drug release from solid dispersions in water-soluble polymers." International Journal of Pharmaceutics 231 (2002) 131-144, Elsevier Science B.V.
Le Cras et al., "Treatment of newborn rats with a VEGF receptor inhibitor causes pulmonary hypertension and abnormal lung structure." Am. J. Physiol. Lung. Cell. Mol. Physiol. vol. 283, pp. L555-L562, 2002.
Crump, Micheal, "Inhibition of raf kinase in the treatment of acute myeloid leukemia," Medline Abstract ISSN:1381-6128, Current Pharmaceutical Design, vol. 8, Issue 25, 2002, pp. 2243-2248.
Cunningham et al., "A Phase I Trial of H- rasAntisense Oligonucleotide ISIS 2503 Administered as a. Continuous intravenous Infusion in Patients with Advanced Carcinoma," Cancer, 2001, American Cancer Society, vol. 92, No. 5, pp. 1265-1271.
Danson et al., "Improving Outcomes in Advanced Malignant Melanoma. Update on Systemic Therapy," *Drugs*, 2005, vol. 65, No. 6, pp. 733-743.
Dasmahapatra et al., "*In vitro*Combination Treatment with Perifosine and UCN-01 Demonstrates Synergism against Prostate (PC-3) and Lung (A549) Epithelial Adenocarcinoma Cell Lines," Clinical Cancer Research, vol. 10, Aug. 1, 2004, pp. 5242-5252.

Daum et al., "The ins and outs of Raf kinases," TIBS 19, Nov. 1994, pp. 474-480.

Dayan et al., "Tertiary Amine Oxidation using HOF-CH$_3$ CN: A Novel Synthesis of N-Oxides," Synthesis, 1999, No. SI, pp. 1427-1430.

DeGrendele, "Activity of the Raf Kinase Inhibitor BAY 43-9006 in Patients with Advanced Solid Tumors," Clinical Colorectal Cancer, May 2003, vol. 3, pp. 16-18.

Dehtling, J. "Große Onkologie-Pipeline" Medizinische Monatsschrift für Pharinazeuten, 2006, Auflage 12914, 2 pages.

Denny, "Prodrug strategies in cancer therapy," European Journal of Medicinal Chemistry. 2001: vol. 36, pp. 577-595.

DeVita et al., "Elevated Perioperative Serum Vascular Endothelial Growth Factor Levels in Patients with Colon Carcinoma," Cancer, 100 (2) pp. 270-278 (2004).

Devlin et al., "GATT and DISCOVERY: Significant Changes in U.S. Patent Law" Screening Fortran, vol. 3, No. 4, pp. 1, 3 and 6 (Dec. 1995).

Doanes et al., "VEGF Stimulates MAPK through a Pathway That Is Unique for Receptor Tyrosine Kinases," Biochem Biophys. Res. Commun. 255: pp. 545-548, 1999.

Dörwald, "Preface," p. IX, in Side Reactions in Organic Synthesis: A Guide to Successful Synthesis Design, Wiley-VCH Verlag GmbH & Co. KGaA (2005).

Downward, J., "Mechanisms and consequence of activation of protein kinase B/Akt," Current Opinion in Cell Biology, vol. 10, 1998, pp. 262-267.

Drevs et al., "Soluble markers for the assessment of biological activity with PTK787/ZK 222584 (PTK/ZK), a vascular endothelial growth factor receptor (VEGFR) tyrosine kinase inhibitor in patients with advanced colorectal cancer from two phase I trials," Annals of Oncology, 16: 558-565 (2005).

Drevs, J., "Soluble Markers for the Detection of Hypoxia under Antiangiogenic Treatment," Anticancer Research, 23: 1159-1162 (2003).

Drevs, J., Die Medizinische Welt, 2006, pp. 3/5, 4/5, 5/5.

"Doxorubicin HCl (ADR)," in drugs: facts and comparisons, 1994 Ed., pp. 2703-2705.

Dudek et al., "Circulating Angiogenic Cytokines in Patients with Advanced Non-Small Cell Lung Cancer: Correlation with Treatment Response and Survival," Cancer Investigation, 23: 193-200 (2005).

Dumas, J. "Protein kinase inhibitors from the urea class," Curr. Opin. In Drug Discovery and Dev., 5(s):718-727, 2002.

Dumas et al., "Discovery of a New Class of p38 Kinase Inhibitors," Bioorganic & Medicinal Chemistry Letters vol. 10, (2000), pp. 2047-2050.

Dumas et al., "1-Phenyl-5-pyrazolyl Ureas: Potent and Selective p38 Kinase Inhibitors," Bioorganic & Medicinal Chemistry Letters, 2000, vol. 10, pp. 2051-2054.

Dumas, J., "Growth factor receptor kinase inhibitors: Recent progress and clinical impact," Current Opinion in Drug Discovery & Development, 2001, vol. 4, No. 4, pp. 378-389.

Dumas, J., "Protein kinase inhibitors: emerging pharmacophores 1997-2000," Expert Opinion on Therapeutic Patents (2001) vol. 11, No. 3, pp. 405-429.

Dumas et al., "Orally Active p38 Kinase Inhibitors from the Urea Class," Poster, 222nd American Cancer Society National Meeting 2001, Med. I 256, 1 page.

Dumas, J., "Raf Kinase Inhibitors," Expert Opinion on Therapeutic Patients, vol. 8, No. 12, pp. 1749-1750, 1998.

Dumas et al., "Recent developments in the discovery of protein kinase inhibitors from the urea class," *Current Opinion in Drug Discovery & Development*, 2004, vol. 7, No. 5, pp. 600-616.

Dumas et al., "Synthesis and Pharmacological Characterization of a Potent, Orally Active p38 Kinase Inhibitor," *Bioorganic & Medicinal Chemistry Letters*, 2002, vol. 12, pp. 1559-1562.

Dunst et al., "Tumor Hypoxia and Systemic Levels of Vascular Endothelial Growth Factor (VEGF) in Head and Neck Cancers," Strahlentherapie und Onkologie, 177(9): 469-473 (2001).

Ebos et al., "Multiple circulating proangiogenic factors induced by sunitinib malate are tumor-independent and correlated with antitumor efficacy" PNAS vol. 104, No. 43, pp. 17069-17074 (Oct. 23, 2007).

Ebrahimi et al., "Cytokines in Pancreatic Carcinoma. Correlation with Phenotypic Characteristics and Prognosis," Cancer, 101(12): 2727-2736 (Published on-line Nov 3, 2004).

Eisen et al., "Phase I trial of BAY 43-9006 (Sorafenib) combined with dacarbazine (DTIC) in metastatic melanoma patients," Abstract #7508, Meeting: *2005 ASCO Annual Meeting*, Category: Melamona, Subcategory: Melamona.

Eisen et al., "Sorafenib in advanced melanoma: a Phase II randomised discontinuation trial analysis" British Journal of Cancer 95, 581-586 (2006).

Eisenhauer et al., "Impact of new non-cytotoxics in the treatment in ovarian cancer," International J. Gynecol. Cancer, 2001, vol. 11, Supplement 1, pp. 68-72.

El-Deiry, Wafik S., "Meeting Report: The International Conference on Tumor Progression and Therapeutic Resistance", Cancer Research, 2005; vol. 65, No. 11, pp. 4475-4484.

Elting et al., "Biomarkers associated with clinical outcomes in TARGETs, a Phase III single-agent, placebo-controlled study of sorafenib in advanced renal cell carcinoma," .Proc. Amer. Assoc. Cancer Res. vol. 47, Abstract #2909, 2006, pp. 683-684.

Escudier et al., "Randomized Phase III trial of the Raf kinase and VEGFR inhibitor sorafenib (BAY 43-9006) in patients with advanced renal cell carcinoma (RCC)," Meeting: 2005 ASCO Annual Meeting, Category: Genitourinary Cancer, Subcategory: Kidney Cancer, 1 page.

Escudier et al., "Sorafenib in Advanced Clear-Cell Renal-Cell Carcinoma" New England Journal of Medicine vol. 356: 125-134 (Jan. 11, 2007).

European Medicines Agency, "CHMP Assessment Report for Nexavar" Doc Ref: EMEA/CHMP/140610/2006, 63 pages. (2006).

Fabian et al., "A small molecule-kinase interaction map for clinical kinase inhibitors," Nature Biotechnology, 2005, vol. 23, No. 3, pp. 329-336, 4 supplementary pages.

Faderl et al., "Angiogenic factors may have a different prognostic role in adult acute lymphoblastic leukemia," Blood, 2005 vol. 106 No. 13, pp. 4303-4307.

Faivre et al., "Molecular basis for sunitinib efficacy and future clinical development" Nature Reviews Drug Discovery, Nature Publishing Group, pp. 734-745, vol. 6 (Sep. 2007).

Fakhari et al., "Upregulation of Vascular Endothelial Growth Factor Receptors is Associated with Advanced Neuroblastoma," Journal of Pediatric Surgery, 37(4): 582-587 (Apr. 2002).

Favaro et al., "Targeted therapy in renal cell carcinoma," Expert Opin. Investig. Drugs 14(10):1251-1258 (2005).

Fiedler et al. "A phase 2 clinical study of SU5416 in patients with refractory acute myeloid leukemia," Blood, 102(8): 2763-2767(prepublished online Jul. 3, 2003).

Feldmann, "Pathogenesis of arthritis: recent research progress," Nature Immunology 2001, vol. 2, No. 9, pp. 771-773.

Fields Virology Second Editon, "Contents,":vol. 1, pp. ix-xiv, Raven Press, NY (1990).

Flaherty et al., "A Phase I Trial of the Oral, Multikinase Inhibitor Sorafenib in Combination with Carboplatin and Paclitaxel" Clin Cancer Res 41(15):4836-4842 (Aug. 1, 2008).

Flaherty et al., "Phase I/II trial of BAY 43-9006 carboplatin (C) and paclitaxel (P) demonstrates preliminary antitumor activity in the expansion cohort of patients with metastatic melanoma," Journal of Clinical Oncology, 2004 ASCO annual meeting proceedings, vol. 22, No. 14S (2004) Supplement: 7507, 4 pages.

Flaherty et al., "Antisense therapeutics: lessons from early clinical trials," Current Opin. in Oncol. 13: 499-505 (2001).

Foekens et al,, "High Tumor Levels of Vascular Endothelial Growth Factor Predict Poor Response to Systemic Therapy in Advanced Breast. Cancer," *Cancer Research*, 2001, vol. 61, pp. 5407-5414.

Forbes et al., "N-(1-Methyl-5-indolyl)-N-(3-methyl-5-isothiazolypurea: A Novel, High-Affinity 5-HT$_{2B}$, Receptor Antagonist," Journal of Medicinal Chemistry, 1995, vol. 38, No. 6, pp. 855-857.

Franco et al., "Dissolution properties and anticonvulsant activity of phenytoin-polyethylene glycol 6000 and -polyvinylpyrrolidone K-30 solid dispersions," International Journal of Pharmaceutics 225 (2001) pp. 63-73.

Fridman et al., "The Minimal Fragments of c-Raf-1 and NF1 That Can Suppress v-Ha-Ras-Induced Malignant Phenotype," The Journal of Biological Chemistry, vol. 269, No. 48, 1994, pp. 30105-30108.

Garcia-López et al., "New Routes for the Synthesis of Pyrrolo[3,2-d]- and [2,3-d]-pyrimidine Systems starting from a Common Pyrrole Derivative," Journal of the Chemical Society, Perkin Transactions 1: Organic and Bio-Organic Chemistry (1972-1999), 1978, pp. 483-487.

Gatzemeier et al., "Phase II trial of single-agent soraferdb in patients with advanced non-small cell lung carcinoma," Journal of Clinical Oncology, 2006 ASCO Annual Meeting Proceedings Part I, vol. 24, No. 18S (Jun. 20 Supplement) 2006, abstract No. 7002, 4 pages.

Geiger et al., "Antitumor Activity of a C-raf Antisense Oligonucleotide in Combination with Standard Chemotherapeutic Agents against Various Human Tumors Transplanted Subcutaneously into Nude Mice," Clinical Cancer Research vol. 3, 1179-1185, Jul. 1997.

Geng et al., "A Specific Antagonist of the p110δ Catalytic Component of Phosphatidylinositol 3'-Kinase, IC486068, Enhances Radiation-Induced Tumor Vascular Destruction," Cancer Research,64, Jul. 2004, pp. 4893-4899.

Gennaro, Alfonso R. "Table of Contents," pp. xiv-xv, in Remington: The Science and Practice of Pharmacy, 20TH Ed. Remington. Lippincott Williams & Wilkins, 2000.

George et al., "VEGF-A, VEGF-C and VEGF-D in Colorectal Cancer Progression," Neoplasia, 3(5): 420- 427 (2001).

George et al., "Prognostic Significance of Plasma Vascular Endothelial Growth Factor Levels in Patients with Hormone-refractory Prostate Cancer Treated on Cancer and Leukemia Group B 9480," Clinical Cancer Research, 7: 1932-1936 (Jul. 2001).

Abou-Alfa et al., "Phase II Study of Sorafenib in Patients with Advanced Hepatocellular Carcinoma" Journal of Clinical Oncology, vol. 24, No. 26, pp. 4293-4300 (Sep. 10, 2006).

Giambartolomei et al., "Sustained activation of the Raf/MEK/Erk pathway in response to EGF in stable cell lines expressing the Hepatitis C Virus (HCV) core protein," Oncogene, Nature Publishing Group, 2001: vol. 20, pp. 2606-2610.

Gills et al., "The development of phosphatidylinositol ether lipid analogues as inhibitors of the serine/threonine kinase, Akt, " Expert Opin. Investig. Drugs, vol. 13, No. 7, 2004, pp. 787-797.

Gollob, "Sorafenib: scientific rationales for single-agent and combination therapy in clear-cell renal cell carcinoma" Pub Med PMID: 16425993, Clin. Genitourin. Cancer 4(3):167-174 (2005) abstract.

Gómez-Esquer et al., "mRNA expression of the angiogenesis markers VEGF and CD105 (endoglin) in human breast cancer," Anticancer Res., 2004, vol. 24, No. 3a, pp. 1581-1585, XP-002455577, abstract.

Grant et al., "Some Hypotensive Thiadiazoles," J. Med. Chem. (1972), 15(10), pp. 1082-1084.

Greene et al., "Contents," pp. xi -xii, in: Protective Groups in Organic Synthesis, 3rd Ed. John Wiley & Sons, Inc., New York, 1999.

Gelasser, "The Importance of Solvates," in: Polymorphism in the Pharmaceutical Industry, Chapter 8, p. 211, 2006, Wiley-VCH Verlug GmbH & Co., KGaA, Weinhelm.

Gridelli et al., "Sorafenib and Sunitinib in the Treatment of Advanced Non-Small Cell Lung Cancer" The Oncologist (2007) 12:191-200.

Guan et al., "H5N1 influenza: A protean pandemic threat," Proc. Natl. Acad, Sci. USA, May 25, 2004; vol. 101, pp. 8156-8161.

Gupta et al., "Sorafenib targets BRAF and VEGFR in metastatic thyroid carcinoma" Journal of Clinical Oncology, 2007 ASCO Annual Meeting Proceedings (Post-Meeting Edition) vol. 25, No. 185 (Jun. 20 Supplement), 2007: 6019 abstract.

Gura, "Systems for identifying new drugs are often faulty." Science,1997; vol. 278, (5340), pp. 1041- 1042, MEDLINE with Full text.

Hahn et al., "Sorafenib," Curr. Opin. Oncol. 18:615-621 (2006).

Hall-Jackson et al., "Paradoxical activation of Raf by a novel Raf inhibitor," Chemistry & Biology. 6: 559- 568 (Jul. 1999).

Han et al., "Targeted Prodrug Design to Optimize Drug Delivery." AAPS Pharmsci. 2000: vol. 2, No. 1, Article 6, 1-11.

Hanna, "Second-Line Treatment of Non-small Cell Lung Cancer: Big Targets, Small Progress; Small Targets, Big Progress?" Journal of Thoracic Oncology vol. 1, No. 9, pp. 927-928 (Nov. 2006).

Hansch et al., "Contents," 21 pages, in: Comprehensive Medicinal Chemistry. The Rational Design, Mechanistic Study & Therapeutic Application of Chemical Compounds, Pergamon Press, Oxford, UK, 1990.

Hanson. "Pulmonary-Allergy, Dermatological, Gastrointestinal & Arthritis Inhibitors of p38 kinase," Exp. Opin. Ther. Patents,1997, vol. 7, No. 7, pp. 729-733.

Hardmann et al., excerpts from chapter 3. Principles of Therapeutics, in: Goodman & Gilman's The Pharmacological Basis of Therapeutics, 9th ed., 1996, pp. 51 and 57-58.

Harris et al., "Soluble Tie2 and Fitt Extracellular Domains in Serum of Patients with Renal Cancer and Response to Antiangiogenic Therapy," Clin. Cancer Res. 7:1992-1997 (2001).

Hayes et al., "Serum vascular endothelial growth factor as a tumour marker in soft tissue sarcoma," British Journal of Surgery, 91:242-247 (Published on-line Nov. 24, 2003).

Hegedus, L.S. "Contents," 4 pages in: Transition Metals in the Synthesis of Complex Organic Molecules, University Science Books, Mill Valley, California, 1994.

Heim et al., "Antitumor effect and potentiation or reduction in cytotoxic drug activity in human colon carcinoma cells by the Raf kinase inhibitor (RKI) BAY 43-9006," International Journal of Clinical Pharmacology and Therapeutics,2003, vol. 41, No. 12, pp. 616-617.

Heim et al., "The Rafkinase inhibitor BAY 43-9006 reduces cellular uptake of platinum compounds and cytotoxicity in human colorectal carcinoma cell lines," Anti-Cancer Drugs,2005, vol. 16, pp. 129-136.

Herlaar et al., "p38 MAPK signalling cascades in inflammatory disease," Molecular Medicine Today, vol. 5, pp. 439-447 (Oct. 1999).

Herrera et al., "Unraveling the complexities of the Raf/MAP kinase pathway for pharmacological. intervention," Trends in Molecular Medicine, 2002, vol. 8, No. 4 (Suppl.), pp. S27-S31.

Higuchi T. et al., "Contents," in: Prodrugs as Novel Drug Delivery Systems, ACS Symposium Series 14, American Chemical Society, Washington, DC, 1975, p. vii.

Higuchi et: al., "Mitochondrial DNA determines androgen dependence in prostate cancer cell lines," Oncogene, 2006, vol. 25, pp. 1437-1445.

Hilger et: al., "Correlation of ERK-phosphorylation and toxicities in patients treated with the Raf kinase inhibitor BAY 43-9006" International Journal of Clinical Pharmacology and Therapeutics, vol. 42, No. 11, pp. 648-649 (2004).

Hilger et al., "ERK1/2 phosphorylation: a biomarker analysis within a phase I study with the new Raf kinase inhibitor BAY 43-9006" International Journal of Clinical Pharmacology and Therapeutics, vol. 40, No. 12, pp. 567-568 (2002).

Hilger et al., "Inhibition of ERK phosphorylation and clinical outcome in patients treated with the Raf kinase inhibitor BAY 43-9006" Proc Am Sac Clin Oncol 21: 2002 (abstr 1916), 3 pages.

Hirasawa et al., "Effect of p38 Mitogen-Activated Protein Kinase on the Replication of Encephalomyocarditis Virus." Journal of Virology, May 2003: vol. 77, No. 10, pp. 5649-5656.

Holmlund et al., "Phase I Trial of C-raf Antisense Oligonucleotide ISIS 5132 (CGP 69846A) By 21-Day Continuous Intravenous infusion (CIV) In Patients With Advanced Cancer," (Meeting abstract), 1998 ASCO Annual Meeting, Abstract No. 811, 2 pages.

Hotte et al., "BAY 43-9006: Early clinical data in patients with advanced solid malignancies," Current Pharmaceutical Design, 8: 2249-2253, 2002.

Hu et al., "Soluble Vascular Endothelial Growth Factor Receptor 1, and Not Receptor 2, Is an Independent Prognostic Factor in Acute Myeloid Leukemia and Myelodyslastic Syndromes," Cancer, 100(9): 1884-1891 (Published on-line Mar. 29, 2004).

Hubbard, "Oncogenic Mutations in B-Raf: Some Losses Yield Gains," Cell vol. 116, Issue 6, 764-766 (2004).

Hyodo et al., "Clinical Significance of Plasma Vascular Endothelial Growth Factor in Gastrointestinal Cancer," European Journal of Cancer, 34(13): 2041-2045 (1998).

Ihle et al., "Molecular pharmacology and antitumor activity of PX-866, a novel inhibitor of phosphoinositide-3-kinase signaling," Molecular Cancer Therapy, vol. 3, No. 7, 2004, pp. 763-772.

Ishigami et al, "Predictive value of vascular endothelial growth factor (VEGF) in metastasis and prognosis of human colorectal cancer," British Journal of Cancer, 78(10): 1379-1384 (1998).

Jacobsen et al., "Vascular Endothelial Growth Factor as Prognostic Factor in Renal Cell Carcinoma," Journal of Urology, 163(1): 343-347 (Jan. 2000).

Jacobsen et al., "Prognostic importance of serum vascular endothelial growth factor in relation to platelet and leukocyte counts in human renal cell carcinoma," European Journal of Cancer Prevention, 2002, 11(3) pp. 245-252.

Jain et al, "Randomized Discontinuation Trial of Sorafenib (BAY 43-9006)," Cancer Biology & Therapy, vol. 5, Issue 10, pp. 1270-1272 (2006).

Jeffcoat et al., "The Metabolism and Toxicity of Halogenated Carbanilides," Drug Metabolism and Disposition, vol. 5, No. 2, pp. 157-166 (1977).

Jimeno et al., "Analysis of Biologic Surrogate Markers from a Children's Oncology Group Phase 1 Trial of Gefitinib in Pediatric Patients with Solid Tumors," Pediatr. Blood Cancer, 49(3): 352-357 (2007).

Jin et al., "Inhibition of AKT survival pathway by a small molecule inhibitor in hiunan endometrial cancer cells," British Journal of Cancer, vol. 91, 2004, pp. 1808-1812.

Johnson et al., "Relationships between drug activity in NCI preclinical in vitro and in vivo models and early clinical trials," British Journal of Cancer, 2001, vol. 84, No. 10, pp. 1424-1431.

Johnston, D, et al., "Elevation of the Epidermal Growth Factor Receptor and Dependent Signaling in Human Papillomavirus-infected Laryngeal Papillomas." Cancer Research, 1999: vol. 59, pp. 968-974.

Jungmayr, P., "Aktueller Stand der Krebstherapie," Deutsche a iotheker Zeitung, Sep. 30, 2004, Auflage ca. 36,000.

Kapouu et al., "TGFβR1 kinase activity, but not p38 activation is required for TGFβR1-induced myofibroblast differentiation and profibrotic gene expression," Molecular Pharmacology Fast Forward, abstract, 2006, www.molpharmaspetjoumals.org, 2 pages.

Karayiannakis et al., "Circulating VEGF Levels in the Serum of Gastric Cancer Patients," Annals of Surgery, 236(1): 37-42 (Jul. 2002).

Karayiannakis et al., "Clinical significance of preoperative serum vascular endothelial growth factor levels in patients with colorectal cancer and the effect of tumor surgery," Surgery, 131(5): 548-555 (May 2002).

Karp et al., "Targeting Vascular Endothelial Growth Factor for Relapsed and Refractory Adult Acute Myelogenous Leukemias: Therapy with Sequential 1-β-D Arabinofuranosylcytosine, Mitoxantrone, and Bevacizumab," Clinical Cancer Research, 10: 3577-3585 (Jun. 1, 2004).

Katritzky et al., "1.18. Azetidines. Azetines, and Azetes: Monocylcic" pp. 507-508 in: Comprehensive Heterocyclic Chemistry II, A Review of the Literature 1982-1995: The Structure, Reactions, Synthesis, And Uses of Heterocyclic; Compounds. Pergamon Press, Oxford, UK, 1996.

Katritzky, Alan R., Tables of Content, in: Comprehensive Organic Functional Group Transformations. Pergamon Press, Oxford, UK, 1995, 25 pages.

Katritzky et al., "Contents," 2 pages, in: Comprehensive Heterocyclic Chemistry, The Structure, Reactions, Synthesis, and Uses of Heterocyclic Compounds. Pergamon Press, Oxford, UK, 1984.

Keller et al., "The role of Raf kinase inhibitor protein (RKIP) in health and disease." Biochemical Pharmacology 68; pp. 1049-1053 (2004).

Kempter et al., "Synthese potentieller Pflanzenschutz- and Schallingsbekampfungsmittel aus substituierten Anilinen," Padagogsische Hochschule, Eingegangen am 1.7.1982, vol. 27, Issue 1, 101-120 (1983).

Kessler et al., "Use of the DNA Flow-Thru Chip, a Three-Dimensional Biochip, for Typing and Subtyping of Influenza Viruses." Journal of Clinical Microbiology. May 2004: vol. 42, pp. 2173-2185.

Khire et al., "Omega-carboxypyridyl substituted ureas as Raf kinase inhibitors: SAR of the amide substituent," Bioorg. Med. Chem. Lett., 2004, vol. 14, pp. 783-786.

Kido, Y., "Vascular Endothelial Growth. Factor (VEGF) Serum Concentration Changes during Chemotherapy in Patients with Lung Cancer," Kurume Medical Journal, 48(1): 43-47 (2001).

Klemm et al., "Chemistry of Thienopyridines. XXXVII. Syntheses in the Cyclopenta, Cyclohexa-, and Cycloheptathieno[2,3-b]pyridine Series. Threee Analogs of 9-Amino-1,2,3,4-tetrahydroacridine [1]," J. Heterocyclic Chem., 27, 1990, pp. 1537-1541.

van Muijlwijk-Koezen et al., "Isoquinoline and Quinazoline Urea Analogues as Antagonists for the Human Adenosine $A_3$ Receptor," J. Med. Chem. 2000, 43, pp. 2227-2238.

Kolch et al., "Raf-1 protein kinase is required for growth of induced NIH/3T3 cells," Nature, vol. 349, Jan. 31, 1991, pp. 426-428.

Kolch et al., "The role of Raf kinases in malignant transformation" Expert reviews in molecular medicine (Apr. 25, 2002) ISSN: 1462-3994 © Cambridge University Press, 18 pages.

Konecny et al., "Association between HER-2/neu and Vascular Endothelial Growth Factor Expression Predicts Clinical Outcome in Primary Breast Cancer Patients," Clinical Cancer Research, 10: 1706-1716 (Mar. 1, 2004).

Korfee et al, "New targeted treatments in lung cancer-overview of clinical trials," Lung Cancer, 45 (Suppl .2): S199-S208 (2004).

Kraft et al., "Vascular Endothelial Growth Factor in the Sera and Effusions of Patients with Malignant and Nonmalignant Disease," Cancer, 85(1): 178-187 (Jan 1, 1999).

Kubo et al., "Herbicidal Activity of 1,3,4-Thiadiazole Derivatives," J. Agr. Food Chem. (1970), 18(1), pp. 60-65.

Kubo et al., "Synthesis and structure-activity relationship of quinazoline-urea derivatives as novel orally active VEGF receptor tyrosine kinase selective inhibitors," Proceedings of the American Association of Cancer Res., 2002, vol. 43, p. 182, abstract No. 913.

Kuefer et al., "Translational research in renal cell cancer. Illustrated by the example of the vascular endothelial growth factor pathway," Der Urologe, 2006, vol. 45, No. 3, pp. 328, 330-335.

Kumar et al., "Drugs targeted against protein kinases" Expert Opin. Emerging Drugs 6(2):303-315 (2001).

Kupsch et ., "Results of a Phase 1 Trial of Sorafenib (BAY 43-9006) in Combination with Oxaliplatin in Patients with Refractory Solid Tumors, Including Colorectal Cancer," Clinical Colorectal Cancer, Cancer Information Group Journal, vol. 5 Issue 3, pp. 188-196, abstract (Sep. 2005).

Kurik et al., "Optical Properties of Segmented Oligourethane with Azomethine Terminal Fragments," Polymer Science, series B, 1996, vol. 38 pp. 2038-2041.

Kyriakis et al., "Raf-i activates MAP kinase-kinase" Nature, 358, 6385, pp. 417-421 (Jul. 30, 1992).

Laack et al., "Pretreatment serum levels of matrix metalloproteinase-9 and vascular endothelial growth factor in non-small-cell lung cancer," Annals of Oncology, 13(10): 1550-1557 (Oct 2002).

Dal Lago et al., "Selected Combination Therapy with Sorafenib: A Review of Clinical Data and Perspectives in Advanced Solid Tumors" the Oncologist, vol. 13, No. 8, pp. 845-858 (Aug 11, 2008).

Lau et al., "Abrogation of c-Raf expression induces apoptosis in tumor cells," Oncogene 16, 1899-1902 (1998).

Lee et al., "BAY-43-9006 Bayer/Onyx," Current Opinion Investigational Drugs, 2003, vol. 4, No. 6, pp. 757-763.

Lee et al., "Bicyclic Imidazoles as a Novel Class of Cytokine Biosynthesis Inhibitors," Annals N.Y. Academy of Science, 1993, vol. 696, pp. 149-170.

Lee et al.: "FTY720 induces apoptosis of human hepatoma cell lines through P13-K-mediated Akt dephosphorylation," Carcinogenesis, vol. 25, No. 12, 2004, pp. 2397-2405.

Lee et al., "Prognostic value of vascular endothelial growth factor expression in colorectal cancer patients," European Journal of Cancer, 36(6): 748-753 (Apr. 2000).

Lee and Heymach, "Emerging Antiangiogenic Agents in Lung Cancer," Clinical Lung Cancer, 7(5): 304- 308 (Mar. 2006).

Legros et al., "Imatinib mesylate (STI571) decreases the vascular endothelial growth factor plasma concentration in patients with chronic myeloid leukemia," Blood, 104(2): 495-501 (Prepublished on-line Feb 19, 2004).

Lemoine, "Overview of *ras*oncogenes and their clinical potential," Chapter 10, In: Mutant Oncogenes: Targets for Therapy? (eds. Lemoine NR & Epeuetos A), Chapman & Hall, London. pp. 85-91.

Lepage et al., "New N-aryl isoxazolecarboxamides and N-isoxazolybenzamides as anticonvulsant agents," *Eur. J. Med. Chem.*, vol. 27, 1992, pp. 581-593.

Leuner et al., "Improving drug solubility for oral delivery using solid dispersions," European Journal of Pharmaceutics and Biopharmaceutics, 50, 2000, pp. 47-60.

Liang et al., "Differential Expression of VEGF and Its Receptors in the Primary Cells of Various Risk Classified Acute Lymphoblastic Leukemia Patients, " Blood 104: Abstract 4446 (2004).

Li et al. "Correlation of Serum VEGF Levels with Clinical Stage, Therapy Efficacy, Tumor Metastasis and Patient Survival in Ovarian Cancer," Anticancer Research, 24: 1973-1980 (2004).

Lin, "Synthesis of 1-(2-Pyridine-1-oxide)-2-(1-Methyl-2-Pyridinium)-Ethane Chloride," OPPI Briefs, vol. 23, No. 1, 1991, pp. 114-115.

Linderholm et al., "Correlation of Vascular Endothelial Growth Factor Content with Recurrences, Survival, and First Relapse Site in Primary Node-Positive Breast Carcinoma After Adjuvant Treatment," Journal of Clinical Oncology, 18(7): 1423-1431 (Apr. 2000).

Linderholm et al., "p53 and Vascular-Endothelial-Growth-Factor (VEGF) Expression Predicts Outcome in 833 Patients with Primary Breast Carcinoma," Int. J. Cancer (Pred. Oncol.): 89(1): 51-62 (2000).

Lissoni et al., "Anti-angiogenic activity of melatonin in advanced cancer patients, " Neuroendocrinology Letters, 2001, 22:45-47.

Lissoni et al., "Chemotherapy and angiogenesis in advanced cancer: vascular endothelial growth factor (VEGF) decline as predictor of disease control during taxol therapy in metastatic breast cancer, " International Journal of Biological markers, 15(4):308-311 (Oct. 1, 2000).

Lissoni et al., "Abnormally enhanced blood concentrations of vascular endothelial growth factor (VEGF) in metastatic cancer patients and their relation to circulating dentric cells, IL-12 and endothelin-1, " Jornal of Biological Regulators and Homostatic Agents, 15(2): 140-144 (Apr. 2001).

Lissoni et al., "Changes in circulating VEGF levels in relation to clinical response during chemotherapy for metastatic cancer, " International Jornal of Biological Markers, 18(2): 152-155 (2003).

Llovet et al., "Molecular Targeted Therapies in Hepatocellular Carcinoma, " Hepatology, vol. 48, No.4, pp. 1312-1327, 2008.

Lockhart et al., "Phase I/Pilot Study of SU5416 (Semaninib) in Combination With Irinotecan/Bolus 5-FU/LV (IFL) in Patients With Metastatic Colorectal Cancer, " American Journal of Clinical Oncology, 29(2):109-115 (Apr. 2006).

Lorigan et al., "Phase II trial of sorafenib combined with dacarbazine in metastatic melanoma patients" ASCO 2006 DTIC abstract, 2 pages (Jan. 11, 2006).

Lowinger et al., "Design and Discovery of Small Molecules Targeting Raf-1 Kinase, " Current Pharmaceutical Design, 2002, vol. 8, pp. 2269-2278.

Lowinger et al., "Discovery of novel class of potent Raf kinase inhibitors: structure activity relationships, " Clinical Cancer Research, Nov. 2000, vol. 6 (Suppl.), p. 4533s, abstract No. 335.

Lowy et al., "Function and Regulation of RAS" Annual Review of Biochemistry, vol. 62, pp. 851-891, 1993.

Ludwig et al., "MEK inhibition impairs influenza B virus propagation without emergence of resistant variants," FEBS Letters, 2004, vol. 561, pp. 37-43.

Luo et al., "Enhancement of radiation effects by pXLG-mENDO in a lung carcinoma model, " Int. J. Radiation Oncology Biol. Phys., 2005, vol. 63, No. 2, pp. 553-564.

Lyons et al., "Discovery of a novel Raf kinase inhibitor, " *Endocrine-Related Cancer*, 2001, vol. 8, pp. 219-225.

Madwed et al., "Pharmacological evaluation of BIRB 796, a selective inhibitor of p38 MAP kinase (MAPK), in animal models of endotoxic shock, inflammation and arthritis, " Inflammation Res., 50:S184, abstract No. W22/03, 2001.

Magnuson et al., "The Raf-1 serine/threonine protein kinase," cancer Biology, vol. 5, 1994, pp. 247-253.

Manenti et al., "Circulating plasma vascular endothelial growth factor in mice bearing human ovarian carcinoma xengraft correlates with tumor progression and response to therapy," Molecular Cancer Therapeutics, 4(5): 715-725 (May 2005).

Mannová et al., "Activation of the N-Ras-P13K-Akt-mTOR Pathway by Hepatitis C Virus: Control of Cell Survival and Viral Replication," Journal of Virology, Jul. 2005, vol. 79, No. 14, pp. 8742-8749.

Markgraf et al., "Strained Heterocyclic Systems. 19. 1-Azatriptycene and Derivatives," Tetrahedron, vol. 47, No. 2, 1991, pp. 183-188.

Marshall, "MAP kinase kinase kinase, MAP kinase kinase, and MAP kinase," Curr. Opin. Genet. Dev. 4: 82-89, 1994.

Marx, J., "Why a New Cancer Drug Works Well, In Some Patients." Science, vol. 304, pp. 658-659, 2004.

McGoon et al., "Screening, Early Detection, and Diagnosis of Pulmonary Arterial Hypertension," CHEST, 2004: 126, pp. 14S-34S.

Medinger et al.. "Hemmung der Tumorangiogenese Neue Therapieoptionen in der Onkologie,"Med Welt, 2006, 57, pp. 437-441.

Med Report Deutschland, "Sorafenib zur Therapie des fortgeschrittenen Nierenzellkarzinoms zugelassen," (2006), 1 page.

Meuillet et al., "In Vivo Molecular Pharmacology and Antitumor Activity of the Targeted Akt Inhibitor PX-316," Oncology Research, vol. 14, 2004. pp. 513-527.

Michaelis, "Phenylharnstoff des 1-Phenyl-3-methyl-5-aminopyrazols,"Justus Liebigs Ann. Chem. (JLACBF) 397, 1913, p. 143.

Milanini et al., "p42/p44 MAP Kinase Module Plays a Key Role in the Transcriptional Regulation of the Vascular Endothelial Growth Factor Gene in Fibroblasts," Journal of Biological Chemistry, 273(29): 18165-18172 (Jul. 17, 1998).

Milano et al., "New molecular targeted therapies in thyroid cancer" Anti-Cancer Drugs (2006) © Lippincott Williams & Wilkins , vol. 17:869-879.

Mills et al., "The Effects of Standard Anthracycline-Based Chemotherapy on Soluble ICAM-1 and Vascular Endothelial Growth Factor Levels in Breast Cancer," Clinical Cancer Research, 10: 4998-5003 (Aug. 1, 2004).

Milojokovic et al., "Immunohistochemical Characterisation of Vascular Endothelial Growth Factor (VEGF) and its Receptors Flt-1 and KDR in Chronic Myeloid Leukaemia (CML) Patients Treated with Imatinib Mesylate," Blood, 104 Abstract 1999 (2004).

Minna et al., "A Bull's Eye for Targeted Lung Cancer Therapy," Science, vol. 304, pp. 1458-1460, 2004.

Mita et al., "The Molecular Target of Rapamycin (mTOR) as a Therapeutic Target Against Cancer." Cancer Biology & Therapy 2:4 Suppl. 1, S169-S177 (Jul./Aug. 2003).

Moelling et al., "Signal Transuction as Target of Gene Therapy," Institute of Medical Virology, University of Zärich, Recent Results in Cancer Research, vol. 142, pp. 63-71 (1996).

Molhoek et al., "Synergistic inhibition of human melanoma proliferation by combination treatment with B-Raf inhibitor BAY 43-9006 and mTOR inhibitor rapamycin," Journal of Translational Medicine (2005) 3:39, pp. 1-11.

Monia, "First-and second-generation antisense oligonucleotide inhibitors targeted against human c-*raf*kinase," (1997) Oligonucleotides as therapeutic agents Wiley, Chichester (Ciba Foundation Symposium 209) pp. 107-123.

Monia et al., "Antitumor activity of a phosphorothioate antisense oligodeoxynucleotide targeted against C- *raf*kinase," Nature Medicine, vol. 2, No. 6, Jun. 1996, pp. 668-675.

Monia et al., "Sequence-specific antitumor activity of a phosphorothioate oligodeoxyribouucleotide targeted to human C-*raf*kinase supports and antisense mechanism of action in *vivo*," Proc. Natl. Acad. Sci USA, vol. 93, 15481-15484 (Dec. 1996).

Morabito et al., Tyrosine Kinase Inhibitors of Vascular Endothelial Growth Factor Receptors I Clinical Trials: Current Status and Future Directions, The Oncologist, 11: 753-764 (2006).

Mori et al., "Differential activation of the c-Jun N-terminal kinase/stress-activated protein kinase and p38 mitogen-activated protein kinase signal transduction pathways in the mouse brain upon infection with neurovirulent influenza A virus," Journal of General Virology, 2003, 84, pp. 2401-2408.

Moore et al., "Phase I study to determine the safety and pharmacokinetics of the novel Raf kinase and VEGFR inhibitor BAY 43-9006, administered for 28 days on/7 days off in patients with advanced, refractory solid tumors," Annals of Oncology, 2005, vol. 16, pp. 1688-1694.

Motzer et al., "Survival and Prognostic Stratification Of 670 Patients With Advanced Renal Cell Carcinoma", J. Clin. Oncol., 17(8):pp. 2530-2540 (1999).

Mross et al., "Drug-drug interaction pharmacokinetic study with the Raf kinase inhibitor (RKI) BAY 43-9006 administered in combination with irinotecan (CPT-11) in patients with solid tumors," International Journal of Clinical Pharmacology and Therapeutics, 2003, vol. 41, No. 12, pp. 618-619.

Mross et al., "Results from an *in vitro* and a clinical/pharmacological phase I study with the combination irinotecan and sorafenib" European Journal of Cancer 43, pp. 55-63 (2007).

Murata et al., "Facile Synthesis of New Pyrrolo[3,4-*d*]pyrimidine-2,4-diones," Chemical and Pharmaceutical Bulletin, vol. 22, No. 5, 1974, pp. 1212-1213.

Murphy et al., "BAY 43-9006 controls tumor growth through inhibition of vascular development," 96th Annual Meeting, Anaheim/Orange County, CA, Apr. 16-20, 2005, abstract No. 2985.

Muthumani et al., "Suppression of HIV-1 viral replication and cellular pathogensis by a novel p38/JNK kinase inhibitor," AIDS. Lippincott Williams & Wilkins, 2004: vol. 18, pp. 739-748.

National Cancer Institute, "Carboplatin and Paclitaxel With or Without Sorafenib in Treating Patients With Unresectable Stage III or Stage IV Melanoma", 7 pages, NCT00110019, clinicaltrials.gov. (2005).

National Cancer Institute, "Paclitaxel, Carboplatin, and Radiation Therapy in Treating Patients Who Are Undergoing Surgery for Stage III Non-Small Cell Lung Cancer," 5 pages, NCT00096226, (2005).

National Cancer Institute, "Sorafenib With or Without Paclitaxel and Carboplatin in Treating Patients With Recurrent Ovarian Cancer, Primary Peritoneal Cancer, or Fallopian Tube Cancer," 5 pages, NCT00096200, (2005).

National Cancer Institute, Clinical Trials (PDQ ® ), "Phase II Randomized Study of ISIS 5132 or ISIS 3521 in Women with Previously Treated Metastatic Breast Cancer," 3 pages, www.cancer.gov website (1998).

National Cancer Institute, Clinical Trials (PDQ® ), "Phase II Randomized Study of ISIS 3521 and ISIS 5132 for Locally Advanced or Metastatic Colorectal Cancer," 3 pages, www.cancer.gov website (1998).

National Cancer Institute, Clinical Trials (PDQ ® ), "Phase II Randomized Study of ISIS 3521 and ISIS 5132 in Patients with Hormone Refractory Prostate Cancer," 3 pages, www.cancer.gov website (1998).

National Cancer Institute, Clinical Trials (PDQ® ), "Phase II Study of ISIS 5132 in Patients with Advanced Pancreatic Cancer," 3 pages, www.cancer.gov website (1999).

National Institutes of Health Clinical Center, "BAY 43-9006 (Sorafenib) to Treat Relapsed Non-Small Cell Lung Cancer", 4 pages, NCT00098254, clinicaltrials.gov (2005).

Naumann et al., "Raf protein serine/threonine kinases" in: Protein Phosphorylation, VCH Verlagsgesellschaft mbH Chapter 7, pp. 203-236 (1996).

Naumann et al., "The Role of Raf Kinases in Development and Growth of Tumors" Recent Results in Cancer Research, vol. 143, pp. 237-244.

Nemunaitis et al., "Phase I Evaluation of ISIS 3521, an Antisense Oligodeoxynucleotide to Protein Kinase C-Alpha, in Patients with Advanced Cancer" Journal of Clinical Oncology, vol. 17, No. 11, pp. 3586-3595 (Nov. 1999).

Neufeld et al., "Vascular endothelial growth factor (VEGF) and its receptors, "The FASEB Journal, 13: 9-22 (Jan. 1999).

"Nexavar Receives FDA Fast Track Designation for Skin Cancer" 4 pages, (Jul. 21, 2006) http:// www.medicalnewstoday.com/articles/47793.php (last visited on Jun. 16, 2008).

Nicholson, K. M. et al.: "The protein kinase B/Akt signalling pathway in human malignancy," Cellular Signalling 14, 2004, pp. 381-395.

Nickel et al., "Carboxylic acid analogues of suramin, potential filaricides," Indian Journal of Chemistry, Feb. 1991, vol. 30B, pp. 182-187.

Nilsson et al., "Vascular Endothelial Growth Factor (VEGF) Pathway," Journal of Thoracic Oncology, 1(8): 768-770 (Oct. 2006).

Noble et al., "Protein Kinase Inhibitors: Insights into Drug Design From Structure," Science, (2004), vol. 303, pp. 1800-1805.

O'Dwyer et al., "c-*raf*-1 Depletion and Tumor Responses in Patients Treated with the c-*raf*-1 Antisense Oligodeoxynucleotide ISIS 5132 (CGP 69846A)," Clinical Cancer Research vol. 5, pp. 3977-3982 (Dec. 1999).

Oka et al., "Constitutive Activation of Mitogen-activated Protein (MAP) Kinases in Human Renal Cell Carcinoma," Cancer Research 55, pp. 4182-4187, (Sep. 15, 1995).

Gollob et al., "Phase II trial of sorafenib (BAY 43-9006) in combination with interferon alpha 2b in patients with metastatic renal cell carcinoma," European Journal of Cancer, 2005, vol. 3, No. 2, pp. 226-227. abstract No. 795.

Osella-Abate et al., "VEGF-165 serum levels and tyrosinase expression in melanoma patients: correlation with the clinical course," Melanoma Research, 12: 325-334 (Aug. 2002).

Oza et al., "Phase II study of CGP 69846A (ISIS 5132) in recurrent epithelial ovarian cancer: an NCIC clinical trials group study (NCIC IND.116)," PubMed Abstract 12694666, Gynecol. Oncol. 2003 Apr: 89(1): 129-133.

Ozols, "New Developments With Carboplatin in the Treatment of Ovarian Cancer," *Seminars in Oncology*, vol. 19, No. 1, Supplement 2, Feb. 1992, pp. 85-89.

Panka et al., "BAY 43-9006 induces apoptosis in melanoma cell lines," 96th Annual Meeting, Anaheim/Orange County, CA, Apr. 16-20, 2005, abstract No. 5328.

Panteva et al., "Hepatitis viruses and the MAPK pathway: is this a survival strategy?" Virus Research, 2003, vol. 92: 131-140.

Paquette, Table of Contents for the Encyclopedia of Reagents for Organic Synthesis, John Wiley, New York, 1994 Table of Contents.

Pavlović-Lažetić et al., "Biointhrmatics analysis of SARS coronavinls genome polymorphism," May 25, 2004, BMC Biointhrmatics, vol. 5:65, 14 pages.

Pederson et al., "Early changes in serum IL-6 and VEGF levels predict clinical outcome following first-line therapy in aggressive non-Hodgkin's lymphoma," Ann. Hematol., 84:510-516 (2005).

Peters, H.D. "Sorafenib bei soliden Tumoren," Focus Onkologie, 2007, Auflage 12000, 6 pages.

Robert et al., "Phase I trial of sorafenib (BAY 43-9006) in combination with interferon alpha-2a in patients with unresectable and/or metastatic renal cell carcinoma and malignant melanoma," European Journal of Cancer, 2005, vol. 3, No. 2, p. 254, Abstract 883.

Hu et al., "Soluble Vascular Endothelial Growth Factor Receptor 1, and Not Receptor 2, Is an Independent Prognostic Factor in Acute Myeloid Leukemia and Myelodysplastic Syndromes," Cancer 2004, vol. 100, No. 9, pp. 1884-1891.

Raez et al., "New developments in chemotherapy for advanced non-small cell lung cancer," Current Opin. Oncol., vol. 18, 2006, pp. 156-161.

Rahmani et al., "Apoptosis Induced by the Kinase Inhibitor BAY 43-9006 in Human Leukemia Cells Involves Down-regulation of Mcl-1 through Inhibition of Translation," J. Biol, Chem. 280(42):35217-35227 (2005).

Rak et al., "Oncogenes and Angiogenesis: Signaling Three-Dimensional Tumor Growth," Journal of Investigative Dermatology Symposium Proceedings (2000) 5, 24-33.

Rak et al., "Oncogenes and Tumor Angiogenesis: Differential Modes of Vascular Endothelial Growth Factor Up-RegUlation in *ras*-transformed Epithelial Cells and Fibroblasts," Cancer Research 60, pp. 490-498, (Jan. 15, 2000).

Rak et al., "Oncogenes as inducers of tumor angiogenesis," Cancer and Metastasis Reviews 14: 263-277, 1995.

Sturm-Ramirez et al., "Reemerging H5N1 Influenza Viruses in Hong Kong in 2002 Are Highly Pathogenic to Ducks," Journal of Virology, May, 2004, 78(9):4892-4901.

Raposo et al., "Catalysis of Nucleophilic Addition of Pyrrolidine to 2-(5H)-Furanone through Chromenone Cleft-Type Receptors," Tetrahedron Letters vol. 37, No. 38, pp. 6947-6950, 1996.

Ratain et al., "Phase II Placebo-Controlled Randomized Discontinuation Trial of Sorafenib in Patients with Metastatic Renal Cell Carcinoma," Journal of Clinical Oncology vol. 24 No. 16, pp. 2505-2512 (Jun. 1, 2006).

Ravi et al., "Activated Raf-1 Causes Growth Arrest in Human Small Cell Lung Cancer Cells," J. Clin. Invest., vol. 101, No. 1, pp. 153-159 (1998).

Reddy et al., "Sorafenib: recent update on activity as a single agent and in combination with interferon-alpha2 in patients with advanced-stage renal cell carcinoma," Clin. Genitourin. Cancer 4:246-248 (2006) abstract.

Redman et al., "p38 Kinase Inhibitors for the Treatment of Arthritis and Osteoporosis: Thienyl, Furyl, and Pyrrolyl Ureas," Bioorganic & Medicinal Chemistry Letters 11 (2001) 9-12.

Regan et al., "Pyrazole Urea-Based Inhibitors of p38 MAP kinase: From Lead Compound to Clinical Candidate." J. Med. Chem. 45:2994-3008, 2002.

Richly et al., "A phase I clinical and pharmacokinetic study of the Raf kinase inhibitor (RKI) BAY 43-9006 administered in combination with doxorubicin in patients with solid tumors," International Journal of Clinical Pharmacology and Therapeutics, 2003, vol. 41, No. 12, pp. 620-621.

Richly et al., "Results of a Phase I trial of sorafenib (BAY 43-9006) in combination with doxorubicin in patients with refractory solid tumors," Annals of Oncology, 2006, 17, pp. 866-873.

Richly et al., "Results of a phase I trial of BAY 43-9006 in combination with doxorubicin in patients with primary hepatic cancer," International Journal of Clinical Pharmacology and Therapeutics, 2004; vol. 42, No. 11, pp. 650-651.

Ridley et al., "Actions of IL-1 are Selectively Controlled by p38 Mitogen-Activated Protein Kinase, Regulation of Prostaglandin H Synthase-2, Metalloproteinases, and IL-6 at Different Levels," The American Association of Immunologists, 1997, J. Immunol. vol. 158, pp. 3165-3173.

Rini and Small, "Biology and Clinical Development of Vascular Endothelial Growth Factor-Targeted Therapy in Renal Cell Carcinoma," Journal of Clinical Oncology, 23(5): 1028-1043 (Feb. 10, 2005).

Robak et al., "Vascular endothelial growth factor and its soluble receptors VEGFR-1 and VEGFR-2 in the serum of patients with systemic lupus erythematosus," Mediators of Inflammation 12(5):293-298 (Oct. 2003).

Robertson et al. "HIV-1 Nomenclature Proposal," Science, Apr. 7. 2000, pp. 55-57. Vol. 288.

Robinson et al., "Enhanced Radiosensitization with Gemcitabine in Mismatch Repair-Deficient HCT116 Cells," Cancer Research 63, 6935-6941 (Oct. 15, 2003).

Robke et al., "Conversion of Aminopyridines into N-Oxides by Caro's Acid Anion (Peroxymonosulfate)," J. Chem. Research (S), 1993, pp. 412-413.

Roche, E. B., "Structural Aspects of Selective Distribution," Chapter 3, in: Design of Biopharmaceutical Properties Through Prodrugs and Analogs, American Pharmaceutical Association, Washington, D.C., 1977, pp. 27-46.

Rodriguez et al., "A sensitive fluorometric enzyme-linked immunosorbent assay that measures vascular endothelial growth factor$_{165}$ in human plasma," Journal of Immunological Methods, 219(1-2): 45-55 (Oct. 1998).

Roman et al., "Human Papillomaviruses: Are We Ready to Type?" Clinical Microbiology Reviews. Apr. 1989: vol. 2, pp. 166-190.

Rowinsky et al., "Sequences of Taxol and Cisplatin: A Phase I and Pharmacologic Study," Journal of Clinical Oncology, vol. 9, No. 9, Sep. 1991, pp. 1692-1703.

Rowinsky et al., "Taxol: The First of the Taxanes, an Important New Class of Antitumor Agents," *Seminars in Oncology*,vol. 19, No. 6, Dec. 1992, pp. 646-662.

Rubin, Lewis J., "Primary Pulmonary Hypertension," New England Journal of Medicine, vol. 336, No. 2, pp. 111-117 (1997).

Rudin et al., "Phase I Trial of ISIS 5132, an Antisense Oligonucleotide Inhibitor of c-raf-1, Administered by 24-hour Weekly Infusion to Patients with Advanced Cancer" Clinical Cancer Research vol. 7, pp. 1214-1220 (May 2001).

Russo et al., "Sintesi Di Derivati 2,6-Sostituiti Del 5H-1,3,4-Tiadiazolo[3,2-a]-s-Triazina-5,7-Dione," Il Farmaco, Ed.Sci. (1978), 33(12), 972-983.

Rydén et al., "Tumor specific VEGF-A and VEGFR2/KDR protein are co-expressed in breast cancer," Breast Cancer Research and Treatment, 82(3):147-154 (Dec. 2003).

Salvatore et al, "BRAF Is a Therapeutic Target in Aggressive Thyroid Carcinoma," Clin. Cancer Res. pp. 1623-1629; 12(5) (Mar. 1, 2006).

Sarkar et al., "Indole-3-Carbinol and Prostate Cancer," Journal of Nutrition 134, 2004, pp. 3493S-3498S.

Serajuddin, "Solid Dispersion of Poorly Water-Soluble Drugs: Early Promises Subsequent Problems, and Recent Breakthroughs," Journal of Pharmaceutical Sciences vol. 88, No. 10, pp. 1058-1066 (Oct. 1999).

Shaked et al., "Cellular and Molecular Surrogate Markers to Monitor Targeted and Non-Targeted Antiangiogenic Drug Activity and Determine Optimal Biologic Dose," Current Cancer Drug Targets, 5: 551-559 (Nov. 2005).

Shelton et al., "Effects of the RAF/MEK/ERK and PI3K/AKT signal transduction pathways on the abrogation of cytokine-dependence and prevention of apoptosis in hematopoietic cells," Oncogene, vol. 22, No. 16, Apr. 2003; pp. 2478-2492.

Shi et al., "Constitutive and Inducible Interleukin 8 Expression by Hypoxia and Acidosis Renders Human Pancreatic Cancer Cells More Tumorigenic and Metastatic," *Clinical Cancer Research*,1999, vol. 5, pp. 3711-3721.

Shimanuki et al., "Role of Serum Vascular Endothelial Growth Factor in the Prediction of Angiogenesis and Prognosis for Non-small Cell Lung Cancer," Lung, 183: 29-42 (2005).

Simone, Joseph, V., "Part XIV. Oncology," in: Cecil Textbook of Medicine, 20th Edition, vol. 1, 2-3-1997. W.B. Saunders Company, pp. 1004-1010.

Sinkula et al., "Rationale for Design of Biologically Reversible Drug Derivatives: Prodrugs," Journal of Pharmaceutical Sciences, vol. 64, No. 2, Feb. 1975, pp. 181-210.

Siu et al., "Phase 1 study of oral raf-1 kinase inhibitor BAY 43-9006 with gemcitabine in patients with advanced solid tumors," Abstract No. 828, Proc. Am. Soc. Clin. Oncol., 2003, vol. 22, p. 207.

Siu et al., "Phase 1 Trial of Sorafenib and Gemcitabine in Advanced Solid Tumors with an Expanded Cohort in Advanced Pancreatic Cancer," Clin. Cancer Res. 12(1):144-151 (2006).

Smith et al., "Discovery of Heterocyclic Ureas as a New Class of Raf Kinase Inhibitors: Identification of a Second Generation Lead by a Combinatorial Chemistry Approach," Bioorganic & Medicinal Chemistry Letters, 2001, vol. 11, pp. 2775-2778.

Smith et al., (Abstract) "Recent Advances in the Research and Development of RAF Kinase Inhibitors," Current Topics in Medicinal Chemistry 6(11):1071-1089 (2006).

Smyth, R.M. et al., "Anchimeric Assistance in the Specific Acid-catalysed Hydration of Benzonitriles" J. Chem. Soc. Perkin Trans. 2 1993 pp, 2171-2174.

Song, Huai-Dong et al., "Cross-host evolution of severe acute respiratory syndrome coronavirus in palm civet and human," Proc. Natl. Acad. Sci. USA 102(7):2430-2435 (2005).

Sorbara et al "BAY-43-9006," Drugs of the Future, 2002, vol. 27, No. 12, pp. 1141-1147.

van Spronsen et al., "Novel treatment strategies in clear-cell metastatic renal cell carcinoma," Anti-Cancer Drugs, 2005, vol. 16, pp. 709-717.

Stadler et al., "A Randomized Phase II Trial of the Antiangiogenic Agent SU5416 in Hormone-Refractory Prostate Cancer," Clinical Cancer Research, 10: 3365-3370 (May 15, 2004).

Stahl et al., "Deregulated Akt3 Activity Promotes Development of Malignant Melanoma," Cancer Research, Vol. 64, No. 19; Oct. 2004; pp. 7002-7010.

Stavchansky et al., "Evaluation of the Bioavailability of a Solid Dispersion of Phenytoin m Polyethylene Glycol 6000 and a Commercial Phenytoin Sodium Capsule in the Dog," Journal of Pharmaceutical Sciences, vol. 73, No. 6, Jun. 1984, pp. 733-736.

Krontiris, "Chapter 71. Molecular and Cellular Biology of Cancer," and Capizzi, "Chapter 72, Principles of Treatment of Cancer," in: Internal Medicine, 4th Edition, Stein, Jay H., MD, Ed., Mosby, 1994, pp. 699-715.

Sternberg et al., "Conspiracy Theory: RAS and RAF Do Not Act Alone" Cell, vol. 95, pp. 447-450 (Nov. 13, 1998).

Stella et al., "Prodrugs and Site-Specific Drug Delivery," Journal of Medicinal Chemistry, vol. 23, No. 12, Dec. 1980, pp. 1275-1282.

Stella et al., "Prodrugs as therapeutics," Exp. Opin. Ther. Patents 14(3): 277-280 (2004).

Stella et al., "Prodrugs. Do They Have Advantages in Clinical Practice?" Drugs, vol. 29, 1985, pp. 455- 473.

Stevenson et al., "Phase I Clinical/Pharmacokinetic and Pharmacodynamic Trial of the c-*raf*-1 Antisense Oligonucleotide ISIS 5132 (CGP 69846A)," The Journal of Clinical Oncology, vol. 17, No7: pp. 2227-2236 (Jul. 1999).

Stöckl et al, "Integrity of c-Raf-1/MEK signal transduction cascade is essential for hepatitis B virus gene expression," Oncogene. Nature Publishing Group, 2003: vol. 22, pp. 2604-2610.

Stokoe et al., "Activation of c-Raf-1 by Ras and Src through different mechanisms: activation *in vivo* and *in vitro*," The Embo Journal, vol. 16 No. 9 pp. 2384-2396 (1997).

Storm et al., "*raf*Oncogenes in Carcinogenesis" Critical Reviews in Oncogenesis, vol. 2, Issue 1, pp. 1-8 (1990).

Strumberg, D., "Preclinical and Clinical Development of the Oral Multikinase Inhibitor Sorafenib in Cancer Treatment," Drugs of Today, 41(12): 773-784 (2005).

Strumberg et al., "Phase I Clinical and Pharmacokinetic Study of the Novel Raf Kinase and Vascular Endothelial Growth Factor Receptor Inhibitor BAY 43-9006 in Patients With Advanced Refractory Solid Tumors," Journal of Clinical Oncology, Feb. 10, 2005, vol. 23, No. 5, pp. 965-972.

Strumberg et al., "Phase I Clinical, Pharmacokinetic and Pharmacodynamic Study of the Raf Kinase Inhibitor BAY 43-9006 in Patients with Locally Advanced or Metastatic Cancer," Proc. Am. Soc. Clin. Oncol. 20: 2001 (abstr 330).

Strumberg et al., "Results of phase I pharmacokinetic and pharmacodynamic studies of the Raf kinase inhibitor BAY 43-9006 in patients with solid tumors," International Journal of Clinical Pharmacology and Therapeutics, 2002, vol. 40, No. 12, pp. 580-581.

Strumberg et al., "Sorafenib Neue Therapieoption in der Onkologie," Krankenhauspharmazie, 2007, vol. 28, pp. 93-97, pp. 1/5, 2/5, 3/5 and 4/5.

Suzuki et al., "The role of p38 mitogen-activated protein kinase in IL-6 and IL-8 production from the TNF-α- or IL-1β-stimulated rheumatoid synovial fibroblasts," FEBS Letters (2000), vol. 465, pp. 23-27.

Swarbrick et al., "Contents," pp, xvii-xviii in: Encyclopedia of Pharmaceutical Technology, 2nd Edition, Marcel Dekker, Inc. 2002.

Swart, Guido W.M., "International Melanoma Research Congress —Foundation for Melanoma Research," IDRUGS: The Investigational Drugs Journal, Aug. 2003; vol. 6, No. 8, pp. 752-754.

Tabellini et al., "Novel 2'-substituted, 3'-deoxy-phosphatidyl-myo-inositiol analogues reduce drug resistance in human leukaemia cell lines with an activated phosphoinositide 3-kinase/Akt pathway," British Journal of Haematology, 126, 2004, pp. 574-582.

Takimoto et al., "Safety and anti-tumor activity of sorafenib (Nexavar®) in combination with other anticancer agents: a review of clinical trials," Cancer Chemotherapy and Pharmacology (2008) 61:535-548.

Tamm et al., "Hypoxia-Induced Interleukin-6 and Interleukin-8 Production Is Mediated by Platelet Activation Factor and Platelet-Derived Factor in Primary Human Lung Cells," Am. J. Respir. Cell Mol. Biol. vol. 19, pp. 653-661, (1998).

Tanaka et al., "Current status and perspective of antiangiogenic therapy for cancer: hepatocellular carcinoma," Int. J. Clin. Oncol. (2006) 11:82-89 (2006).

Tang et al., "Inhaled nitric oxide attenuates pulmonary hypertension and improves lung growth in infant rats after neonatal treatment with a VEGF receptor inhibitor." Am. J. Physiol. Lung Cell, Mol. Physiol. 287:L344-L351 (2004).

Tarzia et al., "Synthesis and anti-inflammatory properties of some pyrrolo(1H,3H) [3,4-d ]pyrimidin-2-ones and pyrrolo=(1H,6H)[3,4-d]pyrimidin-2-ones,"Chemical Abstracts, vol. 91, 1979, 91:74558p.

Teknos et al., "Elevated Serum Vascular Endothelial Growth Factor and Decreased Survival in Advanced Laryngeal Carcinoma," Head & Neck, 24: 1004-1011 (Nov. 2002).

Thaimattam et al,, "3D-QSAR CoMFA, CoMSIA studies on substituted ureas as Raf-1 kinase inhibitors and its confirmation with structure-based studies," Bioorganic & Medicinal Chemistry, 2004, vol. 12, pp. 6415-6425.

Thelen et al., "VEGF-D promotes tumor growth and lymphatic spread in a mouse model of hepatocellular carcinoma" Int. J. Cancer 122, 2471-2481 (2008) © 2008 Wiley-Liss, Inc.

Thompson et al., "Recent progress in targeting the Raf/MEK/ERK pathway with inhibitors in cancer drug discovery," Curr. Opin. Pharmacol., Aug. 2005, vol. 5, No. 4, pp. 350-356.

Tong et al., "Pharmacodynamic Monitoring of BAY 43-9006 (Sorafenib) in Phase I Clinical Trials Involving Solid Tumor and AML/MDS Patients, Using Flow Cytometry to Monitor Activation of the ERK Pathway in Peripheral Blood Cells," Cytometry Part B (Clinical Cytometry) 70B: 107-114 (2006).

Trost et al., "Contents," vols. 1-9, 36 pages in: Comprehensive Organic Synthesis: Selectivity, Strategy & Efficiency in Modern Organic Chemistry, Pergamon Press, Oxford, UK. 1991.

Gupta-Abramson et al., "Phase II Trial of Sorafenib in Advanced Thyroid Cancer" Journal of Clinical Oncology vol. 26, No. 29. pp. 4714-4719 (Oct. 10, 2008).

Veronese et al., "Mechanisms of Hypertension Associated With BAY 43-9006," Journal of Clinical Oncology, 2006, vol. 24, No. 9, pp. 1363-1369.

Vivanco et al., "The Phosphatidylinositol 3-Kinase-AKT Pathway in Human Cancer," Nature Reviews Cancer, vol. 2, Jul. 2002. pp. 489-501.

Vlahos et al., "A Specific Inhibitor of Phosphatidylinositol 3-Kinase, 2-(4-Morpholinyl)-8-phenyl-4H-1- benzopyrart-4-one (LY294002)," The Journal of Biological Chemistry, vol. 269, No. 7, 1994, pp. 5241-5248.

Wakelee et al., "Targeting Angiogenesis with Vascular Endothelial Growth Factor Receptor Small-Molecular Inhibitors: Novel Agents with Potential in Lung Cancer," Clinical Lung Cancer, 7(Suppl 1): S31-S38 (Sep. 2005).

Wald et al.. "Involvement of the CXCL12/CXCR4 pathway in the advanced liver disease that is associated with hepatitis C virus or hepatitis B virus," Eur. J. Immunol., vol. 34, p. 1164-1174 (2004).

Wan et al., "Mechanism of Activation of the RAF-ERK Signaling Pathway by Oncogenic Mutations of B-Raf," Cell, Mar. 19, 2004, vol. 116, pp. 855-867.

Weekly Epidemiological Record, "Influenza," World Health Organization. Apr. 1999; vol. 14, pp. 111-112.

Wermuth, C. G., "Designing Prodrugs and Bioprecursors II: Bioprecursor Prodrugs," in: The Practice of Medicinal Chemistry, Academic Press Limited 1996, pp. 697-715.

White et al., "Heterocyclic Ureas: Inhibitors of Acyl-CoA:Cholesterol O-Acyltransferase as Hypocholesterolemic Agents," J. Med. Chem. 1996, 39, pp. 4382-4395.

Wierzbowska et al., "Circulating VEGF and its soluble receptors sVEGFR-1 and sVEGFR-2 in patients with acute leukemia," Eur. Cytokine Netw., 14(3): 149-153 (Sept. 2003).

Wilhelm et al., "A Novel RAF Kinase Inhibitor Blocks the RAF/MEK/ERK Pathway in Tumor Cells," Poster, 92nd Annual Meeting of the American Association for Cancer Research, Mar. 24-28, 2001, New Orleans, LA USA, 1 page.

Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research, Oct. 1, 2004, Vol. 64, pp. 7099-7109.

Wilhelm et al., "BAY 43-9006: Preclinical Data," Curr Pharm Des, 2002, vol. 8, No. 25, pp. 2255- 2257.

Wilhelm et al., "Discovery and development of sorafenib: a multikinase inhibitor for treating cancer," Nature Reviews, Drug Discovery, 2006, vol. 5, pp. 835-844.

Wilhelm et al., "Preclinical overview of sorafenib, a multikinase inhibitor that targets both Raf and VEGF and PDGF receptor tyrosine kinase signaling," Mol. Cancer Ther., 2008, vol. 7, No. 10, pp. 3129-3140.

Wilkinson Geoffrey, "Contents," 7 pages in: Comprehensive Organometallic Chemistry. The Synthesis, Reactions, and Structures of Organometallic Compounds, Pergamon Press, Oxfrod U.K. 1982: vol. 1-3.

Wilson et al., "The structural basis for the specificity of pyridinylimidazole inhibitors of p38 MAP kinase," Chemistry & Biology, 1997, vol. 4, No. 6, pp, 423-431.

Stollorz, "Die Krebsformel, die der Zufall fand," Frankfurter Allgemeine Sonntagszeitung, Jul. 2, 2006, NR 26, pp. 68-69.

Wissner et al., "Analogues of Platelet Activating Factor. 7. Bis-Aryl Amide and Bis-Aryl Urea Receptor Antagonists of PAF," J. Med Chem.,1992, vol. 35, pp. 4779-4789.

Wojnowski et al., "Endothelial apoptosis in Braf-deficient mice," Nature Genetics vol. 16, pp. 293-297 (Jul. 1997).

Onyx Pharmaceuticals, Inc.,"Novel RAF Kinase Inhibitor Bay 43-9006 Shows Early Signs of Tolerability and Activity in Phase 1B Combination Trials Reported at ASCO," 1 page, (Press Release: Jun. 2, 2003).

Wright et al., "Bovine immunodeficiency Virus Expression in Vitro is Reduced in the Presence of βChemokines, MIP-1α, MIP-1β and RANTES" Veterinary Research Communications. 2002: vol. 26, pp. 239-250.

Wright et al., "Clinical Trials Referral Resource. Current Clinical Trials of BAY 43-9006, Part 1," Oncology, Apr. 2005, vol. 19, No. 4: pp. 499-502.

Wu et al., "Plasma vascular endothelial growth factor is useful in assessing progression of breast cancer post surgery and during adjuvant treatment," International Journal of Oncology, 20: 509-516 (2002).

Xu et al., "Hypoxia-induced Elevation in Interleukin-8 Expression by Human Ovarian Carcinoma Cells," Cancer Research, 1999, vol. 59, pp. 5822-5829.

He et al., "Oral Formulation of a Novel Antiviral Agent, PG301029, in a Mixture of Gelucire 44/14 and DMA (2:1, wt/wt)," AAPS PharmSciTech 2005; vol. 6 (1) Article 1, 5 pages, (http://www.aapsharmscitech.org).

Yamaguchi et al.,"Expression of Vascular Endothelial Growth Factor m Human Hepatocellular Carcinoma," Hepatology, 28(1) pp. 68-77 (1998).

Yang et al. "Akt/Protein Kinase B Signaling Inhibitor-2, a Selective Small Molecule Inhibitor of a Akt Signaling with Antitumor Activity in Cancer Cells Overexpressing Akt," Cancer Research, 64, Jul. 1, 2004, pp. 4394-4399.

Yang et al., "Antiviral chemotherapy control of poxvirus infections through inhibition of cellular signal transduction," The Journal of Clinical Investigation, 2005: 115(2):pp, 379-387.

Yeh et al., "Characterization of severe acute respiratory syndrome coronavirus genomes in Taiwan: Molecular epidemiology and genome evolution," Proc. Natl. Acad. Sci. USA Feb. 24, 2004, 101(8):2542-2547.

Yu et al., "The role of Mc1-1 downregulation in the proapoptotic activity of the multi kinase inhibitor BAY 43-9006," Oncogene 24:6861-6869 (2005).

Zachos et al., "Herpes Simplex Virus Type 1 Infection Stimulates p38/c-Jun N-terminal Mitogen-activated Protein Kinase Pathways and activates Transcription Factor AP-1," Journal of Biological Chemistry, The American Society for Biochemistry and Molecular Biology, Inc, 1999: vol. 274, pp. 5097-5103.

Zangari et al., "Phase II Study of SU5416, a Small Molecule Vascular Endothelial Growth Factor Tyrosine Kinase Receptor Inhibitor, in Patients with Refractory Multiple Myeloma," Clinical Cancer Research, 10: 88-95 (Jan 1, 2004).

Norden-Zfoni, Anat. "Blood-Based Biomarkers of SU11248 Activity and Clinical Outcome in Patients with Metastatic Imatinib-Resistant Gastrointestinal Stromal Tumor," Clin. Cancer, Res. 2007; 13(9):2643-2650 May 1, 2007.

Zhao et al., "Moderate mutation rate in the SARS coronavirus genome and its implications," BMC Evolutionary Biology, 2004, 4:21, 9 pages.

Zhu et al., "From the Cyclooxygenase-2 Inhibitor Celecoxib to a Novel Class of 3- Phosphoinositide-Dependent Protein Kinase-1 Inhibitors," Cancer Research 64, Jun. 15, 2004, pp. 4309-4318.

Carter et al., "Anti-tumor Efficacy of the Orally Active RAF Kinase Inhibitor BAY 43-90006 in Human Tumor Xenograft Model," #4954. Proceedings of the American Association for Cancer Res., 2001, vol. 42, p. 923.

Iwadate et al., MEDLINE/NLM, NLM8336809 "Intra-arterial ACNU, CDDP chemotherapy for brain metastases from lim9 a cancer: comparison of cases with and without intra-arterial mannitol infusion," 1 page, abstract (1998).

Kubo et al., "Synthesis and Structure-Activity Relationship of Quinazoline-Urea Derivatives as Novel Orally Active VEGF Receptor Tyrosine Kinase Selective Inhibitors," Proceedings of the American Association of Cancer Res., 2002, vol. 43, p. 182, abstract No. 913.

Riedl et al., #4956 "Potent RafKinase Inhibitors from the Diphenylurea Class: Structure Activity Relationships," Proceedings of the American Association for Cancer Research, vol. 42, Mar. 2001 (2001-03), p. 923, 92nd Annual Meeting of the American Association for Cancer Research; New Orleans, LA, USA; Mar. 24-28, 2001.

Strumberg et al., abstract No. #2921 "Phase I and Pharmacokinetic Study of the Raf Kinase Inhibitor Bay 43-9006 in Patients with Locally Advanced or Metastic Cancer," Proceedings of the American Association for Cancer Research, vol. 42, Mar. 2001 (2001-03), p. 543, 92nd Annual Meeting of the American Association for Cancer Research;New Orleans, LA, USA; Mar. 24-28, 2001.

Abstract of DE 3305866 A1, Aug. 23, 1984, BASF AG et al.

Abstract of EP 4931 A (Equivalent 4,240,820), Bayer AG, 1 page (1980).

Abstract of EP 16371 (1980), 1 page, Hoffmann-La Roche AG.

Abstract of EP 16371, Oct. 1. 1980, 1 page.

Abstract of EP 116932, Aug. 29, 1984, 2 pages.

Abstract of EP 116932, (1984), 2 pages, BASF AG.

Abstract of EP 0202538, (1986), 3 pages.

Abstract of EP 0202538 A1, Growth Promoting Agents, Nov. 26,1986, 4 pages, Bayer AG.

Abstract of EP 0405233A1, Mitsubishi Kasei Corp., 2 pages (1988).

Abstract of EP 0405233A1, Tetsuo Sekiya et al., 1 page (1988).

Abstract of EP 0676395A2, (1995), 3 pages, Hoechst AG.

Abstract of EP 676395, (U.S. equivalent 5,698,581), Dec. 16, 1997, 1 page.

Patent Abstracts of Japan 02-022650. Jan. 25, 1990, 2 pages, Konica Corp.

esp@cenet Abstracts of Japan 02-022650, Jan. 25, 1990, 1 page.

Patent Abstracts of Japan 02-023337, Jan. 25, 1990, 2 pages, Konica Corp.

Patent Abstracts of Japan 63-214752,Sep. 7, 1988, 2 pages, family member of JP 6-07512 B4, Fuji Photo Film Co. Ltd.

esp@cenet Abstract of Japan 02-023337, 1 page (1988).

Abstract of JP 55162772 A2, Preparation of Substituted Acetic Acid Derivatives, Shiongi & Co., Ltd. Dec. 1980. 1 page.

Esp@cenet Abstract of WO 9822103, May 28, 1998, Philip Hedge et al.

Abstract of WO 9822098 A2, QLT Phototherapeutics Inc. et al., May 28, 1998, 1 page.

Abstract of WO 9822103 A1, Zeneca Limited, published May 28, 1998, 1 page.

Abstract of WO 9852559 A1, Bayer Corp. et al., published Nov. 26, 1998, 1 page.

Abstract of WO 9852562 A1, Verkaik, MSE, et al., published Nov. 26, 1998, 1 page.

Abstract of WO 9900357 A1, Vertex Pharm. Inc., published Jan. 7, 1999, 1 page.

Abstract of WO 9900364 Al, Pharmacia & Upjohn S.P.A. et al., published Jan. 7, 1999, 1 page.

Abstract of WO 9932098 A2, Janssen Pharm NV, published Jul. 1, 1999, 1 page.

Abstract of WO 9932106 A1, Bayer Corp., published Jul. 1, 1999, 1 page.

Abstract of WO 9932148 A1, Beth Israel Deaconess Medical Center et al., pub. Jul. 1, 1999. 1 page.

Abstract of WO 9932436 A1, Bayer Corp., published Jul. 1, 1999, 1 page.
Abstract of WO 9932455 A1, Bayer Corp., published Jul. 1, 1999, 1 page.
Abstract of WO 9932457 A1, Hoechst Marion Roussel Deutschland GmbH et al., published Jul. 01, 1999, 1 page.
Caplus 72:79046, Abstract of CH 479557, "Tuberculostatic and cancerostatic polybasic ureas," Dr. A. Wander, Oct. 15, 1969, 6 pages.
Caplus 84:180049, Abstract JP 56029871, "Substituted acetic acid derivatives," Hamada, Yoshinori et al., Jul. 10, 1981, 1 page.
Caplus 84:43857, Abstract JP 58021626, "Alkanoic acid derivatives containing a pyridine ring," Maeda, Ryozo et al., May 2, 1983, 1 page.
Caplus 86:72448, Abstract JP 57053785, "Pyridine derivatives," Maeda, Ryozo et al., Nov. 15, 1982, 1 page.
Caplus 87:62295, "The metabolism and toxicity of halogenated carbanilides. Biliary metabolites of 3,4,4'-trichlorocarbanilide and 3-trifluoromethy1-4,4'-dichlorocarbanilide in the rat," Chemical Life Science, pp. 157-166, 1977, 1 page.
Caplus 98:78152, Abstract of JP 57185219, "Antitumor benzophenone derivatives," Nov. 15, 1982, 1 page, Chugai Pharmaceutical Co., Ltd.
Caplus 113:106314, Abstract of JP 2022650, "Silver halide color photographic material containing a cyan coupler of 2-ureido-phenol type to improve dye developability and remove lecuo cyan dye," Noboru Mizukura et al. Jan. 25, 1990, 1 page.
Caplus 113:142130, Abstract of JP 2023337, "Silver halide photographic material containing phenolic cyan coupler a colorless cyan coupler," Toshihiko Yagi et al., Jan. 25, 1990, 1 page.
Caplus 125:245169, "Production of murine monoclonal antibodies against sulcofuron and flucofuron by in vitro immunization," G. A. Bonwick et al., J. Immunol, Methods, 196(2), pp. 163-173, 1996, 1 page.
Caplus 126:166148, "Inhibitors of coenzyme A-independent transacylase induce apoptosis in human HL-60 cells," James D. Winkler et al., J. Pharmacol. Exp. Ther. 279(2), pp. 956-966, 1996, 2 pages.
Dearden et al.,"Quantitative structure-biodegradability studies: an investigation of the MITI aromatic compound data-base," in: Biodegradability Prediction, Edited by Willie J.G.M. Peijnenburg et al., NATO ASI Series, 2. Environment - vol. 23, pp. 93-104, 1996.
Caplus 127:293717, "Optical properties of segmented oligourethane with azomethine terminal fragments," National Academy of Science of Ukraine, M. V. Kurik et al., pp. 2038-2041, 1996, 2 pages.
Caplus 127:34137f, "Preparation of quinoline and quinazoline derivatives inhibiting platelet-derived growth factor receptor autophosphorylation," Kazuo Kubo et al., May 15, 1997, WO 97/17329.
Caplus 131:58658k, "Inhibition of raf kinase using symmetrical and unsymmetrical substituted diphenyl ureas," Miller, Scott, et al. Jul. 1, 1999, WO 99 32,436.
Caplus 131:73649b, "Preparation of pyrazolyl aryl ureas and related compomds as p38 kinase inhibitors," Jacques Dumas et al., Jul. 1, 1999, WO 99/32110.
Caplus 131:87909y, "Inhibition of p38 kinase activity using substituted heterocyclic ureas," Jacques Dumas et al., Jul. 1, 1999, WO 99/32111.
Caplus 146:265643 Abstract of Strumberg et al., "Sorafenib - A novel opportunity in oncology," Arzneimitteltherapie 25(1):2-6 (2007) abstract, 1 page.
Kujundzic et al, "Synthesis of 8-methyl-1,2,3,4-tetrattydropyrido[3,4-d] pyrimidine-2,4-diones," Croat. Chem. Acta (1991) 64(4):599-606, Chemical Abstracts vol. 116, No. 21, May 25, 1992, (pp. 741-742) No. 116:214456.
Badran et al., "Novel piperazinyl-substituted pyrimidines as antihypertensive and vasodilators," Revue Roumaine de Chimie (1992), 37(2):238-288, Chemical Abstracts vol. 117:251318.
"Beilstein number" Collection, 28 pp. (1997).
"Beilstein number" Collection, 4 pp. (1997).
Derwent World Patents Index Search, pp. 20-26. (1997).
Dumas, J. "CAS Substructure," May 6, 1997, pp. 1-29.
Scott, Bill, "Substructure (Patent Families)," Aug. 11, 1997, pp. 1-19.
Scott, Bill, "Substructure #2," Nov. 25, 1997, pp. 1-3.
Scott, Bill, "Substructure Search," Dec. 2, 1997. pp. 1-49.
Substructure Search, pp. 1-29. (1997).
Wild, Hamio, "Substructure #1, " search, pp. 1-150, 1996.
A "Notice of References Cited" from the USPTO for U.S. Appl. No. 08/995,749, filing date of Dec. 22, 1997, Inhibition of P38 Kinase Using Symmetrical and Unsymmetrical Diphenyl Ureas, 2 pages.
A "Notice of References Cited" from the USPTO for U.S. Appl. No. 09/083,399, filing date of May 22, 1998, Patent 6187799 issued Feb. 13, 2001, Inhibition of Raf Kinase Activity Using Aryl Ureas, 1 page.
A "Notice of References Cited" from the USPTO for U.S. Appl. No. 09/425,228, filing date of Oct. 22, 1999, Omega-Carboxyaryl Substituted Diphenyl Ureas As Raf Kinase Inhibitors, 3 pages.
A "Notice of References Cited" from the USPTO for U.S. Appl. No. 09/425,229, filing date of Oct. 22, 1999, Omega-Carboxy Aryl Substituted Diphenyl Ureas As p38 Kinase Inhibitors, 1 page.
A "Notice of References Cited" from the USPTO for U.S. Appl. No. 09/458,015, filing date of Dec. 10, 1999, Inhibition Of p38 Kinase Using Symmetrical and Unsymmetrical Diphenyl Ureas, 1 page.
A "Notice of References Cited" from the USPTO for U.S. Appl. No. 09/472,232, filing date of Dec. 27, 1999, Patent 7329670 issued Feb. 12, 2008, Inhibition of Raf Kinase Using Aryl and Heteroaryl Substituted heterocyclic Ureas, 1 page.
A "Notice of References Cited" from the USPTO for U.S. Appl. No. 09/472,232, filing date of Dec. 27, 1999, Patent 7329670 issued Feb. 12, 2008, Inhibition of Raf Kinase Using Aryl and Heteroaryl Substituted Heterocyclic Ureas, 1 page.
A "Notice of References Cited" from the USPTO for U.S. Appl. No. 09/773,604, filing date of Dec. 2, 2001, Publication No. US 2001-0034447-A1, Publication Date Oct. 25, 2001, Omega-carboxyaryl Substituted Diphenyl Ureas as Raf Kinase Inhibitors, 1 page.
A "Notice of References Cited" from the USPTO for U.S. Appl. No. 09/773,659, filing date of Feb. 2, 2001, Publication No. US 2001-0011135 A1, Publication Date: Aug. 2, 2001, Omega-carboxyaryl Substituted Diphenyl Ureas As Raf Kinase Inhibitors, 1 page.
A "Notice of References Cited" from the USPTO for U.S. Appl. No. 09/773,672, filing date of Feb. 2, 2001, Publication No.: US 2001-0016659 A1, Publication Date: Aug. 23, 2001, Omega-carboxyaryl substituted Diphenyl Ureas as Raf Kinase Inhibitors, 1 page.
A "Notice of References Cited" from the USPTO for U.S. Appl. No. 09/773,675, filed of Feb. 2, 2001, Publication No. US 2001-0011136-A1 , Publication Date: Aug. 2, 2001, Omega-Carboxyaryl Substituted Diphenyl Ureas as Raf Kinase Inhibitors, 1 page.
A "Notice of References Cited" from the USPTO for U.S. Appl. No. 09/776,935 filing date of Dec. 22, 1998, Inhibition of p38 Kinase Using Aryl and Heteroaryl Substituted Heterocyclic Ureas, 1 page.
A "Notice of References Cited" from the USPTO for U.S. application 09/776,936, filing date of Dec. 22, 1998, Inhibition of Raf Kinase Using Symmetrical and Unsymmetrical Substituted Diphenyl Ureas, 1 page.
A "Notice of References Cited" from the USPTO for U.S. Appl. No. 09/777,920, filing date of Feb. 7, 2001, Inhibition of Raf kinase using quinolyl, isoquinolyl or pyridyl ureas, 1 page.
A "Notice of References Cited" from the USPTO for U.S. Appl. No. 09/948,915, filing date of Sep. 10, 2001, Omega-Carboxyaryl Substituted Diphenyl Ureas As Raf Kinase Inhibitors, 1 page.
A "Notice of References Cited" from the USPTO for U.S. Appl. No. 10/042,226, filing date of Jan. 11, 2002, Omega-Carboxyaryl Substituted Diphenyl Ureas As Raf Kinase Inhibitors, 1 page.
Co-pending U.S. Appl. No. 09/458,014, filed Dec. 10, 1999, Dumas et al.
Abandoned U.S. Appl. No. 09/776,935 filed Dec. 22, 1998, Dumas et al.
Co-pending U.S. Appl. No. 09/776,936 filed Dec. 22, 1998, Miller et al.
Issued U.S. Appl. No. 09/889,227 filed Jul. 12, 2000, Riedl et al., issued as 7351834, Apr. 1, 2008.
Co-pending U.S. Appl. No. 09/993,647 filed Nov. 27, 2001, Riedl et al, published as 2003-0181442, Sep. 25, 2003.
Issued U.S. Appl. No. 10/060,396 filed Feb. 1, 2002, Miller et al., patent 7517880, issued Apr. 14, 2009, also published as 2004-0102636, May 27, 2004.

Issued U.S. Appl. No. 10/071,248 filed Feb. 11, 2002, Riedl et al., patent 7528255, issued May 5, 2009, also published as 2003-139605, Jul. 24, 2003.

Abandoned U.S. Appl. No. 10/086,417 filed Mar. 4, 2002, Riedl et al., published as 2003-0105091, Jun. 5, 2003.

Abandoned U.S. Appl. No. 10/125,369 filed Apr. 19, 2002, Dumas et al., published as 2003-0207914, Nov. 6, 2003.

Abandoned U.S. Appl. No. 10/308,187 filed Dec. 3, 2002, Carter et al., published as 2003- 0232765, Dec. 18, 2003.

Abandoned U.S. Appl. No. 10/361,844 filed Feb. 11 2003, Dumas et al., published as 2004-0023961, Feb. 5, 2004.

Abandoned U.S. Appl. No. 10/361,850 filed Feb. 11, 2003, Dumas et al., published as US 2003-0216396. Nov. 20, 2003.

Co-pending U.S. Appl. No. 10/361,859 filed Feb. 11, 2003, Dumas et al., published as 2003-0216446.Nov. 20, 2003.

Co-Pending U.S. Appl. No. 10/895,985 filed Jul. 22, 2004. Boyer et al., published as US 2005-0038080, Feb. 17, 2005.

Co-Pending U.S. Appl. No. 11/932,548 filed Oct. 31, 2007, Dumas et al.,.

Co-Pending U.S. Appl. No. 12/084,662 filed May 7, 2008, Sandner et al., published as 2010-0035888, Feb. 11, 2010.

Co-Pending U.S. Appl. No. 12/086,454 filed Jun. 12, 2008, Weber et al.

Co-Pending U.S. Appl. No. 12/093,515 filed Nov. 13, 2008, Wilhelm et al.

Co-Pending U.S. Appl. No. 12/095,611 filed May 30, 2008, Smith et al.

Co-Pending U.S. Appl. No. 12/158,524 filed Jun. 20, 2008, Smith et al.

Co-Pending U.S. Appl. No. 12/294,979 filed Sep. 29, 2008, Wilhelm et al.

Co-Pending U.S. Appl. No. 12/421,690 filed Apr. 10, 2009. Dumas et al.

Co-Pending U.S. Appl. No. 12/444,974 filed Apr. 9, 2009; Grunenberg et al.

Co-Pending U.S. Appl. No. 12/514,129 filed May 8, 2009, Gruneriberg et al.

Co-Pending U.S. Appl. No. 12/514,715 filed May 13, 2009, Stiehl et al.

Co-Pending U.S. Appl. No. 12/520,618 filed Jun. 22, 2009, Smith et al.

Co-Pending U.S. Appl. No. 12/520,609 filed Jun. 22, 2009, Smith et al.

Co-pending U.S. Appl. No. 12/523,652 filed Jul. 17, 2009, Wilhelm et al.

Co-pending U.S. Appl. No. 12/523,697 filed Jul. 17, 2009, Wilhelm et al.

Co-Pending U.S. Appl. No. 12/628,735 filed Dec. 1, 2009, Dumas et al.

Co-Pending U.S. Appl. No. 12/692,845 filed Jan. 25, 2010, Dumas et al.

Co-Pending Application PCT/US09/61506, filed Oct. 21, 2009, Carol Pena.

International search report for International Application No. PCT/US98/10375 dated Sep. 3, 1998, Inhibition Of p38 Kinase Activity by Aryl Ureas, publication No. 98/52558, publication date Nov. 26, 1998, 1 page.

International search report for International Application No. PCT/US98/10376 dated Jul. 30, 1998, Raf Kinase Inhibitors, publication No. WO 98/52559, publication date Nov. 26, 1998, 1 page.

International search report for International Application No. PCT/US98/26078 dated Apr. 2, 1999, Inhibition Of Raf Kinase Using Substituted Heterocyclic Ureas, publication No. WO 99/32106, publication date Jul. 1, 1999, 2 pages.

International search report for international Application No.PCT/US98/26079 dated Apr. 12, 1999, Inhibition of p38 Kinase Activity Using Aryl and Heteroaryl Substituted Heterocyclic Ureas, publication No. WO 99/32110, publication date Jul. 1, 1999, 1 page.

International search report for International Application No. PCT/US98/26080 dated Apr. 12, 1999, Inhibition Of p38 Kinase Using Substituted Heterocyclic Ureas, publication No. WO 99/32111, publication date Jul. 1, 1999, 1 page.

International search report for International Application No. PCT/US98/26081 dated Apr. 2, 1999, Inhibition Of Raf Kinase Using Symmetrical and Unsymmetrical Substituted Diphenyl Ureas, publication No. WO 99/32436, publication date Jul. 1, 1999, 1 page.

International search report for International Application No. PCT/US98/26082 dated May 12, 1999, Inhibition Of Raf Kinase Using Aryl and Heteroaryl Substituted Heterocyclic Ureas, publication No. WO 99/32455, publication date Jul. 1, 1999, 1 page.

International search report for International Application No. PCT/US98/27265, dated Mar. 2, 1999, Inhibition of p38 kinase using symmetrical and unsymmetrical diphenyl ureas, publication No. WO 99/32463, publication date Jul. 1, 1999, 1 page.

International search report for International Application No. PCTIUS00/00648 dated Jun. 29, 2000, Omega-Carboxyaryl Substituted Diphenyl Ureas as RAF Kinase Inhibitors, publication No. WO 00/42012 A1, publication date Jul. 20, 2000, 2 pages.

International search report for International Application No. PCT/US00100768 dated May 16, 2000, Omega-Carboxy Aryl Substituted Diphenyl Ureas As p38 Kinase Inhibitors, publication No. WO 00/41698 A1, publication date Jul. 20, 2000, 1 page.

International search report for International Application No. PCDUS02112064 dated Sep. 20, 2002, Iieteroaryl Ureas Containing Nitrogen Fiftero-Atoms As p38 Kinase Inhibitors, publication No. 02/085859, publication date Oct. 31, 2002, 2 pages.

International search report for International Application No. PCT/US02/12066 dated Sep. 27, 2002, Inhibition Of Raf Kinase Quinolyl, Isoquinolyl or Pyridyl Ureas, publication No. 02/085857, publication date Oct. 31, 2002, 2 pages.

Supplemental search report from the EPO for European application EP 98963809.3 dated Mar. 30, 2001, Inhibition Of Raf Kinase Using Symmetrical and Unsymmetrical Substituted Diphenyl Ureas, publication No. 1049664, publication date Jul. 1, 1999, granted Mar. 16, 2005, 4 pages.

Supplemental search report from the EPO for European application EP 98963810.1 dated Dec. 21, 2000, Inhibition of Raf Kinase Using Aryl and Heteroaryl Substituted Heterocyclic Ureas, publication No. 1056725, publication date Jul. 1, 1999, granted Jun. 17, 2006, 4 pages.

Supplemental search report from the EPO for European application EP 98965981.8 dated Dec. 21, 2000, Inhibition of Raf Kinase Using Substituted Heterocyclic Ureas, publication No. 1047418, publication date Jul. 1, 1999, granted Jul. 27, 2005, 8 pages.

Supplemental search report front the EPO for European application EP 00903239.2 dated Aug. 7, 2002, Omega-Carboxyaryl Substituted Diphenyl Ureas As Raf Kinase Inhibitors, publication No. EP 1140840, published. Jul. 20, 2000, granted Mar. 22, 2006, 6 pages.

Supplemental search report from the EPO for European application EP 00905597.1 dated Feb. 7, 2008, Omega-Carboxyaryl Substituted Diphenyl Ureas As p38 Kinase Inhibitors, publication No. EP 1158985, Jul. 20, 2000, 9 pages.

Belgore et al., "Measurement of free and complexed soluble vascular endothelial growth factor receptor, Flt-1, in fluid samples: development and application of two new immunoassays," Clinical Science, 100: 567-575 (2001).

Belgore et al., "Plasma Levels of Vascular Endothelial Growth Factor (VEGF) and Its Receptor, Flt-1, in Haematological Cancers: A Comparison With Breast Cancer," American Journal of Hematology, 66:59-61 (2001).

Coskun et al., "Significance of serum vascular endothelial growth factor, insulin-like growth factor-I levels and nitric oxide activity in breast cancer patients," The Breast, 12, 104-110 (2003).

Kaya et al., "The prognostic significance of vascular endothelial growth factor levels in sera of non-small cell lung cancer patients," Respiratory Medicine, 98:632-636 (2004).

Kumar et al , "Soluble FLT-1 is Detectable in the Sera of Colorectal and Breast Cancer Patients," Anticancer Research, 22:1877-1880 (2002).

Pasieka et al., "Evaluation of the Levels of bFGF, VEGF, sICAM-1, and sVCAM-1 in Serum of Patients with Thyroid Cancer," Recent Results in Cancer Research, 162:189-194 (2003).

Pegram et al., "Combined Biological Therapy of Breast Cancer Using Monoclonal Antibodies Directed Against HER2/*neu*Protein and Vascular Endothelial Growth Factor," Seminars in Oncology, 29(Suppl. 11):29-37 (2002).

Poon et al., "Prognostic significance of serum vascular endothelial growth factor an endostatin in patients with hepatocellular carcinoma," British Journal of Surgery, 91:1354-1360 (2004).

Ria et al., "Serum levels of angiogenic cytokines decrease after antineoplastic radiotherapy," Cancer Letters, 216:103-107 (2004).

Secord et al., "The relationship between serum vascular endothelial growth factor, persistent disease, and survival at second-look laparotomy in ovarian cancer," Gynecologic Oncology, 94:74-79 (2004).

English abstract of JP 10-306078, Nov. 17, 1998, Patent Abstracts of Japan, 2 pages.

English abstract of JP 08-301841, Nov. 19, 1996, Patent Abstracts of Japan, 2 pages.

English abstract of JP 03-198049, Aug. 29, 1991, Patent Abstracts of Japan, 1 page.

English abstract of JP 03-144634, Jun. 20, 1991, Patent Abstracts of Japan, 1 page.

English abstract of JP 03-053247, Mar. 7, 1991, Patent Abstracts of Japan, 1 page.

English abstract of JP 02-150840, Jun. 11, 1990, Patent Abstracts of Japan, 1 page.

English abstract of JP 02-108048, Apr. 19, 1990, Patent Abstracts of Japan, 1 page.

English abstract of JP 02-105146, Apr. 17, 1990, Patent Abstracts of Japan, 1 page.

English abstract of JP 02-035450, Feb. 6, 1990, Patent Abstracts of Japan, 1 page.

English abstract of JP 01-200254, Aug. 11, 1989, :Patent Abstracts of Japan, 1 page.

English abstract of JP 01-259360, Oct. 17, 1989, Patent Abstracts of Japan, 2 pages.

English abstract of JP 01-102461, Apr. 20, 1989, Patent Abstracts of Japan, 1 page.

English abstract of JP 06-120039, Apr. 28, 1994, Patent Abstracts of Japan, 1 page.

English abstract of JP 05-180862, Jul. 23, 1993, Patent Abstracts of Japan, 1 page.

English abstract of JP 05-163170, Jun. 29, 1993, Patent Abstracts of Japan, 1 page.

English abstract of JP 05-077375, Mar. 30, 1993, Patent Abstracts of Japan, 1 page.

English abstract of JP 05-076072, Mar. 26, 1993, Patent Abstracts of Japan, 2 pages.

English abstract of JP 50-149668 A and JP 56-29871 B, Derwent World Patents Index, Dialog File No. 351, Acc. No. 1488399, 3 pages.

English abstract of JP 53-086033, Jul. 29, 1978, Patent Abstracts of Japan, 1 page.

English abstract of JP 54-032468, Sep. 3, 1979, Patent Abstracts of Japan, 1 page.

English abstract of JP 55-098152, Jul. 25, 1980, Patent Abstracts of Japan, 1 page.

English abstract of JP 64-009455, Jan. 12, 1989, Patent Abstracts of Japan, 1 page.

English abstract of JP 02-023337, Mar. 9, 1979, Patent Abstracts of Japan, 2 pages.

English abstract of EPA 0379915/EP-A, Aug. 1, 1990, 2 pages.

English abstract of DD 253997 A, Feb. 10, 1988, 1 page.

English abstract of DE511468, European Patent Office, 2 pages.

Co-Pending U.S. Appl. No. 12/619,913, filed Nov. 17, 2009, Ranges et al.

ω-CARBOXYL ARYL SUBSTITUTED DIPHENYL UREAS AS P38 KINASE INHIBITORS

CROSS-REFERENCE TO RELATED APPLICATIONS

This application is a continuation of abandoned application Ser. No. 10/086,417, filed Mar. 4, 2002, which is a continuation of abandoned application Ser. No. 09/425,229, filed Oct. 22, 1999 which is a continuation-in-part of abandoned application Ser. No. 09/257,265 filed Feb. 25, 1999. This application claims the benefit of the filing date of U.S. Provisional Application No. 60/115,878, filed Jan. 13, 1999. The content of these applications are incorporated herein by reference.

FIELD OF THE INVENTION

This invention relates to the use of a group of aryl ureas in treating cytokine mediated diseases and proteolytic enzyme mediated diseases, and pharmaceutical compositions for use in such therapy.

BACKGROUND OF THE INVENTION

Two classes of effector molecules which are critical for the progression of rheumatoid arthritis are pro-inflammatory cytokines and tissue degrading proteases. Recently, a family of kinases was described which is instrumental in controlling the transcription and translation of the structural genes coding for these effector molecules.

The mitogen-activated protein (MAP) kinase family is made up of a series of structurally related proline-directed serine/threonine kinases which are activated either by growth factors (such as EGF) and phorbol esters (ERK), or by IL-1, TNFα or stress (p38, JNK). The MAP kinases are responsible for the activation of a wide variety of transcription factors and proteins involved in transcriptional control of cytokine production. A pair of novel protein kinases involved in the regulation of cytokine synthesis was recently described by a group from SmithKline Beecham (Lee et al. *Nature* 1994, 372, 739). These enzymes were isolated based on their affinity to bond to a class of compounds, named CSAIDSs (cytokine suppressive anti-inflammatory drugs) by SKB. The CSAIDs, bicyclic pyridinyl imidazoles, have been shown to have cytokine inhibitory activity both in vitro and in vivo. The isolated enzymes, CSBP-1 and -2 (CSAID binding protein 1 and 2) have been cloned and expressed. A murine homologue for CSBP-2, p38, has also been reported (Han et al. *Science* 1994, 265, 808).

Early studies suggested that CSAIDs function by interfering with m-RNA translational events during cytokine biosynthesis. Inhibition of p38 has been shown to inhibit both cytokine production (eg., TNFα, IL-1, IL-6, IL-8) and proteolytic enzyme production (eg., MMP-1, MMP-3) in vitro and/or in vivo.

Clinical studies have linked TNFα production and/or signaling to a number of diseases including rheumatoid arthritis (Maini. *J. Royal Coll. Physicians London* 1996, 30, 344). In addition, excessive levels of TNFα have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoperosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Diol. Res.* 1989, 308, 463), septic shock (Tracey et al. *Nature* 1987, 330, 662; Girardin et al. *New England J. Med.* 1988, 319, 397), endotoxic shock Beutler et al. *Science* 1985, 229, 869; Aslkenasi et al. *Proc. Nat'l. Acad. Sci. USA* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995-6, 47, 97) including Crohn's disease (van Deventer et al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immunol.* 1995, 46, 111), Jarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Ant. J. Respir. Cell Mol Biol.* 1996, 14, 1044), hepatic failure (Gantner et al. *Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immniuno Rev.* 1989, 112, 49; Taverne et al. *Parasitol Today* 1996, 12, 290) including *Plasmodium falciparum* malaria (Perlmann et al. *Infect. Immunol.* 1997, 65, 116) and cerebral malaria (Rudin et al. *Am. J. Pathol.* 1997, 150, 257), non-insulin-dependent diabetes mellitus (NIDDM; Stephens et al. *J Biol. Chem.* 1997, 272, 971; Ofei et al. *Diabetes* 1996, 45, 881), congestive heart failure (Doyama et al. *Int. J. Cardiol* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), multiple sclerosis (M. S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest,* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633). TNFα levels have also been related to host-versus-graft reactions (Piguet et al. *Immunol. Ser.* 1992, 56, 409) including ischemia reperfusion injury (Colletti et al. *J. Clin. Invest.* 1989, 85, 1333) and allograft rejections including those of the kidney (Naury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). TNFα has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma crazi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdorferi* (Brandt et al. *Infect. Immunol.* 1990, 58, 983), *Treponema pallidum* (Chamberlin et al. *Infect. Immunol.* 1989, 57 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

Because inhibition of p38 leads to inhibition of TNFα production, p38 inhibitors will be useful in treatment of the above listed diseases.

A number of diseases are thought to be mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim, Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1988, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Burns et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), birth control (Woessner et al. *Steroids* 1989, 54, 491), dystrophobic epidermolysis bullosa (Kronberger et al. *J. Invest, Dermatol.* 1982, 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of MMP production, p38 inhibitors will be useful in treatment of the above listed diseases.

Inhibitors of p38 are active in animal models of TNFα production, including a muime lipopolysaccharide (LPS) model of TNFα production. Inhibitors of p38 are active in a number of standard animal models of inflammatory diseases, including carrageenan-induced edema in the rat paw, arachadonic acid-induced edema in the rat paw, arachadonic acid-induced peritonitis in the mouse, fetal rat long bone resorption, murine type II collagen-induced arthritis, and Fruend's adjuvant-induced arthritis in the rat. Thus, inhibitors of p38 will be useful in treating diseases mediated by one or more of the above-mentioned cytokines and/or proteolytic enzymes.

The need for new therapies is especially important in the case of arthritic diseases. The primary disabling effect of osteoarthritis, rheumatoid arthritis and septic arthritis is the progressive loss of articular cartilage and thereby normal joint function. No marketed pharmaceutical agent is able to prevent or slow is cartilage loss, although nonsteroidal anti-inflammatory drugs (NSAIDs) have been given to control pain and swelling. The end result of these diseases is total loss of joint function which is only treatable by joint replacement surgery. P38 inhibitors will halt or reverse the progression of cartilage loss and obviate or delay surgical intervention.

Several patents have appeared claiming polyarylimidazoles and/or compounds containing polyarylimidazoles as inhibitors of p38 (for example, Lee et al. WO 95/07922; Adams et al. WO 95/02591; Adams et al. WO 95/13067; Adams et al. WO 95/31451). It has been reported that arylimidazoles complex to the ferric form of cytochrome P450$_{cam}$ (Harris et al. *Mol. Eng.* 1995, 5, 143, and references therein), causing concern that these compounds may display structure-related toxicity (Howard-Martin et al. *Toxicol. Pathol.* 1987, 15, 369). Therefore, there remains a need for improved p38 inhibitors.

SUMMARY OF THE INVENTION

This invention provides compounds, generally described as aryl ureas, including both aryl and heteroaryl analogues, which inhibit p38 mediated events and thus inhibit the production of cytokines (such as TNFα, IL-1 and IL-8) and proteolytic enzymes (such as MMP-1 and MMP-3). The invention also provides a method of treating a cytokine mediated disease state in humans or mammals, wherein the cytokine is one whose production is affected by p38. Examples of such cytokines include, but are not limited to TNFα, IL-1 and IL-8. The invention also provides a method of treating a protease mediated disease state in humans or mammals, wherein the protease is one whose production is affected by p38. Examples of such proteases include, but are not limited to collagenase (1-1) and stromelysin (MN-3).

Accordingly, these compounds are useful therapeutic agents for such acute and chronic inflammatory and/or immunomodulatory diseases as rheumatoid arthritis, osteoarthritis, septic arthritis, rheumatic fever, bone resorption, postmenopausal osteoperosis, sepsis, gram negative sepsis, septic shock, endotoxic shock, toxic shock syndrome, systemic inflammatory response syndrome, inflammatory bowel diseases including Crohn's disease and ulcerative colitis, Jarisch-Herxheimer reactions, asthma, adult respiratory distress syndrome, acute pulmonary fibrotic diseases, pulmonary sarcoidosis, allergic respiratory diseases, silicosis, coal worker's pneumoconiosis, alveolar injury, hepatic failure, liver disease during acute inflammation, severe alcoholic hepatitis, malaria including *Plasmodium falciparum* malaria and cerebral malaria, non-insulin-dependent diabetes mellitus (NIDDM), congestive heart failure, damage following heart disease, atherosclerosis, Alzheimer's disease, acute encephalitis, brain injury, multiple sclerosis including demyelation and oligiodendrocyte loss in multiple sclerosis, advanced cancer, lymphoid malignancies, tumor metastasis, pancreatitis, including systemic complications in acute pancreatitis, impaired wound healing in infection, inflammation and cancer, periodontal diseases, corneal ulceration, proteinuria, myelodysplastic syndromes, systemic lupus erythematosus, biliary cirrhosis, bowel necrosis, psoriasis, radiation injury, toxicity following administration of monoclonal antibodies such as OKT3, host-versus-graft reactions including ischemia reperfusion injury and allograft rejections including kidney, liver, heart, and skin allograft rejections, lung allograft rejection including chronic lung allograft rejection (obliterative bronchitis) as well as complications due to total hip replacement, and infectious diseases including tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum*, cytomegalovirus, influenza virus, Theiler's encephalomyelitis virus, and the human immunodeficiency virus (HIV).

The present invention, therefore, provides compounds generally described as aryl ureas, including both aryl and heteroaryl analogues, which inhibit the p38 pathway. The invention also provides a method for treatment of p38-mediated disease states in humans or mammals, e.g., disease states mediated by one or more cytokines or proteolytic enzymes produced and/or activated by a p38 mediated process. Thus, the invention is directed to compounds, compositions and methods for the treatment of diseases mediated by p38 kinase wherein a compound of Formula I is administered or a pharmaceutically acceptable salt thereof.

$$A-D-B \qquad (I)$$

In formula I, D is —NH—C(O)—NH—,

A is a substituted moiety of up to 40 carbon atoms of the formula: -L-(M-L$^1$)$_q$, where L is a 5 or 6 membered cyclic structure bound directly to D, L$^1$ comprises a substituted cyclic moiety having at least 5 members, M is a bridging group having at least one atom, q is an integer of from 1-3; and each cyclic structure of L and L$^1$ contains 0-4 members of the group consisting of nitrogen, oxygen and sulfur, and B is a substituted or unsubstituted, up to tricyclic aryl or heteroaryl moiety of up to 30 carbon atoms with at least one 6-member cyclic structure bound directly to D containing 0-4 members of the group consisting of nitrogen, oxygen and sulfur, wherein L$^1$ is substituted by at least one substituent selected from the group consisting of —SO$_2$R$_x$, —C(O)R$_x$ and —C(NR$_y$)R$_z$, R$_y$ is hydrogen or a carbon based moiety of up to 24 carbon atoms optionally containing heteroatoms selected from N, S and O and optionally halosubstituted, up to per halo, R$_z$ is hydrogen or a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen;

R$_x$ is R$_z$ or NR$_a$R$_b$ where R$_a$ and R$_b$ are a) independently hydrogen, a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen, or —OSi(R$_f$)$_3$ where R$_f$ is hydrogen or a carbon based moiety of up to 24 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen; or b) R$_a$ and R$_b$ together form a 5-7 member heterocyclic structure of 1-3 heteroatoms selected from N, S and O, or a substituted 5-7 member heterocyclic structure of 1-3 heteroatoms selected from N, S and O substituted by halogen, hydroxy or carbon based substituents of up to 24 carbon atoms, which optionally contain heteroatoms selected from N, S and O and are optionally substituted by halogen; or c) one of R$_a$ or R$_b$ is —C(O)—, a C$_1$-C$_5$ divalent alkylene group or a substituted C$_1$-C$_5$ divalent alkylene group bound to the moiety L to form a cyclic structure with at least 5 members, wherein the substituents of the substituted C$_1$-C$_5$ divalent alkylene group are selected from the group consisting of halogen, hydroxy, and carbon based substituents of up to 24 carbon atoms, which optionally contain heteroatoms selected from N, S and O and are optionally substituted by halogen;

where B is substituted, L is substituted or L$^1$ is additionally substituted, the substituents are selected from the group consisting of halogen, up to per-halo, and Wn, where n is 0-3;

wherein each W is independently selected from the group consisting of —CN, —CO$_2$R$^7$, —C(O)NR$^7$R$^7$, —C(O)—R$^7$, —NO$_2$, —OR$^7$, —SR$^7$, —NR$^7$R$^7$, —NR$^7$C(O)OR$^7$, —NR$^7$C(O)R$^7$, -Q-Ar, and carbon based moieties of up to 24 carbon atoms, optionally containing heteroatoms selected from N, S and O and optionally substituted by one or more substituents independently selected from the group consisting of —CN, —CO$_2$R$^7$, —C(O)R$^7$, —C(O)NR$^7$R$^7$, —OR$^7$, —SR$^7$, —NR$^7$R$^7$, —NO$_2$, —NR$^7$C(O)R$^7$, —NR$^7$C(O)OR$^7$ and halogen up to per-halo; with each R$^7$ independently selected from H or a carbon based moiety of up to 24 carbon atoms, optionally containing heteroatoms selected from N, S and O and optionally substituted by halogen, wherein Q is —O—, —S—, —N(R$^7$)—, —(CH$_2$)$_m$—, —C(O)—, —CH(OH)—, —(CH$_2$)$_m$O—, —(CH$_2$)$_m$S—, —(CH$_2$)$_m$N(R$^7$)—, —O(CH$_2$)$_m$—, CHX$^a$—, —CX$^a{}_2$—, —S—(CH$_2$)$_m$— and —N(R$^7$)(CH$_2$)$_m$, where m=1-3, and X$^a$ is halogen; and Ar is a 5- or 6-member aromatic structure containing 0-2 members selected from the group consisting of nitrogen, oxygen and sulfur, which is optionally substituted by halogen, up to per-halo, and optionally substituted by Z$_{n1}$, wherein n1 is 0 to 3 and each Z is independently selected from the group consisting of —CN, —CO$_2$R$^7$, —C(O)R$^7$, —C(O)NR$^7$R$^7$, —NO$_2$, —OR$^7$, —SR$^7$—NR$^7$R$^7$, —NR$^7$C(O)OR$^7$, —NR$^7$C(O)R$^7$, and a carbon based moiety of up to 24 carbon atoms, optionally containing heteroatoms selected from N, S and O and optionally substituted by one or more substituents selected from the group consisting of —CN, —CO$_2$R$^7$, —COR$^7$, —C(O)NR$^7$R$^7$, —OR$^7$, —SR$^7$, —NO$_2$, —NR$^7$R$^7$, —NR$^7$C(O)R$^7$, and —NR$^7$C(O)OR$^7$, with R$^7$ as defined above.

In formula I, suitable hetaryl groups include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms. For example, B can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-6- or 7-benzopyrazolyl, 2-, 4-, 5-, 6- or 7-benzoxazolyl, 3-, 4-, 5-, 6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc. For example, B can be 4-methyl-phenyl, 5-methyl-2-thienyl, 4-methyl-2-thienyl, 1-methyl-3-pyrryl, 1-methyl-3-pyrazolyl, 5-methyl-2-thiazolyl or 5-methyl-1,2,4-thiadiazol-2-yl.

Suitable alkyl groups and alkyl portions of groups, e.g., alkoxy, etc. throughout include methyl, ethyl, propyl, butyl, etc., including all straight-chain and branched isomers such as isopropyl, isobutyl, sec-butyl, tert-butyl, etc.

Suitable aryl groups which do not contain heteroatoms include, for example, phenyl and 1- and 2-naphthyl.

The term "cycloalkyl", as used herein, refers to cyclic structures with or without alkyl substituents such that, for example, "$C_4$ cycloakyl" includes methyl substituted cyclopropyl groups as well as cyclobutyl groups. The term "cycloalkyl", as used herein also includes saturated heterocyclic groups.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety.

The invention also relates to compounds per se, of formula I.

The present invention is also directed to pharmaceutically acceptable salts of formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, trifluoromethanesulfonic acid, benzenesulphonic acid, p-toluenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

A number of the compounds of Formula I possess asymmetric carbons and can therefore exist in racemic and optically active forms. Methods of separation of enantiomeric and diastereomeric mixtures are well known to one skilled in the art. The present invention encompasses any isolated racemic or optically active form of compounds described in Formula I which possess p38 kinase inhibitory activity.

General Preparative Methods

The compounds of Formula I may be prepared by use of known chemical reactions and procedures, some from starting materials which are commercially available. Nevertheless, the following general preparative methods are presented to aid one of skill in the art in synthesizing these compounds, with more detailed particular examples being presented in the experimental section describing the working examples.

Substituted anilines may be generated using standard methods (March. *Advanced Organic Chemistry*, $3^{rd}$ Ed.; John Wiley; New York (1985). Larock. *Comprehensive Organic Transformations*; VCH Publishers: New York (1989)). As shown in Scheme I, aryl amines are commonly synthesized by reduction of nitroaryls using a metal catalyst, such as Ni, Pd, or Pt, and H2 or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino- and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, $3^{rd}$ Ed.; John Wiley: New York (1985). Larock. *Comprehensive Organic Transformations*; VCH Publishers: New York (1989)).

Substituted anilines may be generated using standard methods (March. *Advanced Organic Chemistry*, $3^{rd}$ Ed.; John Wiley: New York (1985). Larock. *Comprehensive Organic Transformations*; VCH Publishers: New York (1989)). As shown in Scheme I, aryl amines are commonly synthesized by reduction of nitroaryls using a metal catalyst, such as Ni, Pd, or Pt, and H2 or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino- and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, $3^{rd}$ Ed.; John Wiley: New York (1985). Larock. *Comprehensive Organic Transformations*; VCH Publishers: New York (1989)).

Scheme I
Reduction of Nitroaryls to Aryl Amines

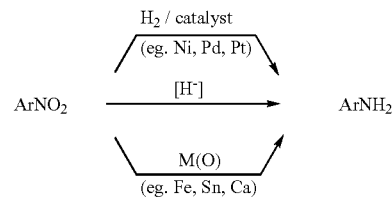

Nitroaryls are commonly formed by electrophilic aromatic nitration using $HNO_3$, or an alternative $NO_2^+$ source. Nitroaryls may be further elaborated prior to reduction. Thus, nitroaryls substituted with

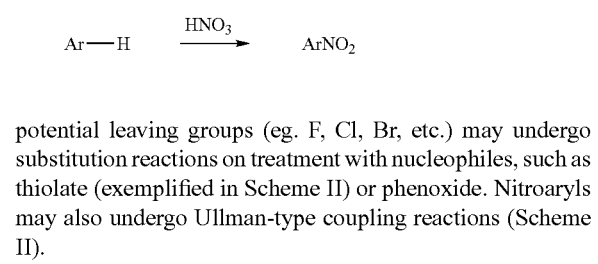

potential leaving groups (eg. F, Cl, Br, etc.) may undergo substitution reactions on treatment with nucleophiles, such as thiolate (exemplified in Scheme II) or phenoxide. Nitroaryls may also undergo Ullman-type coupling reactions (Scheme II).

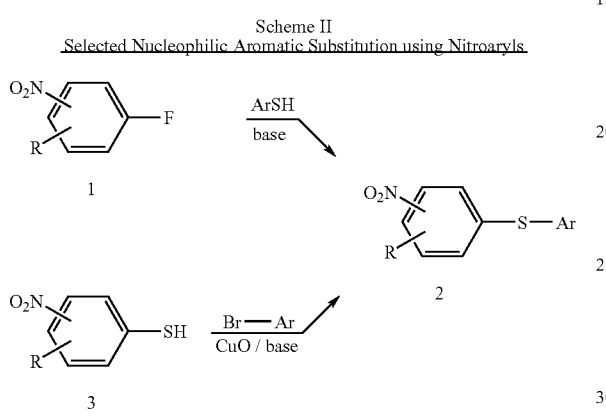

Nitroaryls may also undergo transition metal mediated cross coupling reactions. For example, nitroaryl electrophiles, such as nitroaryl bromides, iodides or triflates, undergo palladium mediated cross coupling reactions with aryl nucleophiles, such as arylboronic acids (Suzuki reactions, exemplified below), aryltins (Stille reactions) or arylzincs (Negishi reaction) to afford the biaryl (5).

Either nitroaryls or anilines may be converted into the corresponding arenesulfonyl chloride (7) on treatment with chlorosulfonic acid. Reaction of the sulfonyl chloride with a fluoride source, such as KF then affords sulfonyl fluoride (8). Reaction of sulfonyl fluoride 8 with trimethylsilyl trifluoromethane in the presence of a fluoride source, such as tris (dimethylamino)sulfonium difluorotrimethylsiliconate (TASF) leads to the corresponding trifluoromethylsulfone (9). Alternatively, sulfonyl chloride 7 may be reduced to the arenethiol (10), for example with zinc amalgum. Reaction of thiol 10 with $CHClF_2$ in the presence of base gives the difluoromethyl mercaptam (11), which may be oxidized to the sulfone (12) with any of a variety of is oxidants, including $CrO_3$-acetic anhydride (Sedova et al. Zh. Org. Khim. 1970, 6, 568).

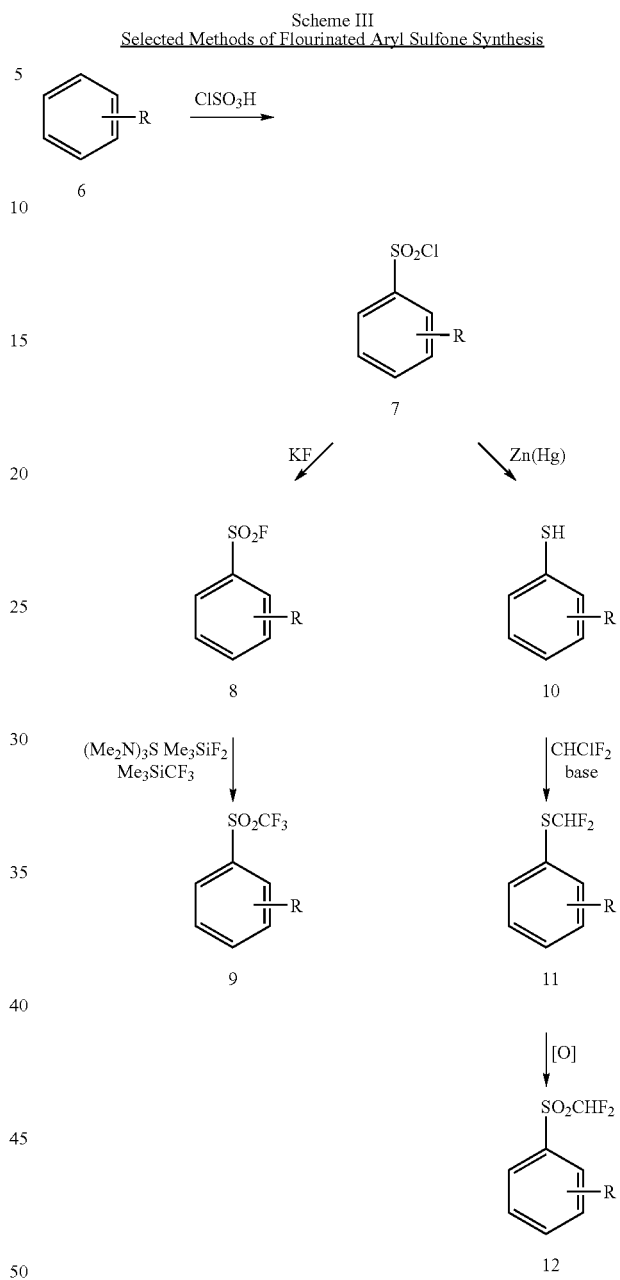

As shown in Scheme TV, non-symmetrical urea formation may involve reaction of an aryl isocyanate (14) with an aryl amine (13). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate. The corresponding carboxylic acid (17) may also be subjected to Curtius-type rearrangements using diphenylphosphoryl azide (DPPA) or a similar reagent.

Scheme IV
Selected Methods of Non-Symmetrical Urea Formation

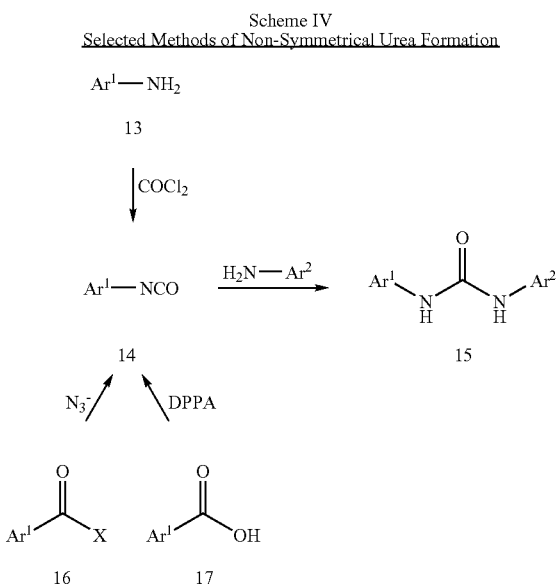

Finally, ureas may be further manipulated using methods familiar to those skilled in the art.

The invention also includes pharmaceutical compositions including a compound of Formula I, and a physiologically acceptable carrier.

The compounds may be administered orally, topically, parenterally, by inhalation or spray, vaginally, rectally or sublingually in dosage unit formulations. The term 'administration by injection' includes intravenous, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Compounds of the invention may also be administrated transdermally using methods known to those skilled in the art (see, for example: Chien; "Transdermal Controlled Systemic Medications"; Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily vaginal dosage regimen will preferably be from 0.01 to 200 mg/Kg of total body weight. The daily rectal dosage regimen will preferably be from 0.01 to 200 mg/Kg of total body weight. The transdermal concentration will preferably be that required to maintain a daily dose of from 0.01 to 200 mg/Kg. The daily topical dosage regimen will preferably be from 0.1 to 200 mg administered between one to four times daily. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for a given patient depends on a variety of factors, including specific activity of the compound administered, the age of the patient, the body weight of the patient, the general health of the patient, the gender of the patient, the diet of the patient, time of administration, route of administration, rate of excretion, drug combination, and the severity of the condition undergoing therapy, etc. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional course of treatment tests.

The compounds of FIG. I are producible from known compounds (or from starting materials which, in turn, are producible from known compounds), e.g., through the general preparative methods shown above. The activity of a given compound to inhibit raf kinase can be routinely assayed, e.g., according to procedures disclosed below. The following examples are for illustrative purposes only and are not intended, nor should they be construed to limit the invention in any way.

The entire disclosure of all applications, patents and publications cited above and below are hereby incorporated by reference, including non-provisional application Ser. No. 09/257,265 filed Feb. 25, 1999 and provisional application Ser. No. 60/115,878, filed on Jan. 13, 1999.

The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg. Unless otherwise stated, the term 'under high vacuum' refers to a vacuum of 0.4-1.0 mmHg.

All temperatures are reported uncorrected in degrees Celsius (° C.). Unless otherwise indicated, all parts and percentages are by weight, Commercial grade reagents and solvents were used without further purification. N-cyclohexyl-N'-(methylpolystyrene)carbodiimide was purchased from Calbiochem-Novabiochem Corp. 3-tert-Butylaniline, 5-tert-butyl-2-methoxyaniline, 4-bromo-3-(trifluoromethyl)aniline, 4-chloro-3-(trifluoromethyl)aniline 2-methoxy-5-(trifluoromethyl)aniline, 4-tert-butyl-2-nitroaniline, 3-amino-2- naphthol, ethyl 4-isocyanatobenzoate, N-acetyl-4-chloro-2-methoxy-5-(trifluoromethylaniline and 4-s chloro-3-(trifluoromethyl)phenyl isocyanate were purchased and used without further purification. Syntheses of 3-amino-2-methoxyquinoline (E. Cho et al. WO 98/00402; A. Cordi et al. EP 542,609; IBID Bioorg. Med. Chem. 3, 1995, 129), 4-(3-carbamoylphenoxy)-1-nitrobenzene (K. Ikawa Yakugaku Zasshi 79, 1959, 760; Chem. Abstr. 53, 1959, 12761b), 3-tert-butylphenyl isocyanate (O. Rohr et al. DE 2,436,108) and 2-methoxy-5-(trifluoromethyl)phenyl isocyanate (K. Inukai et al. JP 42,025,067; IBID Kogyo Kagaku Zasshi 70, 1967, 491) have previously been described.

Thin-layer chromatography (TLC) was performed using Whatman® pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230-400 mesh EM Science® silica gel.

Melting points (mp) were determined using a Thomas-Hoover melting point apparatus or a Mettler FP66 automated melting point apparatus and are uncorrected. Fourier transform infrared spectra were obtained using a Mattson 4020 Galaxy Series spectrophotometer. Proton ($^1$H) nuclear magnetic resonance (NMR) spectra were measured with a General Electric GN-Omega 300 (300 z) spectrometer with either Me$_4$Si (δ 0.00) or residual protonated solvent (CHCl$_3$ δ 7.26; MeOH δ 3.30; DMSO δ 2.49) as standard. Carbon ($^{13}$C)N spectra were measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment were obtained using a Kratos Concept 1-H spectrometer. Chemical ionization mass spectra (CA-MS) were obtained using a Hewlett Packard MS-Engine (5989A) with methane or ammonia as the reagent gas (1×10$^{-4}$ torr to 2.5×10$^{-4}$ torr). The direct insertion desorption chemical ionization (DCI) probe (Vacuumetrics, Inc.) was ramped from 0-1.5 amps in 10 sec and held at 10 amps until all traces of the sample disappeared (~1-2 min). Spectra were scanned from 50-800 amu at 2 sec per scan. HPLC-electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source. Gas chromatography-ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV). Elemental analyses are conducted by Robertson Microlit Labs, Madison N.J.

All compounds displayed NMR spectra, LRMS and either elemental analysis or MS consistent with assigned structures.

| List of Abbreviations and Acronyms: | |
| --- | --- |
| AcOH | acetic acid |
| anh | anhydrous |
| atm | atmosphere(s) |
| BOC | tert-butoxycarbonyl |
| CDI | 1,1'-carbonyl diimidazole |
| conc | concentrated |
| d | day(s) |
| dec | decomposition |
| DMAC | N,N-dimethylacetamide |
| DMPU | 1,3-dimethyl-3,4,5,6-tetrahydro-2(1H)-pyrimidinone |
| DMF | N,N-dimethylformamide |
| DMSO | dimethylsulfoxide |
| DPPA | diphenylphosphoryl azide |
| EDCI | 1-(3-dimethylaminopropyl)-3-ethylcarbodiimide |
| EtOAc | ethyl acetate |
| EtOH | ethanol (100%) |
| Et$_2$O | diethyl ether |
| Et$_3$N | triethylamine |
| h | hour(s) |
| HOBT | 1-hydroxybenzotriazole |
| m-CPBA | 3-chloroperoxybenzoic acid |
| MeOH | methanol |
| pet. ether | petroleum ether (boiling range 30-60° C.) |
| temp. | temperature |
| THF | tetrahydrofuran |
| TFA | trifluoroAcOH |
| Tf | trifluoromethanesulfonyl |

A. General Methods for Synthesis of Substituted Anilines

A1. General Method for Aryl Amine Formation via Ether Formation Followed by Ester Saponification, Curtius Rearrangement, and Carbamate Deprotection. Synthesis of 2-Amino-3-methoxynaphthalene.

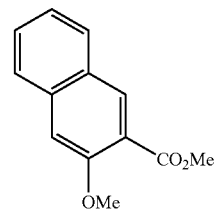

Step 1. Methyl 3-methoxy-2-naphthoate

A slurry of methyl 3-hydroxy-2-naphthoate (10.1 g, 50.1 mmol) and K$_2$CO$_3$ (7.96 g, 57.6 mmol) in DMF (200 mL) was stirred at room temp. for 15 min., then treated with iodomethane (3.43 mL, 55.1 mmol). The mixture was allowed to stir at room temp. overnight, then was treated with water (200 mL). The resulting mixture was extracted with EtOAc (2×200 mL). The combined organic layers were washed with a saturated NaCl solution (100 mL), dried (MgSO$_4$), concentrated under reduced pressure (approximately 0.4 mmHg overnight) to give methyl 3-methoxy-2-naphthoate as an amber oil (10.30 g): $^1$H-NMR DMSO-d$_6$) δ 2.70 (s, 3H), 2.85 (s, 3H), 7.38 (app t, J=8.09 Hz, 1H), 7.44 (s, 1H), 7.53 (app t, J=8.09 Hz, 1H), 7.84 (d, J=8.09 Hz, 1H), 7.90 (s, 1H), 8.21 (s, 1H).

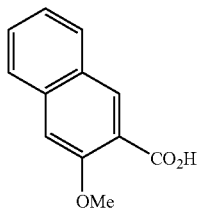

Step 2. 3-Methoxy-2-naphthoic acid

A solution of methyl 3-methoxy-2-naphthoate (6.28 g, 29.10 mmol) and water (10 mL) in MeOH (100 mL) at room temp. was treated with a 1 N NaOH solution (33.4 mL, 33.4 mmol). The mixture was heated at the reflux temp. for 3 h, cooled to room temp., and made acidic with a 10% citric acid solution. The resulting solution was extracted with EtOAc (2×100 mL). The combined organic layers were washed with a saturated NaCl solution, dried (MgSO$_4$) and concentrated under reduced pressure. The residue was triturated with hexane then washed several times with hexane to give 3-methoxy-2-naphthoic acid as a white solid (5.40 g, 92%): $^1$H-NMR (DMSO-d$_6$) δ 3.88 (s, 3H), 7.34-7.41 (m, 2H), 7.49-7.54 (m, 1H), 7.83 (d, J=8.09 Hz, 1H), 7.91 (d, J=8.09 Hz, 1H), 8.19 (s, 1H), 12.83 (br s, 1H).

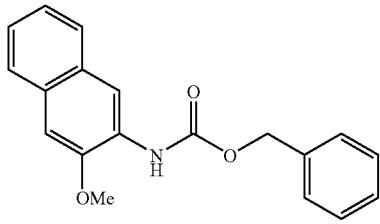

Step 3.
2-(N-(Carbobenzyloxy)amino-3-methoxynaphthalene

A solution of 3-methoxy-2-naphthoic acid (3.36 g, 16.6 mmol) and Et$_3$N (2.59 mL, 18.6 mmol) in anh toluene (70 mL) was stirred at room temp. for 15 min., then treated with a solution of DPPA (5.12 g, 18.6 mmol) in toluene (10 mL) via pipette. The resulting mixture was heated at 80° C. for 2 h. After cooling the mixture to room temp., benzyl alcohol (2.06 mL, 20 mmol) was added via syringe. The mixture was then warmed to 80° C. overnight. The resulting mixture was cooled to room temp., quenched with a 10% citric acid solution, and extracted with EtOAc (2×100 mL). The combined organic layers were washed with a saturated NaCl solution, dried (MgSO$_4$) and concentrated under reduced pressure. The residue was purified by column chromatography (14% EtOAc/86% hexane) to give 2-(N-(carbobenzyloxy)amino-3-methoxynaphthalene as a pale yellow oil (5.1 g, 100%): $^1$H-NMR (DMSO-d$_6$) δ 3.89 (s, 3H), 5.17 (s, 2H), 7.27-7.44 (m, 8H), 7.72-7.75 (m, 2H), 8.20 (s, 1H), 8.76 (s, 1H).

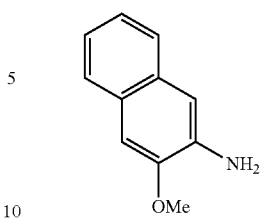

Step 4. 2-Amino-3-methoxynaphthalene

A slurry of 2-(N-(carbobenzyloxy)amino-3-methoxynaphthalene (5.0 g, 16.3 mmol) and 10% Pd/C (0.5 g) in EtOAc (70 mL) was maintained under a H$_2$ atm balloon) at room temp. overnight. The resulting mixture was filtered through Celite® and concentrated under reduced pressure to give 2-amino-3-methoxynaphthalene as a pale pink powder (2.40 g, 85%); $^1$H-NMR (DMSO-d$_6$) δ 3.86 (s, 3H), 6.86 (s, 2H), 7.04-7.16 (m, 2H), 7.43 (d, J=8.0 Hz, 1H), 7.56 (d, J=8.0 Hz, 1H); EI-MS m/z 173 (M$^+$).

A2. Synthesis of ω-Carbamyl Anilines via Formation of a Carbamylpyridine Followed by Nucleophilic Coupling with an Aryl Amine. Synthesis of 4-(2-N-Methylcarbamyl-4-pyridyloxy)aniline

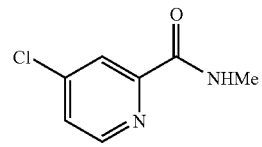

Step 1a. Synthesis of
4-chloro-N-methyl-2-pyridinecarboxamide via the Menisci Reaction Caution: this is a highly hazardous, potentially explosive reaction. To a stirring solution of 4-chloropyridine (10.0 g) in N-methylformamide (250 mL) at room temp. was added conc. H$_2$SO$_4$ (3.55 mL) to generate an exotherm. To this mixture was added H$_2$O$_2$ (30% Wt in H$_2$O, 17 mL) followed by FeSO$_4$·7H$_2$O (0.56 g) to generate another exotherm. The resulting mixture was stirred in the dark at room temp. for 1 h, then warmed slowly over 4 h to 45° C. When bubbling had subsided, the reaction was heated at 60° C. for 16 h. The resulting opaque brown solution was diluted with H$_2$O (700 mL) followed by a 10% NaOH solution (250 mL). The resulting mixture was extracted with EtOAc (3×500 mL). The organic phases were washed separately with a saturated NaCl solution (3×150 mL), then they were combined, dried (MgSO$_4$) and filtered through a pad of silica gel with the aid of EtOAc. The resulting brown oil was purified by column chromatography (gradient from 50% EtOAc/50% hexane to 80% EtOAc/20% hexane). The resulting yellow oil crystallized at 0° C. over 72 h to give 4-chloro-N-methyl-2-pyridinecarboxamide (0.61 g, 5.3%): TLC (50% EtOAc/50% hexane) R$_f$ 0.50; $^1$H NMR (CDCl$_3$) δ 3.04 (d, J=5.1 Hz, 3H), 7.43 (dd, J=5.4, 2.4 Hz, 1H), 7.96 (br s, 1H), 8.21 (s, 1H), 8.44 (d, J=5.1 Hz, 1H); CI-MS m/z 171 ((M+H)$^+$).

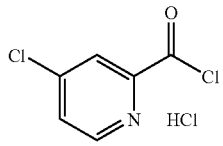

Step 1b. Synthesis of 4-chloropyridine-2-carbonyl chloride HCl salt via picolinic acid Anhydrous DMF (6.0 mL) was slowly added to SOCl$_2$ (180 mL) between 40° and 50° C. The solution was stirred in that temperature range for 10 min. then picolinic acid (60.0 g, 487 mmol) was added in portions over 30 min. The resulting solution was heated at 72° C. (vigorous SO$_2$ evolution) for 16 h to generate a yellow solid precipitate. The resulting mixture was cooled to room temp., diluted with toluene (500 mL) and concentrated to 200 mL. The toluene addition/concentration process was repeated twice. The resulting nearly dry residue was filtered and the solids were washed with toluene (2×200 ml) and dried under high vacuum for 4 h to afford 4-chloro-pyridine-2-carbonyl chloride HCl salt as a yellow-orange solid (92.0 g, 89%).

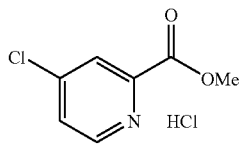

Step 2. Synthesis of methyl 4-chloropyridine-2-carboxylate HCl salt

Anh DMF (100 mL) was slowly added to SOCl$_2$ (300 mL) at 40-48° C. The solution was stirred at that temp. range for 10 min., then picolinic acid (100 g, 812 mmol) was added over 30 min. The resulting solution was heated at 72° C. (vigorous SO$_2$ evolution) for 16 h to generate a yellow solid. The resulting mixture was cooled to room temp., diluted with toluene (500 mL) and concentrated to 200 mL. The toluene addition/concentration process was repeated twice. The resulting nearly dry residue was filtered, and the solids were washed with toluene (50 mL) and dried under high vacuum for 4 hours to afford 4-chloropyridine-2-carbonyl chloride HCl salt as an off-white solid (27.2 g, 16%). This material was set aside.

The red filtrate was added to MeOH (200 mL) at a rate which kept the internal temperature below 55° C. The contents were stirred at room temp. for 45 min., cooled to 5° C. and treated with Et$_2$O (200 mL) dropwise. The resulting solids were filtered, washed with Et$_2$O (200 mL) and dried under reduced pressure at 35° C. to provide methyl 4-chloro-pyridine-2-carboxylate HCl salt as a white solid (110 g, 65%): mp 108-112° C.; $^1$H-NMR (DMSO-d$_6$) δ 3.88 (s, 3H); 7.82 (dd, J=5.5, 2.2 Hz, 1H); 8.08 (d, J=2.2 Hz, 1H); 8.68 (d, J=5.5 Hz, 1H); 10.68 (br s, 1H); HPLC ES-MS m/z 172 ((M+H)$^+$).

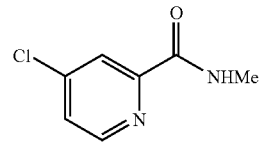

Step 3a. Synthesis of 4-chloro-N-methyl-2-pyridinecarboxamide from methyl 4-chloropyridine-2-carboxylate A suspension of methyl 4-chloropyridine-2-carboxylate HCl salt (89.0 g, 428 mmol) in MeOH (75 mL) at 0° C. was treated with a 2.0 M methylamine solution in THF (1 L) at a rate which kept the internal temp. below 5° C. The resulting mixture was stored at 3° C. for 5 h, then concentrated under reduced pressure. The resulting solids were suspended in EtOAc (1 L) and filtered. The filtrate was washed with a saturated NaCl solution (500 mL), dried (Na$_2$SO$_4$) and concentrated under reduced pressure to afford 4-chloro-N-methyl-2-pyridinecarboxamide as pale-yellow crystals (71.2 g, 97%): mp 41-43° C.; $^1$H-NMR DMSO-d$_6$) δ 2.81 (s, 3H), 7.74 (dd, J=5.1, 2.2 Hz, 1H), 8.00 (d, J=2.2, 1H), 8.61 (d, J=5.1 Hz, 1H), 8.85 (br d, 1H); CI-MS m/z 171 ((M+H)$^+$).

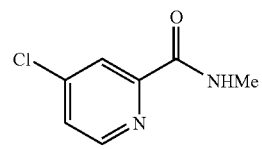

Step 3b. Synthesis of 4-chloro-N-methyl-2-pyridinecarboxamide from 4-chloropyridine-2-carbonyl chloride 4-Chloropyridine-2-carbonyl chloride HCl salt (7.0 g, 32.95 mmol) was added in portions to a mixture of a 2.0 M methylamine solution in THF (100 ml) and MeOH (20 n-L) at 0° C. The resulting mixture was stored at 3° C. for 4 h, then concentrated under reduced pressure. The resulting nearly dry solids were suspended in EtOAc (100 mL) and filtered. The filtrate was washed with a saturated NaCl solution (2×100 mL), dried (Na$_2$SO$_4$) and concentrated under reduced pressure to provide 4-chloro-N-methyl-2-pyridinecarboxamide as a yellow, crystalline solid (4.95 g, 88%): mp 37-40° C.

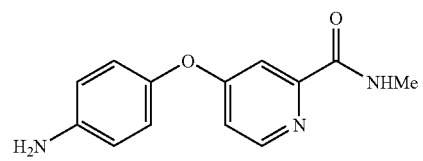

Step 4. Synthesis of 4-(2-(N-methylcarbamoyl)-4-pyridyloxy)aniline

A solution of 4-aminophenol (9.60 g, 88.0 mmol) in anh. DMF (150 mL) was treated with potassium tert-butoxide (10.29 g, 91.7 mmol), and the reddish-brown mixture was stirred at room temp. for 2 h. The contents were treated with 4-chloro-N-methyl-2-pyridinecarboxamide (15.0 g, 87.9 mmol) and K$_2$CO$_3$ (6.50 g, 47.0 mmol) and then heated at 80° C. for 8 h. The mixture was cooled to room temp. and separated between EtOAc (500 mL) and a saturated NaCl solution (500 mL). The aqueous phase was back-extracted with EtOAc (300 mL). The combined organic layers were washed with a saturated NaCl solution (4×1000 mL), dried Na$_2$SO$_4$) and concentrated under reduced pressure. The resulting solids were dried under reduced pressure at 35° C. for 3 h to afford 4-(2-(N-methylcarbamoyl)-4-pyridyloxy)aniline as a light-brown solid 17.9 g, 84%): $^1$H-NMR (DMSO-d$_6$) δ 2.77 (d, J=4.8 Hz, 3H), 5.17 (br s, 2H), 6.64, 6.86 (AA'BB' quartet, J=8.4 Hz, 4H), 7.06 (dd, J=5.5, 2.5 Hz, 1H), 7.33 (d, J=2.5 Hz, 1H), 8.44 (d, J=5.5 Hz, 1H), 8.73 (br d, 1H); HPLC ES-MS m/z 244 ((M+H)$^+$).

A3. General Method for the Synthesis of Anilines by Nucleophilic Aromatic Addition Followed by Nitroarene Reduction. Synthesis of 5-(4-Aminophenoxy)isoindoline-1,3-dione

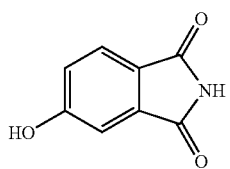

Step 1. Synthesis of 5-hydroxyisoindoline-1,3-dione

To a mixture of ammonium carbonate (5.28 g, 54.9 mmol) in conc. AcOH (25 mL) was slowly added 4-hydroxyphthalic acid (5.0 g, 27.45 mmol). The resulting mixture was heated at 120° C. for 45 min., then the clear, bright yellow mixture was heated at 160° C. for 2 h. The resulting mixture was maintained at 160° C. and was concentrated tot approximately 15 mL, then was cooled to room temp. and adjusted pH 10 with a 1N NaOH solution. This mixture was cooled to 0° C. and slowly acidified to pH 5 using a 1N HCl solution. The resultant precipitate was collected by filtration and dried under reduced pressure to yield 5-hydroxyisoindoline-1,3-dione as a pale yellow powder as product (3.24 g, 72%): $^1$H NMR (DMSO-d$_6$) δ 7.00-7.03 (m, 2H), 7.56 (d, J=9.3 Hz, 1H).

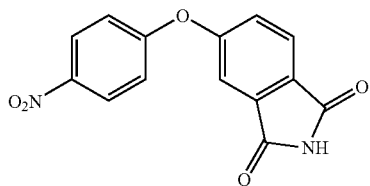

Step 2. Synthesis of 5-(4-nitrophenoxy)isoindoline-1,3-dione

To a stirring slurry of NaH (1.1 g, 44.9 mmol) in DMF (40 mL) at 0° C. was added a solution of 5-hydroxyisoindoline-1,3-dione (3.2 g, 19.6 mmol) in DMF (40 mL) dropwise. The bright yellow-green mixture was allowed to return to room temp. and was stirred for 1 h, then 1-fluoro-4-nitrobenzene (2.67 g, 18.7 mmol) was added via syringe in 3-4 portions. The resulting mixture was heated at 70° C. overnight, then cooled to room temp. and diluted slowly with water (150 mL), and extracted with EtOAc (2×100 mL). The combined organic layers were dried (MgSO$_4$) and concentrated under reduced pressure to give 5-(4-nitrophenoxy)isoindoline-1,3-dione as a yellow solid (3.3 g, 62%): TLC (30% EtOAc/70% hexane) R$_f$ 0.28; 1H NMR (DMSO-d$_6$) δ 7.32 (d, J=12 Hz, 2H), 7.52-7.57 (m, 2H), 7.89 (d, J=7.8 Hz, 1H), 8.29 (d, J=9 Hz, 2H), 11.43 (br s, 1H); CI-MS m/z 285 ((M+H)$^+$, 100%).

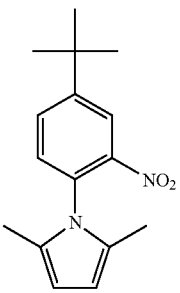

Step 3. Synthesis of 5-(4-aminophenoxy)isoindoline-1,3-dione

A solution of 5-(4-nitrophenoxy)isoindoline-1,3-dione (0.6 g, 2.11 mmol) in conc. AcOH (12 mL) and water (0.1 mL) was stirred under stream of argon while iron powder (0.59 g, 55.9 mmol) was added slowly. This mixture stirred at room temp. for 72 h, then was diluted with water (25 ml) and extracted with EtOAc (3×50 mL). The combined organic layers were dried (MgSO$_4$) and concentrated under reduced pressure to give 5-(4-aminophenoxy)isoindoline-1,3-dione as a brownish solid (0.4 g, 75%): TLC (50% EtOAc/50% hexane) R$_f$ 0.27; $^1$H NMR (DMSO-d$_6$) δ 5.14 (br s, 2H), 6.62 (d, J=8.7 Hz, 2H), 6.84 (d, J=8.7 Hz, 2H), 7.03 (d, J=2.1 Hz, 1H), 7.23 (dd, 1H), 7.75 (d, J=8.4 Hz, 1H), 11.02 (s, 1H); HPLC ES-MS m/z 255 ((M+H)$^+$, 100%).

A4. General Method for the Synthesis of Pyrrolylanilines. Synthesis of 5-tert-Butyl-2-(2,5-dimethylpyrrolyl)aniline Step 1. Synthesis of 1-(4-tert-butyl-2-nitrophenyl)-2,5-dimethylpyrrole To a stirring solution of 2-nitro-4-tert-butylaniline (0.5 g, 2.57 mmol) in cyclohexane (10 mL) was added AcOH (0.1 mL) and acetonylacetone (0.299 g, 2.63 mmol) via syringe. The reaction mixture was heated at 120° C. for 72 h with azeotropic removal of volatiles. The reaction mixture was cooled to room temp., diluted with CH$_2$Cl$_2$ (10 mL) and sequentially washed with a 1N HCl solution (15 mL), a 1N NaOH solution (15 mL) and a saturated NaCl solution (15 mL), dried (MgSO$_4$) and concentrated under reduced pressure. The resulting orange-brown solids were purified via column chromatography (60 g SiO$_2$; gradient from 6% EtOAc/94% hexane to 25% EtOAc/75% hexane) to give 1-(4-tert-butyl-2-nitrophenyl)-2,5-dimethylpyrrole as an orange-yellow solid (0.34 g, 49%)-TLC (15% EtOAc/85% hexane) R$_f$ 0.67; $^1$H NMR (CDCl$_3$) δ 1.34 (s, 9H), 1.89 (s, 6H), 5.84 (s, 2H), 7.19-7.24 (m, 1H), 7.62 (dd, 1H), 7.8 (d, J=2.4 Hz, 1H); CI-MS m/z 273 ((M+H)$^+$, 50%).

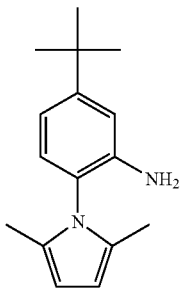

Step 2. Synthesis of
5-tert-Butyl-2-(2,5-dimethylpyrrolyl)aniline

A slurry of 1-(4-tert-butyl-2-nitrophenyl)-2,5-dimethylpyrrole (0.341 g, 1.25 mmol), 10% Pd/C (0.056 g) and EtOAc (50 mL) under an H$_2$ atmosphere (balloon) was stirred for 72 h, then filtered through a pad of Celite®. The filtrate was concentrated under reduced pressure to give 5-tert-butyl-2-(2,5-dimethylpyrrolyl)aniline as yellowish solids (0.30 g, 99%): TLC (10% EtOAc/90% hexane) R$_f$ 0.43; $^1$H NMR (CDCl$_3$) δ 1.28 (s, 9H), 1.87-1.91 (m, 8H), 5.85 (br s, 2H), 6.73-6.96 (m, 3H), 7.28 (br s, 1H).

A5. General Method for the Synthesis of Anilines from Anilines by Nucleophilic Aromatic Substitution. Synthesis of 4-(2-(N-Methylcarbamoyl)-4-pyridyloxy)-2-methylaniline HCl Salt

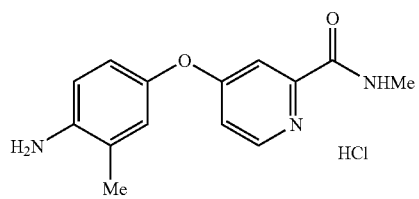

A solution of 4-amino-3-methylphenol (5.45 g, 44.25 mmol) in dry dimethylacetamide (75 mL) was treated with potassium tert-butoxide (10.86 g, 96.77 mmol) and the black mixture was stirred at room temp. until the flask had reached room temp. The contents were then treated with 4-chloro-N-methyl-2-pyridinecarboxamide (method A2, Step 3b; 7.52 g, 44.2 mmol) and heated at 110° C. for 8 h. The mixture was cooled to room temp. and diluted with water (75 mL). The organic layer was extracted with EtOAc (5×100 mL). The combined organic layers were washed with a saturated NaCl solution (200 mL), dried (MgSO$_4$) and concentrated under reduced pressure. The residual black oil was treated with Et$_2$O (50 mL) and sonicated. The solution was then treated with HCl (1 M in Et$_2$O; 100 mL) and stirred at room temp. for 5 min. The resulting dark pink solid (7.04 g, 24.1 mmol) was removed by filtration from solution and stored under anaerobic conditions at 0° C. prior to use: $^1$H NMR (DMSO-d$_6$) δ 2.41 (s, 3H), 2.78 (d, J=4.4 Hz, 3H), 4.93 (br s, 2H), 7.19 (dd, J=8.5, 2.6 Hz, 1H), 7.23 (dd, J=5.5, 2.6 Hz, 1H), 7.26 (d, J=2.6 Hz, 1H), 7.55 (d, 1-2.6 Hz, 1H), 7.64 (d, J=8.8 Hz, 1H), 8.55 (d, J=5.9 Hz, 1H), 8.99 (q, J=4.8 Hz, 1H).

A6. General Method for the Synthesis of Anilines from Hydroxyanilines by N-Protection, Nucleophilic Aromatic Substitution and Deprotection. Synthesis of 4-(2-(N-Methylcarbamoyl)-4-pyridyloxy)-2-chloroaniline

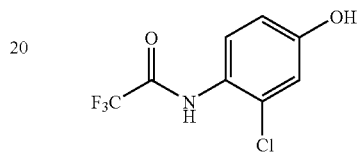

Step 1: Synthesis of
3-Chloro-4-(2,2,2-trifluoroacetylamino)phenol

Iron (3.24 g, 58.00 mmol) was added to stirring TFA (200 mL). To this slurry was added 2-chloro-4-nitrophenol (10.0 g, 58.0 mmol) and trifluoroacetic anhydride (20 mL). This gray slurry was stirred at room temp. for 6 d. The iron was filtered from solution and the remaining material was concentrated under reduced pressure. The resulting gray solid was dissolved in water (20 mL). To the resulting yellow solution was added a saturated NaHCO$_3$ solution (50 mL). The solid which precipitated from solution was removed. The filtrate was slowly quenched with the sodium bicarbonate solution until the product visibly separated from solution (determined was using a mini work-up vial). The slightly cloudy yellow solution was extracted with EtOAc (3×125 mL). The combined organic layers were washed with a saturated NaCl solution (125 mL), dried (MgSO$_4$) and concentrated under reduced pressure. The $^1$H NMR (DMSO-d$_6$) indicated a 1:1 ratio of the nitrophenol starting material and the intended product 3-chloro-4-(2,2,2-trifluoroacetylamino)phenol. The crude material was taken on to the next step without further purification.

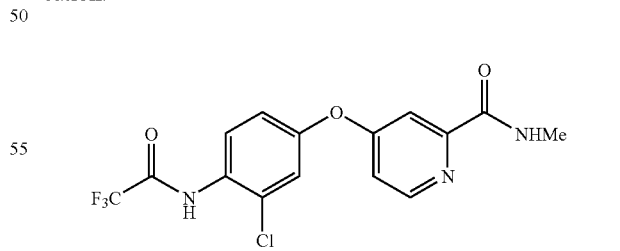

Step 2: Synthesis of 4-(2-(N-Methylcarbamoyl)-4-pyridyloxy)-2-chlorophenyl (222-trifluoro)acetamide A solution of crude 3-chloro-4-(2,2,2-trifluoroacetylamino)phenol (5.62 g, 23.46 mmol) in dry dimethylacetamide (50 mL) was treated with potassium tert-butoxide (5.16 g, 45.98 mmol) and the brownish black mixture was stirred at room temp. until the flask had cooled to room temp. The resulting mixture was treated with 4-chloro-N-methyl-2-pyridinecarboxamide (Method A2, Step 3b; 1.99 g, 11.7 mmol) and heated at 100° C. under argon for 4 d. The black reaction mixture was cooled to room temp. and then poured into cold water (100 mL). The mixture was extracted with EtOAc (3×75 mL) and the combined organic layers were concentrated under reduced pressure. The residual brown oil was purified by column chromatography (gradient from 20% EtOAc/pet. ether to 40% EtOAc/pet. ether) to yield 4-(2-(N-Methylcarbamoyl)-4-pyridyloxy)-2-chlorophenyl (222-trifluoro)acetamide as a yellow solid (8.59 g, 23.0 mmol).

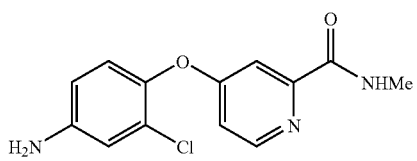

Step 3. Synthesis of 4-(2-(N-Methylcarbamoyl)-4-pyridyloxy)-2-chloroaniline

A solution of crude 4-(2-(N-Methylcarbamoyl)-4-pyridyloxy)-2-chlorophenyl (222-trifluoro)acetamide (8.59 g, 23.0 mmol) in dry 4-dioxane (20 mL) was treated with a 1N NaOH solution (20 mL). This brown solution was allowed to stir for 8 h. To this solution was added EtOAc (40 mL). The green organic layer was extracted with EtOAc (3×40 mL) and the solvent was concentrated to yield 4-(2-(N-Methylcarbamoyl)-4-pyridyloxy)-2-chloroaniline as a green oil that solidified upon standing (2.86 g, 10.30 mmol): $^1$H NMR (DMSO-$d_6$) δ 2.77 (d, J=4.8 Hz, 3H), 5.51 (s, 2H), 6.60 (dd, J=8.5, 2.6 Hz, 1H), 6.76 (d, J=2.6 Hz, 1H), 7.03 (d, J=8.5 Hz, 1H), 7.07 (dd, J=5.5, 2.6, Hz, 1H), 7.27 (d, J=2.6 Hz, 1H), 8.46 (d, J=5.5 Hz, 1H), 8.75 (q, J=4.8, 1H).

A7. General Method for the Deprotection of an Acylated Aniline Synthesis of 4-Chloro-2-methoxy-5-(trifluoromethyl)aniline

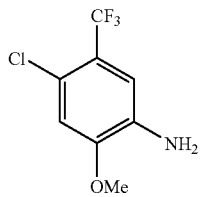

A suspension of 3-chloro-6-(N-acetyl)-4-(trifluoromethyl)anisole (4.00 g, 14.95 mmol) in a 6M HCl solution (24 mL) was heated at the reflux temp. for 1 h. The resulting solution was allowed to cool to room temp. during which time it solidified slightly. The resulting mixture was diluted with water (20 mL) then treated with a combination of solid NaOH and a saturated NaHCO$_3$ solution until the solution was basic. The organic layer was extracted with CH$_2$Cl$_2$ (3×50 nm). The combined organics were dried (MgSO$_4$) and concentrated under reduced pressure to yield 4-chloro-2-methoxy-5-(trifluoromethyl)aniline as a brown oil (3.20 g, 14.2 mmol): $^1$H NMR (DMSO-$d_6$) δ 3.84 (s, 3H), 5.30 (s, 2H), 7.01 (s, 2H).

A8. General Method for Synthesis of ω-Alkoxy-ω-carboxyphenyl Anilines. Synthesis of 4-(3-(N-Methylcarbamoly)-4-methoxyphenoxy)aniline

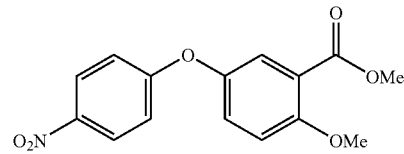

Step 1. 4-(3-Methoxycarbonyl-4-methoxyphenoxy)-1-nitrobenzene

To a solution of 4-(3-carboxy-4-hydroxyphenoxy)-1-nitrobenzene prepared from 2,5-dihydroxybenzoic acid in a manner analogous to that described in Method A13, Step 1, 12 mmol) in acetone (50 mL) was added K$_2$CO$_3$ (5 g) and dimethyl sulfate (3.5 mL). The resulting mixture was heated at the reflux temp. overnight, then cooled to room temp. and filtered through a pad of Celite®. The resulting solution was concentrated under reduced pressure, absorbed onto SiO$_2$, and purified by column chromatography (50% EtOAc/50% hexane) to give 4-(3-methoxycarbonyl-4-methoxyphenoxy)-1-nitrobenzene as a yellow powder (3 g): mp 115-118° C.

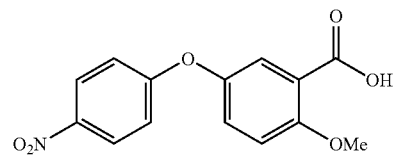

Step 2.
4-(3-Carboxy-4-methoxyphenoxy)-1-nitrobenzene

A mixture of 4-(3-methoxycarbonyl-4-methoxyphenoxy)-1-nitrobenzene (1.2 g), KOH (0.33 g) and water (5 mL) in MeOH (45 mL) was stirred at room temp. overnight and then heated at the reflux temp. for 4 h. The resulting mixture was cooled to room temp. and concentrated under reduced pressure. The residue was dissolved in water (50 mL), and the aqueous mixture was made acidic with a 1N HCl solution. The resulting mixture was extracted with EtOAc (50 mL). The organic layer was dried (MgSO$_4$) and concentrated under reduced pressure to give 4-(3-carboxy-4-methoxyphenoxy)-1-nitrobenzene (1.04 g).

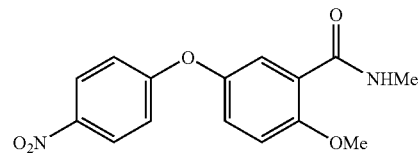

Step 3. 4-(3-(N-Methylcarbamoly)-4-methoxyphenoxy)-1-nitrobenzene

To a solution of 4-(3-carboxy-4-methoxyphenoxy)-1-nitrobenzene (0.50 g, 1.75 mmol) in CH$_2$Cl$_2$ (12 nm) was added SOCl$_2$ (0.64 mL, 8.77 mmol) in portions. The resulting solution was heated at the reflux temp. for 18 h, cooled to room temp., and concentrated under reduced pressure. The resulting yellow solids were dissolved in CH$_2$Cl$_2$ (3 mL) then the resulting solution was treated with a methylamine solution (2.0 M in THF, 3.5 mL, 7.02 mmol) in portions (CAUTION: gas evolution), and stirred at room temp. for 4 h. The resulting mixture was treated with a 1N NaOH solution, then extracted with CH$_2$Cl$_2$ (25 mL). The organic layer was dried (Na$_2$SO$_4$) and concentrated under reduced pressure to give 4-(3-(N-methylcarbamoly)-4-methoxyphenoxy)-1-nitrobenzene as a yellow solid (0.50 g, 95%).

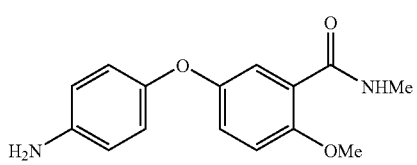

Step 4.
4-(3-(N-Methylcarbamoly)-4-methoxyphenoxy)aniline

A slurry of 4-(3-(N-methylcarbamoly)-4-methoxyphenoxy)-1-nitrobenzene (0.78 g, 2.60 mmol) and 10% Pd/C (0.20 g) in EtOH (55 mL) was stirred under 1 atm of H$_2$ (balloon) for 2.5 d, then was filtered through a pad of Celite®. The resulting solution was concentrated under reduced pressure to afford 4-(3-(N-methylcarbamoly)-4-methoxyphenoxy)aniline as an off-white solid (0.68 g, 96%): TLC (0.1% Et$_3$N/99.9% EtOAc) R$_f$ 0.36.

A9. General Method for Preparation of
ω-Alkylphthalimide-containing Anilines. Synthesis of
5-(4-Aminophenoxy)-2-methylisoindoline-1,3-dione

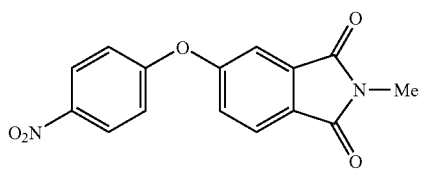

Step 1. Synthesis of
5-(4-Nitrophenoxy)-2-methylisoindoline-1,3-dione

A slurry of 5-(4-nitrophenoxy)isoindoline-1,3-dione (A3 Step 2; 1.0 g, 3.52 mmol) and NaH (0.13 g, 5.27 mmol) in DMF (15 mL) was stirred at room temp. for 1 h, then treated with methyl iodide (0.3 mL, 4.57 mmol). The resulting mixture was stirred at room temp. overnight, then was cooled to ° C. and treated with water (10 mL). The resulting solids were collected and dried under reduced pressure to give 5-(4-nitrophenoxy)-2-methylisoindoline-1,3-dione as a bright yellow solid (0.87 g, 83%): TLC (35% EtOAc/65% hexane) R$_f$ 0.61.

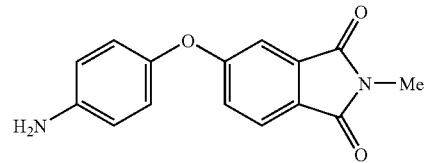

Step 2. Synthesis of
5-(4-Aminophenoxy)-2-methylisoindoline-1,3-dione

A slurry of nitrophenoxy)-2-methylisoindoline-1,3-dione (0.87 g, 2.78 mmol) and 10% Pd/C (0.10 g) in MeOH was stirred under 1 atm of H$_2$ (balloon) overnight. The resulting mixture was filtered through a pad of Celite® and concentrated under reduced pressure. The resulting yellow solids were dissolved in EtOAc (3 mL) and filtered through a plug of SiO$_2$ (60% EtOAc/40% hexane) to afford 5-(4-aminophenoxy)-2-methylisoindoline-1,3-dione as a yellow solid (0.67 g, 86%): TLC (40% EtOAc/60% hexane) R$_f$ 0.27.

A10. General Method for Synthesis of ω-Carbamoylaryl Anilines Through Reaction of ω-Alkoxycarbonylaryl Precursors with Amines. Synthesis of 4-(2-(N-(2-morpholin-4-ylethyl)carbamoyl)pyridyloxy) aniline

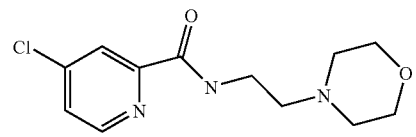

Step 1. Synthesis of 4-Chloro-2-(N-(2-morpholin-4-ylethyl)carbamoyl)pyridine

To a solution of methyl 4-chloropyridine-2-carboxylate HCl salt Method A2, Step 2; 1.01 g, 4.86 mmol) in THF (20 mL) was added 4-(2-aminoethyl)morpholine (2.55 mL, 19.4 mmol) dropwise and the resulting solution was heated at the reflux temp. for 20 h, cooled to room temp., and treated with water (50 mL). The resulting mixture was extracted with EtOAc (50 mL). The organic layer was dried (MgSO$_4$) and concentrated under reduced pressure to afford 4-chloro-2-(N-(2-morpholin-4-ylethyl) carbamoyl)pyridine as a yellow oil (1.25 g, 95%): TLC (10% MeOH/90% EtOAc) R$_f$ 0.50.

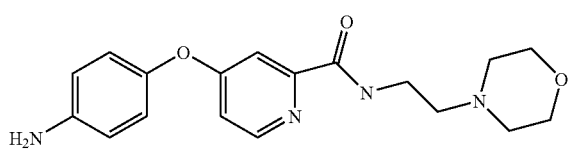

Step 2. Synthesis of 4-(2-(N-(2-Morpholin-4-ylethyl) carbamoyl)pyridyloxy)aniline A solution of 4-aminophenol (0.49 g, 4.52 mmol) and potassium tert-butoxide (0.53 g, 4.75 mol) in DMF (8 mL)

was stirred at room temp. for 2 h, then was sequentially treated with 4-chloro-2-(N-(2-morpholin-4-ylethyl)carbamoyl)pyridine (1.22 g, 4.52 mmol) and $K_2CO_3$ (0.31 g, 2.26 mmol). The resulting mixture was heated at 75° C. overnight, cooled to room temp., and separated between EtOAc (25 mL) and a saturated NaCl solution (25 mL). The aqueous layer was back extracted with EtOAc (25 mL). The combined organic layers were washed with a saturated NaCl solution (3×25 mL) and concentrated under reduced pressure. The resulting brown solids were purified by column chromatography (58 g; gradient from 100% EtOAc to 25% MeOH/75% EtOAc) to afford 4-(2-(N-(2-morpholin-4-ylethyl)carbamoyl)pyridyloxy)aniline (1.0 g, 65%): TLC (10% MeOH/90% EtOAc) $R_f$ 0.32.

A11. General Method for the Reduction of Nitroarenes to Arylamines. Synthesis of 4-(3-Carboxyphenoxy)aniline

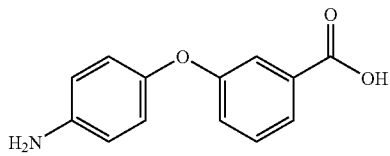

A slurry of 4-(3-carboxyphenoxy)-1-nitrobenzene (5.38 g, 20.7 mmol) and 10% Pd/C (0.50 g) in MeOH (120 mL) was stirred under an H2 atmosphere (balloon) for 2 d. The resulting mixture was filtered through a pad of Celite®, then concentrated under reduced pressure to afford 4-(3-carboxyphenoxy)aniline as a brown solid (2.26 g, 48%): TLC (10% MeOH/90% $CH_2Cl_2$) $R_f$ 0.44 (streaking).

A12. General Method for the Synthesis of Isoindolinone-Containing Anilines. Synthesis of 4-(1-Oxoisoindolin-5-yloxy)aniline

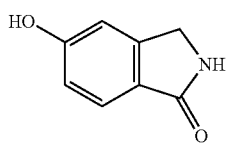

Step 1. Synthesis of 5-hydroxyisoindolin-1-one

To a solution of 5-hydroxyphthalimide (19.8 g, 121 mmol) in AcOH (500 mL) was slowly added zinc dust (47.6 g, 729 mmol) in portions, then the mixture was heated at the reflux temp. for 40 min., filtered hot, and concentrated under reduced pressure. The reaction was repeated on the same scale and the combined oily residue was purified by column chromatography (1.1 Kg $SiO_2$; gradient from 60% EtOAc/40% hexane to 25% MeOH/75% EtOAc) to give 5-hydroxy-isoindolin-1-one (3.77 g): TLC (100% EtOAc) $R_f$ 0.17; HPLC ES-MS m/z 150 ((M+H)$^+$).

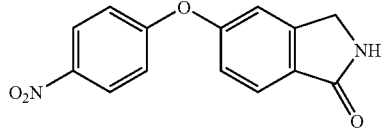

Step 2. Synthesis of 4-(1-isoindolinon-5-yloxy)-1-nitrobenzene

To a slurry of NaH (0.39 g, 16.1 mmol) in DMF at 0° C. was added 5-hydroxyisoindolin-1-one (2.0 g, 13.4 mmol) in portions. The resulting slurry was allowed to warm to room temp. and was stirred for 45 min., then 4-fluoro-1-nitrobenzene was added and then mixture was heated at 70° C. for 3 h. The mixture was cooled to 0° C. and treated with water dropwise until a precipitate formed. The resulting solids were collected to give 4-(1-isoindolinon-5-yloxy)-1-nitrobenzene as a dark yellow solid (3.23 g, 89%): TLC (100% EtOAc) $R_f$ 0.35.

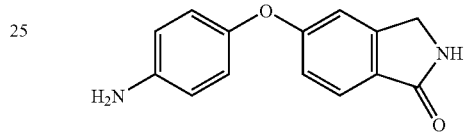

Step 3. Synthesis of 4-(1-oxoisoindolin-5-yloxy)aniline

A slurry of 4-(1-isoindolinon-5-yloxy)-1-nitrobenzene (2.12 g, 7.8 retool) and 10% Pd/C (0.20 g) in EtOH (50 mL) was stirred under an $H_2$ atmosphere balloon) for 4 h, then filtered through a pad of Celite®. The filtrate was concentrated under reduced pressure to afford 4-(1-oxoisoindolin-5-yloxy)aniline as a dark yellow solid: TLC (100% EtOAc) $R_f$ 0.15.

A13. General Method for the Synthesis of co-Carbamoyl Anilines via EDCI-Mediated Amide Formation Followed by Nitroarene Reduction. Synthesis of 4-(3-N-Methylcarbamoylphenoxy)aniline

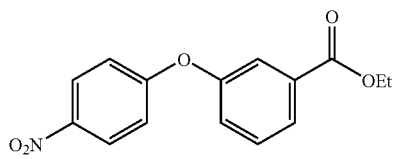

Step 1. Synthesis of 4-(3-ethoxycarbonylphenoxy)-1-nitrobenzene

A mixture of 4-fluoro-1-nitrobenzene (16 mL, 150 mmol), ethyl 3-hydroxybenzoate 25 g, 150 mmol) and $K_2CO_3$ (41 g, 300 mmol) in DMF (125 mL) was heated at the reflux temp. overnight, cooled to room temp. and treated with water (250 mL). The resulting mixture was extracted with EtOAc (3×150 mL). The combined organic phases were sequentially washed with water (3×100 mL) and a saturated NaCl solution (2×100 mL), dried (Na$_2$SO$_4$) and concentrated under reduced pressure. The residue was purified by column chromatography (10% EtOAc/90% hexane) to afford 4-(3-ethoxycarbonylphenoxy)-1-nitrobenzene as an oil (38 g),

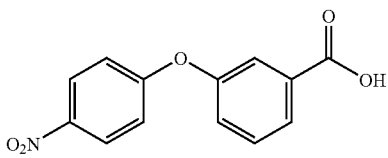

Step 2. Synthesis of
4-(3-carboxyphenoxy)-1-nitrobenzene

To a vigorously stirred mixture of 4-(3-ethoxycarbonylphenoxy)-1-nitrobenzene (5.14 g, 17.9 mmol) in a 3:1 THF/water solution (75 mL) was added a solution LiOH.H$_2$O (1.50 g, 35.8 mmol) in water (36 mL). The resulting mixture was heated at 50° C. overnight, then cooled to room temp., concentrated under reduced pressure, and adjusted to pH 2 with a 1M HCl solution. The resulting bright yellow solids were removed by filtration and washed with hexane to give 4-(3-carboxyphenoxy)-1-nitrobenzene (4.40 g, 95%).

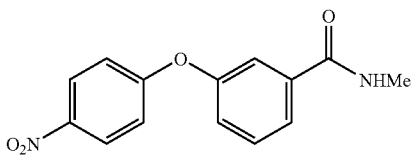

Step 3. Synthesis of
4-(3-(N-methylcarbamoyl)phenoxy)-1-nitrobenzene

A mixture of 4-(3-carboxyphenoxy)-1-nitrobenzene (3.72 g, 14.4 mmol), EDCI.HCl (3.63 g, 18.6 mmol), N-methylmorpholine (1.6 mL, 14.5 mmol) and methylamine (2.0 M in THF 8 mL, 16 mmol) in CH$_2$Cl$_2$ (45 mL) was stirred at room temp. for 3 d, then concentrated under reduced pressure. The residue was dissolved in EtOAc (50 mL) and the resulting mixture was extracted with a 1M HCl solution (50 mL). The aqueous layer was back-extracted with EtOAc (2×50 mL). The combined organic phases were washed with a saturated NaCl solution (50 mL), dried (Na$_2$SO$_4$), and concentrated under reduced pressure to give 4-(3-(N-methylcarbamoyl)phenoxy)-1-nitrobenzene as an oil (1.89 g).

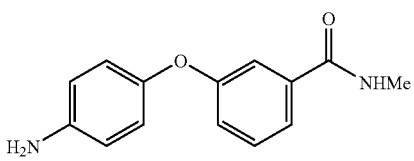

Step 4. Synthesis of
4-(3-(N-methylcarbamoyl)phenoxy)aniline

A slurry of 4-(3-(N-methylcarbamoyl)phenoxy)-1-nitrobenzene (1.89 g, 6.95 mmol) and 5% Pd/C (0.24 g) in EtOAc (20 mL) was stirred under an H2 atm (balloon) overnight. The resulting mixture was filtered through a pad of Celite® and concentrated under reduced pressure. The residue was purified by column chromatography (5% MeOH/95% CH$_2$Cl$_2$). The resulting oil solidified under vacuum overnight to give 4-(3-(N-methylcarbamoyl)phenoxy)aniline as a yellow solid (0.95 g, 56%).

A14. General Method for the Synthesis of
ω-Carbamoyl Anilines via EDCI-Mediated Amide
Formation Followed by Nitroarene Reduction.
Synthesis of
4-3-(5-Methylcarbamoyl)pyridyloxy)aniline

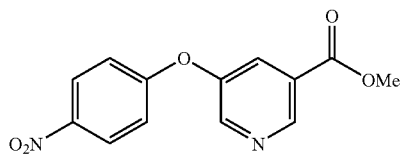

Step 1. Synthesis of
4-(3-(5-methoxycarbonyl)pyridyloxy)-1-nitrobenzene

To a slurry of NaH (0.63 g, 26.1 mmol) in DMF (20 mL) was added a solution of methyl 5-hydroxynicotinate (2.0 g, 13.1 mmol) in DMF (10 mL). The resulting mixture was added to a solution of 4-fluoronitrobenzene (1.4 mL, 13.1 mmol) in DMF (10 mL) and the resulting mixture was heated at 70° C. overnight, cooled to room temp., and treated with MeOH (5 mL) followed by water (50 mL). The resulting mixture was extracted with EtOAc (100 mL). The organic phase was concentrated under reduced pressure. The residue was purified by column chromatography (30% EtOAc/70% hexane) to afford 4-(3-(5-methoxycarbonyl)pyridyloxy)-1-nitrobenzene (0.60 g).

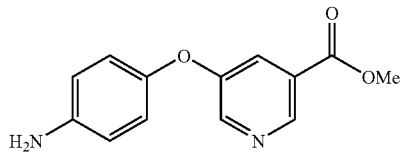

Step 2. Synthesis of
4-(3-(5-methoxycarbonyl)pyridyloxy)aniline

A slurry of 4-(3-(5-methoxycarbonyl)pyridyloxy)-1-nitrobenzene (0.60 g, 2.20 mmol) and 10% Pd/C in MeOH/EtOAc was stirred under an H$_2$ atmosphere (balloon) for 72 h. The resulting mixture was filtered and the filtrate was concentrated under reduced pressure. The residue was purified by column chromatography (gradient from 10% EtOAc/90% hexane to 30% EtOAc/70% hexane to 50% EtOAc/50% hexane) to afford 4-(3-(5-methoxycarbonyl)pyridyloxy)aniline (0.28 g, 60%); $^1$H NMR (CDCl$_3$) δ 3.92 (s, 3H), 6.71 (d, 2H), 6.89 (d, 2H), 7.73 (, 1H), 8.51 (d, 1H), 8.87 (d, 1H).

A15. Synthesis of an Aniline via Electrophilic Nitration Followed by Reduction. Synthesis of 4-(3-Methylsulfamoylphenoxy)aniline

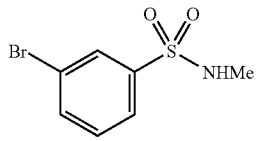

Step 1. Synthesis of N-methyl-3-bromobenzenesulfonamide

To a solution of 3-bromobenzenesulfonyl chloride (2.5 g, 11.2 mmol) in THF (15 mL) at 0° C. was added methylamine (2.0 M in THF; 28 mL, 56 mmol). The resulting solution was allowed to warm to room temp. and was stirred at room temp. overnight. The resulting mixture was separated between EtOAc (25 mL) and a 1 M HCl solution (25 mL). The aqueous phase was back-extracted with EtOAc (2×25 mL). The combined organic phases were sequentially washed with water (2×25 mL) and a saturated NaCl solution (25 mL), dried (MgSO$_4$) and concentrated under reduced pressure to give N-methyl-3-bromobenzenesulfonamide as a white solid (2.8 g, 99%).

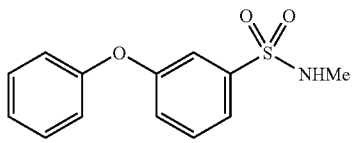

Step 2. Synthesis of 4-(3-(N-methylsulfamoyl)phenyloxy)benzene

To a slurry of phenol (1.9 g, 20 mmol), K$_2$CO$_3$ (6.0 g, 40 mmol), and CuI (4 g, 20 mmol) in DMF (25 mL) was added N-methyl-3-bromobenzenesulfonamide (2.5 g, 10 mmol), and the resulting mixture was stirred at the reflux temp. overnight, cooled to room temp., and separated between EtOAc (50 mL) and a 1 N HCl solution (50 mL). The aqueous layer was back-extracted with EtOAc (2×50 mL). The combined organic phases were sequentially washed with water (2×50 mL) and a saturated NaCl solution (50 mL), dried (MgSO$_4$), and concentrated under reduced pressure. The residual oil was purified by column chromatography (30% EtOAc/70% hexane) to give 4-(3-(N-methylsulfamoyl)phenyloxy)benzene (0.30 g).

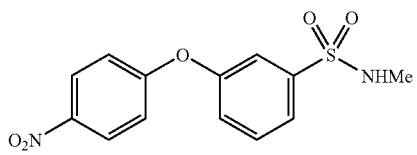

Step 3. Synthesis of 4-(3-(N-methylsulfamoyl)phenyloxy)-1-nitrobenzene

To a solution of 4-(3-(N-methylsulfamoyl)phenyloxy)benzene (0.30 g, 1.14 mmol) in TFA (6 mL) at −10° C. was added NaNO$_2$ (0.097 g, 1.14 mmol) in portions over 5 min. The resulting solution was stirred at −10° C. for 1 h, then was allowed to warm to room temp., and was concentrated under reduced pressure. The residue was separated between EtOAc (10 mL) and water (10 mL). The organic phase was sequentially washed with water (10 mL) and a saturated NaCl solution (10 mL), dried (MgSO$_4$) and concentrated under reduced pressure to give 4-(3-(N-methylsulfamoyl)phenyloxy)-1-nitrobenzene (0.20 g). This material carried on to the next step without further purification.

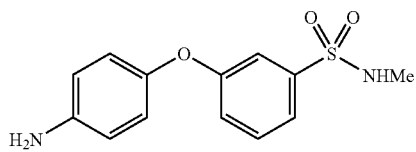

Step 4. Synthesis of 4-(3-(N-methylsulfamoyl)phenyloxy)aniline

A slurry of 4-(3-(N-methylsulfamoyl)phenyloxy)-1-nitrobenzene (0.30 g) and 10% Pd/C (0.030 g) in EtOAc (20 mL) was stirred under an H$_2$ atmosphere (balloon) overnight. The resulting mixture was filtered through a pad of Celite®. The filtrate was concentrated under reduced pressure. The residue was purified by column chromatography (30% EtOAc/70% hexane) to give 4-(3-(N-methylsulfamoyl)phenyloxy)aniline (0.070 g).

A16. Modification of ω-ketones. Synthesis of 4-(4-(1-(N-methoxy)iminoethyl)phenoxyaniline HCl salt

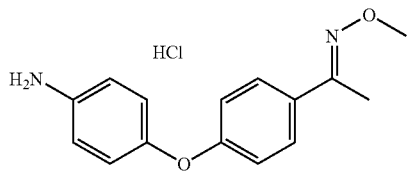

To a slurry of 4-(4-acetylphenoxy)aniline HCl salt (prepared in a manner analogous to Method A13, step 4; 1.0 g, 3.89 mmol) in a mixture of EtOH (10 mL) and pyridine (1.0 mL) was added O-methylhydroxylamine HCl salt (0.65 g, 7.78 mmol, 2.0 equiv.). The resulting solution was heated at the reflux temperature for 30 min, cooled to room temperature and concentrated under reduced pressure. The resulting solids were triturated with water (10 ml) and washed with water to give 4-(4-(1-(N-methoxy)iminoethyl)phenoxyaniline HCl salt as a yellow solid (0.85 g): TLC (50% EtOAc/50% pet. ether) R$_f$ 0.78; $^1$H NMR DMSO-d$_6$) δ 3.90 (s, 3H), 5.70 (s, 3H); HPLC-MS m/z 257 ((M+H)$^+$).

A17. Synthesis of N-(ω-Silyloxyalkyl)amides. Synthesis of 4-(4-(2-(N-(2-Triisopropylsilyloxy)ethylcarbamoyl)pyridyloxyaniline

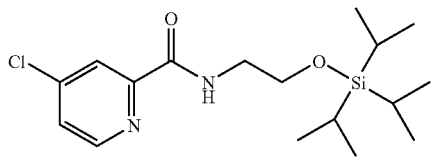

Step 1. 4-Chloro-N-(2-triisopropylsilyloxy)ethylpyridine-2-carboxamide

To a solution of 4-chloro-N-(2-hydroxyethyl)pyridine-2-carboxamide (prepared in a manner analogous to Method A2, Step 3b; 1.5 g, 7.4 mmol) in anh DMF (7 mL) was added triisopropylsilyl chloride (1.59 g, 8.2 mmol, 1.1 equiv.) and imidazole (1.12 g, 16.4 mmol, 2.2 equiv.). The resulting yellow solution was stirred for 3 h at room temp, then was concentrated under reduced pressure. The residue was separated between water (10 mL) and EtOAc (10 mL). The aqueous layer was extracted with EtOAc (3×10 mL). The combined organic phases were dried (MgSO$_4$), and concentrated under reduced pressure to afford 4-chloro-2-(N-(2-triisopropylsilyloxy)ethyl)pyridinecarboxamide as an orange oil (2.32 g, 88%). This material was used in the next step without further purification.

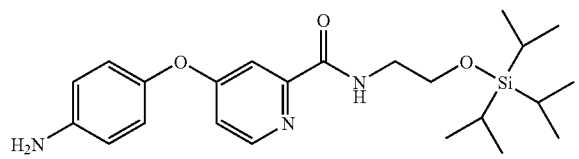

Step 2. 4-(4-(2-(N-(2-Triisopropylsilyloxy)ethylcarbamoyl)pyridyloxyaniline

To a solution of 4-hydroxyaniline (0.70 g, 6.0 mmol) in anh DMF (8 mL) was added potassium tert-butoxide (0.67 g, 6.0 mmol, 1.0 equiv.) in one portion causing an exotherm. When this mixture had cooled to room temperature, a solution of 4-chloro-2-(N-(2-triisopropylsilyloxy)ethyl)pyridinecarboxamide (2.32 g, 6 mmol, 1 equiv.) in DMF (4 mL) was added followed by K$_2$CO$_3$ (0.42 g, 3.0 mmol, 0.50 equiv.). The resulting mixture was heated at 80° C. overnight. An additional portion of potassium tert-butoxide (0.34 g, 3 mmol, 0.5 equiv.) was then added and the mixture was stirred at 80° C. an additional 4 h. The mixture was cooled to 0° C. with an ice/water bath, then water (approx. 1 mL) was slowly added dropwise. The organic layer was extracted with EtOAc (3×10 mL). The combined organic layers were washed with a saturated NaCl solution (20 mL), dried (MgSO$_4$) and concentrated under reduced pressure. The brown oily residue was purified by column chromatography (SiO$_2$; 30% EtOAc/70% pet ether) to afford 4-(4-(2-(N-(2-triisopropylsilyloxy)ethylcarbamoyl)pyridyloxyaniline as a clear light brown oil (0.99 g, 38%).

A18. Synthesis of 2-Pyridinecarboxylate Esters via Oxidation of 2-Methylpyridines. Synthesis of 4-(5-(2-methoxycarbonyl)pyridyloxy)aniline

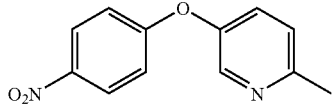

Step 1. 4-(5-(2-Methyl)pyridyloxy)-1-nitrobenzene

A mixture of 5-hydroxy-2-methylpyridine (10.0 g, 91.6 mmol), 1-fluoro-4-nitrobenzene (9.8 mL, 91.6 mmol, 1.0 equiv.), K$_2$CO$_3$ (25 g, 183 mmol, 2.0 equiv.) in DM (100 mL) was heated at the reflux temperature overnight. The resulting mixture was cooled to room temperature, treated with water (200 mL), and extracted with EtOAc (3×100 mL). The combined organic layers were sequentially washed with water (2×100 mL) and a saturated NaCl solution ((100 mL), dried (MgSO$_4$) and concentrated under reduced pressure to give 4-(5-(2-methyl)pyridyloxy)-1-nitrobenzene as a brown solid (12.3 g).

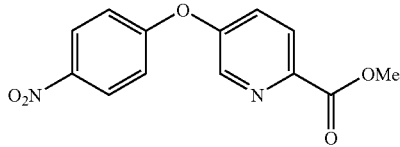

Step 2. Synthesis of 4-(5-(2-Methoxycarbonyl)pyridyloxy)-1-nitrobenzene

A mixture of 4-(5-(2-methyl)pyridyloxy)-1-nitrobenzene (1.70 g, 7.39 mmol) and selenium dioxide (2.50 g, 22.2 mmol, 3.0 equiv.) in pyridine (20 mL) was heated at the reflux temperature for 5 h, then cooled to room temperature. The resulting slurry was filtered, then concentrated under reduced pressure. The residue was dissolved in MeOH (100 nit). The solution was treated with a conc HCl solution (7 mL), then heated at the reflux temperature for 3 h, cooled to room temperature and concentrated under reduced pressure. The residue was separated between EtOAc (50 mL) and a 1N NaOH solution (50 mL). The aqueous layer was extracted with EtOAc (2×50 mL). The combined organic layers were sequentially washed with water (2×50 mL) and a saturated NaCl solution (50 mL), dried (MgSO$_4$) and concentrated under reduced pressure. The residue was purified by column chromatography (SiO$_2$; 50% EtOAc/50% hexane) to afford 4-(5-(2-methoxycarbonyl)pyridyloxy)-1-nitrobenzene (0.70 g).

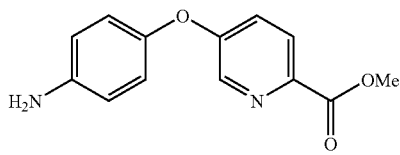

Step 3. Synthesis of 4-(5-(2-Methoxycarbonyl)pyridyloxy)aniline

A slurry of 4-(5-(2-methoxycarbonyl)pyridyloxy)-1-nitrobenzene (0.50 g) and 10% Pd/C (0.050 g) in a mixture of EtOAc (20 mL) and MeOH (5 mL) was placed under a H2 atmosphere (balloon) overnight. The resulting mixture was filtered through a pad of Celite®, and the filtrate was concentrated under reduced pressure. The residue was purified by column chromatography (SiO$_2$; 70% EtOAc/30% hexane) to give 4-(5-(2-methoxycarbonyl)pyridyloxy)aniline (0.40 g).

A19. Synthesis of co-Sulfonylphenyl Anilines. Synthesis of 4-(4-Methylsulfonylphenyoxy)aniline

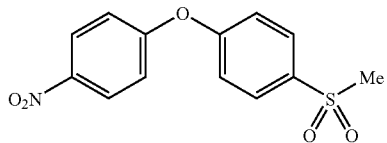

Step 1. 4-(4-Methylsulfonylphenoxy)-1-nitrobenzene: To a solution of 4-(4-methylthiophenoxy)-1-nitrobenzene (2.0 g, 7.7 mmol) in CH$_2$Cl$_2$ (75 mL) at 0° C. was slowly added m-CPBA (57-86%, 4.0 g), and the reaction mixture was stirred at room temperature for 5 h. The reaction mixture was treated with a 1N NaOH solution (25 mL). The organic layer was sequentially washed with a 1N NaOH solution (25 mL), water (25 mL) and a saturated NaCl solution (25 mL), dried (MgSO$_4$), and concentrated under reduced pressure to give 4-(4-methylsulfonylphenoxy)-1-nitrobenzene as a solid (2.1 g).

Step 2. 4-(4-Methylsulfonylphenoxy)-1-aniline: 4-(4-Methylsulfonylphenoxy)-1-nitrobenzene was reduced to the aniline in a manner analogous to that described in Method A18, step 3.

B. Synthesis of Urea Precursors

B1. General Method for the Synthesis of Isocyanates from Anilines Using CDI. Synthesis of 4-Bromo-3-(trifluoromethyl)phenyl Isocyanate

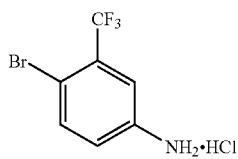

Step 1. Synthesis of 4-bromo-3-(trifluoromethyl)aniline HCl salt

To a solution of 4-bromo-3-(trifluoromethyl)aniline (64 g, 267 mmol) in Et$_2$O (500 mL) was added an HCl solution (1 M in Et$_2$O; 300 mL) dropwise and the resulting mixture was stirred at room temp. for 16 h. The resulting pink-white precipitate was removed by filtration and washed with Et$_2$O (50 mL) and to afford 4-bromo-3-(trifluoromethyl)aniline HCl salt (73 gi, 98%).

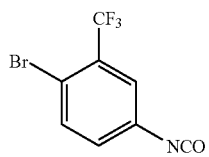

Step 2. Synthesis of 4-bromo-3-(trifluoromethyl)phenyl isocyanate

A suspension of 4-bromo-3-(trifluoromethyl)aniline HCl salt (36.8 g, 133 mmol) in toluene (278 mL) was treated with trichloromethyl chloroformate dropwise and the resulting mixture was heated at the reflux temp. for 18 h. The resulting mixture was concentrated under reduced pressure. The residue was treated with toluene (500 mL), then concentrated under reduced pressure. The residue was treated with CH$_2$Cl$_2$ (500 mL), then concentrated under reduced pressure. The CH$_2$Cl$_2$ treatment/concentration protocol was repeated and resulting amber oil was stored at −20° C. for 16 h, to afford 4-bromo-3-(trifluoromethyl)phenyl isocyanate as a tan solid (35.1 g, 86%): GC-MS m/z 265 (M$^+$).

C. Methods of Urea Formation

C1a. General Method for the Synthesis of Ureas by Reaction of an Isocyanate with an Aniline. Synthesis of N-(4-Chloro-3-(trifluoromethyl)phenyl)-N'-(4-(2-(N-methylcarbamoyl)-4-pyridyloxy)phenyl) Urea

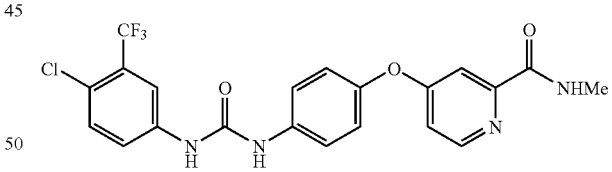

A solution of 4-chloro-3-(trifluoromethyl)phenyl isocyanate (14.60 g, 65.90 mmol) in CH$_2$Cl$_2$ (35 mL) was added dropwise to a suspension of 4-(2-(N-methylcarbamoyl)-4-pyridyloxy)aniline (Method A2, Step 4; 16.0 g, 65.77 mmol) in CH$_2$Cl$_2$ (35 mL) at 0° C. The resulting mixture was stirred at room temp. for 22 h. The resulting yellow solids were removed by filtration, then washed with CH$_2$Cl$_2$ (2×30 mL) and dried under reduced pressure (approximately 1 mmHg) to afford N-(4-chloro-3-(trifluoromethyl)phenyl)-N'-(4-(2-(N-methylcarbamoyl)-4-pyridyloxy)phenyl) urea as an off-white solid (28.5 g, 93%): mp 207-209° C.; $^1$H-NMR (DMSO-d$_6$) δ 2.77 (d, J=4.8 Hz, 3H), 7.16 (m, 3H), 7.37 (d, J=2.5 Hz, 1H), 7.62 (m, 4H), 8.11 (d, J=2.5 Hz, 1H), 8.49 (d, J=5.5 Hz, 1H), 8.77 (br d, 1H), 8.99 (s, 1H), 9.21 (s, 1H); HPLC ES-MS m/z 465 ((M+H)$^+$).

C1b. General Method for the Synthesis of Ureas by Reaction of an Isocyanate with an Aniline. Synthesis of N-(4-Bromo-3-(trifluoromethyl)phenyl)-N'-(4-(2-(N-methylcarbamoyl)-4-pyridyloxy)phenyl) Urea

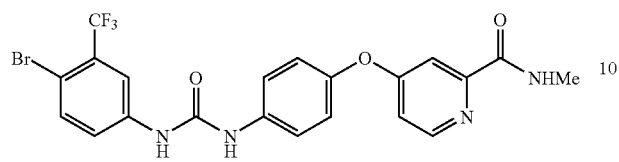

A solution of 4-bromo-3-(trifluoromethyl)phenyl isocyanate (Method B1, Step 2; 8.0 g, 30.1 mmol) in $CH_2Cl_2$ (80 mL) was added dropwise to a solution of 4-(2-(N-methylcarbamoyl)-4-pyridyloxy)aniline (Method A2, Step 4; 7.0 g, 28.8 mmol) in $CH_2Cl_2$ (40 mL) at 0° C. The resulting mixture was stirred at room temp. for 16 h. The resulting yellow solids were removed by filtration, then washed with $CH_2Cl_2$ (2×50 mL) and dried under reduced pressure (approximately 1 mmHg) at 40° C. to afford N-(4-bromo-3-(trifluoromethyl)phenyl)-N'-(4-(2-(N-methylcarbamoyl)-4-pyridyloxy)phenyl) urea as a pale-yellow solid (13.2 g, 90%): mp 203-205° C.; $^1$H-NMR (DMSO-$d_6$) δ 2.77 (d, J=4.8 Hz, 3H), 7.16 (m, 3H), 7.37 (d, J=2.5 Hz, 1H), 7.58 (m, 3H), 7.77 (d, J=8.8 Hz, 1H), 8.11 (d, J=2.5 Hz, 1H), 8.49 (d, J=5.5 Hz, 1H), 8.77 (br d, 1H), 8.99 (s, 1H), 9.21 (s, 1H); HPLC ES-MS m/z 509 ($(M+H)^+$).

C1c. General Method for the Synthesis of Ureas by Reaction of an Isocyanate with an Aniline. Synthesis of N-(4-Chloro-3-(trifluoromethyl)phenyl)-N'-(2-methyl-4-(2-(N-methylcarbamoyl)(4-pyridyloxy))phenyl) Urea

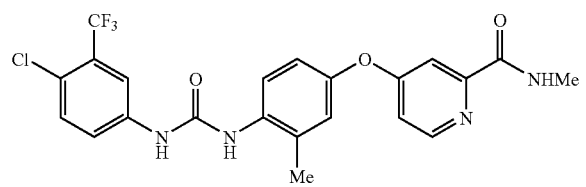

A solution of 2-methyl-4-(2-(N-methylcarbamoyl)(4-pyridyloxy))aniline (Method A5; 0.11 g, 0.45 mmol) in $CH_2Cl_2$ (1 mL) was treated with $Et_3N$ (0.16 mL) and 4-chloro-3-(trifluoromethyl)phenyl isocyanate (0.10 g, 0.45 mmol). The resulting brown solution was stirred at room temp. for 6 d, then was treated with water (5 mL). The aqueous layer was back-extracted with EtOAc (3×5 mL). The combined organic layers were dried ($MgSO_4$) and concentrated under reduced pressure to yield N-(4-chloro-3-(trifluoromethyl)phenyl)-N'-(2-methyl-4-(2-(N-methylcarbamoyl)(4-pyridyloxy))phenyl) urea as a brown oil (0.11 g, 0.22 mmol): $^1$H NMR (DMSO-d) δ 2.27 (s, 3H), 2.77 (d, J=4.8 Hz, 3H), 7.03 (dd, J=8.5, 2.6 Hz, 1H), 7.11 (d, J=2.9 Hz, 1H), 7.15 (dd, J=5.5, 2.6, Hz, 1H), 7.38 (d, J=2.6 Hz, 1H), 7.62 (app d, J=2.6 Hz, 2H), 7.84 (d, J=8.8 Hz, 1H), 8.12 (s, 1H), 8.17 (s, 1H); 8.50 (d, J=5.5 Hz, 1H), 8.78 (q, J=5.2, 1H), 9.52 (s, 1H); HPLC ES-MS m/z 479 ($(M+H)^+$).

C1d. General Method for the Synthesis of Ureas by Reaction of an Isocyanate with an Aniline. Synthesis of N-(4-Chloro-3-(trifluoromethyl)phenyl)-N'-(4-aminophenyl) Urea

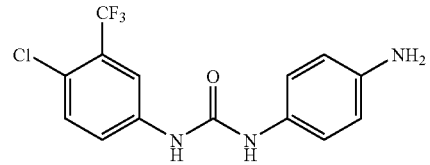

To a solution of 4-chloro-3-(trifluoromethyl)phenyl isocyanate (2.27 g, 10.3 mmol) in $CH_2Cl_2$ (308 mL) was added p-phenylenediamine (3.32 g, 30.7 mmol) in one part. The resulting mixture was stirred at room temp. for 1 h, treated with $CH_2Cl_2$ (100 mL), and concentrated under reduced pressure. The resulting pink solids were dissolved in a mixture of EtOAc (110 mid) and MeOH (15 mL), and the clear solution was washed with a 0.05 N HCl solution. The organic layer was concentrated under reduced pressure to afford impure N-(4-chloro-3-(trifluoromethyl)phenyl)-N-(4-aminophenyl) urea (3.3 g): TLC (100% EtOAc) $R_f$ 0.72.

C1e. General Method for the Synthesis of Ureas by Reaction of an Isocyanate with an Aniline. Synthesis of N-(4-Chloro-3-(trifluoromethyl)phenyl)-N'-(4-ethoxycarbonylphenyl) Urea

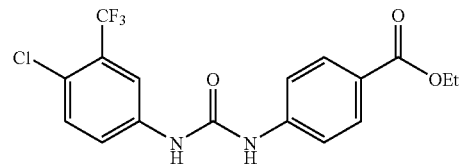

To a solution of ethyl 4-isocyanatobenzoate (3.14 g, 16.4 mmol) in $CH_2Cl_2$ (30 mL) was added 4-chloro-3-(trifluoromethyl)aniline (3.21 g, 16.4 mmol), and the solution was stirred at room temp. overnight. The resulting slurry was diluted with $CH_2Cl_2$ (50 mL) and filtered to afford N-(4-chloro-3-(trifluoromethyl)phenyl)-N-(4-ethoxycarbonylphenyl) urea as a white solid (5.93 g, 97%): TLC (40% EtOAc/60% hexane) $R_f$ 0.44.

C1f. General Method for the Synthesis of Ureas by Reaction of an Isocyanate with an Aniline. Synthesis of N-(4-Chloro-3-(trifluoromethyl)phenyl)-N'-(3-carboxyphenyl) Urea

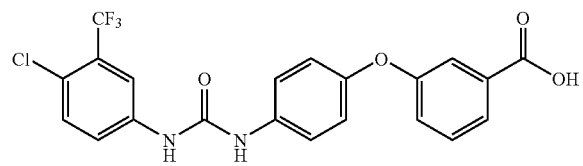

To a solution of 4-chloro-3-(trifluoromethyl)phenyl isocyanate (1.21 g, 5.46 mmol) in $CH_2Cl_2$ (8 mL) was added 4-(3-carboxyphenoxy)aniline (Method A11; 0.81 g, 5.76 mmol) and the resulting mixture was stirred at room temp.

overnight, then treated with MeOH (8 mL), and stirred an additional 2 h. The resulting mixture was concentrated under reduced pressure. The resulting brown solids were triturated with a 1:1 EtOAc/hexane solution to give N-(4-chloro-3-(trifluoromethyl)phenyl)-N'-(3-carboxyphenyl) urea as an off-white solid (1.21 g, 76%).

C2a. General Method for Urea Synthesis by Reaction of an Aniline with N,N-Carbonyl Diimidazole Followed by Addition of a Second Aniline. Synthesis of N-(2-Methoxy-5-(trifluoromethyl)phenyl)-N'-(4-(2-(N-methylcarbamoyl)-4-pyridyloxy)phenyl) Urea

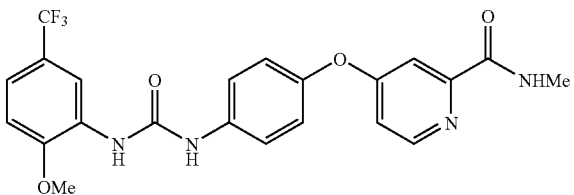

To a solution of 2-methoxy-5-(trifluoromethyl)aniline (0.15 g) in anh CH$_2$Cl$_2$ (15 mL) at 0° C. was added CDI (0.13 g). The resulting solution was allowed to warm to room temp. over 1 h, was stirred at room temp. for 16 h, then was treated with 4-(2-(N-methylcarbamoyl)-4-pyridyloxy)aniline (0.18 g). The resulting yellow solution was stirred at room temp. for 72 h, then was treated with H$_2$O (125 mL). The resulting aqueous mixture was extracted with EtOAc (2×150 mL). The combined organics were washed with a saturated NaCl solution (100 ml), dried (MgSO$_4$) and concentrated under reduced pressure. The residue was triturated (90% EtOAc/10% hexane). The resulting white solids were collected by filtration and washed with EtOAc. The filtrate was concentrated under reduced pressure and the residual oil purified by column chromatography (gradient from 33% EtOAc/67% hexane to 50% EtOAc/50% hexane to 100% EtOAc) to give N-(2-methoxy-5-(trifluoromethyl)phenyl)-N'-(4-(2-(N-methylcarbamoyl)-4-pyridyloxy)phenyl) urea as a light tan solid (0.098 g, 30%): TLC (100% EtOAc) R$_f$ 0.62; $^1$H NMR (DMSO-d$_6$) δ 2.76 (d, J=4.8 Hz, 3H), 3.96 (s, 3H), 7.1-7.6 and 8.4-8.6 (A, 11H), 8.75 (d, J=4.8 Hz, 1H), 9.55 (s, 1H); FAB-MS m/z 461 ((M+H)$^+$).

C2b. General Method for Urea Synthesis by Reaction of an Aniline with N,N'-Carbonyl Diimidazole Followed by Addition of a Second Aniline. Symmetrical Urea's as Side Products of a N,N'-Carbonyl Diimidazole Reaction Procedure. Synthesis of Bis(4-(2-(N-methylcarbamoyl)-4-pyridyloxy)phenyl) Urea To a stirring solution of 3-amino-2-methoxyquinoline (0.14 g) in anhydrous CH$_2$Cl$_2$ (15 mL) at 0 C was added CDI (0.13 g). The resulting solution was allowed to warm to room temp. over 1 h then was stirred at room temp. for 16 h. The resulting mixture was treated with 4-(2-(N-methylcarbamoyl)-4-pyridyloxy)aniline (0.18 g). The resulting yellow solution stirred at room temp. for 72 h, then was treated with water (125 nm). The resulting aqueous mixture was extracted with EtOAc (2×150 mL). The combined organic phases were washed with a saturated NaCl solution (100 mL), dried (MgSO$_4$) and concentrated under reduced pressure. The residue was triturated (90% EtOAc/10% hexane). The resulting white solids were collected by filtration and washed with EtOAc to give bis(4-(2-(N-methylcarbamoyl)-4-pyridyloxy)phenyl) urea (0.081 g, 44%): TLC (100% EtOAc) R$_f$ 0.50; $^1$H NMR (DMSO-d$_6$) δ 2.76 (d, J=5.1 Hz, 6H), 7.1-7.6 (m, 12H), 8.48 (d, J=5.4 Hz, 1H), 8.75 (d, J=4.8 Hz, 2H), 8.86 (s 2H); HPLC ES-MS m/z 513 ((M+H)$^+$).

C2c. General Method for the Synthesis of Ureas by Reaction of an Isocyanate with an Aniline. Synthesis of N-(2-Methoxy-5-(trifluoromethyl)phenyl-N'-(4-(1,3-dioxoisoindolin-5-yloxy)phenyl) Urea

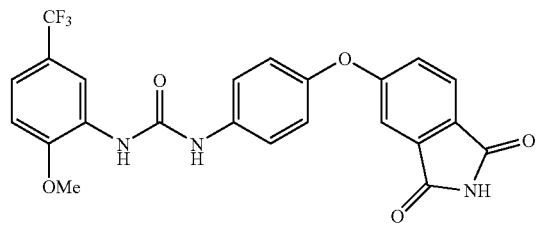

To a stirring solution of 2-methoxy-5-(trifluoromethyl) phenyl isocyanate (0.10 g, 0.47 mmol) in CH$_2$Cl$_2$ (1.5 mL) was added 5-(4-aminophenoxy)isoindoline-1,3-dione (Method A3, Step 3; 0.12 g, 0.47 mmol) in one portion. The resulting mixture was stirred for 12 h, then was treated with CH$_2$Cl$_2$ (10 mL) and MeOH (5 mL). The resulting mixture was sequentially washed with a 1N HCl solution (15 mL) and a saturated NaCl solution (15 mL), dried (MgSO$_4$) and concentrated under reduced pressure to afford N-(2-methoxy-5-(trifluoromethyl)phenyl-N'-(4-(1,3-dioxoisoindolin-5-yloxy)phenyl) urea as a white solid (0.2 g, 96%): TLC (70% EtOAc/30% hexane) R$_f$ 0.50; $^1$H NMR (DMSO-d$_6$) δ 3.95 (s, 3H), 7.31-7.10 (m, 6H), 7.57 (d, J=9.3 Hz, 2H), 7.80 (d, J=8.7 Hz, 1H), 8.53 (br s, 2H), 9.57 (s, 1H), 11.27 (br s, 1H); HPLC ES-MS 472.0 (M+H)$^+$, 100%).

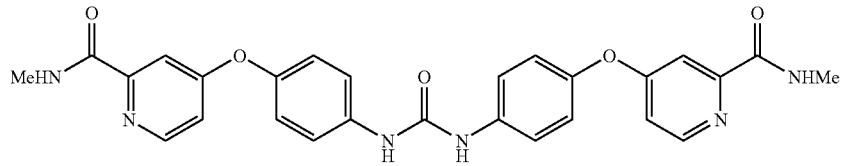

C2d. General Method for Urea Synthesis by Reaction of an Aniline with N,N'-Carbonyl Diimidazole Followed by Addition of a Second Aniline. Synthesis of N-(5-(tert-Butyl)-2-(2,5-dimethylpyrrolyl)phenyl)-N'-(4-(2-(N-methylcarbamoyl)-4-pyridyloxy)phenyl) Urea

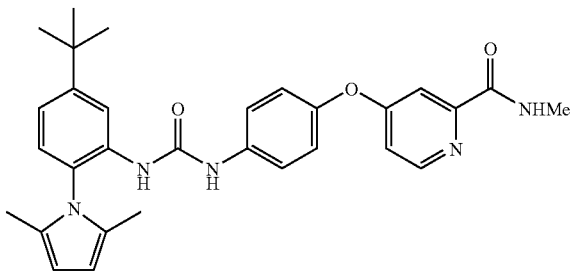

To a stirring solution of CDI (0.21 g, 1.30 mmol) in CH$_2$Cl$_2$ (2 mL) was added 5-(tert-butyl)-2-(2,5-dimethylpyrrolyl)aniline (Method A4, Step 2; 0.30 g, 1.24 mmol) in one portion. The resulting mixture was stirred at room temp. for 4 h, then 4-(2-(N-methylcarbamoyl)-4-pyridyloxy)aniline (0.065 g, 0.267 mmol) was then added in one portion. The resulting mixture was heated at 36° C. overnight, then cooled to room temp. and diluted with EtOAc (5 mL). The resulting mixture was sequentially washed with water (15 mL) and a 1N HCl solution (15 mL), dried (MgSO$_4$), and filtered through a pad of silica gel (50 g) to afford N-(5-(tert-butyl)-2-(2,5-dimethylpyrrolyl)phenyl)-N'-(4-(2-(N-methylcarbamoyl)-4-pyridyloxy)phenyl) urea as a yellowish solid (0.033 g, 24%): TLC (40% EtOAc/60% hexane) R$_f$ 0.24; $^1$H NMR (acetone-d$_6$) δ 1.37 (s, 9H), 1.89 (s, 6H), 2.89 (d, J=4.8 Hz, 3H), 5.83 (s, 2H), 6.87-7.20 (m, 6H), 7.17 (dd, 1H), 7.51-7.58 (m, 3H), 8.43 (d, J=5.4 Hz, 1H), 8.57 (d, J=2.1 Hz, 1H), 8.80 (br s, 1H); HPLC ES-MS 512 ((M+H)$^+$, 100%).

C3. Combinatorial Method for the Synthesis of Diphenyl Ureas Using Triphosgene One of the anilines to be coupled was dissolved in dichloroethane (0.10 M). This solution was added to a 8 mL vial (0.5 mL) containing dichloroethane (1 mL). To this was added a bis(trichloromethyl) carbonate solution (0.12 M in dichloroethane, 0.2 mL, 0.4 equiv.), followed by diisopropylethylamine (0.35 M in dichloroethane, 0.2 ml, 1.2 equiv.). The vial was capped and heat at 80° C. for 5 h, then allowed to cool to room temp for approximately 10 h. The second aniline was added (0.10 M in dichloroethane, 0.5 mL, 1.0 equiv.), followed by diisopropylethylamine (0.35 M in dichloroethane, 0.2 mL, 1.2 equiv.). The resulting mixture was heated at 80° C. for 4 h, cooled to room temperature and treated with MeOH (0.5 mL). The resulting mixture was concentrated under reduced pressure and the products were purified by reverse phase HPLC.

C4. General Method for Urea Synthesis by Reaction of an Aniline with Phosgene Followed by Addition of a Second Aniline. Synthesis of N-(2-Methoxy-5-(trifluoromethyl)phenyl)-N'-(4-(2-(N-methylcarbamoyl)-4-pyridyloxy)phenyl) Urea

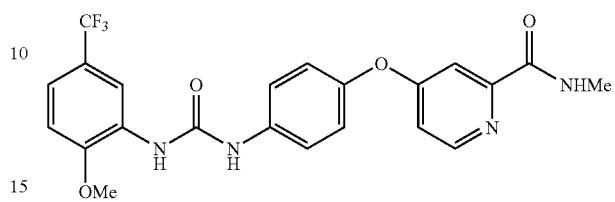

To a stirring solution of phosgene (1.9 M in toluene; 2.07 mL 0.21 g, 1.30 mmol) in CH$_2$Cl$_2$ (20 mL) at 0° C. was added anh pyridine (0.32 mL) followed by 2-methoxy-5-(trifluoromethyl)aniline (0.75 g). The yellow solution was allowed to warm to room temp during which a precipitate formed. The yellow mixture was stirred for 1 h, then concentrated under reduced pressure. The resulting solids were treated with anh toluene (20 mL) followed by 4-(2-(N-methylcarbamoyl)-4-pyridyloxy)aniline (prepared as described in Method A2; 0.30 g) and the resulting suspension was heated at 80° C. for 20 h, then allowed to cool to room temp. The resulting mixture was diluted with water (100 mL), then was made basic with a saturated NaHCO$_3$ solution (2-3 mL). The basic solution was extracted with EtOAc (2×250 mL). The organic layers were separately washed with a saturated NaCl solution, combined, dried (MgSO$_4$), and concentrated under reduced pressure. The resulting pink-brown residue was dissolved in MeOH and absorbed onto SiO$_2$ (100 g). Column chromatography (300 g SiO$_2$; gradient from 1% Et$_3$N/33% EtOAc/66%. hexane to 1% Et$_3$N/99% EtOAc to 1% Et$_3$N/20% MeOH/79% EtOAc) followed by concentration under reduced pressure at 45° C. gave a warm concentrated EtOAc solution, which was treated with hexane (10 mL) to slowly form crystals of N-(2-methoxy-5-(trifluoromethyl)phenyl)-N'-(4-(2-(N-methylcarbamoyl)-4-pyridyloxy)phenyl) urea (0.4 g): TLC (1% Et$_3$N/99% EtOAc) R$_f$ 0.40.

D. Interconversion of Ureas

D1a. Conversion of ω-Aminophenyl Ureas into ω-(Aroylamino)phenyl Ureas. Synthesis of N-(4-Chloro-3-((trifluoromethyl)phenyl)-N'-(4-(3-methoxycarbonylphenyl)carboxyaminophenyl) Urea

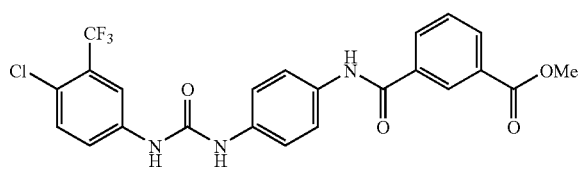

To a solution of N-(4-chloro-3-((trifluoromethyl)phenyl)-N'-(4-aminophenyl) urea (Method C1d; 0.050 g, 1.52 mmol), mono-methyl isophthalate (0.25 g, 1.38 mmol), HOBT.H$_2$O (0.41 g, 3.03 mmol) and N-methylmorpholine (0.33 mL, 3.03 mmol) in DMF (8 mL) was added EDCI.HCl (0.29 g, 1.52 mmol). The resulting mixture was stirred at room temp. overnight, diluted with EtOAc (25 mL) and sequentially washed with water (25 mL) and a saturated NaHCO$_3$ solution (25 ml). The organic layer was dried (Na$_2$SO$_4$) and concentrated under reduced pressure. The resulting solids were triturated with an EtOAc solution (80% EtOAc/20% hexane) to give N-(4-chloro-3-((trifluoromethyl)phenyl)-N-(4-(3-methoxycarbonylphenyl)carboxyaminophenyl) urea (0.27 g, 43%): mp 121-122; TLC (80% EtOAc/20% hexane) R$_f$ 0.75.

D1b. Conversion of ω-Carboxyphenyl Ureas into ω-(Arylcarbamoyl)phenyl Ureas. Synthesis of N-(4-Chloro-3-((trifluoromethyl)phenyl)-N'-(4-(3-methylcarbamoylphenyl)carbamoylphenyl) Urea

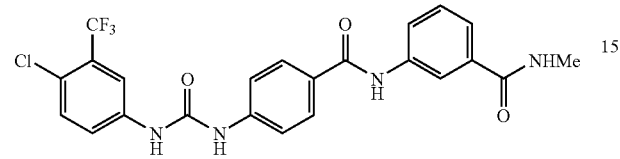

To a solution of N-(4-chloro-3-((trifluoromethyl)phenyl)-N-(4-(3-methylcarbamoylphenyl)carboxyaminophenyl) urea (0.14 g, 0.48 mmol), 3-methylcarbamoylaniline (0.080 g, 0.53 mmol), HOBT-H$_2$O (0.14 g, 1.07 mmol), and N-methylmorpholine (0.5 mL, 1.07 mmol) in DMF (3 mL) at 0° C. was added EDCI.HCl (0.10 g, 0.53 mmol). The resulting mixture was allowed to warm to room temp. and was stirred overnight. The resulting mixture was treated with water (10 mL), and extracted with EtOAc (25 mL). The organic phase was concentrated under reduced pressure. The resulting yellow solids were dissolved in EtOAc (3 mL) then filtered through a pad of silica gel (17 g, gradient from 70% EtOAc/30% hexane to 10% MeOH/90% EtOAc) to give N-(4-chloro-3-((trifluoromethyl)phenyl)-N-(4-(3-methylcarbamoylphenyl) carbamoylphenyl) urea as a white solid (0.097 g, 41%): mp 225-229; TLC (100% EtOAc) R$_f$ 0.23.

D1c. Combinatorial Approach to the Conversion of ω-Carboxyphenyl Ureas into ω-(Arylcarbamoyl)phenyl Ureas. Synthesis of N-(4-Chloro-3-(trifluoromethyl)phenyl)-N'-(4-N-(3-(N-(3-pyridyl)carbamoyl)phenyl)carbamoyl)phenyl) Urea

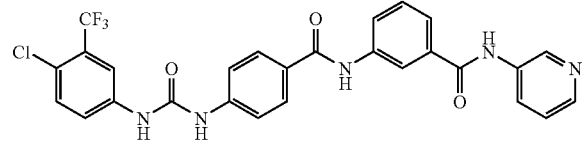

A mixture of N-(4-chloro-3-((trifluoromethyl)phenyl)-N'-(3-carboxyphenyl) urea (Method C1f; 0.030 g, 0.067 mmol) and N-cyclohexyl-N'-(methylpolystyrene)carbodiimide (55 mg) in 1,2-dichloroethane (1 mL) was treated with a solution of 3-aminopyridine in CH$_2$Cl$_2$ (1 M; 0.074 mL, 0.074 mmol). (In cases of insolubility or turbidity, a small amount of DMSO was also added.) The resulting mixture was heated at 36° C. overnight. Turbid reactions were then treated with THF (1 mL) and heating was continued for 18 h. The resulting mixtures were treated with poly(4-isocyanatomethyl)styrene) (0.040 g) and the resulting mixture was stirred at 36° C. for 72 h, then cooled to room temp. and filtered. The resulting solution was filtered through a plug of silica gel (1 g). Concentration under reduced pressure afforded N-(4-chloro-3-((trifluoromethyl)phenyl)-N'-(4-(N-4-(3-(N-(3-pyridyl) carbamoyl)phenyl)carbamoyl)phenyl) urea (0.024 g, 59%): TLC (70% EtOAc/30% hexane) R$_f$ 0.12.

D2. Conversion of ω-Carboalkoxyaryl Ureas into ω-Carbamoylaryl Ureas. Synthesis of N-(4-Chloro-3-((trifluoromethyl)phenyl)-N'-(4-(3-methylcarbamoylphenyl)carboxyaminophenyl) Urea

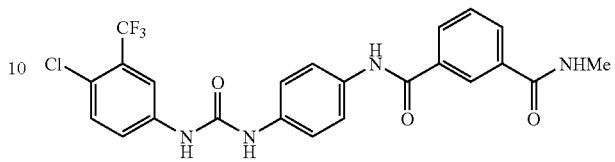

To a sample of N-(4-chloro-3-((trifluoromethyl)phenyl)-N'-(4-(3-carbomethoxyphenyl) carboxyaminophenyl) urea (0.17 g, 0.34 mmol) was added methylamine (2 M in THF; 1 mL, 1.7 mmol) and the resulting mixture was stirred at room temp. overnight, then concentrated under reduced pressure to give N-(4-chloro-3-((trifluoromethyl)phenyl)-N'-(4-(3-methylcarbamoylphenyl)carboxyaminophenyl) urea as a white solid: mp 247; TLC (100% EtOAc) R$_f$ 0.35.

D3. Conversion of ω-Carboalkoxyaryl Ureas into ω-Carboxyaryl Ureas. Synthesis of N-(4-Chloro-3-((trifluoromethyl)phenyl)-N'-(4-carboxyphenyl) Urea

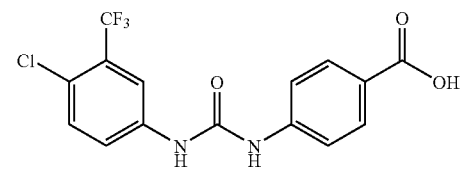

To a slurry of N-(4-chloro-3-((trifluoromethyl)phenyl)-N'-(4-ethoxycarbonylphenyl) urea (Method C1e; 5.93 g, 15.3 mmol) in MeOH (75 mL) was added an aqueous KOH solution (2.5 N, 10 mL, 23 mmol). The resulting mixture was heated at the reflux temp. for 12 h, cooled to room temp., and concentrated under reduced pressure. The residue was diluted with water (50 mL), then treated with a 1 N HCl solution to adjust the pH to 2 to 3. The resulting solids were collected and dried under reduced pressure to give N-(4-chloro-3-((trifluoromethyl)phenyl)-N'-(4-carboxyphenyl) urea as a white solid (5.05 g, 92%).

D4. General Method for the Conversion of ω-Alkoxy Esters into ω-Alkyl Amides. Synthesis of N-(4-Chloro-3-((trifluoromethyl)phenyl)-N'-((4-(3-(5-(2-dimethylaminoethyl)carbamoyl)pyridyl)oxyphenyl) Urea

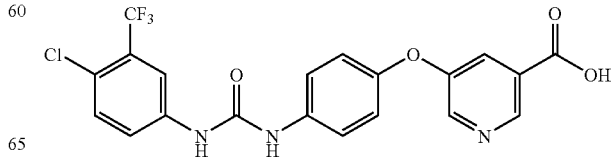

Step 1. Synthesis of N-(4-Chloro-3-(trifluoromethyl) phenyl)-N'-((4-(3-(5-carboxypyridyl)oxyphenyl) Urea N-(4-Chloro-3-(trifluoromethylphenyl)-N'-((4-(3-(5'-methoxycarbonylpyridyl)oxyphenyl) urea was synthesized from 4-chloro-3-(trifluoromethyl)phenyl isocyanate and 4-(3-(5-methoxycarbonylpyridyl)oxyaniline (Method A14, Step 2) in a manner analogous to Method C1a. A suspension of N-(4-chloro-3-(trifluoromethyl)phenyl)-N'-((4-(3-(5-methoxycarbonylpyridyl)oxyphenyl) urea (0.26 g, 0.56 mmol) in MeOH (10 mL) was treated with a solution of KOH (0.14 g, 2.5 mmol) in water (1 mL) and was stirred at room temp. for 1 h. The resulting mixture was adjusted to pH 5 with a 1 N HCl solution. The resulting precipitate was removed by filtration and washed with water. The resulting solids were dissolved in EtOH (10 mL) and the resulting solution was concentrated under reduced pressure. The EtOH/concentration procedure was repeated twice to give N-(4-chloro-3-(trifluoromethyl)phenyl)-N'-((4-(3-(5-carboxypyridyl)oxyphenyl) urea (0.18 g, 71%).

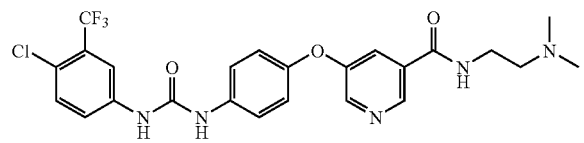

Step 2. Synthesis of N-(4-chloro-3-(trifluoromethyl) phenyl)-N'-((4-(3-(5-(2-dimethylaminoethyl)carbamoyl)pyridyl)oxyphenyl) urea A mixture of N-(4-chloro-3-(trifluoromethyl)phenyl)-N'-((4-(3-(5-carboxypyridyl)oxyphenyl) urea (0.050 g, 0.011 mmol), N,N-dimethylethylenediamine (0.22 mg, 0.17 mmol), HOBT (0.028 g, 0.17 mmol), N-methylmorpholine (0.035 g, 0.28 mmol), and EDCI.HCl (0.032 g, 0.17 mmol) in DMF (2.5 ml) was stirred at room temp. overnight. The resulting solution was separated between EtOAc (50 mL) and water (50 mL). The organic phase was washed with water (35 mL), dried (MgSO$_4$) and concentrated under reduced pressure. The residue was dissolved in a minimal amount of CH$_2$Cl$_2$ (approximately 2 mL). The resulting solution was treated with Et$_2$O dropwise to give N-(4-chloro-3-(trifluoromethyl)phenyl)-N'-((4-(3-(5-(2-dimethylaminoethyl)carbamoyl)pyridyl)oxyphenyl) urea as a white precipitate (0.48 g, 84%: $^1$H NMR (DMSO-d$_6$) δ 2.10 s, 6H), 3.26 (s, H), 7.03 (d, 2H), 7.52 (d, 2H), 7.60 (m, 3H), 8.05 (s, 1H), 8.43 (s, 1H), 8.58 (t, 1H), 8.69 (s, 1H), 8.90 (s, 1H), 9.14 (s, 1H); HPLC ES-MS m/z 522 ((M+H)$_4$).

D5. General Method for the Deprotection of N-(ω-Silyloxyalkyl)amides. Synthesis of N-(4-Chloro-3-((trifluoromethyl)phenyl)-N'-(4-(4-(2-(N-(2-hydroxy)ethylcarbamoyl)pyridyloxyphenyl) Urea To a solution of N-(4-chloro-3-((trifluoromethyl)phenyl)-N'-(4-(4-(2-(N-(2-triisopropylsilyloxy)ethylcarbamoyl)pyridyloxyphenyl) urea (prepared in a manner analogous to Method C1a; 0.25 g, 0.37 mmol) in anh THF (2 mL) was tetrabutylammonium fluoride (1.0 M in THF; 2 mL). The mixture was stirred at room temperature for 5 min, then was treated with water (10 mL). The aqueous mixture was extracted with EtOAc (3×10 mL). The combined organic layers were dried (MgSO$_4$) and concentrated under reduced pressure. The residue was purified by column chromatography (SiO$_2$; gradient from 100% hexane to 40% EtOAc/60% hexane) to give N-(4-chloro-3-((trifluoromethyl)phenyl)-N'-(4-(4-(2-(N-(2-hydroxy)ethylcarbamoyl)pyridyloxyphenyl) urea as a white solid (0.019 g, 10%).

Listed below are compounds listed in the Tables below which have been synthesized according to the Detailed Experimental Procedures given above:

Syntheses of Exemplified Compounds

See Tables for Compound Characterization

Entry 1: 4-(3-N-Methylcarbamoylphenoxy)aniline was prepared according to Method A13. According to Method C3, 3-tert-butylaniline was reacted with bis(trichloromethyl)carbonate followed by 4-(3-N-Methylcarbamoylphenoxy) aniline to afford the urea.

Entry 2: 4-Fluoro-1-nitrobenzene and p-hydroxyacetophenone were reacted according to Method A13, Step 1 to afford the 4-(4-acetylphenoxy)-1-nitrobenzene. 4-(4-Acetylphenoxy)-1-nitrobenzene was reduced according to Method A13, Step 4 to afford 4-(4-acetylphenoxy)aniline. According to Method C3,3-tert-butylaniline was reacted with bis (trichloromethyl) carbonate followed by 4-(4-acetylphenoxy)aniline to afford the urea.

Entry 3: According to Method C2d, 3-tert-butylaniline was treated with CDI, followed by 4-(3-N-methylcarbamoyl)-4-methoxyphenoxy)aniline, which had been prepared according to Method A8, to afford the urea.

Entry 4: 5-tert-Butyl-2-methoxyaniline was converted to 5-tert-butyl-2-methoxyphenyl isocyanate according to Method B1. 4-(3-N-Methylcarbamoylphenoxy)aniline, prepared according to Method A13, was reacted with the isocyanate according to Method C1a to afford the urea.

Entry 5: According to Method C2d, 5-tert-butyl-2-methoxyaniline was reacted with CDI followed by 4-(3-N-methylcarbamoyl)-4-methoxyphenoxy)aniline, which had been prepared according to Method A8, to afford the urea.

Entry 6: 5-(4-Aminophenoxy)isoidoline-1,3-dione was prepared according to Method A3. According to Method 2d, 5-tert-butyl-2-methoxyaniline was reacted with CDI followed by 5-(4-aminophenoxy)isoindoline-1,3-dione to afford the urea.

Entry 7: 4-(1-Oxoisoindolin-5-yloxy)aniline was synthesized according to Method A12. According to Method 2d,

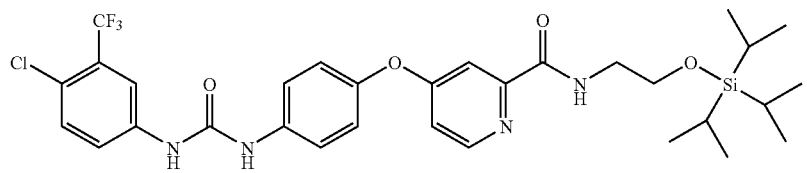

S-tert-butyl-2-methoxyaniline was reacted with CDI followed by 4-(1-oxoisoindolin-5-yloxy)aniline to afford the urea.

Entry 8: 4-(3-N-Methylcarbamoylphenoxy)aniline was synthesized according to Method A13. According to Method C2a, 2-methoxy-5-(trifluoromethyl)aniline was reacted with CDI followed by 4-(3-N-methylcarbamoylphenoxy)aniline to afford the urea.

Entry 9: 4-Hydroxyacetophenone was reacted with 2-chloro-5-nitropyridine to give 4-(4-acetylphenoxy)-5-nitropyridine according to Method A3, Step 2. According to Method A8, Step 4,4-(4-acetylphenoxy)-5-nitropyridine was reduced to 4-(4-acetylphenoxy)-5-aminopyridine. 2-Methoxy-5-(trifluoromethyl)aniline was converted to 2-methoxy-5-(trifluoromethyl)phenyl isocyanate according to Method B1. The isocyanate was reacted with 4-(4-acetylphenoxy)-5-aminopyridine according to Method C1a to afford the urea.

Entry 10: 4-Fluoro-1-nitrobenzene and p-hydroxyacetophenone were reacted according to Method A13, Step 1 to afford the 4-(4-acetylphenoxy)-1-nitrobenzene. 4-(4-Acetylphenoxy)-1-nitrobenzene was reduced according to Method A13, Step 4 to afford 4-(4-acetylphenoxy)aniline. According to Method C3, 5-(trifluoromethyl)-2-methoxybutylaniline was reacted with bis(trichloromethyl) carbonate followed by 4-(4-acetylphenoxy)aniline to afford the urea.

Entry 11: 4-Chloro-N-methyl-2-pyridinecarboxamide, which was synthesized according to Method A2, Step 3a, was reacted with 3-aminophenol according to Method A2, Step 4 using DMAC in place of DMF to give 3-(-2-(N-methylcarbamoyl)-4-pyridyloxy)aniline. According to Method C4, 2-methoxy-5-(trifluoromethyl)aniline was reacted with phosgene followed by 3-(-2-(N-methylcarbamoyl)-4-pyridyloxy)aniline to afford the urea.

Entry 12: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 3-aminophenol according to Method A2, Step 4 using DISC in place of DMF to give 3-(2-carbamoyl-4-pyridyloxy)aniline. According to Method C2a, 2-methoxy-5-(trifluoromethyl)aniline was reacted with phosgene followed by 3-(2-carbamoyl-4-pyridyloxy)aniline to afford the urea.

Entry 13: 4-Chloro-N-methyl-2-pyridinecarboxamide was synthesized according to Method A2, Step 3b. 4-Chloro-N-methyl-2-pyridinecarboxamide was reacted with 4-aminophenol according to Method A2, Step 4 using DMAC in place of DMF to give 4-(2-(N-methylcarbamoyl)-4-pyridyloxy)aniline. According to Method C2a, 2-methoxy-5-(trifluoromethyl)aniline was reacted with CDI followed by 4-(2-(N-methylcarbamoyl)-4-pyridyloxy)aniline to afford the urea.

Entry 14: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 4-aminophenol according to Method A2, Step 4 using DMAC in place of DMF to give 4-(2-carbamoyl-4-pyridyloxy)aniline. According to Method C4,2-methoxy-5-(trifluoromethyl)aniline was reacted with phosgene followed by 4-(2-carbamoyl-4-pyridyloxy)aniline to afford the urea.

Entry 15: According to Method C2d, 5-(trifluoromethyl)-2-methoxyaniline was reacted with CDI followed by 4-(3-N-methylcarbamoyl)-4-methoxyphenoxy)aniline, which had been prepared according to Method A8, to afford the urea.

Entry 16: 4-(2-(N-Methylcarbamoyl)-4-pyridyloxy)-2-methylaniline was synthesized according to Method A5. 5-(Trifluoromethyl)-2-methoxyaniline was converted into 5-(trifluoromethyl)-2-methoxyphenyl isocyanate according to Method B1. The isocyanate was reacted with 4-(2-(N-methylcarbamoyl)-4-pyridyloxy)-2-methylaniline according to Method C1c to afford the urea.

Entry 17: 4-(2-(N-Methylcarbamoyl)-4-pyridyloxy)-2-chloroaniline was synthesized according to Method A6. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-methylcarbamoyl)-4-pyridyloxy)-2-chloroaniline according to Method C1a to afford the urea.

Entry 18: According to Method A2, Step 4,5-amino-2-methylphenol was reacted with 4-chloro-N-methyl-2-pyridinecarboxamide, which had been synthesized according to Method A2, Step 3b, to give 3-(2-(N-methylcarbamoyl)-4-pyridyloxy)-4-methylaniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 3-(2-(N-methylcarbamoyl)-4-pyridyloxy)-4-methylaniline according to Method C1a to afford the urea.

Entry 19: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-ethylcarbamoyl)-4-pyridyloxy)aniline according to Method C1a to afford the urea.

Entry 20: According to Method A2, Step 4,4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-methylcarbamoyl)-4-pyridyloxy)-3-chloro aniline according to Method C1a to afford the urea.

Entry 21: 4-(4-Methylthiophenoxy)-1-nitrobenzene was oxidized according to Method A19, Step 1 to give 4-(4-methylsulfonylphenoxy)-1-nitrobenzene. The nitrobenzene was reduced according to Method A19, Step 2 to give 4-(4-methylsulfonylphenoxy)-1-aniline. According to Method C1a, 5-(trifluoromethyl)-2-methoxyphenyl isocyanate was reacted with 4-(4-methylsulfonylphenoxy)-1-aniline to afford the urea.

Entry 22: 4-(3-carbamoylphenoxy)-1-nitrobenzene was reduced to 4-(3-carbamoylphenoxy)aniline according to Method A15, Step 4. According to Method C1a, 5-(trifluoromethyl)-2-methoxyphenyl isocyanate was reacted with 4-(3-carbamoylphenoxy)aniline to afford the urea.

Entry 23: 5-(4-Aminophenoxy)isoindoline-1,3-dione was synthesized according to Method A3. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 5-(4-aminophenoxy)isoindoline-1,3-dione according to Method C1a to afford the urea.

Entry 24; 4-Chloropyridine-2-carbonyl chloride was reacted with dimethylamine according to Method A2, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N,N-dimethylcarbamoyl)-4-pyridyloxy) an line according to Method C1a to afford the urea.

Entry 25: 4-(1-Oxoisoindolin-5-yloxy)aniline was synthesized according to Method A12. 5-(Trifluoromethyl)-2-methoxyaniline was treated with CDI, followed by 4-(1-oxoisoindolin-5-yloxy)aniline according to Method C2d to afford the urea.

Entry 26: 4-Hydroxyacetophenone was reacted with 4-fluoronitrobenzene according to Method A13, Step 1 to give 4-(4-acetylphenoxy)nitrobenzene. The nitrobenzene was reduced according to Method A13, Step 4 to afford 4-(4-acetylphenoxy)aniline, which was converted to the 4-(4-(1-(N-methoxy)iminoethyl)phenoxyaniline HCl salt according to Method A16. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(4-(1-(N-methoxy)iminoethyl)phenoxyaniline HCl salt to Method C1a to afford the urea.

Entry 27: 4-Chloro-N-methylpyridinecarboxamide was synthesized as described in Method A2, Step 3b. The chloropyridine was reacted with 4-aminothiophenol according to Method A1, Step 4 to give 4-(4-(2-(N-methylcarbamoyl)phenylthio)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(4-(2-(N-methylcarbamoyl)phenylthio)aniline according to Method C1a to afford the urea.

Entry 28: 5-(4-Aminophenoxy)-2-methylisoindoline-1,3-dione was synthesized according to Method A9. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 5-(4-aminophenoxy)-2-methylisoindoline-1,3-dione according to Method C1a to afford the urea.

Entry 29: 4-Chloro-N-methylpyridinecarboxamide was synthesized as: described in Method A2, Step 3b. The chloropyridine was reacted with 3-aminothiophenol according to Method A1, Step 4 to give 3-(4-(2-(N-methylcarbamoyl)phenylthio)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 3-(4-(2-(N-methylcarbamoyl)phenylthio)aniline according to Method C1a to afford the urea.

Entry 30: 4-Chloropyridine-2-carbonyl chloride was reacted with isopropylamine according to Method A2, Step 3b. The resulting 4-chloro-N-isopropyl-2-pyridinecarboxamide was reacted with 4-aminophenol according to Method A2, Step 4 to give 4-(2-(N-isopropylcarbamoyl)-4-pyridyloxy) aniline. 5-(Trifluoromethyl)-2-methoxyaniline was converted into S-(trifluoromethyl)-2-methoxyphenyl isocyanate according to Method B1. 5-(Trifluoromethyl)-2-methoxyphenyl isocyanate was reacted with 4-(2-(N-isopropylcarbamoyl)-4-pyridyloxy)aniline according to Method C1a to afford the urea.

Entry 31: 4-(3-(5-Methoxycarbonyl)pyridyloxy)aniline was synthesized according to Method A14. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(3-(5-methoxycarbonyl)pyridyloxy)aniline according to Method C1a to afford the urea. N-(5-(Trifluoromethyl)-2-methoxyphenyl)-N-(4-(3-(5-methoxycarbonylpyridyl)oxy)phenyl) urea was saponified according to Method D4, Step 1, and the corresponding acid was coupled with 4-(2-aminoethyl)morpholine to afford the amide according to Method D4, Step 2.

Entry 32: 4-(3-(5-Methoxycarbonyl)pyridyloxy)aniline was synthesized according to Method A14. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(3-(5-methoxycarbonyl)pyridyloxy)aniline according to Method C1a to afford the urea. N-(5-(Trifluoromethyl)-2-methoxyphenyl)-N-(4-(3-(5-methoxycarbonylpyridyl)oxy)phenyl) urea was saponified according to Method D4, Step 1, and the corresponding acid was coupled with methylamine according to Method D4, Step 2 to afford the amide, Entry 33: 4-(3-(5-Methoxycarbonyl)pyridyloxy)aniline was synthesized according to Method A14. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(3-(5-methoxycarbonyl)pyridyloxy)aniline according to Method C1a to afford the urea. N-(5-(Trifluoromethyl)-2-methoxyphenyl)-N'-(4-(3-(5-methoxycarbonylpyridyl)oxy)phenyl) urea was saponified according to Method D4, Step 1, and the corresponding acid was coupled with N,N-dimethylethylenediamine according to Method D4, Step 2 to afford the amide Entry 34: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 3-aminopyridine according to Method D1c.

Entry 35: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N-(3-carboxyphenyl) urea, which was coupled with N-(4-fluorophenyl)piperazine according to Method D1c.

Entry 36: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N-(3-carboxyphenyl) urea, which was coupled with 4-fluoroaniline according to Method D1c.

Entry 37: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N-(3-carboxyphenyl) urea, which was coupled with 4-(dimethylamino)aniline according to Method D1c.

Entry 38: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 5-amino-2-methoxypyridine according to Method D1c.

Entry 39: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 4-morpholinoaniline according to Method D1c.

Entry 40: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with N-(2-pyridyl)piperazine according to Method D1c.

Entry 41: 4-(3-(N-Methylcarbamoyl)phenoxy)aniline was synthesized according to Method A13. According to Method C3,4-chloro-3-(trifluoromethyl)aniline was converted to the isocyanate, then reacted with 4-(3-(N-Methylcarbamoyl)phenoxy)aniline to afford the urea.

Entry 42: 4-(2-N-Methylcarbamyl-4-pyridyloxy)aniline was synthesized according to Method A2. 4-Chloro-3-(trifluoromethyl)phenyl isocyanate was reacted with 4-(2-N-methylcarbamyl-4-pyridyloxy)aniline according to Method C1a to afford the urea.

Entry 43: 4-Chloropyridine-2-carbonyl chloride HCl salt was reacted with ammonia according to Method A1, Step 3b to form 4-chloro-2-pyridinecarboxamide. 4-Chloro-2-pyridinecarboxamide was reacted with 4-aminophenol according to Method A2, Step 4 to form 4-(2-carbamoyl-4-pyridyloxy)aniline. According to Method C1a, 4-chloro-3-(trifluoromethyl)phenyl isocyanate was reacted with 4-(2-carbamoyl-4-pyridyloxy)aniline to afford the urea.

Entry 44: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 3-aminophenol according to Method A1, Step 4 to form 3-(2-carbamoyl-4-pyridyloxy)aniline. According to Method C1a, 4-chloro-3-(trifluoromethylphenyl isocyanate was reacted with 3-(2-carbamoyl-4-pyridyloxy)aniline to afford the urea.

Entry 45: 4-Chloro-N-methyl-2-pyridinecarboxamide, which was synthesized according to Method A1, Step 3a, was reacted with 3-aminophenol according to Method A2, Step 4 to form 3-(-2-(N-methylcarbamoyl)-4-pyridyloxy)aniline. According to Method C1a, 4-chloro-3-(trifluoromethylphenyl isocyanate was reacted with 3-(2-(N-methylcarbamoyl)-4-pyridyloxy)aniline to afford the urea.

Entry 46: 5-(4-Aminophenoxy)isoindoline-1,3-dione was synthesized according to Method A3. According to Method C1a, 4-chloro-3-(trifluoromethylphenyl isocyanate was reacted with 5-(4-aminophenoxy)isoindoline-1,3-dione to afford the urea.

Entry 47: 4-(2-(N-Methylcarbamoyl)-4-pyridyloxy)-2-methylaniline was synthesized according to Method A5. According to Method C1c, 4-chloro-3-(trifluoromethyl)phenyl isocyanate was reacted with 5-(4-aminophenoxy)isoindoline-1,3-dione to afford the urea.

Entry 48: 4-(3-N-Methylsulfamoyl)phenyloxy)aniline was synthesized according to Method A15. According to Method C1a, 4-chloro-3-(trifluoromethyl)phenyl isocyanate was reacted with 4-(3-N-methylsulfamoyl)phenyloxy)aniline to afford the urea.

Entry 49: 4-(2-(N-Methylcarbamoyl)-4-pyridyloxy)-2-chloroaniline was synthesized according to Method A6. According to Method C1a, 4-chloro-3-(trifluoromethyl)phenyl isocyanate was reacted with 4-(2-(N-methylcarbamoyl)-4-pyridyloxy)-2-chloroaniline to afford the urea.

Entry 50: According to Method A2, Step 4,5-amino-2-methylphenol was reacted with 4-chloro-N-methyl-2-pyridinecarboxamide, which had been synthesized according to Method A2, Step 3b, to give 3-(2-(N-methylcarbamoyl)-4-pyridyloxy)-4-methylaniline. According to Method C1a, 4-chloro-3-(trifluoromethyl)phenyl isocyanate was reacted with 3-(2-(N-methylcarbamoyl)-4-pyridyloxy)-4-methylaniline to afford the urea.

Entry 51: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. According to Method C1a, 4-chloro-3-(trifluoromethyl)phenyl isocyanate was reacted with 4-(2-(N-ethylcarbamoyl)-4-pyridyloxy)aniline to afford the urea.

Entry 52: According to Method A, Step 4,4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. According to Method C1a, 4-chloro-3-(trifluoromethyl)phenyl isocyanate was reacted with 4-(2-(N-methylcarbamoyl)-4-pyridyloxy)-3-chloroaniline to afford the urea.

Entry 53: 4-(4-Methylthiophenoxy)-1-nitrobenzene was oxidized according to Method A19, Step 1 to give 4-(4-methylsulfonylphenoxy)-1-nitrobenzene. The nitrobenzene was reduced according to Method A19, Step 2 to give 4-(4-methylsulfonylphenoxy)-1-aniline. According to Method C1a, 4-chloro-3-(trifluoromethyl)phenyl isocyanate was reacted with 4-(4-methylsulfonylphenoxy)-1-aniline to afford the urea.

Entry 54: 4-Bromobenzenesulfonyl chloride was reacted with methylamine according to Method A15, Step 1 to afford N-methyl-4-bromobenzenesulfonamide. N-Methyl-4-bromobenzenesulfonamide was coupled with phenol according to Method A15, Step 2 to afford 4-(4-(N-methylsulfamoyl)phenoxy)benzene. 4-(4-(N-Methylsulfamoyl)phenoxy)benzene was converted into 4-(4-(N-methylsulfamoyl)phenoxy)-1-nitrobenzene according to Method A15, Step 3. 4-(4-(N-Methylsulfamoyl)phenoxy)-1-nitrobenzene was reduced to 4-(4-N-methylsulfamoyl)phenyloxy)aniline according to Method A15, Step 4. According to Method C1a, 4-chloro-3-(trifluoromethyl)phenyl isocyanate was reacted with 4-(3-N-methylsulfamoyl)phenyloxy)aniline to afford the urea.

Entry 55: 5-Hydroxy-2-methylpyridine was coupled with 1-fluoro-4-nitrobenzene according to Method A18, Step 1 to give 4-(5-(2-Methyl)pyridyloxy)-1-nitrobenzene. The methylpyridine was oxidized according to the carboxylic acid, then esterified according to Method A18, Step 2 to give 4-(5-(2-methoxycarbonyl)pyridyloxy)-1-nitrobenzene. The nitrobenzene was reduced according the Method A18, Step 3 to give 4-(5-(2-methoxycarbonyl)pyridyloxy)aniline. The aniline was reacted with 4-chloro-3-(trifluoromethyl)phenyl isocyanate according to Method C1a to afford the urea.

Entry 56: 5-Hydroxy-2-methylpyridine was coupled with 1-fluoro-4-nitrobenzene according to Method A18, Step 1 to give 4-(5-(2-Methyl)pyridyloxy)-1-nitrobenzene. The methylpyridine was oxidized according to the carboxylic acid, then esterified according to Method A18, Step 2 to give 4-(5-(2-methoxycarbonyl)pyridyloxy)-1-nitrobenzene. The nitrobenzene was reduced according the Method A18, Step 3 to give 4-(5-(2-methoxycarbonyl)pyridyloxy)aniline. The aniline was reacted with 4-chloro-3-(trifluoromethyl)phenyl isocyanate according to Method C1a to give N-(4-chloro-3-(trifluoromethyl)phenyl)-N'-(4-(2-(methoxycarbonyl)-5-pyridyloxy)phenyl) urea. The methyl ester was reacted with methylamine according to Method D2 to afford N-(4-chloro-3-(trifluoromethyl)phenyl)-N'-(4-(2-(N-methylcarbamoyl)-5-pyridyloxy)phenyl) urea.

Entry 57: N-(4-Chloro-3-(trifluoromethyl)phenyl-N'-(4-aminophenyl) urea was prepared according to Method C1d. N-(4-Chloro-3-(trifluoromethyl)phenyl-N-(4-aminophenyl) urea was coupled with mono-methyl isophthalate according to Method D1a to afford the urea.

Entry 58: N-(4-Chloro-3-(trifluoromethyl)phenyl-N'-(4-aminophenyl) urea was prepared according to Method C1d. N-(4-Chloro-3-(trifluoromethyl)phenyl-N'-(4-aminophenyl) urea was coupled with mono-methyl isophthalate according to Method D1a to afford N-(4-chloro-3-(trifluoromethyl)phenyl-N'-(4-(3-methoxycarbonylphenyl)carboxyaminophenyl) urea. According to Method D2, N-(4-chloro-3-(trifluoromethyl)phenyl-N'-(4-(3-methoxycarbonylphenyl)carboxyaminophenyl) urea was reacted with methylamine to afford the corresponding methyl amide.

Entry 59: 4-Chloropyridine-2-carbonyl chloride was reacted with dimethylamine according to Method M, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. According to Method C1a, 4-chloro-3-(trifluoromethyl)phenyl isocyanate was reacted with 4-(2-(N,N-dimethylcarbamoyl)-4-pyridyloxy)aniline to afford the urea.

Entry 60: 4-Hydroxyacetophenone was reacted with 4-fluoronitrobenzene according to Method A13, Step 1 to give 4-(4-acetylphenoxy)nitrobenzene. The nitrobenzene was reduced according to Method 13, Step 4 to afford 4-(4-acetylphenoxy)aniline, which was converted to the 4-(4-(1-(N-methoxy)iminoethyl)phenoxyaniline HCl salt according to Method A16. According to Method C1a, 4-chloro-3-(trifluoromethyl)phenyl isocyanate was reacted with 4-(4-acetylphenoxy)aniline to afford the urea.

Entry 61: 4-(3-Carboxyphenoxy)-1-nitrobenzene was synthesized according to Method A13, Step 2. 4-(3-Carboxyphenoxy)-1-nitrobenzene was coupled with 4-(2-aminoethyl) morpholine according to Method A13, Step 3 to give 4-(3-(N-(2-morpholinylethyl)carbamoyl)phenoxy)-1-nitrobenzene. According to Method A13 Step 4,4-(3-(N-(2-morpholinylethyl)carbamoyl)phenoxy)-1-nitrobenzene was reduced to 4-(3-(N-(2-morpholinylethyl)carbamoyl)phenoxy)aniline. According to Method C1a, 4-chloro-3-(trifluoromethyl)phenyl isocyanate was reacted with 4-(3-(N-(2-morpholinylethyl)carbamoyl)phenoxy)aniline to afford the urea.

Entry 62: 4-(3-Carboxyphenoxy)-1-nitrobenzene was synthesized according to Method A13, Step 2. 4-(3-Carboxyphenoxy)-1-nitrobenzene was coupled with 1-(2-aminoethyl)piperidine according to Method A13, Step 3 to give 4-(3-(N-(2-piperidylethyl)carbamoyl)phenoxy)-1-nitrobenzene. According to Method A13 Step 4, 4-(3-(N-(2-piperidylethyl)carbamoyl)phenoxy)-1-nitrobenzene was reduced to 4-(3-(N-(2-piperidylethyl)carbamoyl)phenoxy)aniline. According to Method C1a, 4-chloro-3-(trifluoromethyl)phenyl isocyanate was reacted with 4-(3-(N-(2-piperidylethyl)carbamoyl)phenoxy)aniline to afford the urea.

Entry 63: 4-(3-Carboxyphenoxy)-1-nitrobenzene was synthesized according to Method A13, Step 2. 4-(3-Carboxyphenoxy)-1-nitrobenzene was coupled with tetrahydrofurfurylamine according to Method A13, Step 3 to give 4-(3-(N-(tetrahydrofurylmethyl)carbamoyl)phenoxy)-1-nitrobenzene. According to Method A13 Step 4,4-(3-(N-(tetrahydrofurylmethyl)carbamoyl)phenoxy)-1-nitrobenzene was reduced to 4-(3-(N-(tetrahydrofurylmethyl)carbamoyl)phenoxy)aniline. According to Method C1a, 4-chloro-3-(trifluoromethyl)phenyl isocyanate was reacted with 4-(3-(N-(tetrahydrofurylmethyl)carbamoyl)phenoxy)aniline to afford the urea.

Entry 64: 4-(3-Carboxyphenoxy)-1-nitrobenzene was synthesized according to Method A13, Step 2. 4-(3-Carboxyphenoxy)-1-nitrobenzene was coupled with 2-aminomethyl-1-ethylpyrrolidine according to Method A13, Step 3 to give 4-(3-(N-((1-methylpyrrolidinyl)methyl)carbamoyl)phenoxy)-1-nitrobenzene. According to Method A13 Step 4,4-(3-(N-((1-methylpyrrolidinyl)methyl)carbamoyl)phenoxy)-1-nitrobenzene was reduced to 4-(3-(N-((1-methylpyrrolidinyl)methyl)carbamoyl)phenoxy)aniline. According to Method C1a, 4-chloro-3-(trifluoromethyl)phenyl isocyanate was reacted with 4-(3-(N-((1-methylpyrrolidinyl)methyl)carbamoyl)phenoxy)aniline to afford the urea.

Entry 65: 4-Chloro-N-methylpyridinecarboxamide was synthesized as described in Method A2, Step 3b. The chloropyridine was reacted with 4-aminothiophenol according to Method A2, Step 4 to give 4-(4-(2-(N-methylcarbamoyl)phenylthio)aniline. According to Method C1a, 4-chloro-3-(trifluoromethyl)phenyl isocyanate was reacted with 4-(4-(2-(N-methylcarbamoyl)phenylthio)aniline to afford the urea.

Entry 66; 4-Chloropyridine-2-carbonyl chloride was reacted with isopropylamine according to Method A, Step 3b. The resulting 4-chloro-N-isopropyl-2-pyridinecarboxamide was reacted with 4-aminophenol according to Method A2, Step 4 to give 4-(2-(N-isopropylcarbamoyl)-4-pyridyloxy) aniline. According to Method C1a, 4-chloro-3-(trifluoromethyl)phenyl isocyanate was reacted with 4-(2-(N-isopropylcarbamoyl)-4-pyridyloxy)aniline to afford the urea.

Entry 67: N-(4-Chloro-3-(trifluoromethyl)phenyl-N'-(4-ethoxycarbonylphenyl) urea was synthesized according to Method C1e. N-(4-Chloro-3-(trifluoromethyl)phenyl-N'-(4-ethoxycarbonylphenyl) urea was saponified according to Method D3 to give N-(4-chloro-3-(trifluoromethyl)phenyl-N-(4-carboxyphenyl) urea. N-(4-Chloro-3-(trifluoromethyl)phenyl-N'-(4-carboxyphenyl) urea was coupled with 3-methylcarbamoylaniline according to Method D1b to give N-(4-chloro-3-(trifluoromethyl)phenyl-N'-(4-(3-methylcarbamoylphenyl)carbamoylphenyl) urea.

Entry 68: 5-(4-Aminophenoxy)-2-methylisoindoline-1,3-dione was synthesized according to Method A9. According to Method C1a, 4-chloro-3-(trifluoromethyl)phenyl isocyanate was reacted with 5-(4-aminophenoxy)-2-methylisoindoline-1,3-dione to afford the urea.

Entry 69: 4-Chloro-N-methylpyridinecarboxamide was synthesized as described in Method A2, Step 3b. The chloropyridine was reacted with 3-aminothiophenol according to Method A2, Step 4 to give 3-(4-(2-(N-methylcarbamoyl)phenylthio)aniline. According to Method C1a, 4-chloro-3-(trifluoromethyl)phenyl isocyanate was reacted with 3-(4-(2-(N-methylcarbamoyl)phenylthio)aniline to afford the urea.

Entry 70: 4-(2-(N-(2-Morpholin-4-ylethyl)carbamoyl)pyridyloxy)aniline was synthesized according to Method A10. According to Method C1a, 4-chloro-3-(trifluoromethyl)phenyl isocyanate was reacted with 4-(2-(N-(2-morpholin-4-yl-ethyl)carbamoyl)pyridyloxy)aniline to afford the urea.

Entry 71: 4-(3-(5-Methoxycarbonyl)pyridyloxy)aniline was synthesized according to Method A14. 4-Chloro-3-(trifluoromethyl)-2-methoxyphenyl isocyanate was reacted with 4-(3-(5-methoxycarbonyl)pyridyloxy)aniline according to Method C1a to afford the urea. N-(4-Chloro-3-(trifluoromethyl)phenyl)-N-(4-(3-(5-methoxycarbonylpyridyl)oxy)phenyl) urea was saponified according to Method D4, Step 1, and the corresponding acid was coupled with 4-(2-aminoethyl)morpholine to afford the amide.

Entry 72: 4-(3-(5-Methoxycarbonyl)pyridyloxy)aniline was synthesized according to Method A14. 4-Chloro-3-(trifluoromethyl)phenyl isocyanate was reacted with 4-(3-(5-methoxycarbonyl)pyridyloxy)amine according to Method C1a to afford the urea. N-(5-(Trifluoromethyl)-2-methoxyphenyl)-N-(4-(3-(5-methoxycarbonylpyridyl)oxy)phenyl) urea was saponified according to Method D4, Step 1, and the corresponding acid was coupled with methylamine according to Method D4, Step 2 to afford the amide.

Entry 73: 4-(3-(5-Methoxycarbonyl)pyridyloxy)aniline was synthesized according to Method A14. 4-Chloro-3-(trifluoromethyl)phenyl isocyanate was reacted with 4-(3-(5-methoxycarbonyl)pyridyloxy)aniline according to Method C1a to afford the urea. N-(5-(Trifluoromethyl)-2-methoxyphenyl)-N'-(4-(3-(5-methoxycarbonylpyridyl)oxy)phenyl) urea was saponified according to Method D4, Step 1, and the corresponding acid was coupled with N,N-dimethylethylenediamine according to Method D4, Step 2 to afford the amide.

Entry 74: 4-Chloropyridine-2-carbonyl chloride HCl salt was reacted with 2-hydroxyethylamine according to Method A2, Step 3b to form 4-chloro-N-(2-triisopropylsilyloxy)ethylpyridine-2-carboxamide. 4-Chloro-N-(2-triisopropylsilyloxy)ethylpyridine-2-carboxamide was reacted with triisopropylsilyl chloride, followed by 4-aminophenol according to Method A17 to form 4-(4-(2-(N-(2-triisopropylsilyloxy)ethylcarbamoyl)pyridyloxyaniline. According to Method C1a, 4-chloro-3-(trifluoromethyl)phenyl isocyanate was reacted with 4-(4-(2-(N-(2-triisopropylsilyloxy)ethylcarbamoyl)pyridyloxyaniline to afford N-(4-chloro-3-((trifluoromethyl)phenyl)-N'-(4-(4-(2-(N-(2-triisopropylsilyloxy)ethylcarbamoyl)pyridyloxyphenyl) urea.

Entry 75: 4-(3-Carboxyphenoxy)aniline was synthesized according to Method A11. 4-Chloro-3-(trifluoromethyl)phenyl isocyanate was reacted with 4-(3-(5-methoxycarbonyl)pyridyloxy)aniline according to Method C1f to afford the urea, which was coupled with 3-aminopyridine according to Method D1c.

Entry 76: 4-(3-Carboxyphenoxy)aniline was synthesized according to Method A11. 4-Chloro-3-(trifluoromethyl)phenyl isocyanate was reacted with 4-(3-carboxyphenoxy)aniline according to Method C1f to afford the urea, which was coupled with N-(4-acetylphenyl)piperazine according to Method D1c.

Entry 77: 4-(3-Carboxyphenoxy)aniline was synthesized according to Method A11. 4-Chloro-3-(trifluoromethyl)phenyl isocyanate was reacted with 4-(3-carboxyphenoxy)aniline according to Method C1f to afford the urea, which was coupled with 4-fluoroaniline according to Method D1c.

Entry 78: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 4-(dimethylamino)aniline according to Method D1c.

Entry 79: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with N-phenylethylenediamine according to Method D1c.

Entry 80: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 2-methoxyethylamine according to Method D1c.

Entry 81: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 5-amino-2-methoxypyridine according to Method D1c.

Entry 82: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 4-morpholinoaniline according to Method D1c.

Entry 83: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with N-(2-pyridyl)piperazine according to Method D1c.

Entry 84: 4-Chloropyridine-2-carbonyl chloride HCl salt was reacted with 2-hydroxyethylamine according to Method A2, Step 3b to form 4-chloro-N-(2-triisopropylsilyloxy)ethylpyridine-2-carboxamide. 4-Chloro-N-(2-triisopropylsilyloxy)ethylpyridine-2-carboxamide was reacted with triisopropylsilyl chloride, followed by 4-aminophenol according to Method A17 to form 4-(4-(2-(N-(2-triisopropylsilyloxy)ethylcarbamoyl)pyridyloxyaniline. According to Method C1a, 4-chloro-3-(trifluoromethyl)phenyl isocyanate was reacted with 4-(4-(2-(N-(2-triisopropylsilyloxy)ethylcarbamoyl)pyridyloxyaniline to give N-(4-chloro-3-(trifluoromethyl)phenyl)-N'-(4-(4-(2-(N-(2-triisopropylsilyloxy)ethylcarbamoyl)pyridyloxyphenyl) urea. The urea was deprotected according to Method D5 to afford N-(4-chloro-3-((trifluoromethyl)phenyl)-N'-(4-(4-(2-(N-(2-hydroxy)ethylcarbamoyl)pyridyloxyphenyl) urea.

Entry 85: 4-(2-(N-Methylcarbamoyl)-4-pyridyloxy) aniline was synthesized according to Method A2. 4-Bromo-3-(trifluoromethyl)aniline was converted to 4-bromo-3-(trifluoromethyl)phenyl isocyanate according to Method B1. According to Method C1a, 4-bromo-3-(trifluoromethyl)phenyl isocyanate was reacted with 4-(2-(N-methylcarbamoyl)-4-pyridyloxy)aniline to afford the urea.

Entry 86: 4-(2-(N-Methylcarbamoyl)-4-pyridyloxy)-2-chloroaniline was synthesized according to Method A6. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-methylcarbamoyl)-4-pyridyloxy)-2-chloroaniline to afford the urea.

Entry 87: According to Method A2, Step 4,4-amino-2-chlorophenol was reacted with 4-chloro-N-methyl-2-pyridinecarboxamide, which had been synthesized according to Method A2, Step 3b, to give 4-(2-(N-methylcarbamoyl)-4- pyridyloxy)-3-chloroaniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-methylcarbamoyl)-4-pyridyloxy)-3-chloroaniline to afford the urea.

Entry 88: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-ethylcarbamoyl)-4-pyridyloxy)aniline to afford the urea.

Entry 89: 4-Chloro-N-methyl-2-pyridinecarboxamide, which was synthesized according to Method A2, Step 3a, was reacted with 3-aminophenol according to Method A2, Step 4 to form 3-(-2-(N-methylcarbamoyl)-4-pyridyloxy)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 3-(-2-(N-methylcarbamoyl)-4-pyridyloxy)aniline to afford the urea.

Entry 90: According to Method A2, Step 4,5-amino-2-methylphenol was reacted with 4-chloro-N-methyl-2-pyridinecarboxamide, which had been synthesized according to Method A2, Step 3b, to give 3-(2-(N-methylcarbamoyl)-4-pyridyloxy)-4-methylaniline. 4-Bromo-3-(trifluoromethyl)aniline was converted into 4-bromo-3-(trifluoromethyl)phenyl isocyanate according to Method 131. According to Method C1a, 4-bromo-3-(trifluoromethyl)phenyl isocyanate was reacted with 3-(2-(N-methylcarbamoyl)-4-pyridyloxy)-4-methylaniline to afford the urea.

Entry 91: 4-Chloropyridine-2-carbonyl chloride was reacted with dimethylamine according to Method A2, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N,N-dimethylcarbamoyl)-4-pyridyloxy)aniline to afford the urea.

Entry 92: 4-Chloro-N-methylpyridinecarboxamide was synthesized as described in Method A, Step 3b. The chloropyridine was reacted with 4-aminothiophenol according to Method A2, Step 4 to give 4-(4-(2-(N-methylcarbamoyl)phenylthio)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(4-(2-(N-methylcarbamoyl)phenylthio)aniline to afford the urea.

Entry 93: 4-Chloro-N-methylpyridinecarboxamide was synthesized as described in Method A2, Step 3b. The chloropyridine was reacted with 3-aminothiophenol according to Method A2, Step 4 to give 3-(4-(2-(N-methylcarbamoyl)phenylthio)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 3-(4-(2-(N-methylcarbamoyl)phenylthio)aniline to afford the urea.

Entry 94: 4-(2-(N-(2-Morpholin-4-ylethyl)carbamoyl)pyridyloxy)aniline was synthesized according to Method A10. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-(2-Morpholin-4-ylethyl)carbamoyl)pyridyloxy)aniline to afford the urea.

Entry 95: 4-(2-(N-Methylcarbamoyl)-4-pyridyloxy)aniline was synthesized according to Method A2. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-methylcarbamoyl)-4-pyridyloxy)aniline to afford the urea.

Entry 96: 4-(2-(N-Methylcarbamoyl)-4-pyridyloxy)-2-chloroaniline was synthesized according to Method A6. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-methylcarbamoyl)-4-pyridyloxy)-2-chloroaniline afford the urea.

Entry 97: According to Method A1, Step 4,4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-methylcarbamoyl)-4-pyridyloxy)-3-chloroaniline to afford the urea.

Entry 98: 4-Chloro-N-methyl-2-pyridinecarboxamide, which was synthesized according to Method A2, Step 3a, was reacted with 3-aminophenol according to Method A2, Step 4 to form 3-(-2-(N-methylcarbamoyl)-4-pyridyloxy)aniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethylphenyl isocyanate as was reacted with 3-(-2-(N-methylcarbamoyl)-4-pyridyloxy)aniline to afford the urea.

Entry 99: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-ethylcarbamoyl)-4-pyridyloxy)aniline to afford the urea.

Entry 100: 4-Chloropyridine-2-carbonyl chloride was reacted with dimethylamine according to Method A2, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. 4-Chloro-2-methoxy-5-(trifluoromethyl) aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N,N-dimethylcarbamoyl)-4-pyridyloxy)aniline to afford the urea.

Entry 101: 4-Chloro-N-methyl-2-pyridinecarboxamide, which was synthesized according to Method A2, Step 3a, was reacted with 3-aminophenol according to Method A1, Step 4 to form 3-(-2-(N-methylcarbamoyl)-4-pyridyloxy)aniline. 2-Amino-3-methoxynaphthalene was synthesized as described Method A1. According to Method C3,2-amino-3-methoxynaphthalene was reacted with bis(trichloromethyl) carbonate followed by 3-(-2-(N-methylcarbamoyl)-4-pyridyloxy)aniline to form the urea.

Entry 102: 4-(2-(N-Methylcarbamoyl)-4-pyridyloxy) aniline was synthesized according to Method A2. 5-tert-Butyl-2-(2,5-dimethylpyrrolyl)aniline was synthesized according to Method A4. 5-tert-Butyl-2-(2,5-dimethylpyrrolyl) aniline was reacted with CDI followed by 4-(2-(N-methylcarbamoyl)-4-pyridyloxy)aniline according to Method C2d to afford the urea.

Entry 103: 4-Chloro-N-methyl-2-pyridinecarboxamide was synthesized according to Method A2, Step 3b. 4-Chloro-N-methyl-2-pyridinecarboxamide was reacted with 4-aminophenol according to Method A2, Step 4 using DMAC in place of DMF to give 4-(2-(N-methylcarbamoyl)-4-pyridyloxy)aniline. According to Method C2b, reaction of 3-amino-2-methoxyquinoline with CDI followed by 4-(2-(N-methylcarbamoyl)-4-pyridyloxy)aniline afforded bis(4-(2-(N-methylcarbamoyl)-4-pyridlyoxy)phenyl) urea.

Tables

The compounds listed in Tables 1-6 below were synthesized according to the general methods shown above, and the more detailed exemplary procedures are in the entry listings above and characterizations are indicated in the tables.

TABLE 1

3-tert-Butylphenyl Ureas

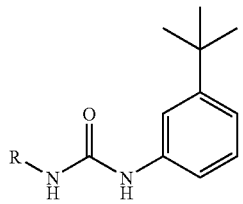

| Entry | R | mp (° C.) | HPLC (min.) | TLC $R_f$ | TLC Solvent System | Mass Spec. [Source] | Synth. Method |
|---|---|---|---|---|---|---|---|
| 1 | (4-methylphenoxy)-3-(N-methylbenzamide) |  |  | 0.22 | 50% EtOAc/ 50% hexane | 418 (M + H)+ (HPLC ES-MS) | A13 C3 |
| 2 | (4-methylphenoxy)-4-acetylphenyl |  |  | 0.58 | 50% EtOAc/ 50% hexane | 403 (M + H)+ (HPLC ES-MS) | A13 C3 |
| 3 | (4-methylphenoxy)-2-methoxy-5-(N-methylbenzamide) | 133-135 |  | 0.68 | 100% EtOAc | 448 (M + H)+ (FAB) | A8 C2d |

TABLE 2
5-tert-Butyl-2-methoxyphenyl Ureas
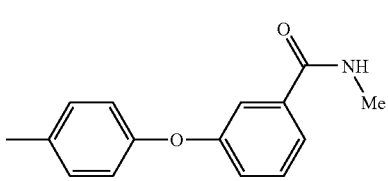
| Entry | R | mp (° C.) | HPLC (min.) | TLC R$_f$ | TLC Solvent System | Mass Spec. [Source] | Synth. Method |
|---|---|---|---|---|---|---|---|
| 4 | 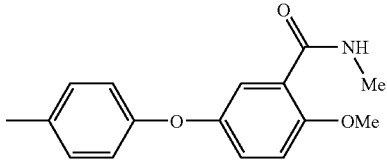 | | 5.93 | | | 448 (M + H)+ (HPLC ES-MS) | A13 B1 C1a |
| 5 | 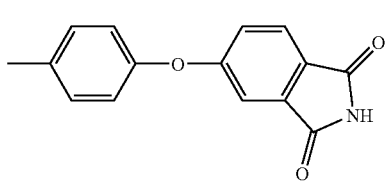 | 120–122 | | 0.67 | 100% EtOAc | 478 (M + H)+ (FAB) | A8 C2d |
| 6 | 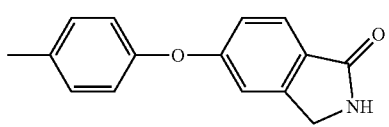 | | | 0.40 | 50% EtOAc/ 50% hexane | 460 (M + H)+ (HPLC ES-MS) | A3 C2d |
| 7 | | | | 0.79 | 50% EtOAc/ 50% hexane | 446 (M + H)+ (HPLC ES-MS) | A12 C2d |

TABLE 3

5-(Trifluoromethyl)-2-methoxyphenyl Ureas

| Entry | R | mp (° C.) | HPLC (min.) | TLC $R_f$ | TLC Solvent System | Mass Spec. [Source] | Synth. Method |
|---|---|---|---|---|---|---|---|
| 8 | 3-(4-methylphenoxy)-N-methylbenzamide | 250 (dec) | | | | 460 (M + H)+ (FAB) | A13 C2a |
| 9 | 4-((5-methylpyridin-2-yl)oxy)acetophenone | 206-208 | | 0.54 | 10% MeOH/ 90% CH2Cl2 | 446 (M + H)+ (HPLC ES-MS) | A3 step 2, A8 step 4, B1, C1a |
| 10 | 4-(4-methylphenoxy)acetophenone | | | 0.33 | 50% EtOAc/ 50% pet ether | 445 (M + H)+ (HPLC ES-MS) | A13 C3 |
| 11 | 4-(3-methylphenoxy)-N-methylpicolinamide | | | 0.20 | 2% Et3N/ 98% EtOAc | 461 (M + H)+ (HPLC ES-MS) | A2 C4 |
| 12 | 4-(3-methylphenoxy)picolinamide | | | 0.27 | 1% Et3N/ 99% EtOAc | 447 (M + H)+ (HPLC ES-MS) | A2 C4 |
| 13 | 4-(4-methylphenoxy)-N-methylpicolinamide | | | 0.62 | 100% EtOAc | 461 (M + H)+ (FAB) | A2 C2a |
| 14 | 4-(4-methylphenoxy)picolinamide | 114-117 | | 0.40 | 1% Et3N/ 99% EtOAc | 447 (M + H)+ (FAB) | A2 C4 |

TABLE 3-continued 5-(Trifluoromethyl)-2-methoxyphenyl Ureas

| Entry | R | mp (° C.) | HPLC (min.) | TLC $R_f$ | TLC Solvent System | Mass Spec. [Source] | Synth. Method |
|---|---|---|---|---|---|---|---|
| 15 | | 232-235 | | 0.54 | 100% EtOAc | 490 (M + H)+ (FAB) | A8 C2d |
| 16 | | 210-213 | | 0.29 | 5% MeOH/ 45% EtOAc/ 50% pet ether | 475 (M + H)+ (HPLC ES-MS) | A5 B1 C1c |
| 17 | | 187-188 | | 0.17 | 50% EtOAc/ 50% pet ether | 495 (M + H)+ (HPLC ES-MS) | A6 B1 C1a |
| 18 | | | | 0.48 | 100% EtOAc | 475 (M + H)+ (HPLC ES-MS) | A2 step 4, B1 C1a |
| 19 | | 194-196 | | 0.31 | 5% MeOH/ 45% EtOAc/ 50% pet ether | 475 (M + H)+ (HPLC ES-MS) | A2 B1 C1a |
| 20 | | 214-216 | | 0.25 | 5% MeOH/ 45% EtOAc/ 50% pet ether | 495 (M + H)+ (HPLC ES-MS) | A2 C1a |
| 21 | | 208-210 | | 0.30 | 50% EtOAc/ 50% hexane | 481 (M + H)+ (HPLC ES-MS) | A19 C2a |

TABLE 3-continued 5-(Trifluoromethyl)-2-methoxyphenyl Ureas

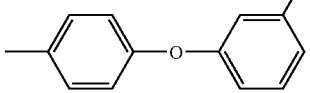

| Entry | R | mp (°C.) | HPLC (min.) | TLC R$_f$ | TLC Solvent System | Mass Spec. [Source] | Synth. Method |
|---|---|---|---|---|---|---|---|
| 22 | 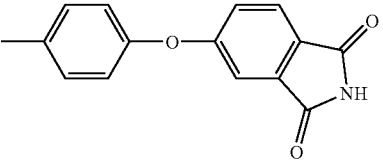 | 188-190 | | 0.30 | 70% EtOAc/ 50% hexane | 447 (M + H)+ (HPLC ES-MS) | A15, step 4, C1a |
| 23 | 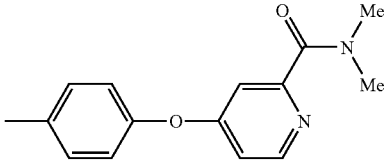 | | | 0.50 | 70% EtOAc/ 30% hexane | 472 (M + H)+ (FAB) | A3 B1 C1a |
| 24 | 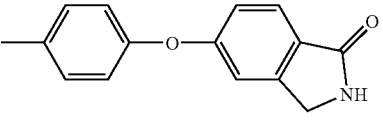 | 203-205 | | 0.13 | 100% EtOAc | 479 (M + H)+ (HPLC ES-MS) | A2 B1 C1a |
| 25 | 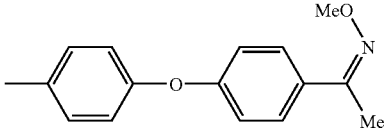 | | | 0.09 | 75% EtOAc/ 25% hexane | 458 (M + H)+ (HPLC ES-MS) | A12 C2d |
| 26 | 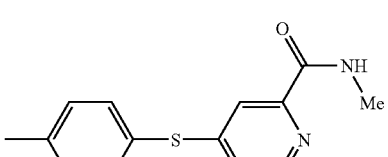 | 169-171 | | 0.67 | 50% EtOAc/ 50% pet ether | 474 (M + H)+ (HPLC ES-MS) | A13 step 1, A13 step 4, A16, B1 C1a |
| 27 | 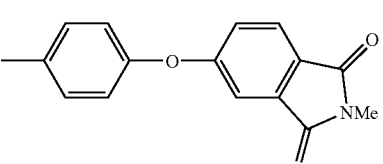 | 218-219 | | 0.40 | 50% EtOAc/ 50% pet ether | 477 (M + H)+ (HPLC ES-MS) | A2 step 3b, A2 step 4, B1, C1a |
| 28 |  | 212-214 | | 0.30 | 40% EtOAc/ 60% hexane | | A9 B1 C1a |

TABLE 3-continued 5-(Trifluoromethyl)-2-methoxyphenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 29 | | | | 0.33 | 50% EtOAc/ 50% pet ether | 474 (M + H)+ (HPLC ES-MS) | A2 step 3b, A2 step 4, B1, C1a |
| 30 | | 210-211 | | | | | A2 B1 C1a |
| 31 | | 210-204 | | 0.43 | 10% MeOH/ CH2Cl2 | | A14 B1 C1a D4 |
| 32 | | 247-249 | | 0.57 | 10% MeOH/ CH2Cl2 | | A14 B1 C1a D4 |
| 33 | | 217-219 | | 0.07 | 10% MeOH/ CH2Cl2 | | A14 B1 C1a D4 |
| 34 | | | | 0.11 | 70% EtOAc/ 30% hexane | | A11 B1 C1f D1c |

TABLE 3-continued

5-(Trifluoromethyl)-2-methoxyphenyl Ureas

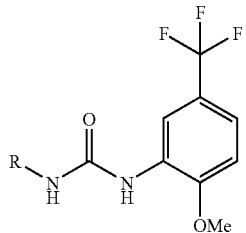

| Entry | R | mp (° C.) | HPLC (min.) | TLC $R_f$ | TLC Solvent System | Mass Spec. [Source] | Synth. Method |
|---|---|---|---|---|---|---|---|
| 35 | 4-F-C6H4-piperazine-C(O)-(3-(4-methylphenoxy)phenyl) | | | 0.38 | 70% EtOAc/ 30% hexane | | A11 B1 C1f D1c |
| 36 | 4-F-C6H4-NH-C(O)-(3-(4-methylphenoxy)phenyl) | | | 0.77 | 70% EtOAc/ 30% hexane | | A11 B1 C1f D1c |
| 37 | 4-(NMe2)-C6H4-NH-C(O)-(3-(4-methylphenoxy)phenyl) | | | 0.58 | 70% EtOAc/ 30% hexane | | A11 B1 C1f D1c |
| 38 | 6-MeO-pyridin-3-yl-NH-C(O)-(3-(4-methylphenoxy)phenyl) | | | 0.58 | 70% EtOAc/ 30% hexane | | A11 B1 C1f D1c |
| 39 | 4-(tetrahydropyran-4-ylamino)-C6H4-NH-C(O)-(3-(4-methylphenoxy)phenyl) | | | 0.17 | 70% EtOAc/ 30% hexane | | A11 B1 C1f D1c |

TABLE 3-continued

5-(Trifluoromethyl)-2-methoxyphenyl Ureas

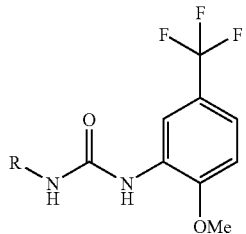

| Entry | R | mp (° C.) | HPLC (min.) | TLC $R_f$ | TLC Solvent System | Mass Spec. [Source] | Synth. Method |
|---|---|---|---|---|---|---|---|
| 40 | (structure) | | | 0.21 | 70% EtOAc/ 30% hexane | | A11 B1 C1f D1c |

TABLE 4

3-(Trifluoromethyl)-4-chlorophenyl Ureas

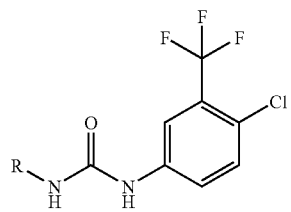

| Entry | R | mp (° C.) | HPLC (min.) | TLC $R_f$ | TLC Solvent System | Mass Spec. [Source] | Synth. Method |
|---|---|---|---|---|---|---|---|
| 41 | (structure) | 163-165 | | 0.08 | 50% EtOAc/ 50% pet ether | 464 (M + H)+ (HPLC ES-MS) | A13 C3 |
| 42 | (structure) | 215 | | 0.06 | 50% EtOAc/ 50% pet ether | 465 (M + H)+ (HPLC ES-MS) | A2 C1a |
| 43 | (structure) | | | 0.10 | 50% EtOAc/ 50% pet ether | 451 (M + H)+ (HPLC ES-MS) | A2 C1a |

TABLE 4-continued
3-(Trifluoromethyl)-4-chlorophenyl Ureas
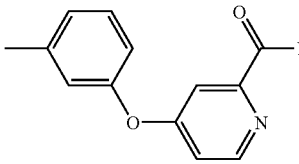
| Entry | R | mp (° C.) | HPLC (min.) | TLC R$_f$ | TLC Solvent System | Mass Spec. [Source] | Synth. Method |
|---|---|---|---|---|---|---|---|
| 44 | 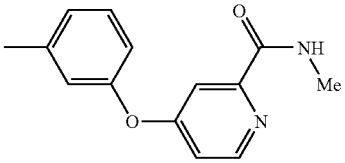 | | | 0.25 | 30% EtOAc/ 70% pet ether | 451 (M + H)+ (HPLC ES-MS) | A2 C1a |
| 45 | 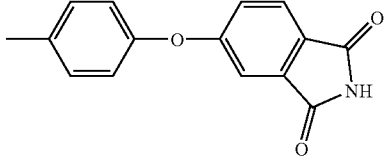 | | | 0.31 | 30% EtOAc/ 70% pet ether | 465 (M + H)+ (HPLC ES-MS) | A2 C1a |
| 46 | 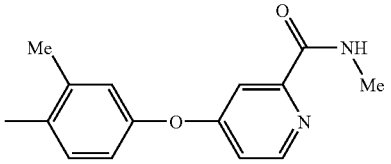 | 176- 179 | | 0.23 | 40% EtOAc/ 60% hexane | 476 (M + H)+ (FAB) | A3 C1a |
| 47 | 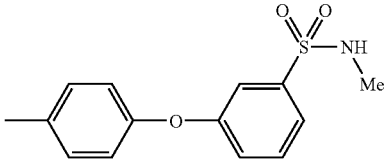 | | | 0.29 | 5% MeOH/ 45% EtOAc/ 50% pet ether | 478 (M + H)+ (HPLC ES-MS) | A5 C1c |
| 48 | 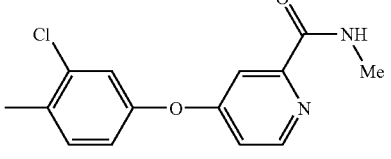 | 206- 209 | | | | | A15 C1a |
| 49 | 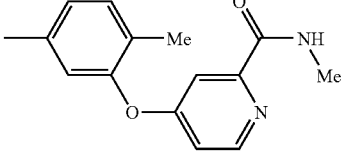 | 147- 151 | | 0.22 | 50% EtOAc/ 50% pet ether | 499 (M + H)+ (HPLC ES-MS) | A6 C1a |
| 50 | | | | 0.54 | 100% EtOAc | 479 (M + H)+ (HPLC ES-MS) | A2 C1a |

TABLE 4-continued
3-(Trifluoromethyl)-4-chlorophenyl Ureas
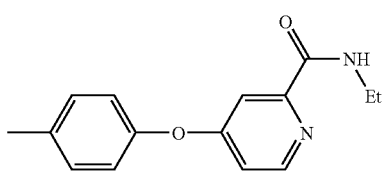
| Entry | R | mp (° C.) | HPLC (min.) | TLC R$_f$ | TLC Solvent System | Mass Spec. [Source] | Synth. Method |
|---|---|---|---|---|---|---|---|
| 51 | 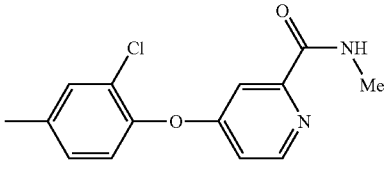 | 187-189 | | 0.33 | 5% MeOH/ 45% EtOAc/ 50% pet ether | 479 (M + H)+ (HPLC ES-MS) | A2 C1a |
| 52 | 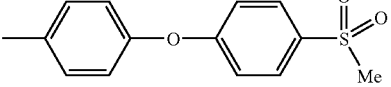 | 219 | | 0.18 | 5% MeOH/ 45% EtOAc/ 50% pet ether | 499 (M + H)+ (HPLC ES-MS) | A2 C1a |
| 53 | 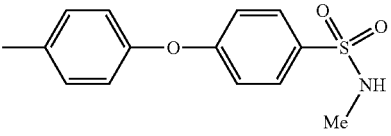 | 246-248 | | 0.30 | 50% EtOAc/ 50% hexane | 485 (M + H)+ (HPLC ES-MS) | A19, C1a |
| 54 | 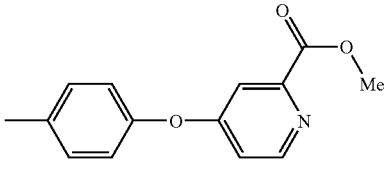 | 196-200 | | 0.30 | 70% EtOAc/ 30% hexane) | 502 (M + H)+ (HPLC ES-MS) | A15 C1a |
| 55 | 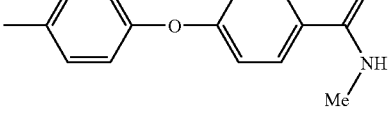 | 228-230 | | 0.30 | 30% EtOAc/ 70% CH2Cl2 | 466 (M + H)+ (HPLC ES-MS) | |
| 56 | 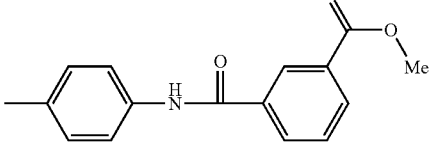 | 238-245 | | | | | |
| 57 |  | 221-222 | | 0.75 | 80% EtOAc/ 20% hexane | 492 (M + H)+ (FAB) | C1d D1a |

TABLE 4-continued 3-(Trifluoromethyl)-4-chlorophenyl Ureas

| Entry | R | mp (° C.) | HPLC (min.) | TLC $R_f$ | TLC Solvent System | Mass Spec. [Source] | Synth. Method |
|---|---|---|---|---|---|---|---|
| 58 | | 247 | | 0.35 | 100% EtOAc | | C1d D1a D2 |
| 59 | | 198-200 | | 0.09 | 100% EtOAc | 479 (M + H)+ (HPLC ES-MS) | A2 C1a |
| 60 | | 158-160 | | 0.64 | 50% EtOAc/ 50% pet ether | | |
| 61 | | 195-197 | | 0.39 | 10% MeOH/ CH2Cl2 | | A13 C1a |
| 62 | | 170-172 | | 0.52 | 10% MeOH/ CH2Cl2 | | A13 C1a |
| 63 | | 168-171 | | 0.39 | 10% MeOH/ CH2Cl2 | | A13 C1a |
| 64 | | 176-177 | | 0.35 | 10% MeOH/ CH2Cl2 | | A13 C1a |

TABLE 4-continued
3-(Trifluoromethyl)-4-chlorophenyl Ureas
| Entry | R | mp (° C.) | HPLC (min.) | TLC R$_f$ | TLC Solvent System | Mass Spec. [Source] | Synth. Method |
|---|---|---|---|---|---|---|---|
| 65 | 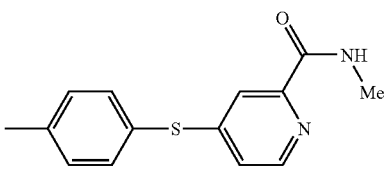 | 130-133 | | | | 487 (M + H)+ (HPLC ES-MS) | A2 B1 C1a |
| 66 | 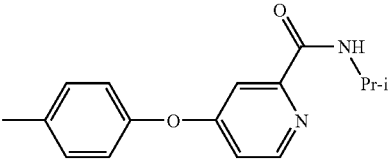 | 155 | | | | | A2 C1a |
| 67 | 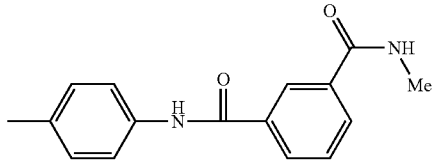 | 225-229 | | 0.23 | 100% EtOAc | | C1e D3 D1b |
| 68 | 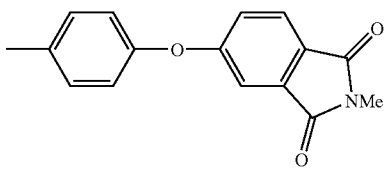 | 234-236 | | 0.29 | 40% EtOAc/ 60% hexane | | A9 C1a |
| 69 | 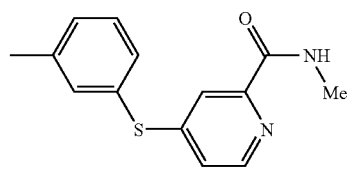 | | | 0.48 | 50% EtOAc/ 50% pet ether | 481 (M + H)+ (HPLC ES-MS) | |
| 70 | 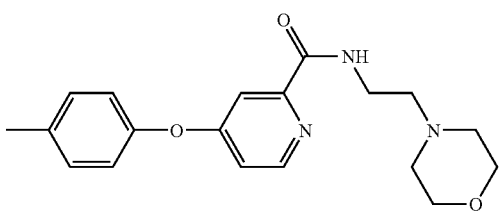 | | | 0.46 | 5% MeOH/ 95% CH2Cl2 | 564 (M + H)+ (HPLC ES-MS) | A10 C1a |

TABLE 4-continued 3-(Trifluoromethyl)-4-chlorophenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 71 | | 199-201 | | 0.50 | 10% MeOH/ CH2Cl2 | | A14 C1a D4 |
| 72 | | 235-237 | | 0.55 | 10% MeOH/ CH2Cl2 | | A14 C1a D4 |
| 73 | | 200-201 | | 0.21 | 50% MeOH/ CH2Cl2 | | A14 C1a D4 |
| 74 | | 145-148 | | | | | |
| 75 | | | | 0.12 | 70% EtOAc/ 30% hexane | 527 (M + H)+ (HPLC ES-MS) | A11 C1f D1c |

TABLE 4-continued
3-(Trifluoromethyl)-4-chlorophenyl Ureas
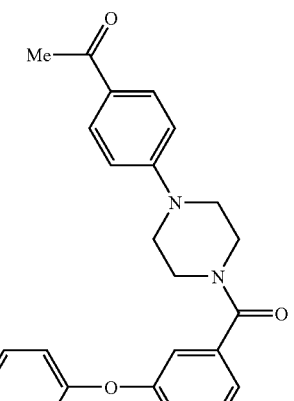
| Entry | R | mp (° C.) | HPLC (min.) | TLC $R_f$ | TLC Solvent System | Mass Spec. [Source] | Synth. Method |
|---|---|---|---|---|---|---|---|
| 76 | 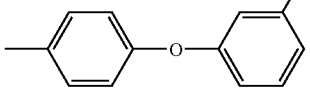 | | | 0.18 | 70% EtOAc/ 30% hexane | | A11 C1f D1c |
| 77 | 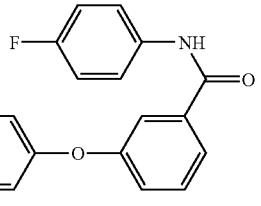 | | | 0.74 | 70% EtOAc/ 30% hexane | | A11 C1f D1c |
| 78 | 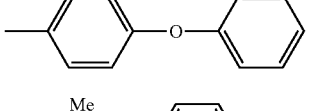 | | | 0.58 | 70% EtOAc/ 30% hexane | | A11 C1f D1c |
| 79 | 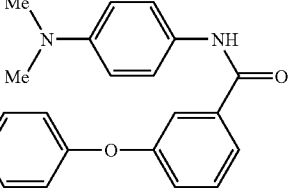 | | | 0.47 | 70% EtOAc/ 30% hexane | 569 (M + H)+ (HPLC ES-MS) | A11 C1f D1c |
| 80 | 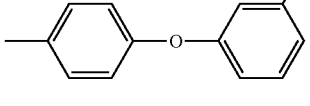 | | | 0.18 | 70% EtOAc/ 30% hexane | 508 (M + H)+ (HPLC ES-MS) | A11 C1f D1c |

TABLE 4-continued 3-(Trifluoromethyl)-4-chlorophenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 81 | | | | 0.58 | 70% EtOAc/ 30% hexane | 557 (M + H)+ (HPLC ES-MS) | A11 C1f D1c |
| 82 | | | | 0.37 | 70% EtOAc/ 30% hexane | 611 (M + H)+ (HPLC ES-MS) | A11 C1f D1c |
| 83 | | | | 0.19 | 70% EtOAc/ 30% hexane | | A11 C1f D1c |
| 84 | | 170 183 | | | | | A2 A17 C1a D5 |

TABLE 5

3-(Trifluoromethyl)-4-bromophenyl Ureas

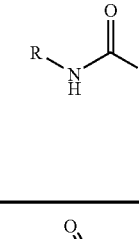

| Entry | R | mp (° C.) | HPLC (min.) | TLC R_f | TLC Solvent System | Mass Spec. [Source] | Synth. Method |
|---|---|---|---|---|---|---|---|
| 85 | 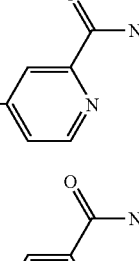 | 186-187 | | 0.13 | 50% EtOAc/ 50% pet ether | 509 (M + H)+ (HPLC ES-MS) | A2 B1 C1a |
| 86 | 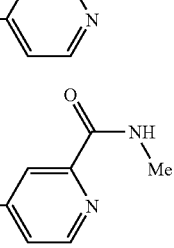 | 150-152 | | 0.31 | 50% EtOAc/ 50% pet ether | 545 (M + H)+ (HPLC ES-MS) | A6 B1 C1a |
| 87 | 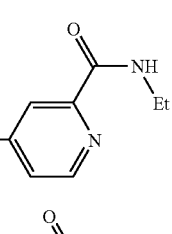 | 217-219 | | 0.16 | 50% EtOAc/ 50% pet ether | 545 (M + H)+ (HPLC ES-MS) | A2 B1 C1a |
| 88 | 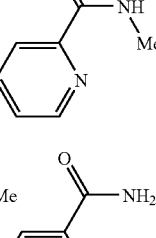 | 183-184 | | 0.31 | 50% EtOAc/ 50% pet ether | 545 (M + H)+ (HPLC ES-MS) | A2 B1 C1a |
| 89 | 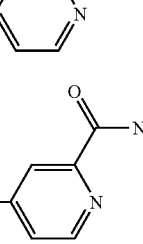 | | | 0.21 | 50% EtOAc/ 50% pet ether | 511 (M + H)+ (HPLC ES-MS) | A2 B1 C1a |
| 90 |  | | | 0.28 | 50% EtOAc/ 50% pet ether | 525 (M + H)+ (HPLC ES-MS) | A2 B1 C1a |
| 91 | | 214-216 | | 0.28 | 50% EtOAc/ 50% pet ether | 522 (M + H)+ (HPLC ES-MS) | A2 B1 C1a |

TABLE 5-continued

3-(Trifluoromethyl)-4-bromophenyl Ureas

| Entry | R | mp (° C.) | HPLC (min.) | TLC R_f | TLC Solvent System | Mass Spec. [Source] | Synth. Method |
|---|---|---|---|---|---|---|---|
| 92 | (4-methylphenyl-S-)pyridine-2-C(O)NHMe | | | 0.47 | 50% EtOAc/ 50% pet ether | 527 (M + H)+ (HPLC ES-MS) | A2 step 3b, A2 step 4, B1, C1a |
| 93 | (3-methylphenyl-S-)pyridine-2-C(O)NHMe | | | 0.46 | 50% EtOAc/ 50% pet ether | 527 (M + H)+ (HPLC ES-MS) | A2 step 3b, A2 step 4, B1, C1a |
| 94 | (4-methylphenyl-O-)pyridine-2-C(O)NH-CH2CH2-morpholine | 145-150 | | 0.41 | 5% MeOH/ 95% CH2Cl2 | | A10 B1 C1a |

TABLE 6

5-(Trifluoromethyl)-4-chloro-2-methoxyphenyl Ureas

| Entry | R | mp (° C.) | HPLC (min.) | TLC R_f | TLC Solvent System | Mass Spec. [Source] | Synth. Method |
|---|---|---|---|---|---|---|---|
| 95 | (4-methylphenyl-O-)pyridine-2-C(O)NHMe | 140-144 | | 0.29 | 5% MeOH/ 45% EtOAc/ 50% pet ether | 495 (M + H)+ (HPLC ES-MS) | A2 A7 B1 C1a |

TABLE 6-continued
5-(Trifluoromethyl)-4-chloro-2-methoxyphenyl Ureas
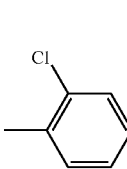
| Entry | R | mp (° C.) | HPLC (min.) | TLC $R_f$ | TLC Solvent System | Mass Spec. [Source] | Synth. Method |
|---|---|---|---|---|---|---|---|
| 96 | 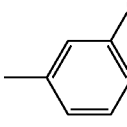 | 244 245 | | 0.39 | 5% MeOH/ 45% EtOAc/ 50% pet ether | 529 (M + H)+ (HPLC ES-MS) | A2 A7 B1 C1a |
| 97 | 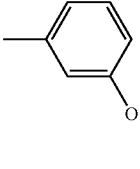 | 220 221 | | 0.25 | 5% MeOH/ 45% EtOAc/ 50% pet ether | 529 (M + H)+ (HPLC ES-MS) | A2 A7 B1 C1a |
| 98 | 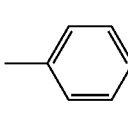 | | | 0.27 | 5% MeOH/ 45% EtOAc/ 50% pet ether | 495 (M + H)+ (HPLC ES-MS) | A2 A7 B1 C1a |
| 99 | 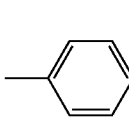 | 180- 181 | | 0.52 | 5% MeOH/ 45% EtOAc/ 50% pet ether | 509 (M + H)+ (HPLC ES-MS) | A2 A7 B1 C1a |
| 100 |  | 162- 165 | | | | | A2 A7 B1 C1a |

TABLE 7

Additional Ureas

| Entry | R | mp (° C.) | HPLC (min.) | TLC $R_f$ | TLC Solvent System | Mass Spec. [Source] | Synth. Method |
|---|---|---|---|---|---|---|---|
| 101 | | 162-165 | | | | | A1 A2 C3 |
| 102 | | | | 0.10 | 50% EtOAc/ 50% hexane | 442 (M + H)+ (HPLC ES-MS) | A2 A4 C2d |
| 103 | | 125-130 | | 0.24 | 40% EtOAc/ 60% hexane | 512 (M + H)+ (FAB) | A2 C2b |

BIOLOGICAL EXAMPLES

P38 Kinase Assay:

The in vitro inhibitory properties of compounds were determined using a p38 kinase inhibition assay. P38 activity was detected using an in vitro kinase assay run in 96-well microtiter plates. Recombinant human p38 (0.5 µg/mL) was mixed with substrate (myelin basic protein, 5 µg/mL) in kinase buffer (25 mM Hepes, 20 mM $MgCl_2$ and 150 mM NaCl) and compound. One µCi/well of $^{33}$P-labeled ATP (10 µM) was added to a final volume of 100 µL. The reaction was run at 32° C. for 30 min. and stopped with a 1M HCl solution. The amount of radioactivity incorporated into the substrate was determined by trapping the labeled substrate onto negatively charged glass fiber filter paper using a 1% phosphoric acid solution and read with a scintillation counter. Negative controls include substrate plus ATP alone.

All compounds exemplified displayed p38 $IC_{50}$s of between 1 nM and 10 µM.

LPS Induced TNFα Production in Mice:

The in vivo inhibitory properties of selected compounds were determined using a murine LPS induced TNFα production in vivo model. BALB/c mice (Charles River Breeding Laboratories; Kingston, N.Y.) in groups of ten were treated with either vehicle or compound by the route noted. After one hour, endotoxin (EB coli lipopolysaccharide (LPS) 100 µg) was administered intraperitoneally (i.p.). After 90 min, animals were euthanized by carbon dioxide asphyxiation and plasma was obtained from individual animals by cardiac puncture into heparinized tubes. The samples were clarified by centrifugation at 12,500×g for 5 min at 4° C. The supernatants were decanted to new tubes, which were stored as needed at −20° C. TNFα levels in sera were measured using a commercial. murine TNF ELISA kit (Genzyme).

The preceding examples can be repeated with similar success by substituting the generically or specifically described reactants and/or operating conditions of this invention for those used in the preceding examples.

From the foregoing discussion, one skilled in the art can easily ascertain the essential characteristics of this invention and, without departing from the spirit and scope thereof, can make various changes and modifications of the invention to adapt it to various usages and conditions.

What is claimed is:

1. A pharmaceutical composition comprising N-(4-chloro-3-(trifluoromethyl)phenyl)-N'-(4-(2-(N-methylcarbamoyl)-4-pyridyloxy)phenyl)urea of the formula X

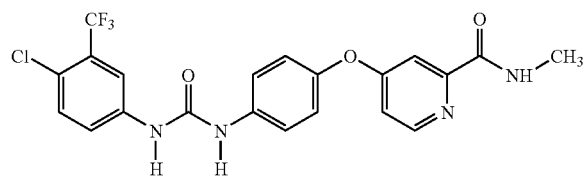

(X)

or a pharmaceutically acceptable salt thereof, and a pharmaceutically acceptable carrier.

2. The pharmaceutical composition of claim 1 wherein the pharmaceutically acceptable salt thereof is a tosylate salt of N-(4-chloro-3-(trifluoromethyl)phenyl)-N'-(4-(2-(N-methylcarbamoyl)-4-pyridyloxy)phenyl)urea of the formula X

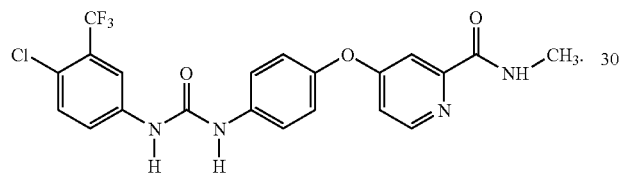

(X)

3. A pharmaceutical composition comprising N-(4-chloro-3-(trifluoromethyl)phenyl)-N'-(4-(2-(N-methylcarbamoyl)-4-pyridyloxy)phenyl)urea of the formula X

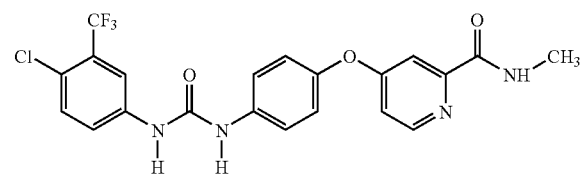

(X)

or a pharmaceutically acceptable salt thereof, and a physiologically acceptable carrier.

4. The pharmaceutical composition of claim 3 wherein the pharmaceutically acceptable salt thereof is a tosylate salt of N-(4-chloro-3-(trifluoromethyl)phenyl)-N'-(4-(2-(N-methylcarbamoyl)-4-pyridyloxy)phenyl)urea of the formula X

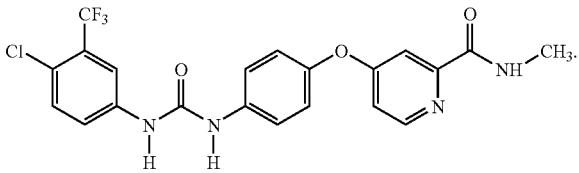

(X)

5. A tablet comprising N-(4-chloro-3-(trifluoromethyl)phenyl)-N'-(4-(2-(N-methylcarbamoyl)-4-pyridyloxy)phenyl)urea of the formula X

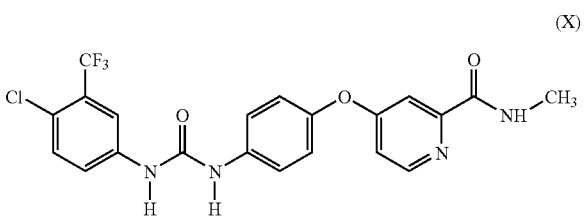

(X)

or a pharmaceutically acceptable salt thereof, and
at least one pharmaceutically acceptable excipient.

6. A tablet of claim 5 wherein the pharmaceutically acceptable salt thereof is a tosylate salt of N-(4-chloro-3-(trifluoromethyl)phenyl)-N'-(4-(2-(N-methylcarbamoyl)-4-pyridyloxy)phenyl)urea of the formula X

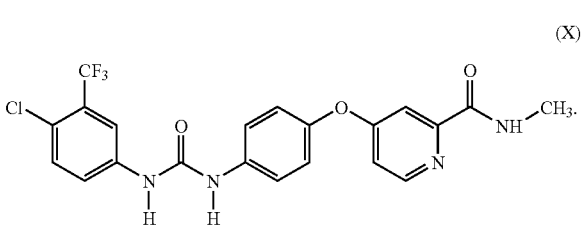

(X)

7. A tablet of claim 5 wherein the pharmaceutically acceptable excipient is a diluent, a granulating agent, a disintegrating agent or a binding agent.

8. A tablet of claim 6 wherein the pharmaceutically acceptable excipient is a diluent, a granulating agent, a disintegrating agent or a binding agent.

* * * * *

UNITED STATES PATENT AND TRADEMARK OFFICE
CERTIFICATE OF CORRECTION

| | | |
|---|---|---|
| PATENT NO. | : 7,897,623 B2 | Page 1 of 1 |
| APPLICATION NO. | : 11/845597 | |
| DATED | : March 1, 2011 | |
| INVENTOR(S) | : Bernd Riedl | |

It is certified that error appears in the above-identified patent and that said Letters Patent is hereby corrected as shown below:

Title page, the text of the section labeled "(75) Inventors" reads:

"Bernd Riedl, Wuppertal (DE); Jacques Dumas, Carlisle, MA (US); Uday R. Khire, Orange, CT (US); Timothy B. Lowinger, Carlisle, MA (US); William J. Scott, Guilford, CT (US); Roger A. Smith, Chester Springs, PA (US); Jill E. Wood, Ft. Collins, CO (US); Mary-Katherine Monahan, Hamden, CT (US); Reina Natero, Hamden, CT (US); Joel Renick, Milford, CT (US); Robert N. Sibley, North Haven, CT (US)"

The text should read:

-- Bernd Riedl, Wuppertal (DE); Jacques Dumas, Carlisle, MA (US); Uday R. Khire, Orange, CT (US); Timothy B. Lowinger, Carlisle, MA (US); William J. Scott, Guilford, CT (US); Roger A. Smith, Chester Springs, PA (US); Jill E. Wood, Ft. Collins, CO (US) --

Signed and Sealed this
Fourteenth Day of June, 2011

David J. Kappos
*Director of the United States Patent and Trademark Office*

Disclaimer

7,897,623 B2 — Bernd Riedl, Wuppertal (DE); Jacques Dumas, Orange, CT (US); Uday Khire, Hamden, CT (US); Timothy B. Lowinger, Nishinomiya (JP); William J. Scott, Guilford, CT (US); Roger A. Smith, Madison, CT (US); Jill E. Wood, North Haven, CT (US); Mary-Katherine Monahan, Hamden, CT (US); Reina Natero, Hamden, CT (US); Joel Renick, Milford, CT ((US); Robert No. Sibley, North Haven, CT (US). OMEGA-CARBOXY ARYL SUBSTITUTED DIPHENYL UREAS AS P38 KINASE INHIBITORS. Patent dated March 1, 2011. Disclaimer filed January 22, 2015, by the assignee, Bayer Healthcare L.L.C.

Hereby disclaims the term of this patent and shall not extend beyond the expiration date of Patent Nos. 7,351,834 and 7,235,576.

*(Official Gazette, February 16, 2016)*